United States Patent
Spencer et al.

(10) Patent No.: US 11,897,938 B2
(45) Date of Patent: Feb. 13, 2024

(54) FACTOR VIII PROTEINS HAVING ANCESTRAL SEQUENCES, EXPRESSION VECTORS, AND USES RELATED THERETO

(71) Applicants: EMORY UNIVERSITY, Atlanta, GA (US); GEORGIA TECH RESEARCH CORPORATION, Atlanta, GA (US)

(72) Inventors: H. Trent Spencer, Marietta, GA (US); Christopher B. Doering, Atlanta, GA (US); Philip M. Zakas, Atlanta, GA (US); Eric Gaucher, Atlanta, GA (US)

(73) Assignees: EMORY UNIVERSITY, Atlanta, GA (US); GEORGIA TECH RESEARCH CORPORATION, Atlanta, GA (US)

( * ) Notice: Subject to any disclaimer, the term of this patent is extended or adjusted under 35 U.S.C. 154(b) by 0 days.

(21) Appl. No.: 17/355,656

(22) Filed: Jun. 23, 2021

(65) Prior Publication Data

US 2021/0388055 A1 Dec. 16, 2021

Related U.S. Application Data

(63) Continuation of application No. 16/874,121, filed on May 14, 2020, now Pat. No. 11,046,750, which is a continuation of application No. 15/547,742, filed as application No. PCT/US2016/015092 on Jan. 27, 2016, now Pat. No. 10,654,910.

(60) Provisional application No. 62/109,964, filed on Jan. 30, 2015.

(51) Int. Cl.
*C07K 14/755* (2006.01)
*A61K 38/00* (2006.01)

(52) U.S. Cl.
CPC ............ *C07K 14/755* (2013.01); *A61K 38/00* (2013.01)

(58) Field of Classification Search
None
See application file for complete search history.

(56) References Cited

U.S. PATENT DOCUMENTS

| 10,654,910 B2 | 5/2020 | Spencer et al. |
| 11,046,750 B2 | 6/2021 | Spencer et al. |
| 2004/0197875 A1 | 10/2004 | Hauser et al. |
| 2007/0166283 A1 | 7/2007 | High et al. |
| 2012/0065136 A1 | 3/2012 | Fay et al. |
| 2013/0296244 A1 | 11/2013 | Lai et al. |

FOREIGN PATENT DOCUMENTS

| WO | 2012061689 | 5/2012 |
| WO | 2013123457 | 8/2013 |

OTHER PUBLICATIONS

Samelson-Jones, Protein-Engineered Coagulation Factors for Hemophilia Gene Therapy, Molecular Therapy: Methods & Clinical Development vol. Mar. 12, 2019, pp. 184-201 (Year: 2019).*
U.S. Appl. No. 15/547,742, Non-Final Office Action, dated May 8, 2019, 12 pages.
U.S. Appl. No. 15/547,742, Notice of Allowance, dated Jan. 13, 2020, 8 pages.
U.S. Appl. No. 16/874,121, Non-Final Office Action, dated Nov. 19, 2020, 5 pages.
U.S. Appl. No. 16/874,121, Notice of Allowance, dated Feb. 25, 2021, 8 pages.
Brown et al., "Bioengineered Coagulation Factor VIII Enables Long-term Correction of Murine Hemophilia a Following Liver-directed Adeno-associated Viral Vector Delivery", Molecular Therapy—Methods and Clinical Development, vol. 1, No. 14036, Aug. 6, 2014, 10 pages.
Doering et al., "Identification of Porcine Coagulation Factor VIII Domains Responsible for High Level Expression via Enhanced Secretion", The Journal of Biological Chemistry, vol. 279, No. 8, Feb. 20, 2004, pp. 6546-6552.
Application No. EP16744021.3, Extended European Search Report, dated Sep. 3, 2018, 7 pages.
Application No. EP16744021.3, Notice of Decision to Grant, dated Jun. 18, 2020, 2 pages.
Application No. EP16744021.3, Office Action, dated May 23, 2019, 6 pages.
Gunasekera et al., "Factor VIII Gene Variants and Inhibitor Risk in African American Hemophilia a Patients", Blood, vol. 126, No. 7, Aug. 13, 2015, pp. 895-904.
Hussain et al., "Three Novel F8 Mutations in Sporadic Haemophilia A Cases", Springerplus, vol. 1, No. 10, 2012, 3 pages.
Lind et al., "Novel Forms of B-domain-deleted Recombinant Factor Viii Molecules: Construction and Biochemical Characterization", European Journal of Biochemistry, vol. 232, No. 1, Aug. 15, 1995, pp. 19-27.
Mcintosh et al., "Therapeutic Levels of Fviii Following a Single Peripheral Vein Administration of Raav Vector Encoding a Novel Human Factor VIII Variant", Blood, vol. 121, No. 17, Apr. 25, 2013, pp. 3335-3344.
Ngo et al., "Crystal Structure of Human Factor VIII: Implications for the Formation of the Factor IXa-Factor VIIIa Complex", Structure, vol. 16, No. 4, Apr. 2008, pp. 597-606.
Application No. PCT/US2016/015092, International Preliminary Report on Patentability, dated Aug. 10, 2017, 7 pages.
Application No. PCT/US2016/015092, International Search Report and Written Opinion, dated Jun. 23, 2016, 11 pages.

(Continued)

*Primary Examiner* — Thomas S Heard
(74) *Attorney, Agent, or Firm* — Kilpatrick Townsend & Stockton LLP

(57) ABSTRACT

This disclosure relates to recombinant or chimeric FVIII proteins, variants, and vectors encoding the proteins containing one or more ancestral mutations. In certain embodiments, one or more protein domains comprise amino acid sequences that are derived from ancestrally reconstructed amino acid sequences. In certain embodiments, the disclosure relates to pharmaceutical compositions comprising the proteins or vectors and related methods of inducing blood clotting.

9 Claims, 8 Drawing Sheets

Specification includes a Sequence Listing.

(56) References Cited

OTHER PUBLICATIONS

Powell, "Recombinant Factor Viii in the Management of Hemophilia a: Current Use and Future Promise", Therapeutics and Clinical Risk Management, vol. 5, 2009, pp. 391-402.
Schwarz et al., "F8 Haplotype and Inhibitor Risk: Results from the Hemophilia Inhibitor Genetics Study (HIGS) Combined Cohort", Haemophilia, vol. 19, No. 1, Jan. 2013, pp. 113-118.
Shen et al., "The Tertiary Structure and Domain Organization of Coagulation Factor VIII", Blood, vol. 111, No. 3, Feb. 1, 2008, pp. 1240-1247.
Zakas et al., "Expanding the Ortholog Approach for Hemophilia Treatment Complicated by Factor VIII Inhibitors", Journal of Thrombosis and Haemostasis, vol. 13, No. 1, Jan. 2015, pp. 72-81.

\* cited by examiner

SEQUENCE LISTING

```
<160> NUMBER OF SEQ ID NOS: 277

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110
```

```
His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
        515                 520                 525
```

-continued

```
Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
930                 935                 940
```

```
Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Thr Glu Ser Gly Arg Leu Phe
        980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

Gln Arg Thr His Gly Lys Asn Ser Leu Asn Ser Gly Gln Gly Pro
        1130                1135                1140

Ser Pro Lys Gln Leu Val Ser Leu Gly Pro Glu Lys Ser Val Glu
        1145                1150                1155

Gly Gln Asn Phe Leu Ser Glu Lys Asn Lys Val Val Val Gly Lys
        1160                1165                1170

Gly Glu Phe Thr Lys Asp Val Gly Leu Lys Glu Met Val Phe Pro
        1175                1180                1185

Ser Ser Arg Asn Leu Phe Leu Thr Asn Leu Asp Asn Leu His Glu
        1190                1195                1200

Asn Asn Thr His Asn Gln Glu Lys Lys Ile Gln Glu Glu Ile Glu
        1205                1210                1215

Lys Lys Glu Thr Leu Ile Gln Glu Asn Val Val Leu Pro Gln Ile
        1220                1225                1230

His Thr Val Thr Gly Thr Lys Asn Phe Met Lys Asn Leu Phe Leu
        1235                1240                1245

Leu Ser Thr Arg Gln Asn Val Glu Gly Ser Tyr Asp Gly Ala Tyr
        1250                1255                1260

Ala Pro Val Leu Gln Asp Phe Arg Ser Leu Asn Asp Ser Thr Asn
        1265                1270                1275

Arg Thr Lys Lys His Thr Ala His Phe Ser Lys Lys Gly Glu Glu
        1280                1285                1290

Glu Asn Leu Glu Gly Leu Gly Asn Gln Thr Lys Gln Ile Val Glu
        1295                1300                1305

Lys Tyr Ala Cys Thr Thr Arg Ile Ser Pro Asn Thr Ser Gln Gln
        1310                1315                1320

Asn Phe Val Thr Gln Arg Ser Lys Arg Ala Leu Lys Gln Phe Arg
        1325                1330                1335
```

```
Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725
```

```
Gly Met Ser Ser Ser Pro His Val Leu Arg Asn Arg Ala Gln Ser
        1730                1735                1740

Gly Ser Val Pro Gln Phe Lys Lys Val Val Phe Gln Glu Phe Thr
        1745                1750                1755

Asp Gly Ser Phe Thr Gln Pro Leu Tyr Arg Gly Glu Leu Asn Glu
        1760                1765                1770

His Leu Gly Leu Leu Gly Pro Tyr Ile Arg Ala Glu Val Glu Asp
        1775                1780                1785

Asn Ile Met Val Thr Phe Arg Asn Gln Ala Ser Arg Pro Tyr Ser
        1790                1795                1800

Phe Tyr Ser Ser Leu Ile Ser Tyr Glu Glu Asp Gln Arg Gln Gly
        1805                1810                1815

Ala Glu Pro Arg Lys Asn Phe Val Lys Pro Asn Glu Thr Lys Thr
        1820                1825                1830

Tyr Phe Trp Lys Val Gln His His Met Ala Pro Thr Lys Asp Glu
        1835                1840                1845

Phe Asp Cys Lys Ala Trp Ala Tyr Phe Ser Asp Val Asp Leu Glu
        1850                1855                1860

Lys Asp Val His Ser Gly Leu Ile Gly Pro Leu Leu Val Cys His
        1865                1870                1875

Thr Asn Thr Leu Asn Pro Ala His Gly Arg Gln Val Thr Val Gln
        1880                1885                1890

Glu Phe Ala Leu Phe Phe Thr Ile Phe Asp Glu Thr Lys Ser Trp
        1895                1900                1905

Tyr Phe Thr Glu Asn Met Glu Arg Asn Cys Arg Ala Pro Cys Asn
        1910                1915                1920

Ile Gln Met Glu Asp Pro Thr Phe Lys Glu Asn Tyr Arg Phe His
        1925                1930                1935

Ala Ile Asn Gly Tyr Ile Met Asp Thr Leu Pro Gly Leu Val Met
        1940                1945                1950

Ala Gln Asp Gln Arg Ile Arg Trp Tyr Leu Leu Ser Met Gly Ser
        1955                1960                1965

Asn Glu Asn Ile His Ser Ile His Phe Ser Gly His Val Phe Thr
        1970                1975                1980

Val Arg Lys Lys Glu Glu Tyr Lys Met Ala Leu Tyr Asn Leu Tyr
        1985                1990                1995

Pro Gly Val Phe Glu Thr Val Glu Met Leu Pro Ser Lys Ala Gly
        2000                2005                2010

Ile Trp Arg Val Glu Cys Leu Ile Gly Glu His Leu His Ala Gly
        2015                2020                2025

Met Ser Thr Leu Phe Leu Val Tyr Ser Asn Lys Cys Gln Thr Pro
        2030                2035                2040

Leu Gly Met Ala Ser Gly His Ile Arg Asp Phe Gln Ile Thr Ala
        2045                2050                2055

Ser Gly Gln Tyr Gly Gln Trp Ala Pro Lys Leu Ala Arg Leu His
        2060                2065                2070

Tyr Ser Gly Ser Ile Asn Ala Trp Ser Thr Lys Glu Pro Phe Ser
        2075                2080                2085

Trp Ile Lys Val Asp Leu Leu Ala Pro Met Ile Ile His Gly Ile
        2090                2095                2100

Lys Thr Gln Gly Ala Arg Gln Lys Phe Ser Ser Leu Tyr Ile Ser
        2105                2110                2115
```

```
Gln Phe Ile Ile Met Tyr Ser Leu Asp Gly Lys Lys Trp Gln Thr
    2120            2125                2130

Tyr Arg Gly Asn Ser Thr Gly Thr Leu Met Val Phe Phe Gly Asn
    2135            2140                2145

Val Asp Ser Ser Gly Ile Lys His Asn Ile Phe Asn Pro Pro Ile
    2150            2155                2160

Ile Ala Arg Tyr Ile Arg Leu His Pro Thr His Tyr Ser Ile Arg
    2165            2170                2175

Ser Thr Leu Arg Met Glu Leu Met Gly Cys Asp Leu Asn Ser Cys
    2180            2185                2190

Ser Met Pro Leu Gly Met Glu Ser Lys Ala Ile Ser Asp Ala Gln
    2195            2200                2205

Ile Thr Ala Ser Ser Tyr Phe Thr Asn Met Phe Ala Thr Trp Ser
    2210            2215                2220

Pro Ser Lys Ala Arg Leu His Leu Gln Gly Arg Ser Asn Ala Trp
    2225            2230                2235

Arg Pro Gln Val Asn Asn Pro Lys Glu Trp Leu Gln Val Asp Phe
    2240            2245                2250

Gln Lys Thr Met Lys Val Thr Gly Val Thr Thr Gln Gly Val Lys
    2255            2260                2265

Ser Leu Leu Thr Ser Met Tyr Val Lys Glu Phe Leu Ile Ser Ser
    2270            2275                2280

Ser Gln Asp Gly His Gln Trp Thr Leu Phe Phe Gln Asn Gly Lys
    2285            2290                2295

Val Lys Val Phe Gln Gly Asn Gln Asp Ser Phe Thr Pro Val Val
    2300            2305                2310

Asn Ser Leu Asp Pro Pro Leu Leu Thr Arg Tyr Leu Arg Ile His
    2315            2320                2325

Pro Gln Ser Trp Val His Gln Ile Ala Leu Arg Met Glu Val Leu
    2330            2335                2340

Gly Cys Glu Ala Gln Asp Leu Tyr
    2345            2350

<210> SEQ ID NO 2
<211> LENGTH: 2324
<212> TYPE: PRT
<213> ORGANISM: artificial sequence
<220> FEATURE:
<223> OTHER INFORMATION: ancestral

<400> SEQUENCE: 2

Met Gln Ile Ala Leu Phe Thr Cys Phe Phe Leu Ser Leu Phe Asn Phe
1               5                   10                  15

Cys Ser Ser Ala Thr Arg Arg Tyr Tyr Leu Gly Ala Val Glu Leu Ser
            20                  25                  30

Trp Asn Tyr Met Gln Ser Asp Leu Leu Ser Val Leu His Thr Asp Thr
        35                  40                  45

Arg Phe Leu Pro Arg Met Pro Thr Ser Phe Pro Phe Asn Thr Ser Ile
    50                  55                  60

Met Tyr Lys Lys Thr Val Phe Val Glu Tyr Met Asp His Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Ile Thr Leu Lys Asn Met Ala
            100                 105                 110
```

```
Ser His Pro Val Ser Leu His Ala Val Gly Val Ser Tyr Trp Lys Ala
            115                 120                 125
Ser Glu Gly Ala Glu Tyr Glu Asp Gln Thr Ser Gln Arg Glu Lys Glu
130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                165                 170                 175
Ser Tyr Leu Ser His Val Asp Leu Val Lys Asp Leu Asn Ser Gly Leu
            180                 185                 190
Ile Gly Ala Leu Leu Val Cys Lys Glu Gly Ser Leu Ser Lys Glu Arg
        195                 200                 205
Thr Gln Met Leu His Gln Phe Val Leu Leu Phe Ala Val Phe Asp Glu
    210                 215                 220
Gly Lys Ser Trp His Ser Glu Thr Lys Asp Ser Phe Thr Gln Ala Met
225                 230                 235                 240
Asp Ser Ala Ser Thr Arg Ala Trp Pro Lys Met His Thr Val Asn Gly
                245                 250                 255
Tyr Val Asn Arg Ser Leu Pro Gly Leu Ile Gly Cys His Arg Lys Ser
            260                 265                 270
Val Tyr Trp His Val Ile Gly Met Gly Thr Thr Pro Glu Val His Ser
    275                 280                 285
Ile Phe Leu Glu Gly His Thr Phe Leu Val Arg Asn His Arg Gln Ala
    290                 295                 300
Ser Leu Glu Ile Ser Pro Ile Thr Phe Leu Thr Ala Gln Thr Leu Leu
305                 310                 315                 320
Ile Asp Leu Gly Gln Phe Leu Leu Phe Cys His Ile Ser Ser His Lys
                325                 330                 335
His Asp Gly Met Glu Ala Tyr Val Lys Val Asp Ser Cys Pro Glu Glu
            340                 345                 350
Pro Gln Trp Gln Lys Lys Asn Asn Glu Glu Met Glu Asp Tyr Asp Asp
        355                 360                 365
Asp Leu Asp Ser Glu Met Asp Met Phe Thr Leu Asp Asp Asn Ser
    370                 375                 380
Pro Phe Ile Gln Ile Arg Ser Val Ala Lys Lys Tyr Pro Lys Thr Trp
385                 390                 395                 400
Ile His Tyr Ile Ser Ala Glu Glu Asp Trp Asp Tyr Ala Pro Ser
                405                 410                 415
Val Leu Thr Ser Asp Asp Gly Ser Tyr Lys Ser Gln Tyr Leu Ser Asn
            420                 425                 430
Gly Pro His Arg Ile Gly Arg Lys Tyr Lys Val Arg Phe Ile Ala
        435                 440                 445
Tyr Thr Asp Glu Thr Phe Lys Thr Arg Glu Thr Ile Gln His Glu Ser
    450                 455                 460
Gly Ile Leu Gly Pro Leu Leu Tyr Gly Glu Val Gly Asp Thr Leu Leu
465                 470                 475                 480
Ile Ile Phe Lys Asn Gln Ala Ser Arg Pro Tyr Asn Ile Tyr Pro His
                485                 490                 495
Gly Ile Thr Asp Val Ser Pro Leu His Ser Arg Arg Leu Pro Arg Gly
            500                 505                 510
Ile Lys His Val Lys Asp Leu Pro Ile Arg Pro Gly Glu Ile Phe Lys
        515                 520                 525
```

-continued

Tyr Lys Trp Thr Val Thr Val Glu Asp Gly Pro Thr Lys Ser Asp Pro
            530                 535                 540

Arg Cys Leu Thr Arg Tyr Tyr Ser Ser Phe Ile Asn Pro Glu Arg Asp
545                 550                 555                 560

Leu Ala Ser Gly Leu Ile Gly Pro Leu Leu Ile Cys Tyr Lys Glu Ser
                565                 570                 575

Val Asp Gln Arg Gly Asn Gln Met Met Ser Asp Lys Arg Asn Val Ile
            580                 585                 590

Leu Phe Ser Val Phe Asp Glu Asn Gln Ser Trp Tyr Ile Thr Glu Asn
                595                 600                 605

Met Gln Arg Phe Leu Pro Asn Ala Ala Asp Thr Gln Pro Gln Asp Pro
        610                 615                 620

Glu Phe Gln Ala Ser Asn Ile Met His Ser Ile Asn Gly Tyr Val Phe
625                 630                 635                 640

Asp Ser Leu Gln Leu Thr Val Cys Leu His Glu Val Ala Tyr Trp Tyr
                645                 650                 655

Ile Leu Ser Val Gly Ala Gln Thr Asp Phe Leu Ser Ile Phe Phe Ser
                660                 665                 670

Gly Tyr Thr Phe Lys His Lys Met Val Tyr Glu Asp Thr Leu Thr Leu
            675                 680                 685

Phe Pro Phe Ser Gly Glu Thr Val Phe Met Ser Met Glu Asn Pro Gly
690                 695                 700

Leu Trp Val Leu Gly Cys His Asn Ser Asp Phe Arg Lys Arg Gly Met
705                 710                 715                 720

Thr Ala Leu Leu Lys Val Ser Ser Cys Asp Lys Ser Thr Ser Asp Tyr
                725                 730                 735

Tyr Glu Glu Ile Tyr Glu Asp Ile Pro Thr Gln Leu Val Asn Asp Asn
            740                 745                 750

Asn Val Ile Glu Pro Arg Ser Phe Phe Gln Asn Ser Asn His Pro Asn
            755                 760                 765

Thr Arg Lys Lys Lys Phe Lys Ala Thr Thr Ile Pro Glu Asn Asp Ile
        770                 775                 780

Glu Lys Ile Glu Pro Gln Phe Gly Glu Thr Ala Glu Met Leu Lys Val
785                 790                 795                 800

Gln Ser Val Ser Ser Ser Asp Leu Leu Met Leu Leu Gly Gln Ser Pro
                805                 810                 815

Thr Pro His Gly Leu Ser Leu Ser Asp Asn Gln Glu Ala Ile Tyr Glu
            820                 825                 830

Ala Ile Pro Asp Asp His Ser Pro Asp Ala Ile Asp Ser Asn Glu Gly
            835                 840                 845

Pro Ser Lys Val Thr Gln Leu Arg Pro Glu Leu His His Ser Gly Lys
        850                 855                 860

Ile Val Phe Thr Pro Glu Pro Gly Leu Gln Leu Arg Ser Asn Lys Asn
865                 870                 875                 880

Leu Glu Thr Thr Ile Glu Val Lys Trp Lys Lys Leu Asp Leu Gln Val
                885                 890                 895

Ser Ser Leu Pro Asn Asn Leu Met Thr Thr Thr Ile Leu Ser Asp Asn
                900                 905                 910

Leu Thr Ala Thr Ser Glu Lys Thr Asp Ser Ser Gly Ser Pro Asp Met
        915                 920                 925

Pro Val His Phe Ser Ser Lys Leu Ser Thr Thr Ala Phe Gly Lys Lys
        930                 935                 940

-continued

```
Ser Tyr Pro Leu Ile Gly Ser His Val Pro Leu Asn Ile Ser Glu Arg
945                 950                 955                 960

Asn Ser Asp Ser Asn Leu Leu Asp Ala Thr Leu Met Asn Asn Gln Glu
                965                 970                 975

Ser Ser Leu Gly Asp Asn Ile Ser Ser Met Glu Asn Asp Arg Leu Leu
            980                 985                 990

Lys Glu Lys Arg Phe His Gly Ile Ala Leu Leu Thr Lys Asp Asn Thr
        995                 1000                1005

Leu Phe Lys Asp Asn Ile Ser Leu Met Lys Thr Asn Lys Thr Tyr
    1010                1015                1020

Asn His Ser Thr Thr Asn Gly Lys Ala His Ile Asp Ser Pro Thr
    1025                1030                1035

Ser Ile Glu Asn Ser Thr Ala Val Leu Gln Asp Thr Ile Leu Lys
    1040                1045                1050

Ile Asn Ser Glu Ile Gln Glu Val Thr Ser Leu Ile His Asp Gly
    1055                1060                1065

Thr Leu Ser Gly Lys Asn Thr Thr Tyr Leu Arg Leu Asn His Met
    1070                1075                1080

Leu Asn Arg Thr Thr Ser Ser Lys Asn Lys Glu Ile Phe His Gln
    1085                1090                1095

Lys Asp Glu Asp Pro Val Pro Gln Asp Thr Glu Asn Thr Ile Met
    1100                1105                1110

Pro Phe Phe Lys Met Leu Phe Leu Pro Glu Ser Ala Asn Trp Met
    1115                1120                1125

Lys Arg Thr Asn Gly Asn Asn Ser Leu Asn Ser Glu Gln Gly Pro
    1130                1135                1140

Ser Pro Lys Gln Leu Val Tyr Leu Met Leu Glu Lys Ser Val Lys
    1145                1150                1155

Asn Gln Asn Phe Leu Ser Glu Lys Asn Lys Val Ile Val Glu Gln
    1160                1165                1170

Asp Glu Phe Thr Lys Asp Thr Gly Leu Lys Asp Met Val Phe Pro
    1175                1180                1185

Ser Asn Met Ser Ile Phe Leu Thr Thr Leu Ala Asn Val Gln Glu
    1190                1195                1200

Asn Asp Met His Asn Gln Glu Lys Asn Ile Gln Glu Glu Ile Glu
    1205                1210                1215

Lys Glu Ala Leu Ile Glu Glu Lys Val Val Leu Pro Gln Val His
    1220                1225                1230

Ile Ala Thr Gly Ser Lys Asn Phe Leu Lys Asp Ile Phe Phe Leu
    1235                1240                1245

Gly Thr Arg Gln Asn Val Ser Leu Asp Glu Asp Ile Tyr Val Pro
    1250                1255                1260

Val Leu Gln Asp Ile Ser Ser Ile Asn Asn Ser Thr Asn Thr Val
    1265                1270                1275

Glu Ile His Met Ala His Phe Phe Lys Arg Arg Glu Asp Glu Glu
    1280                1285                1290

Thr Asn Ser Glu Gly Leu Val Asn Lys Thr Arg Glu Met Val Lys
    1295                1300                1305

Asn Tyr Pro Ser Gln Lys Asn Ile Ile Thr Gln Arg Ser Lys Arg
    1310                1315                1320

Ala Leu Gly Gln Phe Arg Leu Pro Leu Ala Ser Thr Gln Trp Pro
    1325                1330                1335
```

```
Gln Thr Met Asn Tyr Leu Thr Gln Ser Ile Ile Thr Gln Ile Asp
    1340                1345                1350

His Ser Lys Glu Gly Glu Lys Ser Ile Thr Gln Ser Ser Leu Ser
    1355                1360                1365

Asp Ser Ser Met Ile Lys Ser Thr Thr Gln Thr Asn Ser Ser Gly
    1370                1375                1380

Leu His Ile Val Lys Thr Ser Ala Phe Pro Pro Thr Asp Leu Lys
    1385                1390                1395

Arg Ile Pro Phe Gln Asp Lys Phe Phe His Val Leu Ala Ser Ser
    1400                1405                1410

Tyr Thr Tyr Asp Phe Lys Thr Lys Ser Ser Arg Ile Gln Glu Ser
    1415                1420                1425

Ser His Phe Leu Lys Glu Thr Lys Ile Asn Asn Ser Ser Leu Ala
    1430                1435                1440

Ile Leu Pro Trp Glu Met Ile Ile Asn Gln Gly Lys Phe Ala Ser
    1445                1450                1455

Pro Gly Thr Ser Asn Thr Asn Ser Val Thr Tyr Lys Lys Leu Glu
    1460                1465                1470

Asn Ile Val Leu Leu Lys Pro Val Leu Pro Glu Glu Ser Gly Lys
    1475                1480                1485

Val Glu Leu Leu Pro Gln Val Ser Ile His Glu Glu Leu Leu
    1490                1495                1500

Pro Thr Glu Thr Ser His Gly Ser Pro Gly His Leu Asp Leu Met
    1505                1510                1515

Lys Glu Val Phe Leu Gln Lys Thr Gln Gly Pro Ile Lys Trp Asn
    1520                1525                1530

Lys Ala Lys Arg His Gly Glu Ser Glu Leu Lys Gly Thr Thr Glu
    1535                1540                1545

Ser Ser Glu Lys Thr Pro Ser Lys Leu Leu Asp His Leu Ala Trp
    1550                1555                1560

Asp Asn His Tyr Ala Ala Gln Ile Pro Lys Asp Lys Trp Lys Ser
    1565                1570                1575

Lys Glu Lys Ser Pro Glu Ile Thr Ser Ile Lys Arg Glu Asp Thr
    1580                1585                1590

Ile Leu Ser Leu Asn Pro His Glu Asn Asn His Ser Ile Val Ala
    1595                1600                1605

Asn Glu Lys Gln Asn Trp Pro Gln Arg Glu Ala Thr Trp Val Lys
    1610                1615                1620

Gln Gly Gln Thr Gln Arg Leu Cys Ser Gln Asn Pro Pro Val Leu
    1625                1630                1635

Lys Arg His Gln Arg Glu Leu Ser Ala Leu Gln Ser Glu Gln Glu
    1640                1645                1650

Ala Thr Asp Tyr Asp Asp Ser Ile Thr Ile Glu Thr Asn Glu Asp
    1655                1660                1665

Phe Asp Ile Tyr Gly Glu Asp Ile Lys Gln Gly Pro Arg Ser Phe
    1670                1675                1680

Gln Gln Lys Thr Arg His Tyr Phe Ile Ala Ala Val Glu Arg Leu
    1685                1690                1695

Trp Asp Tyr Gly Met Ser Thr Ser Pro His Val Leu Arg Asn Arg
    1700                1705                1710

Asp Gln Ser Gly Asn Ala Pro Gln Phe Lys Lys Val Val Phe Gln
    1715                1720                1725
```

```
Glu Phe Thr Asp Gly Ser Phe Ser Gln Pro Leu Tyr Arg Gly Glu
    1730                1735                1740

Leu Asn Glu His Leu Gly Leu Leu Gly Pro Tyr Ile Arg Ala Glu
    1745                1750                1755

Val Glu Asp Asn Ile Met Val Thr Phe Lys Asn Gln Ala Ser Arg
    1760                1765                1770

Pro Tyr Ser Phe Tyr Ser Ser Leu Ile Ser Tyr Lys Glu Asp Gln
    1775                1780                1785

Arg Gln Gly Glu Glu Pro Arg Arg Asn Phe Val Lys Pro Asn Glu
    1790                1795                1800

Thr Lys Ile Tyr Phe Trp Lys Val Gln His His Met Ala Pro Thr
    1805                1810                1815

Glu Asp Glu Phe Asp Cys Lys Ala Trp Ala Tyr Phe Ser Asp Val
    1820                1825                1830

Asp Leu Glu Arg Asp Met His Ser Gly Leu Ile Gly Pro Leu Leu
    1835                1840                1845

Ile Cys His Thr Asn Thr Leu Asn Pro Ala His Gly Arg Gln Val
    1850                1855                1860

Ala Val Gln Glu Phe Ala Leu Phe Phe Thr Ile Phe Asp Glu Thr
    1865                1870                1875

Lys Ser Trp Tyr Phe Thr Glu Asn Val Glu Arg Asn Cys Lys Thr
    1880                1885                1890

Pro Cys Asn Ile Gln Met Glu Asp Pro Thr Leu Lys Glu Asn Tyr
    1895                1900                1905

Arg Phe His Ala Ile Asn Gly Tyr Val Met Asp Thr Leu Pro Gly
    1910                1915                1920

Leu Val Met Ala Gln Asp Gln Arg Ile Arg Trp Tyr Leu Leu Ser
    1925                1930                1935

Met Gly Ser Asn Glu Asn Ile Gln Ser Ile His Phe Ser Gly His
    1940                1945                1950

Val Phe Thr Val Arg Lys Lys Glu Glu Tyr Lys Met Ala Val Tyr
    1955                1960                1965

Asn Leu Tyr Pro Gly Val Phe Glu Thr Val Glu Met Leu Pro Ser
    1970                1975                1980

Arg Ala Gly Ile Trp Arg Val Glu Cys Leu Ile Gly Glu His Leu
    1985                1990                1995

Gln Ala Gly Met Ser Thr Leu Phe Leu Val Tyr Ser Lys Gln Cys
    2000                2005                2010

Gln Ile Pro Leu Gly Met Ala Ser Gly Ser Ile Arg Asp Phe Gln
    2015                2020                2025

Ile Thr Ala Ser Gly His Tyr Gly Gln Trp Ala Pro Asn Leu Ala
    2030                2035                2040

Arg Leu His His Ser Gly Ser Ile Asn Ala Trp Ser Thr Lys Glu
    2045                2050                2055

Pro Phe Ser Trp Ile Lys Val Asp Leu Leu Thr Pro Met Ile Ile
    2060                2065                2070

His Gly Ile Lys Thr Gln Gly Ala Arg Gln Lys Phe Ser Ser Leu
    2075                2080                2085

Tyr Ile Ser Gln Phe Ile Ile Met Tyr Ser Leu Asp Gly Lys Lys
    2090                2095                2100

Trp Leu Ser Tyr Arg Gly Asn Ser Thr Gly Thr Leu Met Val Phe
    2105                2110                2115
```

```
Phe Gly Asn Val Asp Ser Ser Gly Ile Lys His Asn Ser Phe Asn
    2120                2125                2130

Pro Pro Ile Ile Ala Arg Tyr Ile Arg Leu His Pro Thr His Ser
    2135                2140                2145

Ser Ile Arg Ser Thr Leu Arg Met Glu Leu Met Gly Cys Asp Leu
    2150                2155                2160

Asn Ser Cys Ser Ile Pro Leu Gly Met Glu Asn Lys Val Ile Ser
    2165                2170                2175

Asp Thr Gln Ile Thr Ala Ser Ser Tyr Phe Thr Asn Met Phe Ala
    2180                2185                2190

Thr Trp Ser Pro Ser Gln Ala Arg Leu His Leu Gln Gly Arg Thr
    2195                2200                2205

Asn Ala Trp Arg Pro Gln Val Asn Asp Pro Lys Glu Trp Leu Gln
    2210                2215                2220

Val Asp Leu Gln Lys Thr Met Lys Val Thr Gly Ile Ile Thr Gln
    2225                2230                2235

Gly Val Lys Ser Leu Phe Thr Ser Met Phe Val Lys Glu Phe Leu
    2240                2245                2250

Ile Ser Ser Ser Gln Asp Gly His His Trp Thr His Ile Leu His
    2255                2260                2265

Asn Gly Lys Val Lys Val Phe Gln Gly Asn Gln Asp Ser Ser Thr
    2270                2275                2280

Pro Met Val Asn Ser Leu Asp Pro Pro Leu Leu Thr Arg Tyr Leu
    2285                2290                2295

Arg Ile His Pro Gln Ile Trp Glu His Gln Ile Ala Leu Arg Leu
    2300                2305                2310

Glu Ile Leu Gly Cys Glu Ala Gln Gln Leu Tyr
    2315                2320

<210> SEQ ID NO 3
<211> LENGTH: 19
<212> TYPE: PRT
<213> ORGANISM: artificial sequence
<220> FEATURE:
<223> OTHER INFORMATION: ancestral

<400> SEQUENCE: 3

Met Gln Ile Ala Leu Phe Thr Cys Phe Phe Leu Ser Leu Phe Asn Phe
1               5                   10                  15

Cys Ser Ser

<210> SEQ ID NO 4
<211> LENGTH: 372
<212> TYPE: PRT
<213> ORGANISM: artificial sequence
<220> FEATURE:
<223> OTHER INFORMATION: ancestral

<400> SEQUENCE: 4

Ala Thr Arg Arg Tyr Tyr Leu Gly Ala Val Glu Leu Ser Trp Asn Tyr
1               5                   10                  15

Met Gln Ser Asp Leu Leu Ser Val Leu His Thr Asp Thr Arg Phe Leu
                20                  25                  30

Pro Arg Met Pro Thr Ser Phe Pro Phe Asn Thr Ser Ile Met Tyr Lys
            35                  40                  45

Lys Thr Val Phe Val Glu Tyr Met Asp His Leu Phe Asn Ile Ala Lys
        50                  55                  60
```

Pro Arg Pro Pro Trp Met Gly Leu Leu Gly Pro Thr Ile Trp Thr Glu
65                  70                  75                  80

Val His Asp Thr Val Ile Thr Leu Lys Asn Met Ala Ser His Pro
            85                  90                  95

Val Ser Leu His Ala Val Gly Val Ser Tyr Trp Lys Ala Ser Glu Gly
                100                 105                 110

Ala Glu Tyr Glu Asp Gln Thr Ser Gln Arg Glu Lys Glu Asp Asp Lys
            115                 120                 125

Val Phe Pro Gly Glu Ser His Thr Tyr Val Trp Gln Val Leu Lys Glu
130                 135                 140

Asn Gly Pro Met Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ser Lys Glu Arg Thr Gln Met
            180                 185                 190

Leu His Gln Phe Val Leu Leu Phe Ala Val Phe Asp Glu Gly Lys Ser
            195                 200                 205

Trp His Ser Glu Thr Lys Asp Ser Phe Thr Gln Ala Met Asp Ser Ala
210                 215                 220

Ser Thr Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255

His Val Ile Gly Met Gly Thr Thr Pro Glu Val His Ser Ile Phe Leu
            260                 265                 270

Glu Gly His Thr Phe Leu Val Arg Asn His Arg Gln Ala Ser Leu Glu
            275                 280                 285

Ile Ser Pro Ile Thr Phe Leu Thr Ala Gln Thr Leu Leu Ile Asp Leu
290                 295                 300

Gly Gln Phe Leu Leu Phe Cys His Ile Ser Ser His Lys His Asp Gly
305                 310                 315                 320

Met Glu Ala Tyr Val Lys Val Asp Ser Cys Pro Glu Glu Pro Gln Trp
            325                 330                 335

Gln Lys Lys Asn Asn Glu Glu Met Glu Asp Tyr Asp Asp Leu Asp
            340                 345                 350

Ser Glu Met Asp Met Phe Thr Leu Asp Asp Asp Asn Ser Pro Phe Ile
            355                 360                 365

Gln Ile Arg Ser
    370

<210> SEQ ID NO 5
<211> LENGTH: 367
<212> TYPE: PRT
<213> ORGANISM: artificial sequence
<220> FEATURE:
<223> OTHER INFORMATION: ancestral

<400> SEQUENCE: 5

Val Ala Lys Lys Tyr Pro Lys Thr Trp Ile His Tyr Ile Ser Ala Glu
1               5                   10                  15

Glu Glu Asp Trp Asp Tyr Ala Pro Ser Val Leu Thr Ser Asp Asp Gly
            20                  25                  30

Ser Tyr Lys Ser Gln Tyr Leu Ser Asn Gly Pro His Arg Ile Gly Arg
        35                  40                  45

Lys Tyr Lys Lys Val Arg Phe Ile Ala Tyr Thr Asp Glu Thr Phe Lys
 50                  55                  60

Thr Arg Glu Thr Ile Gln His Glu Ser Gly Ile Leu Gly Pro Leu Leu
 65                  70                  75                  80

Tyr Gly Glu Val Gly Asp Thr Leu Leu Ile Ile Phe Lys Asn Gln Ala
                 85                  90                  95

Ser Arg Pro Tyr Asn Ile Tyr Pro His Gly Ile Thr Asp Val Ser Pro
            100                 105                 110

Leu His Ser Arg Arg Leu Pro Arg Gly Ile Lys His Val Lys Asp Leu
            115                 120                 125

Pro Ile Arg Pro Gly Glu Ile Phe Lys Tyr Lys Trp Thr Val Thr Val
130                 135                 140

Glu Asp Gly Pro Thr Lys Ser Asp Pro Arg Cys Leu Thr Arg Tyr Tyr
145                 150                 155                 160

Ser Ser Phe Ile Asn Pro Glu Arg Asp Leu Ala Ser Gly Leu Ile Gly
                165                 170                 175

Pro Leu Leu Ile Cys Tyr Lys Glu Ser Val Asp Gln Arg Gly Asn Gln
            180                 185                 190

Met Met Ser Asp Lys Arg Asn Val Ile Leu Phe Ser Val Phe Asp Glu
            195                 200                 205

Asn Gln Ser Trp Tyr Ile Thr Glu Asn Met Gln Arg Phe Leu Pro Asn
210                 215                 220

Ala Ala Asp Thr Gln Pro Gln Asp Pro Glu Phe Gln Ala Ser Asn Ile
225                 230                 235                 240

Met His Ser Ile Asn Gly Tyr Val Phe Asp Ser Leu Gln Leu Thr Val
                245                 250                 255

Cys Leu His Glu Val Ala Tyr Trp Tyr Ile Leu Ser Val Gly Ala Gln
            260                 265                 270

Thr Asp Phe Leu Ser Ile Phe Phe Ser Gly Tyr Thr Phe Lys His Lys
            275                 280                 285

Met Val Tyr Glu Asp Thr Leu Thr Leu Phe Pro Phe Ser Gly Glu Thr
290                 295                 300

Val Phe Met Ser Met Glu Asn Pro Gly Leu Trp Val Leu Gly Cys His
305                 310                 315                 320

Asn Ser Asp Phe Arg Lys Arg Gly Met Thr Ala Leu Leu Lys Val Ser
                325                 330                 335

Ser Cys Asp Lys Ser Thr Ser Asp Tyr Tyr Glu Glu Ile Tyr Glu Asp
            340                 345                 350

Ile Pro Thr Gln Leu Val Asn Asp Asn Asn Val Ile Glu Pro Arg
            355                 360                 365

<210> SEQ ID NO 6
<211> LENGTH: 885
<212> TYPE: PRT
<213> ORGANISM: artificial sequence
<220> FEATURE:
<223> OTHER INFORMATION: ancestral

<400> SEQUENCE: 6

Ser Phe Phe Gln Asn Ser Asn His Pro Asn Thr Arg Lys Lys Lys Phe
 1               5                  10                  15

Lys Ala Thr Thr Ile Pro Glu Asn Asp Ile Glu Lys Ile Glu Pro Gln
                 20                  25                  30

Phe Gly Glu Thr Ala Glu Met Leu Lys Val Gln Ser Val Ser Ser Ser
             35                  40                  45

```
Asp Leu Leu Met Leu Leu Gly Gln Ser Pro Thr Pro His Gly Leu Ser
     50                  55                  60

Leu Ser Asp Asn Gln Glu Ala Ile Tyr Glu Ala Ile Pro Asp Asp His
 65              70                  75                      80

Ser Pro Asp Ala Ile Asp Ser Asn Glu Gly Pro Ser Lys Val Thr Gln
                 85                  90                  95

Leu Arg Pro Glu Leu His His Ser Gly Lys Ile Val Phe Thr Pro Glu
            100                 105                 110

Pro Gly Leu Gln Leu Arg Ser Asn Lys Asn Leu Glu Thr Thr Ile Glu
        115                 120                 125

Val Lys Trp Lys Lys Leu Asp Leu Gln Val Ser Ser Leu Pro Asn Asn
    130                 135                 140

Leu Met Thr Thr Thr Ile Leu Ser Asp Asn Leu Thr Ala Thr Ser Glu
145                 150                 155                 160

Lys Thr Asp Ser Ser Gly Ser Pro Asp Met Pro Val His Phe Ser Ser
                165                 170                 175

Lys Leu Ser Thr Thr Ala Phe Gly Lys Lys Ser Tyr Pro Leu Ile Gly
            180                 185                 190

Ser His Val Pro Leu Asn Ile Ser Glu Arg Asn Ser Asp Ser Asn Leu
    195                 200                 205

Leu Asp Ala Thr Leu Met Asn Asn Gln Glu Ser Ser Leu Gly Asp Asn
210                 215                 220

Ile Ser Ser Met Glu Asn Asp Arg Leu Leu Lys Glu Lys Arg Phe His
225                 230                 235                 240

Gly Ile Ala Leu Leu Thr Lys Asp Asn Thr Leu Phe Lys Asp Asn Ile
                245                 250                 255

Ser Leu Met Lys Thr Asn Lys Thr Tyr Asn His Ser Thr Thr Asn Gly
            260                 265                 270

Lys Ala His Ile Asp Ser Pro Thr Ser Ile Glu Asn Ser Thr Ala Val
    275                 280                 285

Leu Gln Asp Thr Ile Leu Lys Ile Asn Ser Glu Ile Gln Glu Val Thr
290                 295                 300

Ser Leu Ile His Asp Gly Thr Leu Ser Gly Lys Asn Thr Thr Tyr Leu
305                 310                 315                 320

Arg Leu Asn His Met Leu Asn Arg Thr Thr Ser Ser Lys Asn Lys Glu
                325                 330                 335

Ile Phe His Gln Lys Asp Glu Asp Pro Val Pro Gln Asp Thr Glu Asn
            340                 345                 350

Thr Ile Met Pro Phe Phe Lys Met Leu Phe Leu Pro Glu Ser Ala Asn
    355                 360                 365

Trp Met Lys Arg Thr Asn Gly Asn Asn Ser Leu Asn Ser Glu Gln Gly
370                 375                 380

Pro Ser Pro Lys Gln Leu Val Tyr Leu Met Leu Glu Lys Ser Val Lys
385                 390                 395                 400

Asn Gln Asn Phe Leu Ser Glu Lys Asn Lys Val Ile Val Glu Gln Asp
                405                 410                 415

Glu Phe Thr Lys Asp Thr Gly Leu Lys Asp Met Val Phe Pro Ser Asn
            420                 425                 430

Met Ser Ile Phe Leu Thr Thr Leu Ala Asn Val Gln Glu Asn Asp Met
        435                 440                 445

His Asn Gln Glu Lys Asn Ile Gln Glu Glu Ile Glu Lys Glu Ala Leu
    450                 455                 460
```

```
Ile Glu Glu Lys Val Val Leu Pro Gln Val His Ile Ala Thr Gly Ser
465                 470                 475                 480

Lys Asn Phe Leu Lys Asp Ile Phe Phe Leu Gly Thr Arg Gln Asn Val
            485                 490                 495

Ser Leu Asp Glu Asp Ile Tyr Val Pro Val Leu Gln Asp Ile Ser Ser
            500                 505                 510

Ile Asn Asn Ser Thr Asn Thr Val Glu Ile His Met Ala His Phe Phe
            515                 520                 525

Lys Arg Arg Glu Asp Glu Thr Asn Ser Glu Gly Leu Val Asn Lys
530                 535                 540

Thr Arg Glu Met Val Lys Asn Tyr Pro Ser Gln Lys Asn Ile Ile Thr
545                 550                 555                 560

Gln Arg Ser Lys Arg Ala Leu Gly Gln Phe Arg Leu Pro Leu Ala Ser
            565                 570                 575

Thr Gln Trp Pro Gln Thr Met Asn Tyr Leu Thr Gln Ser Ile Ile Thr
            580                 585                 590

Gln Ile Asp His Ser Lys Glu Gly Lys Ser Ile Thr Gln Ser Ser
            595                 600                 605

Leu Ser Asp Ser Ser Met Ile Lys Ser Thr Thr Gln Thr Asn Ser Ser
610                 615                 620

Gly Leu His Ile Val Lys Thr Ser Ala Phe Pro Pro Thr Asp Leu Lys
625                 630                 635                 640

Arg Ile Pro Phe Gln Asp Lys Phe Phe His Val Leu Ala Ser Ser Tyr
            645                 650                 655

Thr Tyr Asp Phe Lys Thr Lys Ser Ser Arg Ile Gln Glu Ser Ser His
            660                 665                 670

Phe Leu Lys Glu Thr Lys Ile Asn Asn Ser Ser Leu Ala Ile Leu Pro
            675                 680                 685

Trp Glu Met Ile Ile Asn Gln Gly Lys Phe Ala Ser Pro Gly Thr Ser
            690                 695                 700

Asn Thr Asn Ser Val Thr Tyr Lys Lys Leu Glu Asn Ile Val Leu Leu
705                 710                 715                 720

Lys Pro Val Leu Pro Glu Glu Ser Gly Lys Val Glu Leu Leu Pro Gln
            725                 730                 735

Val Ser Ile His Glu Glu Leu Leu Pro Thr Glu Thr Ser His Gly
            740                 745                 750

Ser Pro Gly His Leu Asp Leu Met Lys Glu Val Phe Leu Gln Lys Thr
            755                 760                 765

Gln Gly Pro Ile Lys Trp Asn Lys Ala Lys Arg His Gly Glu Ser Glu
            770                 775                 780

Leu Lys Gly Thr Thr Glu Ser Ser Glu Lys Thr Pro Ser Lys Leu Leu
785                 790                 795                 800

Asp His Leu Ala Trp Asp Asn His Tyr Ala Ala Gln Ile Pro Lys Asp
            805                 810                 815

Lys Trp Lys Ser Lys Glu Lys Ser Pro Glu Ile Thr Ser Ile Lys Arg
            820                 825                 830

Glu Asp Thr Ile Leu Ser Leu Asn Pro His Glu Asn Asn His Ser Ile
            835                 840                 845

Val Ala Asn Glu Lys Gln Asn Trp Pro Gln Arg Glu Ala Thr Trp Val
850                 855                 860
```

```
Lys Gln Gly Gln Thr Gln Arg Leu Cys Ser Gln Asn Pro Val Leu
865                 870                 875                 880

Lys Arg His Gln Arg
            885

<210> SEQ ID NO 7
<211> LENGTH: 38
<212> TYPE: PRT
<213> ORGANISM: artificial sequence
<220> FEATURE:
<223> OTHER INFORMATION: ancestral

<400> SEQUENCE: 7

Glu Leu Ser Ala Leu Gln Ser Glu Gln Glu Ala Thr Asp Tyr Asp Asp
1               5                   10                  15

Ser Ile Thr Ile Glu Thr Asn Glu Asp Phe Asp Ile Tyr Gly Glu Asp
                20                  25                  30

Ile Lys Gln Gly Pro Arg
        35

<210> SEQ ID NO 8
<211> LENGTH: 330
<212> TYPE: PRT
<213> ORGANISM: artificial sequence
<220> FEATURE:
<223> OTHER INFORMATION: ancestral

<400> SEQUENCE: 8

Ser Phe Gln Gln Lys Thr Arg His Tyr Phe Ile Ala Ala Val Glu Arg
1               5                   10                  15

Leu Trp Asp Tyr Gly Met Ser Thr Ser Pro His Val Leu Arg Asn Arg
                20                  25                  30

Asp Gln Ser Gly Asn Ala Pro Gln Phe Lys Lys Val Val Phe Gln Glu
            35                  40                  45

Phe Thr Asp Gly Ser Phe Ser Gln Pro Leu Tyr Arg Gly Glu Leu Asn
        50                  55                  60

Glu His Leu Gly Leu Leu Gly Pro Tyr Ile Arg Ala Glu Val Glu Asp
65                  70                  75                  80

Asn Ile Met Val Thr Phe Lys Asn Gln Ala Ser Arg Pro Tyr Ser Phe
                85                  90                  95

Tyr Ser Ser Leu Ile Ser Tyr Lys Glu Asp Gln Arg Gln Gly Glu Glu
                100                 105                 110

Pro Arg Arg Asn Phe Val Lys Pro Asn Glu Thr Lys Ile Tyr Phe Trp
            115                 120                 125

Lys Val Gln His His Met Ala Pro Thr Glu Asp Glu Phe Asp Cys Lys
        130                 135                 140

Ala Trp Ala Tyr Phe Ser Asp Val Asp Leu Glu Arg Asp Met His Ser
145                 150                 155                 160

Gly Leu Ile Gly Pro Leu Leu Ile Cys His Thr Asn Thr Leu Asn Pro
                165                 170                 175

Ala His Gly Arg Gln Val Ala Val Gln Glu Phe Ala Leu Phe Phe Thr
            180                 185                 190

Ile Phe Asp Glu Thr Lys Ser Trp Tyr Phe Thr Glu Asn Val Glu Arg
        195                 200                 205

Asn Cys Lys Thr Pro Cys Asn Ile Gln Met Glu Asp Pro Thr Leu Lys
    210                 215                 220
```

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
            245                 250                 255

Ser Met Gly Ser Asn Glu Asn Ile Gln Ser Ile His Phe Ser Gly His
            260                 265                 270

Val Phe Thr Val Arg Lys Lys Glu Tyr Lys Met Ala Val Tyr Asn
            275                 280                 285

Leu Tyr Pro Gly Val Phe Glu Thr Val Glu Met Leu Pro Ser Arg Ala
            290                 295                 300

Gly Ile Trp Arg Val Glu Cys Leu Ile Gly Glu His Leu Gln Ala Gly
305                 310                 315                 320

Met Ser Thr Leu Phe Leu Val Tyr Ser Lys
            325                 330

<210> SEQ ID NO 9
<211> LENGTH: 153
<212> TYPE: PRT
<213> ORGANISM: artificial sequence
<220> FEATURE:
<223> OTHER INFORMATION: ancestral

<400> SEQUENCE: 9

Gln Cys Gln Ile Pro Leu Gly Met Ala Ser Gly Ser Ile Arg Asp Phe
1               5                   10                  15

Gln Ile Thr Ala Ser Gly His Tyr Gly Gln Trp Ala Pro Asn Leu Ala
            20                  25                  30

Arg Leu His His Ser Gly Ser Ile Asn Ala Trp Ser Thr Lys Glu Pro
        35                  40                  45

Phe Ser Trp Ile Lys Val Asp Leu Leu Thr Pro Met Ile Ile His Gly
    50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Leu Ser Tyr
                85                  90                  95

Arg Gly Asn Ser Thr Gly Thr Leu Met Val Phe Phe Gly Asn Val Asp
            100                 105                 110

Ser Ser Gly Ile Lys His Asn Ser Phe Asn Pro Pro Ile Ile Ala Arg
        115                 120                 125

Tyr Ile Arg Leu His Pro Thr His Ser Ser Ile Arg Ser Thr Leu Arg
    130                 135                 140

Met Glu Leu Met Gly Cys Asp Leu Asn
145                 150

<210> SEQ ID NO 10
<211> LENGTH: 160
<212> TYPE: PRT
<213> ORGANISM: artificial sequence
<220> FEATURE:
<223> OTHER INFORMATION: ancestral

<400> SEQUENCE: 10

Ser Cys Ser Ile Pro Leu Gly Met Glu Asn Lys Val Ile Ser Asp Thr
1               5                   10                  15

Gln Ile Thr Ala Ser Ser Tyr Phe Thr Asn Met Phe Ala Thr Trp Ser
            20                  25                  30

```
Pro Ser Gln Ala Arg Leu His Leu Gln Gly Arg Thr Asn Ala Trp Arg
        35                  40                  45

Pro Gln Val Asn Asp Pro Lys Glu Trp Leu Gln Val Asp Leu Gln Lys
    50                  55                  60

Thr Met Lys Val Thr Gly Ile Ile Thr Gln Gly Val Lys Ser Leu Phe
65                  70                  75                  80

Thr Ser Met Phe Val Lys Glu Phe Leu Ile Ser Ser Ser Gln Asp Gly
                85                  90                  95

His His Trp Thr His Ile Leu His Asn Gly Lys Val Lys Val Phe Gln
                100                 105                 110

Gly Asn Gln Asp Ser Ser Thr Pro Met Val Asn Ser Leu Asp Pro Pro
            115                 120                 125

Leu Leu Thr Arg Tyr Leu Arg Ile His Pro Gln Ile Trp Glu His Gln
        130                 135                 140

Ile Ala Leu Arg Leu Glu Ile Leu Gly Cys Glu Ala Gln Gln Leu Tyr
145                 150                 155                 160

<210> SEQ ID NO 11
<211> LENGTH: 2354
<212> TYPE: PRT
<213> ORGANISM: artificial sequence
<220> FEATURE:
<223> OTHER INFORMATION: ancestral

<400> SEQUENCE: 11

Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
                100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
        130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
                180                 185                 190

Ile Gly Ala Leu Leu Val Cys Arg Glu Gly Ser Leu Ala Lys Glu Arg
            195                 200                 205

Thr Gln Thr Leu His Lys Phe Val Leu Leu Phe Ala Val Phe Asp Glu
        210                 215                 220

Gly Lys Ser Trp His Ser Glu Thr Lys Asp Ser Leu Met Gln Asp Met
225                 230                 235                 240
```

-continued

```
Asp Ser Ala Ser Ala Arg Ala Trp Pro Lys Met His Thr Val Asn Gly
            245                 250                 255
Tyr Val Asn Arg Ser Leu Pro Gly Leu Ile Gly Cys His Arg Lys Ser
                260                 265                 270
Val Tyr Trp His Val Ile Gly Met Gly Thr Thr Pro Glu Val His Ser
            275                 280                 285
Ile Phe Leu Glu Gly His Thr Phe Leu Val Arg Asn His Arg Gln Ala
        290                 295                 300
Ser Leu Glu Ile Ser Pro Ile Thr Phe Leu Thr Ala Gln Thr Leu Leu
305                 310                 315                 320
Met Asp Leu Gly Gln Phe Leu Leu Phe Cys His Ile Ser Ser His Gln
                325                 330                 335
His Asp Gly Met Glu Ala Tyr Val Lys Val Asp Ser Cys Pro Glu Glu
            340                 345                 350
Pro Gln Leu Arg Met Lys Asn Asn Glu Glu Glu Asp Tyr Asp Asp
        355                 360                 365
Asp Leu Ala Asp Ser Glu Met Asp Val Val Arg Phe Asp Asp Asp Asn
    370                 375                 380
Ser Pro Ser Phe Ile Gln Ile Arg Ser Val Ala Lys Lys His Pro Lys
385                 390                 395                 400
Thr Trp Val His Tyr Ile Ala Ala Glu Glu Asp Trp Asp Tyr Ala
                405                 410                 415
Pro Ser Val Leu Thr Pro Asp Asp Arg Ser Tyr Lys Ser Gln Tyr Leu
            420                 425                 430
Asn Asn Gly Pro Gln Arg Ile Gly Arg Lys Tyr Lys Lys Val Arg Phe
        435                 440                 445
Met Ala Tyr Thr Asp Glu Thr Phe Lys Thr Arg Glu Ala Ile Gln Tyr
    450                 455                 460
Glu Ser Gly Ile Leu Gly Pro Leu Leu Tyr Gly Glu Val Gly Asp Thr
465                 470                 475                 480
Leu Leu Ile Ile Phe Lys Asn Gln Ala Ser Arg Pro Tyr Asn Ile Tyr
                485                 490                 495
Pro His Gly Ile Thr Asp Val Arg Pro Leu His Ser Gly Arg Leu Pro
            500                 505                 510
Lys Gly Val Lys His Leu Lys Asp Leu Pro Ile Leu Pro Gly Glu Ile
        515                 520                 525
Phe Lys Tyr Lys Trp Thr Val Thr Val Glu Asp Gly Pro Thr Lys Ser
    530                 535                 540
Asp Pro Arg Cys Leu Thr Arg Tyr Tyr Ser Ser Phe Ile Asn Leu Glu
545                 550                 555                 560
Arg Asp Leu Ala Ser Gly Leu Ile Gly Pro Leu Leu Ile Cys Tyr Lys
                565                 570                 575
Glu Ser Val Asp Gln Arg Gly Asn Gln Met Met Ser Asp Lys Arg Asn
            580                 585                 590
Val Ile Leu Phe Ser Val Phe Asp Glu Asn Arg Ser Trp Tyr Leu Thr
        595                 600                 605
Glu Asn Met Gln Arg Phe Leu Pro Asn Ala Ala Gly Val Gln Pro Gln
    610                 615                 620
Asp Pro Glu Phe Gln Ala Ser Asn Ile Met His Ser Ile Asn Gly Tyr
625                 630                 635                 640
Val Phe Asp Ser Leu Gln Leu Ser Val Cys Leu His Glu Val Ala Tyr
                645                 650                 655
```

-continued

```
Trp Tyr Ile Leu Ser Ile Gly Ala Gln Thr Asp Phe Leu Ser Val Phe
                660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Ser Thr Tyr Leu Leu Ser
            740                 745                 750

Glu Asn Asn Val Ile Glu Pro Arg Ser Phe Ser Gln Asn Ser Arg His
        755                 760                 765

Pro Ser Thr Arg Gln Lys Gln Phe Lys Ala Thr Thr Ile Pro Glu Asn
    770                 775                 780

Asp Ile Glu Lys Ile Asp Pro Gln Phe Gly Arg Thr Gln Met Leu
785                 790                 795                 800

Lys Val Gln Ser Val Ser Ser Asp Leu Leu Met Leu Leu Gly Gln
                805                 810                 815

Ser Pro Thr Pro His Gly Leu Ser Leu Ser Asp Leu Gln Glu Ala Thr
            820                 825                 830

Tyr Glu Ala Ile Pro Asp Asp His Ser Pro Gly Ala Ile Asp Ser Asn
        835                 840                 845

Glu Gly Pro Ser Glu Val Ala His Leu Arg Pro Glu Leu His His Ser
    850                 855                 860

Gly Asp Met Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
                885                 890                 895

Lys Val Ser Ser Ser Asn Asn Leu Met Thr Ser Pro Thr Ile Pro
            900                 905                 910

Ser Asp Asn Leu Ala Ala Gly Thr Glu Lys Thr Gly Ser Leu Gly Pro
        915                 920                 925

Pro Asn Met Pro Val His Phe Asp Ser Gln Leu Asp Thr Thr Val Phe
    930                 935                 940

Gly Lys Lys Ser Ser Pro Leu Ile Gly Ser Gly Val Pro Leu Ser Leu
945                 950                 955                 960

Ser Glu Arg Asn Asn Asp Ser Lys Leu Leu Glu Ala Ala Leu Met Asn
                965                 970                 975

Ser Gln Glu Ser Ser Leu Gly Lys Asn Val Ser Ser Met Glu Ser Asp
            980                 985                 990

Arg Leu Phe Lys Glu Lys Arg Ala His Gly Pro Ala Leu Leu Thr Lys
        995                1000                1005

Asp Asn Ala Leu Phe Lys Val Asn Ile Ser Leu Val Lys Thr Asn
    1010                1015                1020

Lys Thr Ser Asn Asn Ser Thr Thr Asn Arg Lys Thr His Ile Asp
    1025                1030                1035

Gly Pro Thr Leu Leu Ile Glu Asn Ser Thr Ser Val Trp Gln Asp
    1040                1045                1050

Ile Leu Glu Ser Asp Thr Glu Phe Gln Glu Val Thr Ser Leu Ile
    1055                1060                1065
```

```
His Asp Lys Met Leu Met Asp Lys Asn Thr Thr Ala Leu Arg Leu
    1070            1075            1080

Asn His Val Ser Asn Lys Thr Thr Ser Ser Lys Asn Met Glu Met
    1085            1090            1095

Val His Gln Lys Lys Glu Gly Pro Val Pro Pro Asp Ala Glu Asn
    1100            1105            1110

Pro Asp Met Ser Phe Phe Lys Met Leu Phe Leu Pro Glu Ser Ala
    1115            1120            1125

Asn Trp Ile Lys Arg Thr His Gly Lys Asn Ser Leu Asn Ser Gly
    1130            1135            1140

Gln Gly Pro Ser Pro Lys Gln Leu Ile Ser Leu Gly Ser Glu Lys
    1145            1150            1155

Ser Val Lys Asp Gln Asn Phe Leu Ser Glu Lys Asn Lys Val Val
    1160            1165            1170

Val Gly Glu Asp Glu Phe Thr Lys Asp Thr Gly Leu Lys Glu Met
    1175            1180            1185

Ile Phe Pro Ser Ser Arg Asn Ile Phe Leu Thr Asn Leu Ala Asn
    1190            1195            1200

Val His Glu Asn Asp Thr His Asn Gln Glu Lys Lys Ile Gln Glu
    1205            1210            1215

Glu Ile Glu Arg Lys Glu Thr Leu Ile Gln Glu Asn Val Val Leu
    1220            1225            1230

Pro Gln Val Tyr Thr Val Thr Gly Thr Lys Asn Phe Met Lys Asn
    1235            1240            1245

Leu Phe Leu Leu Ser Thr Arg Gln Asn Val Glu Gly Leu Asp Glu
    1250            1255            1260

Gly Ala Tyr Ala Pro Val Leu Gln Asp Thr Arg Ser Leu Asn Asp
    1265            1270            1275

Ser Thr Asn Arg Thr Glu Ile His Met Ala His Phe Ser Lys Lys
    1280            1285            1290

Arg Glu Glu Glu Asn Leu Glu Gly Leu Gly Asn Gln Thr Lys Gln
    1295            1300            1305

Met Val Glu Lys Tyr Pro Ser Thr Thr Arg Met Ser Pro Asn Pro
    1310            1315            1320

Ser Gln Gln Asn Val Ile Thr Gln Arg Gly Lys Arg Ala Leu Lys
    1325            1330            1335

Gln Phe Arg Leu Pro Leu Glu Glu Thr Glu Leu Glu Lys Gly Leu
    1340            1345            1350

Ile Val Asp Asp Thr Ser Thr Gln Trp Ser Lys Asn Met Lys Tyr
    1355            1360            1365

Leu Thr Gln Ser Thr Leu Thr Gln Ile Asp Tyr Asn Glu Lys Glu
    1370            1375            1380

Lys Lys Ala Ile Thr Gln Ser Pro Leu Ser Asp Cys Leu Met Arg
    1385            1390            1395

Asn His Ser Ile Thr Gln Thr Asn Ser Ser Ala Leu Pro Ile Ala
    1400            1405            1410

Lys Val Ser Ala Phe Pro Ser Ile Arg Pro Thr Asp Leu Thr Arg
    1415            1420            1425

Val Pro Ser Gln Asp Asn Ser Ser His Leu Leu Ala Ser Ala Tyr
    1430            1435            1440

Arg Lys Lys Ser Ser Gly Val Gln Glu Ser Ser His Phe Leu Gln
    1445            1450            1455
```

```
Gly Ala Lys Arg Asn Asn Leu Ser Leu Ala Ile Leu Thr Leu Glu
    1460                1465                1470

Met Ile Gly Asn Gln Arg Lys Val Gly Ser Leu Gly Thr Ser Ala
    1475                1480                1485

Thr Asn Ser Val Met Tyr Lys Lys Leu Glu Asn Thr Val Leu Leu
    1490                1495                1500

Lys Pro Gly Leu Pro Glu Ala Ser Gly Lys Val Glu Leu Leu Pro
    1505                1510                1515

Lys Val His Ile His Gln Lys Asp Leu Phe Pro Thr Glu Thr Ser
    1520                1525                1530

Asn Gly Ser Pro Gly His Leu Asp Leu Met Glu Glu Ile Leu Leu
    1535                1540                1545

Gln Lys Thr Gln Gly Ala Ile Lys Trp Asn Lys Thr Asn Arg Pro
    1550                1555                1560

Gly Lys Val Pro Phe Leu Lys Gly Ala Thr Glu Ser Ser Glu Lys
    1565                1570                1575

Thr Pro Ser Lys Leu Leu Gly Pro Leu Ala Trp Asp Asn Gln Tyr
    1580                1585                1590

Ala Thr Gln Ile Pro Lys Glu Glu Trp Lys Ser Gln Glu Lys Ser
    1595                1600                1605

Pro Glu Asn Thr Ala Phe Lys Thr Lys Asp Thr Ile Leu Ser Leu
    1610                1615                1620

Asn Pro Cys Glu Ser Asn His Ala Ile Ala Ala Ile Asn Glu Gly
    1625                1630                1635

Gln Asp Arg Pro Gln Arg Glu Ala Thr Trp Ala Lys Gln Gly Gly
    1640                1645                1650

Thr Gly Arg Leu Cys Ser Gln Asn Pro Pro Val Leu Lys Arg His
    1655                1660                1665

Gln Arg Glu Ile Thr Leu Thr Thr Leu Gln Ser Asp Gln Glu Glu
    1670                1675                1680

Ile Asp Tyr Asp Asp Thr Ile Ser Ile Glu Thr Lys Arg Glu Asp
    1685                1690                1695

Phe Asp Ile Tyr Gly Glu Asp Glu Asn Gln Ser Pro Arg Ser Phe
    1700                1705                1710

Gln Lys Lys Thr Arg His Tyr Phe Ile Ala Ala Val Glu Arg Leu
    1715                1720                1725

Trp Asp Tyr Gly Met Ser Arg Ser Pro His Val Leu Arg Asn Arg
    1730                1735                1740

Ala Gln Ser Gly Ser Val Pro Gln Phe Lys Lys Val Val Phe Gln
    1745                1750                1755

Glu Phe Thr Asp Gly Ser Phe Thr Gln Pro Leu Tyr Arg Gly Glu
    1760                1765                1770

Leu Asn Glu His Leu Gly Leu Leu Gly Pro Tyr Ile Arg Ala Glu
    1775                1780                1785

Val Glu Asp Asn Ile Met Val Thr Phe Lys Asn Gln Ala Ser Arg
    1790                1795                1800

Pro Tyr Ser Phe Tyr Ser Ser Leu Ile Ser Tyr Glu Glu Asp Gln
    1805                1810                1815

Arg Gln Gly Ala Glu Pro Arg Lys Asn Phe Val Lys Pro Asn Glu
    1820                1825                1830

Thr Lys Thr Tyr Phe Trp Lys Val Gln His His Met Ala Pro Thr
    1835                1840                1845
```

```
Lys Asp Glu Phe Asp Cys Lys Ala Trp Ala Tyr Phe Ser Asp Val
    1850                1855                1860

Asp Leu Glu Lys Asp Met His Ser Gly Leu Ile Gly Pro Leu Leu
    1865                1870                1875

Ile Cys His Thr Asn Thr Leu Asn Pro Ala His Gly Arg Gln Val
    1880                1885                1890

Thr Val Gln Glu Phe Ala Leu Phe Phe Thr Ile Phe Asp Glu Thr
    1895                1900                1905

Lys Ser Trp Tyr Phe Thr Glu Asn Met Glu Arg Asn Cys Arg Ala
    1910                1915                1920

Pro Cys Asn Ile Gln Met Glu Asp Pro Thr Phe Lys Glu Asn Tyr
    1925                1930                1935

Arg Phe His Ala Ile Asn Gly Tyr Val Met Asp Thr Leu Pro Gly
    1940                1945                1950

Leu Val Met Ala Gln Asp Gln Arg Ile Arg Trp Tyr Leu Leu Ser
    1955                1960                1965

Met Gly Ser Asn Glu Asn Ile His Ser Ile His Phe Ser Gly His
    1970                1975                1980

Val Phe Thr Val Arg Lys Lys Glu Glu Tyr Lys Met Ala Val Tyr
    1985                1990                1995

Asn Leu Tyr Pro Gly Val Phe Glu Thr Val Glu Met Leu Pro Ser
    2000                2005                2010

Lys Ala Gly Ile Trp Arg Val Glu Cys Leu Ile Gly Glu His Leu
    2015                2020                2025

His Ala Gly Met Ser Thr Leu Phe Leu Val Tyr Ser Lys Gln Cys
    2030                2035                2040

Gln Thr Pro Leu Gly Met Ala Ser Gly His Ile Arg Asp Phe Gln
    2045                2050                2055

Ile Thr Ala Ser Gly Gln Tyr Gly Gln Trp Ala Pro Lys Leu Ala
    2060                2065                2070

Arg Leu His Tyr Ser Gly Ser Ile Asn Ala Trp Ser Thr Lys Glu
    2075                2080                2085

Pro Phe Ser Trp Ile Lys Val Asp Leu Leu Ala Pro Met Ile Ile
    2090                2095                2100

His Gly Ile Lys Thr Gln Gly Ala Arg Gln Lys Phe Ser Ser Leu
    2105                2110                2115

Tyr Ile Ser Gln Phe Ile Ile Met Tyr Ser Leu Asp Gly Lys Lys
    2120                2125                2130

Trp Gln Thr Tyr Arg Gly Asn Ser Thr Gly Thr Leu Met Val Phe
    2135                2140                2145

Phe Gly Asn Val Asp Ser Ser Gly Ile Lys His Asn Ile Phe Asn
    2150                2155                2160

Pro Pro Ile Ile Ala Arg Tyr Ile Arg Leu His Pro Thr His Tyr
    2165                2170                2175

Ser Ile Arg Ser Thr Leu Arg Met Glu Leu Met Gly Cys Asp Leu
    2180                2185                2190

Asn Ser Cys Ser Met Pro Leu Gly Met Glu Ser Lys Ala Ile Ser
    2195                2200                2205

Asp Ala Gln Ile Thr Ala Ser Ser Tyr Phe Thr Asn Met Phe Ala
    2210                2215                2220

Thr Trp Ser Pro Ser Gln Ala Arg Leu His Leu Gln Gly Arg Thr
    2225                2230                2235
```

```
Asn Ala Trp Arg Pro Gln Val Asn Asn Pro Lys Glu Trp Leu Gln
    2240                2245                2250

Val Asp Phe Gln Lys Thr Met Lys Val Thr Gly Ile Thr Thr Gln
    2255                2260                2265

Gly Val Lys Ser Leu Leu Thr Ser Met Tyr Val Lys Glu Phe Leu
    2270                2275                2280

Ile Ser Ser Ser Gln Asp Gly His His Trp Thr Leu Phe Phe Gln
    2285                2290                2295

Asn Gly Lys Val Lys Val Phe Gln Gly Asn Gln Asp Ser Phe Thr
    2300                2305                2310

Pro Val Val Asn Ser Leu Asp Pro Pro Leu Leu Thr Arg Tyr Leu
    2315                2320                2325

Arg Ile His Pro Gln Ser Trp Val His Gln Ile Ala Leu Arg Leu
    2330                2335                2340

Glu Val Leu Gly Cys Glu Ala Gln Gln Leu Tyr
    2345                2350

<210> SEQ ID NO 12
<211> LENGTH: 19
<212> TYPE: PRT
<213> ORGANISM: artificial sequence
<220> FEATURE:
<223> OTHER INFORMATION: ancestral

<400> SEQUENCE: 12

Met Gln Ile Glu Leu Ser Thr Cys Phe Phe Leu Cys Leu Leu Gln Phe
1               5                   10                  15

Ser Phe Ser

<210> SEQ ID NO 13
<211> LENGTH: 374
<212> TYPE: PRT
<213> ORGANISM: artificial sequence
<220> FEATURE:
<223> OTHER INFORMATION: ancestral

<400> SEQUENCE: 13

Ala Thr Arg Arg Tyr Tyr Leu Gly Ala Val Glu Leu Ser Trp Asp Tyr
1               5                   10                  15

Met Gln Ser Asp Leu Leu Ser Glu Leu His Val Asp Thr Arg Phe Pro
                20                  25                  30

Pro Arg Val Pro Arg Ser Phe Pro Phe Asn Thr Ser Val Met Tyr Lys
            35                  40                  45

Lys Thr Val Phe Val Glu Phe Thr Asp His Leu Phe Asn Ile Ala Lys
        50                  55                  60

Pro Arg Pro Pro Trp Met Gly Leu Leu Gly Pro Thr Ile Gln Ala Glu
65                  70                  75                  80

Val Tyr Asp Thr Val Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Asp Asp Gln Thr Ser Gln Arg Glu Lys Glu Asp Asp Lys
        115                 120                 125

Val Phe Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Leu
145                 150                 155                 160
```

```
Ser His Val Asp Leu Val Lys Asp Leu Asn Ser Gly Leu Ile Gly Ala
            165                 170                 175

Leu Leu Val Cys Arg Glu Gly Ser Leu Ala Lys Glu Arg Thr Gln Thr
        180                 185                 190

Leu His Lys Phe Val Leu Leu Phe Ala Val Phe Asp Glu Gly Lys Ser
        195                 200                 205

Trp His Ser Glu Thr Lys Asp Ser Leu Met Gln Asp Met Asp Ser Ala
        210                 215                 220

Ser Ala Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
            245                 250                 255

His Val Ile Gly Met Gly Thr Thr Pro Glu Val His Ser Ile Phe Leu
        260                 265                 270

Glu Gly His Thr Phe Leu Val Arg Asn His Arg Gln Ala Ser Leu Glu
        275                 280                 285

Ile Ser Pro Ile Thr Phe Leu Thr Ala Gln Thr Leu Leu Met Asp Leu
        290                 295                 300

Gly Gln Phe Leu Leu Phe Cys His Ile Ser Ser His Gln His Asp Gly
305                 310                 315                 320

Met Glu Ala Tyr Val Lys Val Asp Ser Cys Pro Glu Glu Pro Gln Leu
                325                 330                 335

Arg Met Lys Asn Asn Glu Glu Glu Asp Tyr Asp Asp Leu Ala
            340                 345                 350

Asp Ser Glu Met Asp Val Val Arg Phe Asp Asp Asp Asn Ser Pro Ser
        355                 360                 365

Phe Ile Gln Ile Arg Ser
    370

<210> SEQ ID NO 14
<211> LENGTH: 367
<212> TYPE: PRT
<213> ORGANISM: artificial sequence
<220> FEATURE:
<223> OTHER INFORMATION: ancestral

<400> SEQUENCE: 14

Val Ala Lys Lys His Pro Lys Thr Trp Val His Tyr Ile Ala Ala Glu
1               5                   10                  15

Glu Glu Asp Trp Asp Tyr Ala Pro Ser Val Leu Thr Pro Asp Asp Arg
                20                  25                  30

Ser Tyr Lys Ser Gln Tyr Leu Asn Asn Gly Pro Gln Arg Ile Gly Arg
            35                  40                  45

Lys Tyr Lys Lys Val Arg Phe Met Ala Tyr Thr Asp Glu Thr Phe Lys
        50                  55                  60

Thr Arg Glu Ala Ile Gln Tyr Glu Ser Gly Ile Leu Gly Pro Leu Leu
65                  70                  75                  80

Tyr Gly Glu Val Gly Asp Thr Leu Leu Ile Ile Phe Lys Asn Gln Ala
                85                  90                  95

Ser Arg Pro Tyr Asn Ile Tyr Pro His Gly Ile Thr Asp Val Arg Pro
            100                 105                 110

Leu His Ser Gly Arg Leu Pro Lys Gly Val Lys His Leu Lys Asp Leu
        115                 120                 125

Pro Ile Leu Pro Gly Glu Ile Phe Lys Tyr Lys Trp Thr Val Thr Val
    130                 135                 140
```

Glu Asp Gly Pro Thr Lys Ser Asp Pro Arg Cys Leu Thr Arg Tyr Tyr
145                 150                 155                 160

Ser Ser Phe Ile Asn Leu Glu Arg Asp Leu Ala Ser Gly Leu Ile Gly
                165                 170                 175

Pro Leu Leu Ile Cys Tyr Lys Glu Ser Val Asp Gln Arg Gly Asn Gln
            180                 185                 190

Met Met Ser Asp Lys Arg Asn Val Ile Leu Phe Ser Val Phe Asp Glu
        195                 200                 205

Asn Arg Ser Trp Tyr Leu Thr Glu Asn Met Gln Arg Phe Leu Pro Asn
    210                 215                 220

Ala Ala Gly Val Gln Pro Gln Asp Pro Glu Phe Gln Ala Ser Asn Ile
225                 230                 235                 240

Met His Ser Ile Asn Gly Tyr Val Phe Asp Ser Leu Gln Leu Ser Val
                245                 250                 255

Cys Leu His Glu Val Ala Tyr Trp Tyr Ile Leu Ser Ile Gly Ala Gln
                260                 265                 270

Thr Asp Phe Leu Ser Val Phe Phe Ser Gly Tyr Thr Phe Lys His Lys
            275                 280                 285

Met Val Tyr Glu Asp Thr Leu Thr Leu Phe Pro Phe Ser Gly Glu Thr
        290                 295                 300

Val Phe Met Ser Met Glu Asn Pro Gly Leu Trp Val Leu Gly Cys His
305                 310                 315                 320

Asn Ser Asp Phe Arg Asn Arg Gly Met Thr Ala Leu Leu Lys Val Ser
                325                 330                 335

Ser Cys Asp Arg Asn Thr Gly Asp Tyr Tyr Glu Asp Thr Tyr Glu Asp
                340                 345                 350

Ile Ser Thr Tyr Leu Leu Ser Glu Asn Asn Val Ile Glu Pro Arg
            355                 360                 365

<210> SEQ ID NO 15
<211> LENGTH: 910
<212> TYPE: PRT
<213> ORGANISM: artificial sequence
<220> FEATURE:
<223> OTHER INFORMATION: ancestral

<400> SEQUENCE: 15

Ser Phe Ser Gln Asn Ser Arg His Pro Ser Thr Arg Gln Lys Gln Phe
1               5                   10                  15

Lys Ala Thr Thr Ile Pro Glu Asn Asp Ile Glu Lys Ile Asp Pro Gln
                20                  25                  30

Phe Gly Glu Arg Thr Gln Met Leu Lys Val Gln Ser Val Ser Ser Ser
            35                  40                  45

Asp Leu Leu Met Leu Leu Gly Gln Ser Pro Thr Pro His Gly Leu Ser
        50                  55                  60

Leu Ser Asp Leu Gln Glu Ala Thr Tyr Glu Ala Ile Pro Asp Asp His
65                  70                  75                  80

Ser Pro Gly Ala Ile Asp Ser Asn Glu Gly Pro Ser Glu Val Ala His
                85                  90                  95

Leu Arg Pro Glu Leu His His Ser Gly Asp Met Val Phe Thr Pro Glu
            100                 105                 110

Pro Gly Leu Gln Leu Arg Leu Asn Glu Asn Leu Gly Thr Thr Ile Ala
        115                 120                 125

Val Glu Leu Lys Lys Leu Asp Leu Lys Val Ser Ser Ser Asn Asn
        130                 135                 140

```
Leu Met Thr Ser Pro Thr Ile Pro Ser Asp Asn Leu Ala Ala Gly Thr
145                 150                 155                 160

Glu Lys Thr Gly Ser Leu Gly Pro Pro Asn Met Pro Val His Phe Asp
            165                 170                 175

Ser Gln Leu Asp Thr Thr Val Phe Gly Lys Lys Ser Ser Pro Leu Ile
        180                 185                 190

Gly Ser Gly Val Pro Leu Ser Leu Ser Glu Arg Asn Asn Asp Ser Lys
    195                 200                 205

Leu Leu Glu Ala Ala Leu Met Asn Ser Gln Glu Ser Ser Leu Gly Lys
    210                 215                 220

Asn Val Ser Ser Met Glu Ser Asp Arg Leu Phe Lys Glu Lys Arg Ala
225                 230                 235                 240

His Gly Pro Ala Leu Leu Thr Lys Asp Asn Ala Leu Phe Lys Val Asn
                245                 250                 255

Ile Ser Leu Val Lys Thr Asn Lys Thr Ser Asn Asn Ser Thr Thr Asn
            260                 265                 270

Arg Lys Thr His Ile Asp Gly Pro Thr Leu Leu Ile Glu Asn Ser Thr
        275                 280                 285

Ser Val Trp Gln Asp Ile Leu Glu Ser Asp Thr Glu Phe Gln Glu Val
    290                 295                 300

Thr Ser Leu Ile His Asp Lys Met Leu Met Asp Lys Asn Thr Thr Ala
305                 310                 315                 320

Leu Arg Leu Asn His Val Ser Asn Lys Thr Thr Ser Ser Lys Asn Met
                325                 330                 335

Glu Met Val His Gln Lys Lys Glu Gly Pro Val Pro Pro Asp Ala Glu
                340                 345                 350

Asn Pro Asp Met Ser Phe Phe Lys Met Leu Phe Leu Pro Glu Ser Ala
            355                 360                 365

Asn Trp Ile Lys Arg Thr His Gly Lys Asn Ser Leu Asn Ser Gly Gln
    370                 375                 380

Gly Pro Ser Pro Lys Gln Leu Ile Ser Leu Gly Ser Glu Lys Ser Val
385                 390                 395                 400

Lys Asp Gln Asn Phe Leu Ser Glu Lys Asn Lys Val Val Val Gly Glu
                405                 410                 415

Asp Glu Phe Thr Lys Asp Thr Gly Leu Lys Glu Met Ile Phe Pro Ser
            420                 425                 430

Ser Arg Asn Ile Phe Leu Thr Asn Leu Ala Asn Val His Glu Asn Asp
    435                 440                 445

Thr His Asn Gln Glu Lys Lys Ile Gln Glu Glu Ile Glu Arg Lys Glu
450                 455                 460

Thr Leu Ile Gln Glu Asn Val Val Leu Pro Gln Val Tyr Thr Val Thr
465                 470                 475                 480

Gly Thr Lys Asn Phe Met Lys Asn Leu Phe Leu Leu Ser Thr Arg Gln
                485                 490                 495

Asn Val Glu Gly Leu Asp Glu Gly Ala Tyr Ala Pro Val Leu Gln Asp
            500                 505                 510

Thr Arg Ser Leu Asn Asp Ser Thr Asn Arg Thr Glu Ile His Met Ala
    515                 520                 525

His Phe Ser Lys Lys Arg Glu Glu Asn Leu Glu Gly Leu Gly Asn
530                 535                 540

Gln Thr Lys Gln Met Val Glu Lys Tyr Pro Ser Thr Thr Arg Met Ser
545                 550                 555                 560
```

```
Pro Asn Pro Ser Gln Gln Asn Val Ile Thr Gln Arg Gly Lys Arg Ala
            565                 570                 575

Leu Lys Gln Phe Arg Leu Pro Leu Glu Glu Thr Glu Leu Glu Lys Gly
        580                 585                 590

Leu Ile Val Asp Asp Thr Ser Thr Gln Trp Ser Lys Asn Met Lys Tyr
    595                 600                 605

Leu Thr Gln Ser Thr Leu Thr Gln Ile Asp Tyr Asn Glu Lys Glu Lys
610                 615                 620

Lys Ala Ile Thr Gln Ser Pro Leu Ser Asp Cys Leu Met Arg Asn His
625                 630                 635                 640

Ser Ile Thr Gln Thr Asn Ser Ser Ala Leu Pro Ile Ala Lys Val Ser
                645                 650                 655

Ala Phe Pro Ser Ile Arg Pro Thr Asp Leu Thr Arg Val Pro Ser Gln
            660                 665                 670

Asp Asn Ser Ser His Leu Leu Ala Ser Ala Tyr Arg Lys Lys Ser Ser
        675                 680                 685

Gly Val Gln Glu Ser Ser His Phe Leu Gln Gly Ala Lys Arg Asn Asn
    690                 695                 700

Leu Ser Leu Ala Ile Leu Thr Leu Glu Met Ile Gly Asn Gln Arg Lys
705                 710                 715                 720

Val Gly Ser Leu Gly Thr Ser Ala Thr Asn Ser Val Met Tyr Lys Lys
                725                 730                 735

Leu Glu Asn Thr Val Leu Leu Lys Pro Gly Leu Pro Glu Ala Ser Gly
            740                 745                 750

Lys Val Glu Leu Leu Pro Lys Val His Ile His Gln Lys Asp Leu Phe
        755                 760                 765

Pro Thr Glu Thr Ser Asn Gly Ser Pro Gly His Leu Asp Leu Met Glu
    770                 775                 780

Glu Ile Leu Leu Gln Lys Thr Gln Gly Ala Ile Lys Trp Asn Lys Thr
785                 790                 795                 800

Asn Arg Pro Gly Lys Val Pro Phe Leu Lys Gly Ala Thr Glu Ser Ser
                805                 810                 815

Glu Lys Thr Pro Ser Lys Leu Leu Gly Pro Leu Ala Trp Asp Asn Gln
            820                 825                 830

Tyr Ala Thr Gln Ile Pro Lys Glu Glu Trp Lys Ser Gln Glu Lys Ser
        835                 840                 845

Pro Glu Asn Thr Ala Phe Lys Thr Lys Asp Thr Ile Leu Ser Leu Asn
    850                 855                 860

Pro Cys Glu Ser Asn His Ala Ile Ala Ala Ile Asn Glu Gly Gln Asp
865                 870                 875                 880

Arg Pro Gln Arg Glu Ala Thr Trp Ala Lys Gln Gly Gly Thr Gly Arg
                885                 890                 895

Leu Cys Ser Gln Asn Pro Pro Val Leu Lys Arg His Gln Arg
            900                 905                 910

<210> SEQ ID NO 16
<211> LENGTH: 41
<212> TYPE: PRT
<213> ORGANISM: artificial sequence
<220> FEATURE:
<223> OTHER INFORMATION: ancestral

<400> SEQUENCE: 16

Glu Ile Thr Leu Thr Thr Leu Gln Ser Asp Gln Glu Glu Ile Asp Tyr
1               5                   10                  15
```

Asp Asp Thr Ile Ser Ile Glu Thr Lys Arg Glu Asp Phe Asp Ile Tyr
            20                  25                  30

Gly Glu Asp Glu Asn Gln Ser Pro Arg
            35                  40

<210> SEQ ID NO 17
<211> LENGTH: 330
<212> TYPE: PRT
<213> ORGANISM: artificial sequence
<220> FEATURE:
<223> OTHER INFORMATION: ancestral

<400> SEQUENCE: 17

Ser Phe Gln Lys Lys Thr Arg His Tyr Phe Ile Ala Ala Val Glu Arg
1               5                   10                  15

Leu Trp Asp Tyr Gly Met Ser Arg Ser Pro His Val Leu Arg Asn Arg
            20                  25                  30

Ala Gln Ser Gly Ser Val Pro Gln Phe Lys Lys Val Val Phe Gln Glu
        35                  40                  45

Phe Thr Asp Gly Ser Phe Thr Gln Pro Leu Tyr Arg Gly Glu Leu Asn
    50                  55                  60

Glu His Leu Gly Leu Leu Gly Pro Tyr Ile Arg Ala Glu Val Glu Asp
65                  70                  75                  80

Asn Ile Met Val Thr Phe Lys Asn Gln Ala Ser Arg Pro Tyr Ser Phe
                85                  90                  95

Tyr Ser Ser Leu Ile Ser Tyr Glu Glu Asp Gln Arg Gln Gly Ala Glu
            100                 105                 110

Pro Arg Lys Asn Phe Val Lys Pro Asn Glu Thr Lys Thr Tyr Phe Trp
        115                 120                 125

Lys Val Gln His His Met Ala Pro Thr Lys Asp Glu Phe Asp Cys Lys
    130                 135                 140

Ala Trp Ala Tyr Phe Ser Asp Val Asp Leu Glu Lys Asp Met His Ser
145                 150                 155                 160

Gly Leu Ile Gly Pro Leu Leu Ile Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
        195                 200                 205

Asn Cys Arg Ala Pro Cys Asn Ile Gln Met Glu Asp Pro Thr Phe Lys
    210                 215                 220

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Val Tyr Asn
        275                 280                 285

Leu Tyr Pro Gly Val Phe Glu Thr Val Glu Met Leu Pro Ser Lys Ala
    290                 295                 300

Gly Ile Trp Arg Val Glu Cys Leu Ile Gly Glu His Leu His Ala Gly
305                 310                 315                 320

Met Ser Thr Leu Phe Leu Val Tyr Ser Lys
                325                 330

```
<210> SEQ ID NO 18
<211> LENGTH: 153
<212> TYPE: PRT
<213> ORGANISM: artificial sequence
<220> FEATURE:
<223> OTHER INFORMATION: ancestral

<400> SEQUENCE: 18

Gln Cys Gln Thr Pro Leu Gly Met Ala Ser Gly His Ile Arg Asp Phe
1               5                   10                  15

Gln Ile Thr Ala Ser Gly Gln Tyr Gly Gln Trp Ala Pro Lys Leu Ala
            20                  25                  30

Arg Leu His Tyr Ser Gly Ser Ile Asn Ala Trp Ser Thr Lys Glu Pro
        35                  40                  45

Phe Ser Trp Ile Lys Val Asp Leu Leu Ala Pro Met Ile Ile His Gly
    50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Gln Thr Tyr
                85                  90                  95

Arg Gly Asn Ser Thr Gly Thr Leu Met Val Phe Gly Asn Val Asp
            100                 105                 110

Ser Ser Gly Ile Lys His Asn Ile Phe Asn Pro Pro Ile Ile Ala Arg
        115                 120                 125

Tyr Ile Arg Leu His Pro Thr His Tyr Ser Ile Arg Ser Thr Leu Arg
    130                 135                 140

Met Glu Leu Met Gly Cys Asp Leu Asn
145                 150

<210> SEQ ID NO 19
<211> LENGTH: 160
<212> TYPE: PRT
<213> ORGANISM: artificial sequence
<220> FEATURE:
<223> OTHER INFORMATION: ancestral

<400> SEQUENCE: 19

Ser Cys Ser Met Pro Leu Gly Met Glu Ser Lys Ala Ile Ser Asp Ala
1               5                   10                  15

Gln Ile Thr Ala Ser Ser Tyr Phe Thr Asn Met Phe Ala Thr Trp Ser
            20                  25                  30

Pro Ser Gln Ala Arg Leu His Leu Gln Gly Arg Thr Asn Ala Trp Arg
        35                  40                  45

Pro Gln Val Asn Asn Pro Lys Glu Trp Leu Gln Val Asp Phe Gln Lys
    50                  55                  60

Thr Met Lys Val Thr Gly Ile Thr Thr Gln Gly Val Lys Ser Leu Leu
65                  70                  75                  80

Thr Ser Met Tyr Val Lys Glu Phe Leu Ile Ser Ser Ser Gln Asp Gly
                85                  90                  95

His His Trp Thr Leu Phe Phe Gln Asn Gly Lys Val Lys Val Phe Gln
            100                 105                 110

Gly Asn Gln Asp Ser Phe Thr Pro Val Val Asn Ser Leu Asp Pro Pro
        115                 120                 125

Leu Leu Thr Arg Tyr Leu Arg Ile His Pro Gln Ser Trp Val His Gln
    130                 135                 140
```

Ile Ala Leu Arg Leu Glu Val Leu Gly Cys Glu Ala Gln Gln Leu Tyr
145                 150                 155                 160

<210> SEQ ID NO 20
<211> LENGTH: 2359
<212> TYPE: PRT
<213> ORGANISM: artificial sequence
<220> FEATURE:
<223> OTHER INFORMATION: ancestral

<400> SEQUENCE: 20

Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Gln Phe Val Leu Leu Phe Ala Val Phe Asp Glu
    210                 215                 220

Gly Lys Ser Trp His Ser Glu Thr Lys Asp Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

```
Pro Gln Leu Arg Met Lys Asn Glu Glu Glu Asp Tyr Asp Asp
        355                 360                 365

Asp Leu Tyr Asp Ser Glu Met Asp Val Val Arg Phe Asp Asp Asn
    370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asp Asp Arg Ser Tyr Lys Ser Gln Tyr Leu
            420                 425                 430

Asn Asn Gly Pro Gln Arg Ile Gly Arg Lys Tyr Lys Lys Val Arg Phe
            435                 440                 445

Met Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
            595                 600                 605

Glu Asn Met Gln Arg Phe Leu Pro Asn Ala Ala Gly Val Gln Pro Gln
    610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
            740                 745                 750

Glu Asn Asn Val Ile Glu Pro Arg Ser Phe Ser Gln Asn Ser Arg His
            755                 760                 765
```

```
Pro Ser Thr Arg Gln Lys Gln Phe Lys Ala Thr Thr Ile Pro Glu Asn
    770             775                 780

Asp Ile Glu Lys Ile Asp Pro Gln Phe Gly Arg Thr Gln Met Leu
785             790                 795                 800

Lys Val Gln Ser Val Ser Ser Asp Leu Leu Met Leu Leu Gly Gln
            805                 810                 815

Ser Pro Thr Pro His Gly Leu Ser Leu Ser Asp Leu Gln Glu Ala Thr
            820                 825                 830

Tyr Glu Ala Ile Pro Asp Asp His Ser Pro Gly Ala Ile Asp Ser Asn
            835                 840                 845

Glu Gly Pro Ser Glu Val Ala His Leu Arg Pro Glu Leu His His Ser
    850                 855                 860

Gly Asp Met Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
            885                 890                 895

Lys Val Ser Ser Ser Asn Asn Leu Met Thr Ser Pro Thr Ile Pro
            900                 905                 910

Ser Asp Asn Leu Ala Ala Gly Thr Glu Lys Thr Gly Ser Leu Gly Pro
            915                 920                 925

Pro Asn Met Pro Val His Phe Ser Ser Gln Leu Gly Thr Thr Val Phe
            930                 935                 940

Gly Lys Lys Ser Ser Pro Leu Ile Gly Ser Gly Val Pro Leu Asn Leu
945                 950                 955                 960

Ser Glu Arg Asn Asn Asp Ser Lys Leu Leu Glu Ala Ala Leu Met Asn
                965                 970                 975

Ser Gln Glu Ser Ser Leu Gly Lys Asn Val Ser Ser Met Glu Ser Asp
            980                 985                 990

Arg Leu Phe Lys Glu Lys Arg Val His Gly Pro Ala Leu Leu Thr Lys
            995                 1000                1005

Asp Asn Ala Leu Phe Lys Val Asn Ile Ser Leu Val Lys Thr Asn
    1010                1015                1020

Lys Thr Ser Asn Asn Ser Thr Thr Asn Arg Lys Thr His Ile Asp
    1025                1030                1035

Gly Pro Thr Leu Leu Ile Glu Asn Ser Thr Ser Val Trp Gln Asp
    1040                1045                1050

Ile Ile Leu Glu Ser Asp Thr Glu Phe Gln Glu Val Thr Ser Leu
    1055                1060                1065

Ile His Asp Glu Met Leu Met Asp Lys Asn Thr Thr Ala Leu Arg
    1070                1075                1080

Leu Asn His Val Ser Asn Lys Thr Thr Ser Ser Lys Asn Met Glu
    1085                1090                1095

Met Val His Gln Lys Lys Glu Gly Pro Val Pro Asp Ala Glu
    1100                1105                1110

Asn Pro Asp Met Ser Phe Phe Lys Met Leu Phe Leu Pro Glu Ser
    1115                1120                1125

Ala Asn Trp Ile Lys Arg Thr His Gly Lys Asn Ser Leu Asn Ser
    1130                1135                1140

Gly Gln Gly Pro Ser Pro Lys Gln Leu Ile Ser Leu Gly Ser Glu
    1145                1150                1155

Lys Ser Val Lys Asp Gln Asn Phe Leu Ser Glu Lys Asn Lys Val
    1160                1165                1170
```

-continued

Val Val Gly Glu Asp Glu Phe Thr Lys Asp Thr Gly Leu Lys Glu
1175                    1180                1185

Met Ile Phe Pro Asn Ser Arg Ser Ile Phe Leu Thr Asn Leu Ala
1190                    1195                1200

Asn Val Gln Glu Asn Asp Thr His Asn Gln Glu Lys Lys Phe Gln
1205                    1210                1215

Glu Glu Ile Glu Arg Lys Glu Thr Leu Ile Gln Glu Asn Val Val
1220                    1225                1230

Leu Pro Gln Val Tyr Thr Val Thr Gly Thr Lys Asn Phe Leu Lys
1235                    1240                1245

Asn Leu Phe Leu Leu Ser Thr Arg Gln Asn Val Glu Gly Leu Asp
1250                    1255                1260

Glu Gly Thr Tyr Ala Pro Val Leu Gln Asp Thr Arg Ser Leu Asn
1265                    1270                1275

Asp Ser Thr Asn Arg Ala Glu Ile His Met Ala His Phe Ser Lys
1280                    1285                1290

Arg Arg Glu Glu Glu Asn Leu Glu Gly Leu Gly Asn Gln Thr Lys
1295                    1300                1305

Gln Met Val Glu Lys Tyr Pro Ser Thr Thr Arg Met Ser Pro Asn
1310                    1315                1320

Pro Ser Gln Gln Asn Val Ile Thr Gln Arg Gly Lys Arg Ala Leu
1325                    1330                1335

Lys Gln Phe Arg Leu Pro Leu Glu Glu Thr Glu Leu Glu Lys Gly
1340                    1345                1350

Leu Ile Val Asp Asp Thr Ser Thr Gln Trp Ser Lys Asn Met Lys
1355                    1360                1365

Tyr Leu Thr Gln Ser Thr Leu Thr Gln Ile Asp Tyr Asn Glu Lys
1370                    1375                1380

Glu Lys Lys Ala Ile Thr Gln Ser Pro Leu Ser Asp Cys Ser Met
1385                    1390                1395

Arg Asn His Ser Ile Thr Gln Thr Asn Ser Ser Ala Leu Pro Ile
1400                    1405                1410

Ala Lys Val Ser Ala Phe Pro Ser Ile Arg Pro Thr Asp Leu Thr
1415                    1420                1425

Lys Ile Pro Ser Gln Asp Asn Ser Ser His Leu Leu Ala Ser Ala
1430                    1435                1440

Tyr Ser Tyr Thr Phe Arg Glu Lys Ser Ser Gly Val Gln Glu Ser
1445                    1450                1455

Ser His Phe Leu Gln Gly Ala Lys Arg Asn Asn Leu Ser Leu Ala
1460                    1465                1470

Ile Leu Thr Leu Glu Met Ile Arg Asn Gln Glu Lys Val Gly Ser
1475                    1480                1485

Leu Gly Thr Ser Ala Thr Asn Ser Val Met Tyr Lys Lys Leu Glu
1490                    1495                1500

Asn Thr Val Leu Leu Lys Pro Gly Leu Pro Glu Ala Ser Gly Lys
1505                    1510                1515

Val Glu Leu Leu Pro Lys Val His Ile His Gln Glu Asp Leu Phe
1520                    1525                1530

Pro Thr Glu Thr Ser Asn Gly Ser Pro Gly His Leu Asp Leu Met
1535                    1540                1545

Glu Glu Ile Leu Leu Gln Lys Thr Gln Gly Ala Ile Lys Trp Asn
1550                    1555                1560

```
Lys Thr Asn Arg Pro Gly Lys Val Pro Phe Leu Lys Gly Ala Thr
1565                1570                1575

Glu Ser Ser Glu Lys Thr Pro Ser Lys Leu Leu Gly Pro Leu Ala
    1580                1585                1590

Trp Asp Asn Gln Tyr Ala Thr Gln Ile Pro Lys Glu Glu Trp Lys
1595                1600                1605

Ser Gln Glu Lys Ser Pro Lys Asn Thr Ala Phe Lys Thr Lys Asp
    1610                1615                1620

Thr Ile Leu Ser Leu Asn Pro Cys Glu Asn Asn His Ala Ile Ala
1625                1630                1635

Ala Ile Asn Glu Gly Gln Asp Arg Pro Gln Arg Glu Ala Thr Trp
    1640                1645                1650

Ala Lys Gln Gly Gly Thr Gly Arg Leu Cys Ser Gln Asn Pro Pro
1655                1660                1665

Val Leu Lys Arg His Gln Arg Glu Ile Thr Leu Thr Thr Leu Gln
    1670                1675                1680

Ser Glu Gln Glu Glu Ile Asp Tyr Asp Asp Thr Ile Ser Ile Glu
1685                1690                1695

Thr Lys Arg Glu Asp Phe Asp Ile Tyr Gly Glu Asp Glu Asn Gln
    1700                1705                1710

Gly Pro Arg Ser Phe Gln Lys Arg Thr Arg His Tyr Phe Ile Ala
1715                1720                1725

Ala Val Glu Arg Leu Trp Asp Tyr Gly Met Ser Arg Ser Pro His
    1730                1735                1740

Val Leu Arg Asn Arg Ala Gln Ser Gly Ser Val Pro Gln Phe Lys
1745                1750                1755

Lys Val Val Phe Gln Glu Phe Thr Asp Gly Ser Phe Thr Gln Pro
    1760                1765                1770

Leu Tyr Arg Gly Glu Leu Asn Glu His Leu Gly Leu Leu Gly Pro
1775                1780                1785

Tyr Ile Arg Ala Glu Val Glu Asp Asn Ile Met Val Thr Phe Lys
    1790                1795                1800

Asn Gln Ala Ser Arg Pro Tyr Ser Phe Tyr Ser Ser Leu Ile Ser
1805                1810                1815

Tyr Glu Glu Asp Gln Arg Gln Gly Ala Glu Pro Arg Lys Asn Phe
    1820                1825                1830

Val Lys Pro Asn Glu Thr Lys Thr Tyr Phe Trp Lys Val Gln His
1835                1840                1845

His Met Ala Pro Thr Lys Asp Glu Phe Asp Cys Lys Ala Trp Ala
    1850                1855                1860

Tyr Phe Ser Asp Val Asp Leu Glu Lys Asp Met His Ser Gly Leu
1865                1870                1875

Ile Gly Pro Leu Leu Ile Cys His Thr Asn Thr Leu Asn Pro Ala
    1880                1885                1890

His Gly Arg Gln Val Thr Val Gln Glu Phe Ala Leu Phe Phe Thr
1895                1900                1905

Ile Phe Asp Glu Thr Lys Ser Trp Tyr Phe Thr Glu Asn Met Glu
    1910                1915                1920

Arg Asn Cys Arg Ala Pro Cys Asn Ile Gln Met Glu Asp Pro Thr
1925                1930                1935

Phe Lys Glu Asn Tyr Arg Phe His Ala Ile Asn Gly Tyr Val Met
    1940                1945                1950
```

```
Asp Thr Leu Pro Gly Leu Val Met Ala Gln Asp Gln Arg Ile Arg
    1955            1960                1965

Trp Tyr Leu Leu Ser Met Gly Ser Asn Glu Asn Ile His Ser Ile
    1970            1975                1980

His Phe Ser Gly His Val Phe Thr Val Arg Lys Lys Glu Glu Tyr
    1985            1990                1995

Lys Met Ala Val Tyr Asn Leu Tyr Pro Gly Val Phe Glu Thr Val
    2000            2005                2010

Glu Met Leu Pro Ser Lys Ala Gly Ile Trp Arg Val Glu Cys Leu
    2015            2020                2025

Ile Gly Glu His Leu His Ala Gly Met Ser Thr Leu Phe Leu Val
    2030            2035                2040

Tyr Ser Lys Gln Cys Gln Thr Pro Leu Gly Met Ala Ser Gly His
    2045            2050                2055

Ile Arg Asp Phe Gln Ile Thr Ala Ser Gly Gln Tyr Gly Gln Trp
    2060            2065                2070

Ala Pro Lys Leu Ala Arg Leu His Tyr Ser Gly Ser Ile Asn Ala
    2075            2080                2085

Trp Ser Thr Lys Glu Pro Phe Ser Trp Ile Lys Val Asp Leu Leu
    2090            2095                2100

Ala Pro Met Ile Ile His Gly Ile Lys Thr Gln Gly Ala Arg Gln
    2105            2110                2115

Lys Phe Ser Ser Leu Tyr Ile Ser Gln Phe Ile Ile Met Tyr Ser
    2120            2125                2130

Leu Asp Gly Lys Lys Trp Gln Thr Tyr Arg Gly Asn Ser Thr Gly
    2135            2140                2145

Thr Leu Met Val Phe Phe Gly Asn Val Asp Ser Ser Gly Ile Lys
    2150            2155                2160

His Asn Ile Phe Asn Pro Pro Ile Ile Ala Arg Tyr Ile Arg Leu
    2165            2170                2175

His Pro Thr His Tyr Ser Ile Arg Ser Thr Leu Arg Met Glu Leu
    2180            2185                2190

Met Gly Cys Asp Leu Asn Ser Cys Ser Met Pro Leu Gly Met Glu
    2195            2200                2205

Ser Lys Ala Ile Ser Asp Ala Gln Ile Thr Ala Ser Ser Tyr Phe
    2210            2215                2220

Thr Asn Met Phe Ala Thr Trp Ser Pro Ser Gln Ala Arg Leu His
    2225            2230                2235

Leu Gln Gly Arg Thr Asn Ala Trp Arg Pro Gln Val Asn Asn Pro
    2240            2245                2250

Lys Glu Trp Leu Gln Val Asp Phe Gln Lys Thr Met Lys Val Thr
    2255            2260                2265

Gly Ile Thr Thr Gln Gly Val Lys Ser Leu Leu Thr Ser Met Tyr
    2270            2275                2280

Val Lys Glu Phe Leu Ile Ser Ser Ser Gln Asp Gly His His Trp
    2285            2290                2295

Thr Leu Phe Leu Gln Asn Gly Lys Val Lys Val Phe Gln Gly Asn
    2300            2305                2310

Gln Asp Ser Phe Thr Pro Val Val Asn Ser Leu Asp Pro Pro Leu
    2315            2320                2325

Leu Thr Arg Tyr Leu Arg Ile His Pro Gln Ser Trp Val His Gln
    2330            2335                2340
```

```
Ile Ala Leu Arg Leu Glu Val Leu Gly Cys Glu Ala Gln Gln Leu
    2345                2350                2355
Tyr

<210> SEQ ID NO 21
<211> LENGTH: 19
<212> TYPE: PRT
<213> ORGANISM: artificial sequence
<220> FEATURE:
<223> OTHER INFORMATION: ancestral

<400> SEQUENCE: 21

Met Gln Ile Glu Leu Ser Thr Cys Phe Phe Leu Cys Leu Leu Gln Phe
1               5                   10                  15

Ser Phe Ser

<210> SEQ ID NO 22
<211> LENGTH: 374
<212> TYPE: PRT
<213> ORGANISM: artificial sequence
<220> FEATURE:
<223> OTHER INFORMATION: ancestral

<400> SEQUENCE: 22

Ala Thr Arg Arg Tyr Tyr Leu Gly Ala Val Glu Leu Ser Trp Asp Tyr
1               5                   10                  15

Met Gln Ser Asp Leu Leu Ser Glu Leu His Val Asp Thr Arg Phe Pro
                20                  25                  30

Pro Arg Val Pro Arg Ser Phe Pro Phe Asn Thr Ser Val Met Tyr Lys
            35                  40                  45

Lys Thr Val Phe Val Glu Phe Thr Asp His Leu Phe Asn Ile Ala Lys
        50                  55                  60

Pro Arg Pro Pro Trp Met Gly Leu Leu Gly Pro Thr Ile Arg Ala Glu
65                  70                  75                  80

Val Tyr Asp Thr Val Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Asp Asp Gln Thr Ser Gln Arg Glu Lys Glu Asp Asp Lys
        115                 120                 125

Val Phe Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Ala Lys Glu Arg Thr Gln Thr
            180                 185                 190

Leu His Gln Phe Val Leu Leu Phe Ala Val Phe Asp Glu Gly Lys Ser
        195                 200                 205

Trp His Ser Glu Thr Lys Asp Ser Leu Thr Gln Ala Met Asp Ser Ala
    210                 215                 220

Ser Ala Arg Ala Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255
```

```
His Val Ile Gly Met Gly Thr Thr Pro Glu Val His Ser Ile Phe Leu
            260                 265                 270
Glu Gly His Thr Phe Leu Val Arg Asn His Arg Gln Ala Ser Leu Glu
        275                 280                 285
Ile Ser Pro Ile Thr Phe Leu Thr Ala Gln Thr Leu Leu Met Asp Leu
    290                 295                 300
Gly Gln Phe Leu Leu Phe Cys His Ile Ser Ser His Gln His Asp Gly
305                 310                 315                 320
Met Glu Ala Tyr Val Lys Val Asp Ser Cys Pro Glu Pro Gln Leu
                325                 330                 335
Arg Met Lys Asn Asn Glu Glu Glu Asp Tyr Asp Asp Asp Leu Tyr
            340                 345                 350
Asp Ser Glu Met Asp Val Val Arg Phe Asp Asp Asp Asn Ser Pro Pro
        355                 360                 365
Phe Ile Gln Ile Arg Ser
    370

<210> SEQ ID NO 23
<211> LENGTH: 367
<212> TYPE: PRT
<213> ORGANISM: artificial sequence
<220> FEATURE:
<223> OTHER INFORMATION: ancestral

<400> SEQUENCE: 23

Val Ala Lys Lys His Pro Lys Thr Trp Val His Tyr Ile Ala Ala Glu
1               5                   10                  15
Glu Glu Asp Trp Asp Tyr Ala Pro Ser Val Leu Thr Pro Asp Asp Arg
            20                  25                  30
Ser Tyr Lys Ser Gln Tyr Leu Asn Gly Pro Gln Arg Ile Gly Arg
        35                  40                  45
Lys Tyr Lys Lys Val Arg Phe Met Ala Tyr Thr Asp Glu Thr Phe Lys
50                  55                  60
Thr Arg Glu Ala Ile Gln Tyr Glu Ser Gly Ile Leu Gly Pro Leu Leu
65                  70                  75                  80
Tyr Gly Glu Val Gly Asp Thr Leu Leu Ile Ile Phe Lys Asn Gln Ala
                85                  90                  95
Ser Arg Pro Tyr Asn Ile Tyr Pro His Gly Ile Thr Asp Val Ser Pro
            100                 105                 110
Leu His Ser Gly Arg Leu Pro Lys Gly Val Lys His Leu Lys Asp Leu
        115                 120                 125
Pro Ile Leu Pro Gly Glu Ile Phe Lys Tyr Lys Trp Thr Val Thr Val
    130                 135                 140
Glu Asp Gly Pro Thr Lys Ser Asp Pro Arg Cys Leu Thr Arg Tyr Tyr
145                 150                 155                 160
Ser Ser Phe Ile Asn Leu Glu Arg Asp Leu Ala Ser Gly Leu Ile Gly
                165                 170                 175
Pro Leu Leu Ile Cys Tyr Lys Glu Ser Val Asp Gln Arg Gly Asn Gln
            180                 185                 190
Met Met Ser Asp Lys Arg Asn Val Ile Leu Phe Ser Val Phe Asp Glu
        195                 200                 205
Asn Arg Ser Trp Tyr Leu Thr Glu Asn Met Gln Arg Phe Leu Pro Asn
    210                 215                 220
Ala Ala Gly Val Gln Pro Gln Asp Pro Glu Phe Gln Ala Ser Asn Ile
225                 230                 235                 240
```

```
Met His Ser Ile Asn Gly Tyr Val Phe Asp Ser Leu Gln Leu Ser Val
                245                 250                 255

Cys Leu His Glu Val Ala Tyr Trp Tyr Ile Leu Ser Val Gly Ala Gln
                260                 265                 270

Thr Asp Phe Leu Ser Val Phe Phe Ser Gly Tyr Thr Phe Lys His Lys
                275                 280                 285

Met Val Tyr Glu Asp Thr Leu Thr Leu Phe Pro Phe Ser Gly Glu Thr
                290                 295                 300

Val Phe Met Ser Met Glu Asn Pro Gly Leu Trp Val Leu Gly Cys His
305                 310                 315                 320

Asn Ser Asp Phe Arg Asn Arg Gly Met Thr Ala Leu Leu Lys Val Ser
                325                 330                 335

Ser Cys Asp Arg Asn Thr Gly Asp Tyr Tyr Glu Asp Thr Tyr Glu Asp
                340                 345                 350

Ile Pro Thr Tyr Leu Leu Ser Glu Asn Asn Val Ile Glu Pro Arg
                355                 360                 365

<210> SEQ ID NO 24
<211> LENGTH: 915
<212> TYPE: PRT
<213> ORGANISM: artificial sequence
<220> FEATURE:
<223> OTHER INFORMATION: ancestral

<400> SEQUENCE: 24

Ser Phe Ser Gln Asn Ser Arg His Pro Ser Thr Arg Gln Lys Gln Phe
1               5                   10                  15

Lys Ala Thr Thr Ile Pro Glu Asn Asp Ile Glu Lys Ile Asp Pro Gln
                20                  25                  30

Phe Gly Glu Arg Thr Gln Met Leu Lys Val Gln Ser Val Ser Ser Ser
                35                  40                  45

Asp Leu Leu Met Leu Leu Gly Gln Ser Pro Thr Pro His Gly Leu Ser
                50                  55                  60

Leu Ser Asp Leu Gln Glu Ala Thr Tyr Glu Ala Ile Pro Asp Asp His
65                  70                  75                  80

Ser Pro Gly Ala Ile Asp Ser Asn Glu Gly Pro Ser Glu Val Ala His
                85                  90                  95

Leu Arg Pro Glu Leu His His Ser Gly Asp Met Val Phe Thr Pro Glu
                100                 105                 110

Pro Gly Leu Gln Leu Arg Leu Asn Glu Asn Leu Gly Thr Thr Ile Ala
                115                 120                 125

Val Glu Leu Lys Lys Leu Asp Leu Lys Val Ser Ser Ser Asn Asn
                130                 135                 140

Leu Met Thr Ser Pro Thr Ile Pro Ser Asp Asn Leu Ala Ala Gly Thr
145                 150                 155                 160

Glu Lys Thr Gly Ser Leu Gly Pro Pro Asn Met Pro Val His Phe Ser
                165                 170                 175

Ser Gln Leu Gly Thr Thr Val Phe Gly Lys Lys Ser Ser Pro Leu Ile
                180                 185                 190

Gly Ser Gly Val Pro Leu Asn Leu Ser Glu Arg Asn Asn Asp Ser Lys
                195                 200                 205

Leu Leu Glu Ala Ala Leu Met Asn Ser Gln Glu Ser Ser Leu Gly Lys
                210                 215                 220

Asn Val Ser Ser Met Glu Ser Asp Arg Leu Phe Lys Glu Lys Arg Val
225                 230                 235                 240
```

```
His Gly Pro Ala Leu Leu Thr Lys Asp Asn Ala Leu Phe Lys Val Asn
                245                 250                 255

Ile Ser Leu Val Lys Thr Asn Lys Thr Ser Asn Asn Ser Thr Thr Asn
                260                 265                 270

Arg Lys Thr His Ile Asp Gly Pro Thr Leu Leu Ile Glu Asn Ser Thr
                275                 280                 285

Ser Val Trp Gln Asp Ile Ile Leu Glu Ser Asp Thr Glu Phe Gln Glu
                290                 295                 300

Val Thr Ser Leu Ile His Asp Glu Met Leu Met Asp Lys Asn Thr Thr
305                 310                 315                 320

Ala Leu Arg Leu Asn His Val Ser Asn Lys Thr Thr Ser Ser Lys Asn
                325                 330                 335

Met Glu Met Val His Gln Lys Lys Glu Gly Pro Val Pro Pro Asp Ala
                340                 345                 350

Glu Asn Pro Asp Met Ser Phe Phe Lys Met Leu Phe Leu Pro Glu Ser
                355                 360                 365

Ala Asn Trp Ile Lys Arg Thr His Gly Lys Asn Ser Leu Asn Ser Gly
                370                 375                 380

Gln Gly Pro Ser Pro Lys Gln Leu Ile Ser Leu Gly Ser Glu Lys Ser
385                 390                 395                 400

Val Lys Asp Gln Asn Phe Leu Ser Glu Lys Asn Lys Val Val Val Gly
                405                 410                 415

Glu Asp Glu Phe Thr Lys Asp Thr Gly Leu Lys Glu Met Ile Phe Pro
                420                 425                 430

Asn Ser Arg Ser Ile Phe Leu Thr Asn Leu Ala Asn Val Gln Glu Asn
                435                 440                 445

Asp Thr His Asn Gln Glu Lys Lys Phe Gln Glu Glu Ile Glu Arg Lys
                450                 455                 460

Glu Thr Leu Ile Gln Glu Asn Val Val Leu Pro Gln Val Tyr Thr Val
465                 470                 475                 480

Thr Gly Thr Lys Asn Phe Leu Lys Asn Leu Phe Leu Leu Ser Thr Arg
                485                 490                 495

Gln Asn Val Glu Gly Leu Asp Glu Gly Thr Tyr Ala Pro Val Leu Gln
                500                 505                 510

Asp Thr Arg Ser Leu Asn Asp Ser Thr Asn Arg Ala Glu Ile His Met
                515                 520                 525

Ala His Phe Ser Lys Arg Arg Glu Glu Glu Asn Leu Glu Gly Leu Gly
                530                 535                 540

Asn Gln Thr Lys Gln Met Val Glu Lys Tyr Pro Ser Thr Thr Arg Met
545                 550                 555                 560

Ser Pro Asn Pro Ser Gln Gln Asn Val Ile Thr Gln Arg Gly Lys Arg
                565                 570                 575

Ala Leu Lys Gln Phe Arg Leu Pro Leu Glu Glu Thr Glu Leu Glu Lys
                580                 585                 590

Gly Leu Ile Val Asp Asp Thr Ser Thr Gln Trp Ser Lys Asn Met Lys
                595                 600                 605

Tyr Leu Thr Gln Ser Thr Leu Thr Gln Ile Asp Tyr Asn Glu Lys Glu
                610                 615                 620

Lys Lys Ala Ile Thr Gln Ser Pro Leu Ser Asp Cys Ser Met Arg Asn
625                 630                 635                 640

His Ser Ile Thr Gln Thr Asn Ser Ser Ala Leu Pro Ile Ala Lys Val
                645                 650                 655
```

```
Ser Ala Phe Pro Ser Ile Arg Pro Thr Asp Leu Thr Lys Ile Pro Ser
            660                 665                 670

Gln Asp Asn Ser Ser His Leu Leu Ala Ser Ala Tyr Ser Tyr Thr Phe
        675                 680                 685

Arg Glu Lys Ser Ser Gly Val Gln Glu Ser Ser His Phe Leu Gln Gly
    690                 695                 700

Ala Lys Arg Asn Asn Leu Ser Leu Ala Ile Leu Thr Leu Glu Met Ile
705                 710                 715                 720

Arg Asn Gln Glu Lys Val Gly Ser Leu Gly Thr Ser Ala Thr Asn Ser
                725                 730                 735

Val Met Tyr Lys Lys Leu Glu Asn Thr Val Leu Leu Lys Pro Gly Leu
            740                 745                 750

Pro Glu Ala Ser Gly Lys Val Glu Leu Leu Pro Lys Val His Ile His
        755                 760                 765

Gln Glu Asp Leu Phe Pro Thr Glu Thr Ser Asn Gly Ser Pro Gly His
    770                 775                 780

Leu Asp Leu Met Glu Glu Ile Leu Leu Gln Lys Thr Gln Gly Ala Ile
785                 790                 795                 800

Lys Trp Asn Lys Thr Asn Arg Pro Gly Lys Val Pro Phe Leu Lys Gly
                805                 810                 815

Ala Thr Glu Ser Ser Glu Lys Thr Pro Ser Lys Leu Leu Gly Pro Leu
            820                 825                 830

Ala Trp Asp Asn Gln Tyr Ala Thr Gln Ile Pro Lys Glu Glu Trp Lys
        835                 840                 845

Ser Gln Glu Lys Ser Pro Lys Asn Thr Ala Phe Lys Thr Lys Asp Thr
    850                 855                 860

Ile Leu Ser Leu Asn Pro Cys Glu Asn Asn His Ala Ile Ala Ala Ile
865                 870                 875                 880

Asn Glu Gly Gln Asp Arg Pro Gln Arg Glu Ala Thr Trp Ala Lys Gln
                885                 890                 895

Gly Gly Thr Gly Arg Leu Cys Ser Gln Asn Pro Pro Val Leu Lys Arg
            900                 905                 910

His Gln Arg
    915

<210> SEQ ID NO 25
<211> LENGTH: 41
<212> TYPE: PRT
<213> ORGANISM: artificial sequence
<220> FEATURE:
<223> OTHER INFORMATION: ancestral

<400> SEQUENCE: 25

Glu Ile Thr Leu Thr Thr Leu Gln Ser Glu Gln Glu Glu Ile Asp Tyr
1               5                   10                  15

Asp Asp Thr Ile Ser Ile Glu Thr Lys Arg Glu Asp Phe Asp Ile Tyr
            20                  25                  30

Gly Glu Asp Glu Asn Gln Gly Pro Arg
        35                  40

<210> SEQ ID NO 26
<211> LENGTH: 330
<212> TYPE: PRT
<213> ORGANISM: artificial sequence
<220> FEATURE:
<223> OTHER INFORMATION: ancestral
```

<400> SEQUENCE: 26

```
Ser Phe Gln Lys Arg Thr Arg His Tyr Phe Ile Ala Ala Val Glu Arg
1               5                   10                  15

Leu Trp Asp Tyr Gly Met Ser Arg Ser Pro His Val Leu Arg Asn Arg
            20                  25                  30

Ala Gln Ser Gly Ser Val Pro Gln Phe Lys Lys Val Phe Gln Glu
        35                  40                  45

Phe Thr Asp Gly Ser Phe Thr Gln Pro Leu Tyr Arg Gly Glu Leu Asn
    50                  55                  60

Glu His Leu Gly Leu Leu Gly Pro Tyr Ile Arg Ala Glu Val Glu Asp
65              70                  75                  80

Asn Ile Met Val Thr Phe Lys Asn Gln Ala Ser Arg Pro Tyr Ser Phe
                85                  90                  95

Tyr Ser Ser Leu Ile Ser Tyr Glu Glu Asp Gln Arg Gln Gly Ala Glu
            100                 105                 110

Pro Arg Lys Asn Phe Val Lys Pro Asn Glu Thr Lys Thr Tyr Phe Trp
        115                 120                 125

Lys Val Gln His His Met Ala Pro Thr Lys Asp Glu Phe Asp Cys Lys
    130                 135                 140

Ala Trp Ala Tyr Phe Ser Asp Val Asp Leu Glu Lys Asp Met His Ser
145                 150                 155                 160

Gly Leu Ile Gly Pro Leu Leu Ile Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
        195                 200                 205

Asn Cys Arg Ala Pro Cys Asn Ile Gln Met Glu Asp Pro Thr Phe Lys
    210                 215                 220

Glu Asn Tyr Arg Phe His Ala Ile Asn Gly Tyr Val Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Val Tyr Asn
        275                 280                 285

Leu Tyr Pro Gly Val Phe Glu Thr Val Glu Met Leu Pro Ser Lys Ala
    290                 295                 300

Gly Ile Trp Arg Val Glu Cys Leu Ile Gly Glu His Leu His Ala Gly
305                 310                 315                 320

Met Ser Thr Leu Phe Leu Val Tyr Ser Lys
                325                 330
```

<210> SEQ ID NO 27
<211> LENGTH: 153
<212> TYPE: PRT
<213> ORGANISM: artificial sequence
<220> FEATURE:
<223> OTHER INFORMATION: ancestral

<400> SEQUENCE: 27

```
Gln Cys Gln Thr Pro Leu Gly Met Ala Ser Gly His Ile Arg Asp Phe
1               5                   10                  15
```

```
Gln Ile Thr Ala Ser Gly Gln Tyr Gly Gln Trp Ala Pro Lys Leu Ala
            20                  25                  30

Arg Leu His Tyr Ser Gly Ser Ile Asn Ala Trp Ser Thr Lys Glu Pro
        35                  40                  45

Phe Ser Trp Ile Lys Val Asp Leu Leu Ala Pro Met Ile Ile His Gly
    50                  55                  60

Ile Lys Thr Gln Gly Ala Arg Gln Lys Phe Ser Ser Leu Tyr Ile Ser
65                  70                  75                  80

Gln Phe Ile Ile Met Tyr Ser Leu Asp Gly Lys Lys Trp Gln Thr Tyr
                85                  90                  95

Arg Gly Asn Ser Thr Gly Thr Leu Met Val Phe Phe Gly Asn Val Asp
            100                 105                 110

Ser Ser Gly Ile Lys His Asn Ile Phe Asn Pro Pro Ile Ile Ala Arg
        115                 120                 125

Tyr Ile Arg Leu His Pro Thr His Tyr Ser Ile Arg Ser Thr Leu Arg
130                 135                 140

Met Glu Leu Met Gly Cys Asp Leu Asn
145                 150

<210> SEQ ID NO 28
<211> LENGTH: 160
<212> TYPE: PRT
<213> ORGANISM: artificial sequence
<220> FEATURE:
<223> OTHER INFORMATION: ancestral

<400> SEQUENCE: 28

Ser Cys Ser Met Pro Leu Gly Met Glu Ser Lys Ala Ile Ser Asp Ala
1               5                   10                  15

Gln Ile Thr Ala Ser Ser Tyr Phe Thr Asn Met Phe Ala Thr Trp Ser
            20                  25                  30

Pro Ser Gln Ala Arg Leu His Leu Gln Gly Arg Thr Asn Ala Trp Arg
        35                  40                  45

Pro Gln Val Asn Asn Pro Lys Glu Trp Leu Gln Val Asp Phe Gln Lys
    50                  55                  60

Thr Met Lys Val Thr Gly Ile Thr Thr Gln Gly Val Lys Ser Leu Leu
65                  70                  75                  80

Thr Ser Met Tyr Val Lys Glu Phe Leu Ile Ser Ser Ser Gln Asp Gly
                85                  90                  95

His His Trp Thr Leu Phe Leu Gln Asn Gly Lys Val Lys Val Phe Gln
            100                 105                 110

Gly Asn Gln Asp Ser Phe Thr Pro Val Val Asn Ser Leu Asp Pro Pro
        115                 120                 125

Leu Leu Thr Arg Tyr Leu Arg Ile His Pro Gln Ser Trp Val His Gln
130                 135                 140

Ile Ala Leu Arg Leu Glu Val Leu Gly Cys Glu Ala Gln Gln Leu Tyr
145                 150                 155                 160

<210> SEQ ID NO 29
<211> LENGTH: 2360
<212> TYPE: PRT
<213> ORGANISM: artificial sequence
<220> FEATURE:
<223> OTHER INFORMATION: ancestral

<400> SEQUENCE: 29

Met Arg Ile Glu Leu Pro Cys Cys Phe Phe Leu Cys Leu Leu Pro Phe
1               5                   10                  15
```

```
Ser Phe Gly Ala Thr Arg Arg Tyr Tyr Leu Gly Ala Val Glu Leu Ser
            20                  25                  30

Trp Asp Tyr Val His Ser Asp Leu Leu Ser Val Leu His Val Pro Thr
        35                  40                  45

Gly Phe Pro Gly Arg Val Gly Arg Lys Phe Pro Phe Ser Thr Ser Val
    50                  55                  60

Arg Tyr Lys Lys Thr Val Phe Val Glu Phe Thr Asp His Leu Phe Thr
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Thr Leu Lys Asn Leu Ala
                100                 105                 110

Ser His Pro Phe Ser Leu His Ala Val Gly Val Thr Tyr Trp Lys Ala
        115                 120                 125

Ser Glu Gly Ala Gly Tyr Asp Asp Glu Thr Ser Gln Arg Glu Lys Glu
    130                 135                 140

Asp Asp Lys Val Asp Pro Gly Lys Thr His Thr Tyr Val Trp Glu Val
145                 150                 155                 160

Leu Lys Asp Asn Gly Pro Thr Ala Ser Asp Pro Pro Cys Leu Thr Tyr
                165                 170                 175

Ser Tyr Leu Ser Tyr Val Asp Leu Val Lys Asp Leu Asn Ser Gly Leu
            180                 185                 190

Ile Gly Ala Leu Leu Val Cys Arg Pro Gly Ala Leu Ala Lys Asp Gly
        195                 200                 205

Thr Gln Thr Leu His Glu Phe Val Leu Leu Phe Ala Val Phe Asp Glu
    210                 215                 220

Gly Lys Ser Trp Tyr Pro Glu Pro Asn Glu Ser Leu Thr Gln Ala Leu
225                 230                 235                 240

Asp Thr Gly Thr Pro Arg Pro Trp Pro Lys Leu His Thr Val Asn Gly
                245                 250                 255

Tyr Val Asn Gly Ser Leu Pro Gly Leu Ile Gly Cys His Lys Arg Pro
            260                 265                 270

Val Tyr Trp His Val Ile Gly Leu Gly Thr Thr Pro Glu Val His Ser
        275                 280                 285

Ile Phe Leu Glu Gly His Thr Phe Leu Val Arg Asn His Arg His Ala
    290                 295                 300

Thr Leu Glu Ile Ser Pro Ile Thr Phe Leu Thr Ala Gln Thr Leu Leu
305                 310                 315                 320

Thr Asp Leu Gly Arg Phe Leu Leu Phe Cys His Ile Pro Ala His Gln
                325                 330                 335

His Asp Gly Met Glu Ala Tyr Val Lys Val Asp Val Cys Pro Glu Glu
            340                 345                 350

Pro Lys Leu Arg Met Arg Ala Asp Ala Pro Glu Glu Asp Tyr Tyr Asp
        355                 360                 365

Asp Leu Tyr Asp Leu Asp Met Asp Val Ile Arg Phe Asp Asp Asp
    370                 375                 380

Ser Pro Pro Phe Ile Gly Val Arg Ala Phe Ala Lys His Pro Lys
385                 390                 395                 400

Thr Trp Ile His Tyr Ile Ala Ala Glu Glu Val Asp Trp Asp Tyr Ala
                405                 410                 415

Pro Ile Val Pro Thr Tyr Leu Asp Arg Ser Tyr Lys Ser Gln Tyr Leu
            420                 425                 430
```

```
Glu Ala Gly Pro Gln Arg Ile Gly Arg Lys Tyr Lys Lys Val Arg Phe
            435                 440                 445

Val Ala Tyr Thr Asp Gly Thr Phe Lys Thr Arg Lys Val Ile Gln Tyr
450                 455                 460

Asp Thr Gly Ile Leu Gly Pro Leu Leu Tyr Gly Glu Val Gly Asp Thr
465                 470                 475                 480

Leu Leu Ile Val Phe Lys Asn Leu Ala Ser Arg Pro Tyr Asn Ile Tyr
                485                 490                 495

Pro His Gly Leu Thr Ser Val Ser Pro Leu His Pro Gly Arg Leu Pro
                500                 505                 510

Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Gly Ser
            530                 535                 540

Asp Pro Arg Cys Leu Thr Arg Tyr Tyr Tyr Ser Phe Ile Asn Pro Val
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Arg
            580                 585                 590

Phe Ile Leu Phe Ser Val Phe Asp Glu Asn Arg Ser Trp Tyr Leu Thr
            595                 600                 605

Glu Asn Ile Gln Arg Phe Cys Pro Asp Ala Ala Gly Val Gln Pro Gln
            610                 615                 620

Asp Pro Glu Phe Tyr Ala Ser Asn Val Met His Ser Ile Asn Gly Tyr
625                 630                 635                 640

Val Phe Asp Asn Leu His Leu Lys Leu Cys Leu His Glu Val Ala Tyr
                645                 650                 655

Trp Tyr Val Leu Ser Val Gly Ala Gln Thr Asp Phe Leu Ser Val Phe
            660                 665                 670

Phe Ser Gly Tyr Thr Phe Lys His Lys Met Val Phe Glu Asp Thr Leu
            675                 680                 685

Thr Leu Phe Pro Phe Ser Gly Glu Thr Val Phe Met Ser Met Glu Lys
            690                 695                 700

Pro Gly Leu Trp Val Leu Gly Cys Leu Asn Pro Asp Phe Arg Asp Arg
705                 710                 715                 720

Gly Met Trp Ala Leu Leu Lys Val Ser Ser Cys Asp Arg Asp Pro Gly
                725                 730                 735

Leu Tyr Tyr Gly Asp Asp Tyr Asp Leu Ile Pro Thr Tyr Leu Leu Asn
                740                 745                 750

Glu Asn Asn Val Leu Glu Pro Arg Gly Phe Pro Lys Asn Lys Arg Trp
            755                 760                 765

Pro Arg Leu Cys Leu Arg Lys Phe Lys Ala Val Thr Ser Pro Glu Lys
770                 775                 780

Asp Ile Glu Lys Leu Asp Pro Gln Phe Gly Glu Arg Thr Gln Cys Leu
785                 790                 795                 800

Arg Ala Gln Pro Leu Lys Phe Ser Asp Leu Leu Met Leu Leu Gly Gln
                805                 810                 815

Asn Pro Asp Pro His Gly Leu Ser Leu Ser Asp Leu Thr Glu Ala Thr
            820                 825                 830

Tyr Glu Pro Ile Pro Tyr Asp Ser Phe Pro Gly Pro Val Gly Asn Ser
            835                 840                 845
```

```
Thr Gly Pro Ser Glu Val Val His Leu Arg Pro Glu Leu His His Ala
    850                 855                 860

Gly Asp Ala Gly Phe Tyr Pro Glu Gly Gly Leu Leu Leu Phe Gly Lys
865                 870                 875                 880

Glu Arg Leu Gly Pro Thr Val Ala Val Glu Leu Lys Lys Leu Asp Leu
                    885                 890                 895

Lys Leu His Lys Ser Val Asp Asn Val Met Phe Ser Pro Thr Ala Pro
                900                 905                 910

Leu Asp Asn Leu Glu Lys Gly Leu Lys Gly Thr Gly Thr Leu Gly Pro
            915                 920                 925

Leu Lys Glu Pro Val Arg Phe Ser Gly His Leu Gly Pro Thr Val Phe
        930                 935                 940

Gly Lys Lys Glu Thr Gly Leu Ile Gly Ser Gly Val Pro Leu Gln Leu
945                 950                 955                 960

Ser Asp Arg Asp His Asp Ser Arg Leu Leu Glu Arg Val Leu Leu Asn
                965                 970                 975

Asp Glu Glu Ser Pro Leu Gly Leu Asn Val Thr Ser Leu Lys Pro Asp
                980                 985                 990

Arg Pro Phe Lys Asp Lys Arg Val His Gly Pro Ala Ser Leu Thr Lys
            995                 1000                1005

Asp Asn Ala Leu Phe Lys Gly Asn Ile Thr Leu Val Lys Leu Asp
    1010                1015                1020

Lys Thr Pro Asp Asn Thr Thr Asn Arg Lys Thr Tyr Val Asp
    1025                1030                1035

Gly Pro Ala Leu Leu Lys Glu Asn Gly Thr Pro Val Trp Leu Asp
    1040                1045                1050

Ile Leu Glu Asn Asp Thr Arg Phe Gln Glu Val Ala Ser Leu Gly
    1055                1060                1065

Phe Tyr Glu Thr Phe Gln Asp Gly Lys Leu Thr Ala Pro Gly Leu
    1070                1075                1080

Asp His Val Leu Asn Lys Thr Thr Ser Ser Lys Asn Gly Glu Val
    1085                1090                1095

Phe Phe Glu Lys Lys Val Glu Pro Val Pro Leu Asp Ala Glu Arg
    1100                1105                1110

Pro Pro Ala Pro Phe Lys Asp Leu Phe Leu Pro Arg Thr Ala
    1115                1120                1125

Asn Trp Leu Leu Asp Thr His Gly Lys Ala Asp Leu Arg Ala Gly
    1130                1135                1140

Gln Gly Pro Ser Pro Lys Gln Leu Ile Ser Leu Gly Ser Asp Lys
    1145                1150                1155

Ser Gly Asp Gly Glu His Phe Leu Ser Ala Lys Ser Lys Val Arg
    1160                1165                1170

Leu Gly Pro Asp Lys Phe Thr Lys Gly Thr Gly Leu Leu Glu Met
    1175                1180                1185

Ile Phe Pro Gly Arg Lys Asp Ile Phe Leu Thr Ser Leu Val Thr
    1190                1195                1200

Val Gln Glu Asn Asp Thr Leu Ile Leu Gly Lys Lys Phe Gln Glu
    1205                1210                1215

Ala Ile Glu Arg Lys Glu Thr Leu Ile Gln Glu Asn Val Asp Leu
    1220                1225                1230

Pro Lys Leu Tyr Val Val Ala Gly Thr Arg Asn Phe Leu Lys Asp
    1235                1240                1245
```

```
Leu Phe Leu Leu His Thr Arg Thr Asn Leu Thr Leu Asp Gly Pro
    1250                1255                1260

Asp Glu Gly Asp Tyr Ala Pro Leu Leu Gln Asp Thr Arg Tyr Leu
    1265                1270                1275

Asn Gly Lys Val Pro Pro Ala Gly Val His Leu Val His Gly Ser
    1280                1285                1290

Lys Leu Leu Glu Ala Ala Asp Leu Glu Gly Leu Leu His Lys Thr
    1295                1300                1305

Lys Arg Met Val Leu Asp Tyr Pro Ser Thr Thr Arg Thr Ala Pro
    1310                1315                1320

Lys Pro Cys Asp Gln Asn Cys Ile Thr His Arg Gly Lys Arg Ala
    1325                1330                1335

Leu Lys Gln Phe Gly Leu Pro Leu Glu Glu Thr Glu Leu Glu Arg
    1340                1345                1350

Gly Leu Val Asp Lys Asp Arg Ala Leu Lys Gly Arg Lys Asn Met
    1355                1360                1365

Gly Tyr Leu Thr Gly Gly Thr Leu Thr Lys Ile Asp Tyr Asn Asp
    1370                1375                1380

Arg Ala Lys Arg Leu Val Ala Arg Pro Pro Leu Val Asp Cys Thr
    1385                1390                1395

Ala Arg Asp His Gly Val Thr Gly Thr Asp Gly Pro Ala Gly Pro
    1400                1405                1410

Ile Arg Gly Val Ser Ala Phe Pro Pro Ile Arg Pro Thr Asp Leu
    1415                1420                1425

Thr Lys Leu Pro Ser His Asp Asn Ser Ser His Leu Pro Ala Ala
    1430                1435                1440

Ala Cys Gly Tyr Thr Phe Arg Glu Lys Ser Ser Gly Val Arg Gly
    1445                1450                1455

Gly Ser His Phe Leu Gln Gly Ala Lys Arg Thr Ser Leu Thr Ser
    1460                1465                1470

Ala Tyr Leu Thr Leu Lys Thr Ile Arg Gly Glu Glu Lys Val Ser
    1475                1480                1485

Ser Leu Gly Thr Ser Ala Asp Thr Pro Pro Thr Tyr Lys Lys Leu
    1490                1495                1500

Glu Asn Thr Val Leu Leu Lys Pro Gly Leu Pro Glu Val Val Gly
    1505                1510                1515

Lys Val Glu Gly Leu Pro Lys Pro His Val Trp Glu Ala Asp Leu
    1520                1525                1530

Phe Pro Thr Pro Thr Gly Asn Gly Thr Pro Gly His Leu Asp Leu
    1535                1540                1545

Lys Glu Glu Trp Leu Leu Gln Lys Leu Gln Gly Ala Ile Lys Leu
    1550                1555                1560

Ser Lys Val Lys Arg Pro Gly Asp Phe Pro Phe Leu Lys Gly Ala
    1565                1570                1575

Thr Glu Ile Leu Glu Lys Arg Pro Ser Lys Leu Leu Gly Pro Leu
    1580                1585                1590

Pro Trp Asp Gly Gln Tyr Leu Thr Gln Ile Leu Arg Asp Glu Trp
    1595                1600                1605

Lys Leu Lys His Lys Ser Pro Lys Asn Thr Val Phe Lys Thr Lys
    1610                1615                1620

Asp Ala Ile Leu Pro Leu Ser Gly Cys Glu Asn Val His Gly Val
    1625                1630                1635
```

```
Asp Gly Ile Asn Glu Gly Arg Asp Arg Leu Gln Lys Ala Ala Thr
    1640                1645                1650

Trp Ala Lys Gln Gly Gly Thr Glu Arg Leu Cys Ser Arg Glu Pro
    1655                1660                1665

Pro Val Leu Lys Asn His Lys Arg Glu Ile Thr Leu Thr Thr Leu
    1670                1675                1680

Gln Pro Glu Lys Glu Lys Ile Asp Tyr Asp Asp Tyr Leu Lys Pro
    1685                1690                1695

Glu Thr Asp Arg Asp Asp Phe Asp Ile Tyr Gly Glu Asp Glu Asn
    1700                1705                1710

Gln Gly Pro Arg Thr Phe Thr Gly Arg Thr Arg His Tyr Phe Ile
    1715                1720                1725

Ala Ala Val Glu Arg Leu Trp Asp Tyr Gly Met Ser Arg Pro Pro
    1730                1735                1740

His Phe Leu Arg Asn Arg Ala Arg Gly Gly Arg Val Pro Phe Phe
    1745                1750                1755

Lys Lys Val Val Phe Arg Gly Phe Leu Asp Gly Ser Phe Thr Gln
    1760                1765                1770

Pro Leu Tyr Arg Gly Glu Leu Asp Glu His Leu Gly Leu Leu Gly
    1775                1780                1785

Pro Tyr Ile Arg Ala Glu Val Asp Asp Val Ile Met Val Thr Phe
    1790                1795                1800

Lys Asn Leu Ala Ser Arg Pro Tyr Ser Phe Tyr Ser Ser Leu Leu
    1805                1810                1815

Pro Tyr Glu Gly Gly Leu Gly Gln Gly Ser Glu Pro Arg Lys Glu
    1820                1825                1830

Val Val Lys Pro Gly Glu Leu Arg Thr Tyr Phe Trp Lys Val Leu
    1835                1840                1845

Pro His Met Ala Pro Thr Val Asp Glu Phe Asp Cys Lys Ala Trp
    1850                1855                1860

Ala Tyr Phe Ser Asp Val Asp Leu Glu Lys Asp Leu His Ser Gly
    1865                1870                1875

Leu Val Gly Pro Leu Leu Ile Cys Arg Pro Gly Thr Leu Ser Pro
    1880                1885                1890

Ala Phe Gly Arg Gln Leu Thr Val Gln Glu Phe Ala Leu Leu Phe
    1895                1900                1905

Thr Ile Phe Asp Glu Thr Lys Ser Trp Tyr Phe Thr Glu Asn Met
    1910                1915                1920

Glu Arg Asn Cys Pro Pro Cys Gln Ile Gln Pro Asp Asp Pro
    1925                1930                1935

Asp Phe Arg Arg Ser Tyr Arg Phe His Ala Ile Asn Gly Tyr Val
    1940                1945                1950

Met Asp Thr Leu Pro Gly Leu Val Met Ala Gln Asp Gln Arg Val
    1955                1960                1965

Arg Trp Tyr Leu Leu Ser Val Gly Gly Thr Glu Asp Ile His Ser
    1970                1975                1980

Val Tyr Phe His Gly His Val Phe Thr Val Arg Lys Lys His Glu
    1985                1990                1995

Tyr Arg Met Gly Val Tyr Asn Leu Tyr Pro Gly Val Phe Gly Thr
    2000                2005                2010

Val Glu Met Leu Pro Ser Lys Pro Gly Ile Trp Arg Val Glu Cys
    2015                2020                2025
```

-continued

Leu Val Gly Glu His Leu Gln Ala Gly Met Ser Thr Leu Phe Leu
2030              2035              2040

Val Tyr Asp Pro Lys Cys Gln Thr Pro Leu Gly Leu Ala Ser Gly
2045              2050              2055

His Ile Arg Asp Ala Gln Ile Thr Ala Ser Gly Gln Tyr Gly Gln
2060              2065              2070

Trp Ala Pro Arg Leu Ala Arg Leu His Tyr Ser Gly Ser Val Asn
2075              2080              2085

Ala Trp Ser Thr Lys Asp Pro Phe Ser Trp Ile Lys Val Asp Leu
2090              2095              2100

Leu Arg Pro Met Ile Leu His Gly Ile Lys Thr Gln Gly Ala Arg
2105              2110              2115

Gln Lys Phe Ser Ser Leu Tyr Ile Ser Gln Phe Ile Ile Phe Tyr
2120              2125              2130

Gly Leu Asp Gly Lys Arg Trp Lys Arg Tyr Arg Gly Asn Ala Thr
2135              2140              2145

Gly Thr Leu Met Val Phe Phe Gly Asn Val Asp Ala Thr Gly Val
2150              2155              2160

Lys His Asn Arg Phe Asn Pro Pro Ile Ile Ala Arg Tyr Ile Arg
2165              2170              2175

Leu His Pro Thr His Tyr Ser Ile Arg Thr Thr Leu Arg Met Glu
2180              2185              2190

Leu Ile Gly Cys Asp Leu Asn Ser Cys Ser Met Pro Leu Gly Met
2195              2200              2205

Glu Asn Lys Ala Ile Ser Asp Ala Gln Ile Thr Ala Ser Ser Tyr
2210              2215              2220

Phe Thr Asn Met Phe Ala Thr Trp Ala Pro Ser Gln Ala Arg Leu
2225              2230              2235

His Leu Gln Gly Arg Thr Asn Ala Trp Arg Pro Lys Val Asn Ser
2240              2245              2250

Pro Lys Glu Trp Leu Gln Val Asp Phe Glu Lys Thr Met Arg Val
2255              2260              2265

Thr Gly Ile Val Thr Gln Gly Ala Lys Ser Leu Leu Thr Ser Met
2270              2275              2280

Tyr Val Lys Glu Phe Leu Val Ser Ser Ser Gln Asp Gly His Arg
2285              2290              2295

Trp Thr Pro Phe Leu Gln Asp Gly Lys Val Lys Val Phe Lys Gly
2300              2305              2310

Asn Gln Asp His Phe Thr Pro Val Val Asn Ser Leu Asp Pro Pro
2315              2320              2325

Leu Leu Thr Arg Tyr Leu Arg Ile His Pro Arg Arg Trp Val His
2330              2335              2340

His Ile Ala Leu Arg Leu Glu Phe Leu Gly Cys Asp Ala Gln Gln
2345              2350              2355

Leu Tyr
2360

<210> SEQ ID NO 30
<211> LENGTH: 2362
<212> TYPE: PRT
<213> ORGANISM: artificial sequence
<220> FEATURE:
<223> OTHER INFORMATION: ancestral

<400> SEQUENCE: 30

```
Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Asp Leu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Asp Asp Gln Thr Ser Gln Arg Glu Lys Glu
130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
210                 215                 220

Gly Lys Ser Trp His Ser Glu Thr Asn Glu Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Asp Tyr Asp Asp
        355                 360                 365

Asp Leu Tyr Asp Ser Asp Met Asp Val Val Arg Phe Asp Asp Asp Asn
370                 375                 380

Ser Pro Pro Phe Ile Gln Ile Arg Ser Val Ala Lys Lys His Pro Lys
385                 390                 395                 400
```

```
Thr Trp Val His Tyr Ile Ala Glu Glu Asp Trp Asp Tyr Ala
            405             410             415

Pro Ser Val Leu Thr Pro Asn Asp Arg Ser Tyr Lys Ser Gln Tyr Leu
            420             425             430

Asn Asn Gly Pro Gln Arg Ile Gly Arg Lys Tyr Lys Val Arg Phe
            435             440             445

Met Ala Tyr Thr Asp Glu Thr Phe Lys Thr Arg Glu Ala Ile Gln Tyr
450             455             460

Glu Ser Gly Ile Leu Gly Pro Leu Leu Tyr Gly Glu Val Gly Asp Thr
465             470             475             480

Leu Leu Ile Ile Phe Lys Asn Gln Ala Ser Arg Pro Tyr Asn Ile Tyr
            485             490             495

Pro His Gly Ile Thr Asp Val Ser Pro Leu His Ser Gly Arg Leu Pro
            500             505             510

Lys Gly Val Lys His Leu Lys Asp Leu Pro Ile Leu Pro Gly Glu Ile
            515             520             525

Phe Lys Tyr Lys Trp Thr Val Thr Val Glu Asp Gly Pro Thr Lys Ser
            530             535             540

Asp Pro Arg Cys Leu Thr Arg Tyr Tyr Ser Ser Phe Ile Asn Leu Glu
545             550             555             560

Arg Asp Leu Ala Ser Gly Leu Ile Gly Pro Leu Leu Ile Cys Tyr Lys
                565             570             575

Glu Ser Val Asp Gln Arg Gly Asn Gln Met Met Ser Asp Lys Arg Asn
            580             585             590

Val Ile Leu Phe Ser Val Phe Asp Glu Asn Arg Ser Trp Tyr Leu Thr
            595             600             605

Glu Asn Met Gln Arg Phe Leu Pro Asn Ala Ala Gly Val Gln Pro Gln
            610             615             620

Asp Pro Glu Phe Gln Ala Ser Asn Ile Met His Ser Ile Asn Gly Tyr
625             630             635             640

Val Phe Asp Ser Leu Gln Leu Ser Val Cys Leu His Glu Val Ala Tyr
                645             650             655

Trp Tyr Ile Leu Ser Val Gly Ala Gln Thr Asp Phe Leu Ser Val Phe
                660             665             670

Phe Ser Gly Tyr Thr Phe Lys His Lys Met Val Tyr Glu Asp Thr Leu
            675             680             685

Thr Leu Phe Pro Phe Ser Gly Glu Thr Val Phe Met Ser Met Glu Asn
            690             695             700

Pro Gly Leu Trp Val Leu Gly Cys His Asn Ser Asp Phe Arg Asn Arg
705             710             715             720

Gly Met Thr Ala Leu Leu Lys Val Ser Ser Cys Asp Arg Asn Thr Gly
                725             730             735

Asp Tyr Tyr Glu Asp Thr Tyr Glu Asp Ile Pro Thr Tyr Leu Leu Asn
            740             745             750

Glu Asn Asn Val Ile Glu Pro Arg Ser Phe Ser Gln Asn Ser Arg His
            755             760             765

Pro Ser Thr Arg Gln Lys Gln Phe Lys Ala Thr Thr Thr Pro Glu Asn
770             775             780

Asp Ile Glu Lys Ile Asp Pro Gln Phe Gly Glu Arg Thr Gln Leu Leu
785             790             795             800

Lys Val Gln Ser Val Ser Ser Asp Leu Leu Met Leu Leu Gly Gln
            805             810             815
```

-continued

Ser Pro Thr Pro His Gly Leu Ser Leu Ser Asp Leu Gln Glu Ala Thr
                820                 825                 830

Tyr Glu Ala Ile Pro Asp Asp His Ser Pro Gly Ala Ile Glu Ser Asn
            835                 840                 845

Glu Gly Pro Ser Glu Val Ala His Leu Arg Pro Glu Leu His His Ser
850                 855                 860

Gly Asp Met Val Phe Thr Pro Glu Pro Gly Leu Gln Leu Arg Leu Asn
865                 870                 875                 880

Glu Asn Leu Gly Thr Thr Ile Thr Val Glu Leu Lys Lys Leu Asp Leu
                885                 890                 895

Lys Val Ser Ser Ser Asn Asn Leu Met Thr Ser Pro Thr Ile Pro
            900                 905                 910

Ser Asp Asn Leu Ala Ala Gly Thr Glu Lys Thr Gly Ser Leu Gly Pro
            915                 920                 925

Pro Asn Met Pro Val His Phe Ser Ser Gln Leu Gly Thr Ile Val Phe
930                 935                 940

Gly Lys Lys Ser Ser Pro Leu Ile Gly Ser Gly Val Pro Leu Asn Leu
945                 950                 955                 960

Ser Glu Arg Asp Asn Asp Ser Lys Leu Leu Glu Ala Ala Leu Met Asn
            965                 970                 975

Ser Gln Glu Ser Ser Leu Gly Lys Asn Val Ser Ser Met Glu Ser Asp
            980                 985                 990

Arg Leu Phe Lys Glu Lys Arg Val His Gly Pro Ala Ser Leu Thr Lys
            995                 1000                1005

Asp Asn Ala Leu Phe Lys Val Asn Ile Ser Leu Val Lys Thr Asn
        1010                1015                1020

Lys Thr Pro Asn Asn Ser Thr Thr Asn Arg Lys Thr His Ile Asp
    1025                1030                1035

Gly Pro Thr Leu Leu Ile Glu Asn Ser Thr Ser Val Trp Gln Asp
    1040                1045                1050

Ile Leu Glu Asn Asp Thr Glu Phe Gln Glu Val Thr Ser Leu Ile
    1055                1060                1065

His Asp Glu Met Phe Met Asp Lys Asn Thr Thr Ala Leu Gly Leu
    1070                1075                1080

Asn His Val Ser Asn Lys Thr Thr Ser Ser Lys Asn Met Glu Met
    1085                1090                1095

Val His Gln Lys Lys Glu Gly Pro Val Pro Leu Asp Ala Glu Asn
    1100                1105                1110

Pro Asp Met Ser Phe Phe Lys Met Leu Phe Leu Pro Asp Ser Ala
    1115                1120                1125

Asn Trp Ile Lys Arg Thr His Gly Lys Asn Ser Leu Ser Ser Gly
    1130                1135                1140

Gln Gly Pro Ser Pro Lys Gln Leu Ile Ser Leu Gly Ser Glu Lys
    1145                1150                1155

Ser Val Lys Asp Gln Asn Phe Leu Ser Glu Lys Asn Lys Val Val
    1160                1165                1170

Val Gly Glu Asp Glu Phe Thr Lys Asp Thr Gly Leu Lys Glu Met
    1175                1180                1185

Ile Phe Pro Asn Ser Lys Ser Ile Phe Leu Thr Asn Leu Ala Asn
    1190                1195                1200

Val Gln Glu Asn Asp Thr His Asn Gln Glu Lys Lys Phe Gln Glu
    1205                1210                1215

```
Glu Ile Glu Arg Lys Glu Thr Leu Ile Gln Glu Asn Val Val Leu
    1220            1225            1230

Pro Gln Val Tyr Thr Val Thr Gly Thr Lys Asn Phe Leu Lys Asn
    1235            1240            1245

Leu Phe Leu Leu Ser Thr Arg Gln Asn Val Thr Val Glu Gly Leu
    1250            1255            1260

Asp Glu Gly Thr Tyr Ala Pro Val Leu Gln Asp Thr Arg Ser Leu
    1265            1270            1275

Asn Asp Ser Ala Asn Arg Ala Gly Ile His Met Ala His Phe Ser
    1280            1285            1290

Lys Arg Arg Glu Glu Ala Glu Thr Asn Leu Glu Gly Leu Gly Asn
    1295            1300            1305

Gln Thr Lys Gln Met Val Glu Lys Tyr Pro Ser Thr Thr Arg Met
    1310            1315            1320

Ser Pro Asn Pro Ser Gln Gln Asn Val Ile Thr Gln Arg Gly Lys
    1325            1330            1335

Arg Ala Leu Lys Gln Phe Arg Leu Pro Leu Glu Glu Ile Glu Leu
    1340            1345            1350

Glu Arg Gly Leu Ile Val Asn Asp Thr Ser Thr Gln Trp Ser Lys
    1355            1360            1365

Asn Met Lys Tyr Leu Thr Gln Gly Thr Leu Thr Gln Ile Asp Tyr
    1370            1375            1380

Asn Glu Lys Glu Lys Arg Ala Ile Thr Gln Ser Pro Leu Ser Asp
    1385            1390            1395

Cys Ser Met Arg Asn His Ser Ile Thr Gln Thr Asn Gly Ser Ala
    1400            1405            1410

Leu Pro Ile Ala Lys Val Ser Ala Phe Pro Ser Ile Arg Pro Thr
    1415            1420            1425

Asp Leu Thr Lys Ile Pro Ser Gln Asp Asn Ser Ser His Leu Leu
    1430            1435            1440

Ala Ser Ala Cys Ser Tyr Thr Phe Arg Glu Lys Ser Ser Gly Val
    1445            1450            1455

Gln Glu Ser Ser His Phe Leu Gln Gly Ala Lys Arg Asn Asn Leu
    1460            1465            1470

Ser Leu Ala Ile Leu Thr Leu Glu Met Ile Arg Gly Gln Glu Lys
    1475            1480            1485

Val Ser Ser Leu Gly Thr Ser Ala Thr Asn Pro Leu Met Tyr Lys
    1490            1495            1500

Lys Leu Glu Asn Thr Val Leu Leu Lys Pro Gly Leu Pro Glu Ala
    1505            1510            1515

Ser Gly Lys Val Glu Leu Leu Pro Lys Val His Val His Gln Glu
    1520            1525            1530

Asp Leu Phe Pro Thr Glu Thr Ser Asn Gly Ser Pro Gly His Leu
    1535            1540            1545

Asp Leu Met Glu Glu Ile Leu Leu Gln Lys Thr Gln Gly Ala Ile
    1550            1555            1560

Lys Leu Asn Lys Val Asn Arg Pro Gly Lys Val Pro Phe Leu Lys
    1565            1570            1575

Gly Ala Thr Glu Ser Ser Glu Lys Thr Pro Ser Lys Leu Leu Gly
    1580            1585            1590

Pro Leu Ala Trp Asp Asn Gln Tyr Ala Thr Gln Ile Pro Arg Glu
    1595            1600            1605
```

```
Glu  Trp  Lys  Ser  Gln  Glu  Lys  Ser  Pro  Lys  Asn  Thr  Ala  Phe  Lys
    1610                1615                1620

Thr  Lys  Asp  Thr  Ile  Leu  Pro  Leu  Asn  Pro  Cys  Glu  Asn  Asn  His
    1625                1630                1635

Ala  Ile  Ala  Ala  Ile  Asn  Glu  Gly  Gln  Asp  Arg  Pro  Gln  Arg  Glu
    1640                1645                1650

Ala  Thr  Trp  Ala  Lys  Gln  Gly  Gly  Thr  Gly  Arg  Leu  Cys  Ser  Gln
    1655                1660                1665

Asn  Pro  Pro  Val  Leu  Lys  Arg  His  Gln  Arg  Glu  Ile  Thr  Leu  Thr
    1670                1675                1680

Thr  Leu  Gln  Pro  Glu  Gln  Glu  Lys  Ile  Asp  Tyr  Asp  Asp  Thr  Ile
    1685                1690                1695

Ser  Ile  Glu  Thr  Lys  Arg  Glu  Asp  Phe  Asp  Ile  Tyr  Gly  Glu  Asp
    1700                1705                1710

Glu  Asn  Gln  Gly  Pro  Arg  Ser  Phe  Gln  Lys  Arg  Thr  Arg  His  Tyr
    1715                1720                1725

Phe  Ile  Ala  Ala  Val  Glu  Arg  Leu  Trp  Asp  Tyr  Gly  Met  Ser  Arg
    1730                1735                1740

Ser  Pro  His  Ala  Leu  Arg  Asn  Arg  Ala  Gln  Ser  Gly  Ser  Val  Pro
    1745                1750                1755

Gln  Phe  Lys  Lys  Val  Val  Phe  Gln  Glu  Phe  Thr  Asp  Gly  Ser  Phe
    1760                1765                1770

Thr  Gln  Pro  Leu  Tyr  Arg  Gly  Glu  Leu  Asn  Glu  His  Leu  Gly  Leu
    1775                1780                1785

Leu  Gly  Pro  Tyr  Ile  Arg  Ala  Glu  Val  Glu  Asp  Asn  Ile  Met  Val
    1790                1795                1800

Thr  Phe  Lys  Asn  Gln  Ala  Ser  Arg  Pro  Tyr  Ser  Phe  Tyr  Ser  Ser
    1805                1810                1815

Leu  Ile  Ser  Tyr  Glu  Glu  Asp  Gln  Arg  Gln  Gly  Ala  Glu  Pro  Arg
    1820                1825                1830

Lys  Asn  Phe  Val  Lys  Pro  Asn  Glu  Thr  Lys  Thr  Tyr  Phe  Trp  Lys
    1835                1840                1845

Val  Gln  His  His  Met  Ala  Pro  Thr  Lys  Asp  Glu  Phe  Asp  Cys  Lys
    1850                1855                1860

Ala  Trp  Ala  Tyr  Phe  Ser  Asp  Val  Asp  Leu  Glu  Lys  Asp  Met  His
    1865                1870                1875

Ser  Gly  Leu  Ile  Gly  Pro  Leu  Leu  Ile  Cys  Arg  Thr  Asn  Thr  Leu
    1880                1885                1890

Asn  Pro  Ala  His  Gly  Arg  Gln  Val  Thr  Val  Gln  Glu  Phe  Ala  Leu
    1895                1900                1905

Phe  Phe  Thr  Ile  Phe  Asp  Glu  Thr  Lys  Ser  Trp  Tyr  Phe  Thr  Glu
    1910                1915                1920

Asn  Met  Glu  Arg  Asn  Cys  Arg  Ala  Pro  Cys  Asn  Ile  Gln  Met  Glu
    1925                1930                1935

Asp  Pro  Thr  Phe  Lys  Glu  Asn  Tyr  Arg  Phe  His  Ala  Ile  Asn  Gly
    1940                1945                1950

Tyr  Val  Met  Asp  Thr  Leu  Pro  Gly  Leu  Val  Met  Ala  Gln  Asp  Gln
    1955                1960                1965

Arg  Ile  Arg  Trp  Tyr  Leu  Leu  Ser  Met  Gly  Ser  Asn  Glu  Asn  Ile
    1970                1975                1980

His  Ser  Ile  His  Phe  Ser  Gly  His  Val  Phe  Thr  Val  Arg  Lys  Lys
    1985                1990                1995
```

-continued

```
Glu Glu Tyr Lys Met Ala Val Tyr Asn Leu Tyr Pro Gly Val Phe
    2000                2005                2010

Glu Thr Val Glu Met Leu Pro Ser Lys Ala Gly Ile Trp Arg Val
    2015                2020                2025

Glu Cys Leu Ile Gly Glu His Leu Gln Ala Gly Met Ser Thr Leu
    2030                2035                2040

Phe Leu Val Tyr Ser Lys Gln Cys Gln Thr Pro Leu Gly Met Ala
    2045                2050                2055

Ser Gly Arg Ile Arg Asp Phe Gln Ile Thr Ala Ser Gly Gln Tyr
    2060                2065                2070

Gly Gln Trp Ala Pro Lys Leu Ala Arg Leu His Tyr Ser Gly Ser
    2075                2080                2085

Ile Asn Ala Trp Ser Thr Lys Asp Pro Phe Ser Trp Ile Lys Val
    2090                2095                2100

Asp Leu Leu Ala Pro Met Ile Ile His Gly Ile Lys Thr Gln Gly
    2105                2110                2115

Ala Arg Gln Lys Phe Ser Ser Leu Tyr Ile Ser Gln Phe Ile Ile
    2120                2125                2130

Met Tyr Ser Leu Asp Gly Lys Lys Trp Gln Ser Tyr Arg Gly Asn
    2135                2140                2145

Ser Thr Gly Thr Leu Met Val Phe Phe Gly Asn Val Asp Ser Ser
    2150                2155                2160

Gly Ile Lys His Asn Ile Phe Asn Pro Pro Ile Ile Ala Arg Tyr
    2165                2170                2175

Ile Arg Leu His Pro Thr His Tyr Ser Ile Arg Ser Thr Leu Arg
    2180                2185                2190

Met Glu Leu Met Gly Cys Asp Leu Asn Ser Cys Ser Met Pro Leu
    2195                2200                2205

Gly Met Glu Ser Lys Ala Ile Ser Asp Ala Gln Ile Thr Ala Ser
    2210                2215                2220

Ser Tyr Phe Thr Asn Met Phe Ala Thr Trp Ser Pro Ser Gln Ala
    2225                2230                2235

Arg Leu His Leu Gln Gly Arg Thr Asn Ala Trp Arg Pro Gln Val
    2240                2245                2250

Asn Asn Pro Lys Glu Trp Leu Gln Val Asp Phe Gln Lys Thr Met
    2255                2260                2265

Lys Val Thr Gly Ile Thr Thr Gln Gly Val Lys Ser Leu Leu Thr
    2270                2275                2280

Ser Met Tyr Val Lys Glu Phe Leu Ile Ser Ser Ser Gln Asp Gly
    2285                2290                2295

His His Trp Thr Leu Phe Leu Gln Asn Gly Lys Val Lys Val Phe
    2300                2305                2310

Gln Gly Asn Gln Asp Ser Phe Thr Pro Val Val Asn Ser Leu Asp
    2315                2320                2325

Pro Pro Leu Leu Thr Arg Tyr Leu Arg Ile His Pro Gln Ser Trp
    2330                2335                2340

Val His Gln Ile Ala Leu Arg Leu Glu Val Leu Gly Cys Glu Ala
    2345                2350                2355

Gln Gln Leu Tyr
    2360

<210> SEQ ID NO 31
<211> LENGTH: 2351
```

```
<212> TYPE: PRT
<213> ORGANISM: artificial sequence
<220> FEATURE:
<223> OTHER INFORMATION: ancestral

<400> SEQUENCE: 31

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Thr Arg
        35                  40                  45

Phe Pro Pro Arg Val Pro Arg Ser Phe Pro Phe Asn Thr Ser Val Val
    50                  55                  60

Tyr Lys Lys Thr Val Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Val Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380
```

-continued

| | | | | | | | | | | | | | | |
|---|---|---|---|---|---|---|---|---|---|---|---|---|---|---|
Pro | Ser | Phe | Ile | Gln | Ile | Arg | Ser | Val | Ala | Lys | Lys | His | Pro | Lys | Thr
385 | | | | 390 | | | | | 395 | | | | | 400

Trp Val His Tyr Ile Ala Ala Glu Glu Glu Asp Trp Asp Tyr Ala Pro
                405                    410                    415

Ser Val Leu Ala Pro Asp Asp Arg Ser Tyr Lys Ser Gln Tyr Leu Asn
            420                    425                    430

Asn Gly Pro Gln Arg Ile Gly Arg Lys Tyr Lys Lys Val Arg Phe Met
        435                    440                    445

Ala Tyr Thr Asp Glu Thr Phe Lys Thr Arg Glu Ala Ile Gln His Glu
    450                    455                    460

Ser Gly Ile Leu Gly Pro Leu Leu Tyr Gly Glu Val Gly Asp Thr Leu
465                    470                    475                  480

Leu Ile Ile Phe Lys Asn Gln Ala Ser Arg Pro Tyr Asn Ile Tyr Pro
                485                    490                  495

His Gly Ile Thr Asp Val Arg Pro Leu Tyr Ser Arg Arg Leu Pro Lys
            500                    505                    510

Gly Val Lys His Leu Lys Asp Phe Pro Ile Leu Pro Gly Glu Ile Phe
        515                    520                    525

Lys Tyr Lys Trp Thr Val Thr Val Glu Asp Gly Pro Thr Lys Ser Asp
    530                    535                    540

Pro Arg Cys Leu Thr Arg Tyr Tyr Ser Ser Phe Ile Asn Met Glu Arg
545                    550                    555                  560

Asp Leu Ala Ser Gly Leu Ile Gly Pro Leu Leu Ile Cys Tyr Lys Glu
                565                    570                  575

Ser Val Asp Gln Arg Gly Asn Gln Ile Met Ser Asp Lys Arg Asn Val
            580                    585                    590

Ile Leu Phe Ser Val Phe Asp Glu Asn Arg Ser Trp Tyr Leu Thr Glu
        595                    600                    605

Asn Ile Gln Arg Phe Leu Pro Asn Pro Ala Gly Val Gln Leu Glu Asp
    610                    615                    620

Pro Glu Phe Gln Ala Ser Asn Ile Met His Ser Ile Asn Gly Tyr Val
625                    630                    635                  640

Phe Asp Ser Leu Gln Leu Ser Val Cys Leu His Glu Val Ala Tyr Trp
                645                    650                  655

Tyr Ile Leu Ser Ile Gly Ala Gln Thr Asp Phe Leu Ser Val Phe Phe
            660                    665                  670

Ser Gly Tyr Thr Phe Lys His Lys Met Val Tyr Glu Asp Thr Leu Thr
        675                    680                    685

Leu Phe Pro Phe Ser Gly Glu Thr Val Phe Met Ser Met Glu Asn Pro
    690                    695                    700

Gly Leu Trp Ile Leu Gly Cys His Asn Ser Asp Phe Arg Asn Arg Gly
705                    710                    715                  720

Met Thr Ala Leu Leu Lys Val Ser Ser Cys Asp Lys Asn Thr Gly Asp
            725                    730                  735

Tyr Tyr Glu Asp Ser Tyr Glu Asp Ile Ser Thr Tyr Leu Leu Ser Lys
        740                    745                    750

Asn Asn Ala Ile Glu Pro Arg Ser Phe Ser Gln Asn Ser Arg His Pro
        755                    760                    765

Ser Thr Arg Gln Lys Gln Phe Asn Ala Thr Thr Ile Pro Glu Asn Asp
    770                    775                    780

Ile Glu Lys Thr Asp Pro Trp Phe Ala His Arg Thr Pro Met Pro Lys
785                    790                    795                  800

```
Val Gln Asn Val Ser Ser Ser Asp Leu Leu Met Leu Arg Gln Ser
            805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
    850                 855                 860

Asp Met Val Phe Thr Pro Glu Pro Gly Leu Gln Leu Arg Leu Asn Glu
865                 870                 875                 880

Lys Leu Gly Thr Thr Ala Ala Thr Glu Leu Lys Lys Leu Asp Phe Lys
            885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Asn Met
            915                 920                 925

Pro Val His Tyr Asp Ser Gln Leu Asp Thr Thr Leu Phe Gly Lys Lys
            930                 935                 940

Ser Ser Pro Leu Ile Glu Ser Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
            980                 985                 990

Lys Glu Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
            1010                1015                1020

Asn Asn Ser Ala Thr Asn Arg Lys Thr His Ile Asp Gly Pro Ser
            1025                1030                1035

Leu Leu Ile Glu Asn Ser Pro Ser Val Trp Gln Asn Ile Leu Glu
            1040                1045                1050

Ser Asp Thr Glu Phe Gln Lys Val Thr Pro Leu Ile His Asp Arg
            1055                1060                1065

Met Leu Met Asp Lys Asn Ala Thr Ala Leu Arg Leu Asn His Met
            1070                1075                1080

Ser Asn Lys Thr Thr Ser Ser Lys Asn Met Glu Met Val Gln Gln
            1085                1090                1095

Lys Lys Glu Gly Pro Ile Pro Pro Asp Ala Glu Asn Pro Asp Met
            1100                1105                1110

Ser Phe Phe Lys Met Leu Phe Leu Pro Glu Ser Ala Asn Trp Ile
            1115                1120                1125

Gln Arg Thr His Gly Lys Asn Ser Leu Asn Ser Gly Gln Gly Pro
            1130                1135                1140

Ser Pro Lys Gln Leu Val Ser Leu Gly Pro Glu Lys Ser Val Glu
            1145                1150                1155

Gly Gln Asn Phe Leu Ser Glu Lys Asn Lys Val Val Gly Lys
            1160                1165                1170

Gly Glu Phe Thr Lys Asp Val Gly Leu Lys Glu Met Val Phe Pro
            1175                1180                1185

Ser Ser Arg Asn Leu Phe Leu Thr Asn Leu Asp Asn Leu His Glu
            1190                1195                1200
```

```
Asn Asn Thr His Asn Gln Glu Lys Lys Ile Gln Glu Glu Ile Glu
    1205                1210                1215

Arg Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Glu Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Pro Arg Thr Thr Arg Ile Ser Pro Asn Pro Ser Gln Gln
    1310                1315                1320

Asn Phe Val Thr Gln Arg Gly Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Thr Gln Ala Asn Arg Ser Pro Leu Pro Ile Ala Lys Val Ser
    1400                1405                1410

Ser Phe Pro Ser Ile Arg Pro Ile Asp Leu Thr Arg Val Leu Phe
    1415                1420                1425

Gln Asp Asn Ser Ser His Leu Pro Ala Pro Ser Tyr Arg Lys Lys
    1430                1435                1440

Asp Ser Gly Val Gln Glu Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Leu Lys Pro Gly
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Glu Thr
    1535                1540                1545

Glu Gly Ala Ile Lys Trp Asn Glu Ala Asn Arg Pro Gly Lys Ile
    1550                1555                1560

Pro Phe Leu Arg Val Ala Thr Glu Ser Ser Ala Lys Thr Pro Ser
    1565                1570                1575

Lys Leu Leu Gly Pro Leu Ala Trp Asp Asn His Tyr Gly Thr Gln
    1580                1585                1590
```

```
Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ile Asn Glu Gly Gln Asn Lys
1625                1630                1635

Pro Glu Ile Glu Val Thr Trp Ala Lys Gln Gly Gly Thr Glu Arg
1640                1645                1650

Leu Cys Ser Gln Asn Pro Pro Val Leu Lys Arg His Gln Arg Glu
1655                1660                1665

Ile Thr Leu Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Lys Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980
```

| | | | | | | | | | | | |
|---|---|---|---|---|---|---|---|---|---|---|---|
| Val | Arg | Lys | Lys | Glu | Glu | Tyr | Lys | Met | Ala | Val | Tyr | Asn | Leu | Tyr |

Val Arg Lys Lys Glu Glu Tyr Lys Met Ala Val Tyr Asn Leu Tyr
1985                1990              1995

Pro Gly Val Phe Glu Thr Val Glu Met Leu Pro Ser Lys Ala Gly
2000                2005              2010

Ile Trp Arg Val Glu Cys Leu Ile Gly Glu His Leu His Ala Gly
2015                2020              2025

Met Ser Thr Leu Phe Leu Val Tyr Ser Asn Lys Cys Gln Thr Pro
2030                2035              2040

Leu Gly Met Ala Ser Gly His Ile Arg Asp Phe Gln Ile Thr Ala
2045                2050              2055

Ser Gly Gln Tyr Gly Gln Trp Ala Pro Lys Leu Ala Arg Leu His
2060                2065              2070

Tyr Ser Gly Ser Ile Asn Ala Trp Ser Thr Lys Glu Pro Phe Ser
2075                2080              2085

Trp Ile Lys Val Asp Leu Leu Ala Pro Met Ile Ile His Gly Ile
2090                2095              2100

Lys Thr Gln Gly Ala Arg Gln Lys Phe Ser Ser Leu Tyr Ile Ser
2105                2110              2115

Gln Phe Ile Ile Met Tyr Ser Leu Asp Gly Lys Lys Trp Gln Thr
2120                2125              2130

Tyr Arg Gly Asn Ser Thr Gly Thr Leu Met Val Phe Phe Gly Asn
2135                2140              2145

Val Asp Ser Ser Gly Ile Lys His Asn Ile Phe Asn Pro Pro Ile
2150                2155              2160

Ile Ala Arg Tyr Ile Arg Leu His Pro Thr His Tyr Ser Ile Arg
2165                2170              2175

Ser Thr Leu Arg Met Glu Leu Met Gly Cys Asp Leu Asn Ser Cys
2180                2185              2190

Ser Met Pro Leu Gly Met Glu Ser Lys Ala Ile Ser Asp Ala Gln
2195                2200              2205

Ile Thr Ala Ser Ser Tyr Phe Thr Asn Met Phe Ala Thr Trp Ser
2210                2215              2220

Pro Ser Lys Ala Arg Leu His Leu Gln Gly Arg Ser Asn Ala Trp
2225                2230              2235

Arg Pro Gln Val Asn Asn Pro Lys Glu Trp Leu Gln Val Asp Phe
2240                2245              2250

Gln Lys Thr Met Lys Val Thr Gly Ile Thr Thr Gln Gly Val Lys
2255                2260              2265

Ser Leu Leu Thr Ser Met Tyr Val Lys Glu Phe Leu Ile Ser Ser
2270                2275              2280

Ser Gln Asp Gly His His Trp Thr Leu Phe Phe Gln Asn Gly Lys
2285                2290              2295

Val Lys Val Phe Gln Gly Asn Gln Asp Ser Phe Thr Pro Val Val
2300                2305              2310

Asn Ser Leu Asp Pro Pro Leu Leu Thr Arg Tyr Leu Arg Ile His
2315                2320              2325

Pro Gln Ser Trp Val His Gln Ile Ala Leu Arg Met Glu Val Leu
2330                2335              2340

Gly Cys Glu Ala Gln Glu Leu Tyr
2345                2350

<210> SEQ ID NO 32
<211> LENGTH: 2351
<212> TYPE: PRT

<213> ORGANISM: artificial sequence
<220> FEATURE:
<223> OTHER INFORMATION: ancestral

<400> SEQUENCE: 32

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Val Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380
```

```
Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Ile Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
            770                 775                 780

Ile Glu Lys Thr Asp Pro Trp Phe Ala His Arg Thr Pro Met Pro Lys
785                 790                 795                 800
```

```
Val Gln Asn Val Ser Ser Ser Asp Leu Leu Met Leu Leu Arg Gln Ser
                    805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Gln Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Glu Asn Pro Asp Met
    1100                1105                1110

Ser Phe Phe Lys Met Leu Phe Leu Pro Glu Ser Ala Ser Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200
```

```
Asn Asn Thr His Asn Gln Glu Lys Lys Ile Gln Glu Glu Ile Glu
         1205                1210                1215

Arg Lys Glu Thr Leu Ile Gln Glu Asn Val Val Leu Pro Gln Ile
         1220                1225                1230

His Thr Val Thr Gly Thr Lys Asn Phe Met Lys Asn Leu Phe Leu
         1235                1240                1245

Leu Ser Thr Arg Gln Asn Val Glu Gly Ser Tyr Glu Gly Ala Tyr
         1250                1255                1260

Ala Pro Val Leu Gln Asp Phe Arg Ser Leu Asn Asp Ser Thr Asn
         1265                1270                1275

Arg Thr Lys Lys His Thr Ala His Phe Ser Lys Lys Gly Glu Glu
         1280                1285                1290

Glu Asn Leu Glu Gly Leu Gly Asn Gln Thr Lys Gln Ile Val Glu
         1295                1300                1305

Lys Tyr Ala Cys Thr Thr Arg Ile Ser Pro Asn Thr Ser Gln Gln
         1310                1315                1320

Asn Phe Val Thr Gln Arg Ser Lys Arg Ala Leu Lys Gln Phe Arg
         1325                1330                1335

Leu Pro Leu Glu Glu Thr Glu Leu Glu Lys Arg Ile Ile Val Asp
         1340                1345                1350

Asp Thr Ser Thr Gln Trp Ser Lys Asn Met Lys His Leu Thr Pro
         1355                1360                1365

Ser Thr Leu Thr Gln Ile Asp Tyr Asn Glu Lys Glu Lys Gly Ala
         1370                1375                1380

Ile Thr Gln Ser Pro Leu Ser Asp Cys Leu Thr Arg Ser His Ser
         1385                1390                1395

Ile Pro Gln Ala Asn Arg Ser Pro Leu Pro Ile Ala Lys Val Ser
         1400                1405                1410

Ser Phe Pro Ser Ile Arg Pro Ile Tyr Leu Thr Arg Val Leu Phe
         1415                1420                1425

Gln Asp Asn Ser Ser His Leu Pro Ala Ala Ser Tyr Arg Lys Lys
         1430                1435                1440

Asp Ser Gly Val Gln Glu Ser Ser His Phe Leu Gln Gly Ala Lys
         1445                1450                1455

Lys Asn Asn Leu Ser Leu Ala Ile Leu Thr Leu Glu Met Thr Gly
         1460                1465                1470

Asp Gln Arg Glu Val Gly Ser Leu Gly Thr Ser Ala Thr Asn Ser
         1475                1480                1485

Val Thr Tyr Lys Lys Val Glu Asn Thr Val Leu Pro Lys Pro Gly
         1490                1495                1500

Leu Pro Lys Thr Ser Gly Lys Val Glu Leu Leu Pro Lys Val His
         1505                1510                1515

Ile Tyr Gln Lys Asp Leu Phe Pro Thr Glu Thr Ser Asn Gly Ser
         1520                1525                1530

Pro Gly His Leu Asp Leu Val Glu Gly Ser Leu Leu Gln Glu Thr
         1535                1540                1545

Glu Gly Ala Ile Lys Trp Asn Glu Ala Asn Arg Pro Gly Lys Ile
         1550                1555                1560

Pro Phe Leu Arg Val Ala Thr Glu Ser Ser Ala Lys Thr Pro Ser
         1565                1570                1575

Lys Leu Leu Gly Pro Leu Ala Trp Asp Asn His Tyr Gly Thr Gln
         1580                1585                1590
```

```
Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Lys Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980
```

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Ile Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His His Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 33
<211> LENGTH: 2360

```
<212> TYPE: PRT
<213> ORGANISM: artificial sequence
<220> FEATURE:
<223> OTHER INFORMATION: ancestral

<400> SEQUENCE: 33
```

| | | | | | | | | | | | | | | |
|---|---|---|---|---|---|---|---|---|---|---|---|---|---|---|
| Met | Gln | Ile | Glu | Leu | Ser | Thr | Cys | Phe | Phe | Leu | Cys | Leu | Leu | Gln | Phe |
| 1 | | | | 5 | | | | | 10 | | | | | 15 | |
| Ser | Phe | Ser | Ala | Thr | Arg | Arg | Tyr | Tyr | Leu | Gly | Ala | Val | Glu | Leu | Ser |
| | | | 20 | | | | | 25 | | | | | 30 | | |
| Trp | Tyr | Asp | Met | Gln | Ser | Asp | Leu | Leu | Ser | Glu | Leu | His | Val | Asp | Thr |
| | | | 35 | | | | | 40 | | | | | 45 | | |
| Arg | Phe | Pro | Pro | Arg | Met | Pro | Arg | Ser | Phe | Pro | Phe | Asn | Thr | Ser | Val |
| | 50 | | | | | 55 | | | | | 60 | | | | |
| Met | Tyr | Lys | Lys | Thr | Val | Phe | Val | Glu | Phe | Thr | Asp | His | Leu | Phe | Asn |
| 65 | | | | | 70 | | | | | 75 | | | | | 80 |
| Ile | Ala | Lys | Pro | Arg | Pro | Pro | Trp | Met | Gly | Leu | Leu | Gly | Pro | Thr | Ile |
| | | | | 85 | | | | | 90 | | | | | 95 | |
| Trp | Ala | Glu | Val | Tyr | Asp | Thr | Val | Val | Ile | Thr | Leu | Lys | Asn | Met | Ala |
| | | | 100 | | | | | 105 | | | | | 110 | | |
| Ser | His | Pro | Val | Ser | Leu | His | Ala | Val | Gly | Val | Ser | Tyr | Trp | Lys | Ala |
| | | | 115 | | | | | 120 | | | | | 125 | | |
| Ser | Glu | Gly | Ala | Glu | Tyr | Asp | Asp | Gln | Thr | Ser | Gln | Arg | Glu | Lys | Glu |
| | 130 | | | | | 135 | | | | | 140 | | | | |
| Asp | Asp | Lys | Val | Phe | Pro | Gly | Glu | Ser | His | Thr | Tyr | Val | Trp | Gln | Val |
| 145 | | | | | 150 | | | | | 155 | | | | | 160 |
| Leu | Lys | Glu | Asn | Gly | Pro | Met | Ala | Ser | Asp | Pro | Pro | Cys | Leu | Thr | Tyr |
| | | | | 165 | | | | | 170 | | | | | 175 | |
| Ser | Tyr | Leu | Ser | His | Val | Asp | Leu | Val | Lys | Asp | Leu | Asn | Ser | Gly | Leu |
| | | | 180 | | | | | 185 | | | | | 190 | | |
| Ile | Gly | Ala | Leu | Leu | Val | Cys | Arg | Glu | Gly | Ser | Leu | Ala | Lys | Glu | Arg |
| | | | 195 | | | | | 200 | | | | | 205 | | |
| Thr | Gln | Met | Leu | His | Gln | Phe | Val | Leu | Leu | Phe | Ala | Val | Phe | Asp | Glu |
| | 210 | | | | | 215 | | | | | 220 | | | | |
| Gly | Lys | Ser | Trp | His | Ser | Glu | Thr | Lys | Gly | Ser | Leu | Thr | Gln | Ala | Met |
| 225 | | | | | 230 | | | | | 235 | | | | | 240 |
| Asp | Ser | Ala | Ser | Ala | Arg | Ala | Trp | Pro | Lys | Met | His | Thr | Val | Asn | Gly |
| | | | | 245 | | | | | 250 | | | | | 255 | |
| Tyr | Val | Asn | Arg | Ser | Leu | Pro | Gly | Leu | Ile | Gly | Cys | His | Arg | Lys | Ser |
| | | | 260 | | | | | 265 | | | | | 270 | | |
| Val | Tyr | Trp | His | Val | Ile | Gly | Met | Gly | Thr | Thr | Pro | Glu | Val | His | Ser |
| | | | 275 | | | | | 280 | | | | | 285 | | |
| Ile | Phe | Leu | Glu | Gly | His | Thr | Phe | Leu | Val | Arg | Asn | His | Arg | Gln | Ala |
| | 290 | | | | | 295 | | | | | 300 | | | | |
| Ser | Leu | Glu | Ile | Ser | Pro | Ile | Thr | Phe | Leu | Thr | Ala | Gln | Thr | Leu | Leu |
| 305 | | | | | 310 | | | | | 315 | | | | | 320 |
| Met | Asp | Leu | Gly | Gln | Phe | Leu | Leu | Phe | Cys | His | Ile | Ser | Ser | His | Gln |
| | | | | 325 | | | | | 330 | | | | | 335 | |
| His | Asp | Gly | Met | Glu | Ala | Tyr | Val | Lys | Val | Asp | Ser | Cys | Pro | Glu | Glu |
| | | | 340 | | | | | 345 | | | | | 350 | | |
| Pro | Gln | Leu | Arg | Met | Lys | Asn | Asn | Glu | Glu | Glu | Asp | Tyr | Asp | Asp |
| | | | 355 | | | | | 360 | | | | | 365 | |
| Asp | Leu | Leu | Asp | Ser | Glu | Met | Asp | Val | Phe | Arg | Phe | Asp | Asp | Asp | Asn |
| | 370 | | | | | 375 | | | | | 380 | | | | |

```
Ser Pro Pro Phe Ile Gln Ile Arg Ser Val Ala Lys Lys His Pro Lys
385                 390                 395                 400

Thr Trp Ile His Tyr Ile Ala Glu Glu Asp Trp Asp Tyr Ala
            405                 410                 415

Pro Ser Val Leu Thr Ser Asp Asp Arg Ser Tyr Lys Ser Gln Tyr Leu
            420                 425                 430

Asn Asn Gly Pro Gln Arg Ile Gly Arg Lys Tyr Lys Val Arg Phe
            435                 440                 445

Met Ala Tyr Thr Asp Glu Thr Phe Lys Thr Arg Glu Thr Ile Gln Tyr
450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
                500                 505                 510

Lys Gly Val Lys His Leu Lys Asp Leu Pro Ile Leu Pro Gly Glu Ile
                515                 520                 525

Phe Lys Tyr Lys Trp Thr Val Thr Val Glu Asp Gly Pro Thr Lys Ser
            530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
            595                 600                 605

Glu Asn Met Gln Arg Phe Leu Pro Asn Ala Ala Gly Val Gln Pro Gln
            610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
                660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
                740                 745                 750

Glu Asn Asn Val Ile Glu Pro Arg Ser Phe Ser Gln Asn Ser Arg His
            755                 760                 765

Pro Ser Thr Arg Gln Lys Gln Phe Lys Ala Thr Thr Ile Pro Glu Asn
            770                 775                 780

Asp Ile Glu Lys Ile Asp Pro Gln Phe Gly Glu Arg Thr Gln Met Leu
785                 790                 795                 800
```

```
Lys Val Gln Ser Val Ser Ser Asp Leu Leu Met Leu Gly Gln
            805                 810                 815

Ser Pro Thr Pro His Gly Leu Ser Leu Ser Asp Leu Gln Glu Ala Thr
            820                 825                 830

Tyr Glu Ala Ile Pro Asp Asp His Ser Pro Gly Ala Ile Asp Ser Asn
            835                 840                 845

Glu Gly Pro Ser Glu Val Ala His Leu Arg Pro Glu Leu His His Ser
        850                 855                 860

Gly Asp Ile Val Phe Thr Pro Glu Pro Gly Leu Gln Leu Arg Leu Asn
865                 870                 875                 880

Glu Asn Leu Gly Thr Thr Ile Ala Val Glu Leu Lys Lys Leu Asp Leu
            885                 890                 895

Lys Val Ser Ser Ser Pro Asn Asn Leu Met Thr Ser Pro Thr Ile Pro
            900                 905                 910

Ser Asp Asn Leu Ala Ala Gly Thr Glu Lys Thr Gly Ser Leu Gly Pro
            915                 920                 925

Pro Asn Met Pro Val His Phe Ser Ser Gln Leu Ser Thr Thr Val Phe
        930                 935                 940

Gly Lys Lys Ser Ser Pro Leu Ile Gly Ser Gly Val Pro Leu Asn Leu
945                 950                 955                 960

Ser Glu Arg Asn Asn Asp Ser Lys Leu Leu Glu Ala Ala Leu Met Asn
            965                 970                 975

Ser Gln Glu Ser Ser Leu Gly Lys Asn Val Ser Ser Met Glu Ser Asp
            980                 985                 990

Arg Leu Phe Lys Glu Lys Arg Val His Gly Pro Ala Leu Leu Thr Lys
            995                1000                1005

Asp Asn Ala Leu Phe Lys Val Asn Ile Ser Leu Ile Lys Thr Asn
        1010                1015                1020

Lys Thr Ser Asn Asn Ser Thr Thr Asn Arg Lys Thr His Ile Asp
        1025                1030                1035

Gly Pro Thr Leu Leu Ile Glu Asn Ser Thr Ser Val Trp Gln Asp
        1040                1045                1050

Thr Ile Leu Glu Ser Asp Thr Glu Phe Gln Glu Val Thr Ser Leu
        1055                1060                1065

Ile His Asp Glu Met Leu Met Asp Lys Asn Thr Thr Ala Leu Arg
        1070                1075                1080

Leu Asn His Val Ser Asn Lys Thr Thr Ser Ser Lys Asn Met Glu
        1085                1090                1095

Met Val His Gln Lys Lys Glu Gly Pro Val Pro Pro Asp Ala Glu
        1100                1105                1110

Asn Pro Asp Met Ser Phe Phe Lys Met Leu Phe Leu Pro Glu Ser
        1115                1120                1125

Ala Asn Trp Ile Lys Arg Thr His Gly Lys Asn Ser Leu Asn Ser
        1130                1135                1140

Gly Gln Gly Pro Ser Pro Lys Gln Leu Ile Ser Leu Gly Ser Glu
        1145                1150                1155

Lys Ser Val Lys Asp Gln Asn Phe Leu Ser Glu Lys Asn Lys Val
        1160                1165                1170

Val Val Gly Glu Asp Glu Phe Thr Lys Asp Thr Gly Leu Lys Glu
        1175                1180                1185

Met Ile Phe Pro Asn Asn Arg Ser Ile Phe Leu Thr Asn Leu Ala
        1190                1195                1200
```

```
Asn Val Gln Glu Asn Asp Thr His Asn Gln Glu Lys Lys Phe Gln
1205                1210                1215

Glu Glu Ile Glu Arg Lys Glu Ala Leu Ile Gln Glu Asn Val Val
1220                1225                1230

Leu Pro Gln Val Tyr Thr Val Thr Gly Thr Lys Asn Phe Leu Lys
1235                1240                1245

Asn Leu Phe Leu Leu Ser Thr Arg Gln Asn Ile Gly Leu Asp Glu
1250                1255                1260

Gly Thr Tyr Ala Pro Val Leu Gln Asp Thr Arg Ser Leu Asn Asp
1265                1270                1275

Ser Thr Asn Arg Ala Glu Ile His Met Ala His Phe Ser Lys Arg
1280                1285                1290

Arg Glu Glu Glu Thr Asn Leu Glu Gly Leu Gly Asn Gln Thr
1295                1300                1305

Lys Gln Met Val Glu Lys Tyr Pro Ser Thr Thr Arg Met Ser Pro
1310                1315                1320

Asn Pro Ser Gln Gln Asn Val Ile Thr Gln Arg Gly Lys Arg Ala
1325                1330                1335

Leu Lys Gln Phe Arg Leu Pro Leu Glu Glu Thr Glu Leu Glu Lys
1340                1345                1350

Gly Leu Ile Val Asp Asp Thr Ser Thr Gln Trp Ser Lys Asn Met
1355                1360                1365

Lys Tyr Leu Thr Gln Ser Thr Leu Thr Gln Ile Asp Tyr Asn Glu
1370                1375                1380

Lys Glu Lys Lys Ala Ile Thr Gln Ser Pro Leu Ser Asp Ser Pro
1385                1390                1395

Met Arg Asn His Ser Ile Thr Gln Met Asn Ser Ser Ala Leu Pro
1400                1405                1410

Ile Ala Lys Ile Ser Ala Phe Pro Ser Ile Arg Pro Thr Asp Leu
1415                1420                1425

Thr Lys Ile Pro Ser Gln Asp Asn Ser Ser His Phe Leu Ala Ser
1430                1435                1440

Ala Tyr Asn Tyr Thr Phe Arg Glu Lys Ser Ser Gly Val Gln Glu
1445                1450                1455

Ser Ser His Phe Leu Gln Gly Ala Lys Arg Asn Asn Leu Ser Leu
1460                1465                1470

Ala Ile Leu Pro Leu Glu Met Ile Arg Asn Gln Glu Lys Val Gly
1475                1480                1485

Ser Leu Gly Thr Ser Ala Thr Asn Ser Val Met Tyr Lys Lys Leu
1490                1495                1500

Glu Asn Thr Val Leu Leu Lys Pro Gly Leu Pro Glu Ala Ser Gly
1505                1510                1515

Lys Val Glu Leu Leu Pro Lys Val Pro Ile His Gln Glu Asp Leu
1520                1525                1530

Phe Pro Thr Glu Thr Ser His Gly Ser Pro Gly His Leu Asp Leu
1535                1540                1545

Met Glu Glu Ile Leu Leu Gln Lys Thr Gln Gly Ala Ile Lys Trp
1550                1555                1560

Asn Lys Thr Asn Arg Pro Gly Lys Val Pro Phe Leu Lys Gly Ala
1565                1570                1575

Thr Glu Ser Ser Glu Lys Thr Pro Ser Lys Leu Leu Gly Pro Leu
1580                1585                1590
```

```
Ala Trp Asp Asn Gln Tyr Ala Thr Gln Ile Pro Lys Glu Glu Trp
1595                1600                1605

Lys Ser Gln Glu Lys Ser Pro Lys Asn Thr Ala Phe Lys Thr Lys
1610                1615                1620

Asp Thr Ile Leu Ser Leu Asn Pro Cys Glu Asn Asn His Ala Ile
1625                1630                1635

Ala Ala Ile Asn Glu Gly Gln Asp Arg Pro Gln Arg Glu Ala Thr
1640                1645                1650

Trp Ala Lys Gln Gly Gly Thr Gly Arg Leu Cys Ser Gln Asn Pro
1655                1660                1665

Pro Val Leu Lys Arg His Gln Arg Glu Ile Thr Leu Thr Thr Leu
1670                1675                1680

Gln Ser Glu Gln Glu Glu Ile Asp Tyr Asp Asp Thr Ile Ser Ile
1685                1690                1695

Glu Thr Lys Arg Glu Asp Phe Asp Ile Tyr Gly Glu Asp Glu Asn
1700                1705                1710

Gln Gly Pro Arg Ser Phe Gln Lys Arg Thr Arg His Tyr Phe Ile
1715                1720                1725

Ala Ala Val Glu Arg Leu Trp Asp Tyr Gly Met Ser Arg Ser Pro
1730                1735                1740

His Val Leu Arg Asn Arg Asp Gln Ser Gly Ser Val Pro Gln Phe
1745                1750                1755

Lys Lys Val Val Phe Gln Glu Phe Thr Asp Gly Ser Phe Thr Gln
1760                1765                1770

Pro Leu Tyr Arg Gly Glu Leu Asn Glu His Leu Gly Leu Leu Gly
1775                1780                1785

Pro Tyr Ile Arg Ala Glu Val Glu Asp Asn Ile Met Val Thr Phe
1790                1795                1800

Lys Asn Gln Ala Ser Arg Pro Tyr Ser Phe Tyr Ser Ser Leu Ile
1805                1810                1815

Ser Tyr Lys Glu Asp Gln Arg Gln Gly Ala Glu Pro Arg Lys Asn
1820                1825                1830

Phe Val Lys Pro Asn Glu Thr Lys Thr Tyr Phe Trp Lys Val Gln
1835                1840                1845

His His Met Ala Pro Thr Lys Asp Glu Phe Asp Cys Lys Ala Trp
1850                1855                1860

Ala Tyr Phe Ser Asp Val Asp Leu Glu Lys Asp Met His Ser Gly
1865                1870                1875

Leu Ile Gly Pro Leu Leu Ile Cys His Thr Asn Thr Leu Asn Pro
1880                1885                1890

Ala His Gly Arg Gln Val Thr Val Gln Glu Phe Ala Leu Phe Phe
1895                1900                1905

Thr Ile Phe Asp Glu Thr Lys Ser Trp Tyr Phe Thr Glu Asn Met
1910                1915                1920

Glu Arg Asn Cys Arg Ala Pro Cys Asn Ile Gln Met Glu Asp Pro
1925                1930                1935

Thr Phe Lys Glu Asn Tyr Arg Phe His Ala Ile Asn Gly Tyr Val
1940                1945                1950

Met Asp Thr Leu Pro Gly Leu Val Met Ala Gln Asp Gln Arg Ile
1955                1960                1965

Arg Trp Tyr Leu Leu Ser Met Gly Ser Asn Glu Asn Ile His Ser
1970                1975                1980
```

```
Ile His Phe Ser Gly His Val Phe Thr Val Arg Lys Lys Glu Glu
    1985                1990                1995

Tyr Lys Met Ala Val Tyr Asn Leu Tyr Pro Gly Val Phe Glu Thr
    2000                2005                2010

Val Glu Met Leu Pro Ser Lys Ala Gly Ile Trp Arg Val Glu Cys
    2015                2020                2025

Leu Ile Gly Glu His Leu His Ala Gly Met Ser Thr Leu Phe Leu
    2030                2035                2040

Val Tyr Ser Lys Gln Cys Gln Ile Pro Leu Gly Met Ala Ser Gly
    2045                2050                2055

His Ile Arg Asp Phe Gln Ile Thr Ala Ser Gly Gln Tyr Gly Gln
    2060                2065                2070

Trp Ala Pro Lys Leu Ala Arg Leu His Tyr Ser Gly Ser Ile Asn
    2075                2080                2085

Ala Trp Ser Thr Lys Glu Pro Phe Ser Trp Ile Lys Val Asp Leu
    2090                2095                2100

Leu Ala Pro Met Ile Ile His Gly Ile Lys Thr Gln Gly Ala Arg
    2105                2110                2115

Gln Lys Phe Ser Ser Leu Tyr Ile Ser Gln Phe Ile Ile Met Tyr
    2120                2125                2130

Ser Leu Asp Gly Lys Lys Trp Gln Thr Tyr Arg Gly Asn Ser Thr
    2135                2140                2145

Gly Thr Leu Met Val Phe Phe Gly Asn Val Asp Ser Ser Gly Ile
    2150                2155                2160

Lys His Asn Ile Phe Asn Pro Pro Ile Ile Ala Arg Tyr Ile Arg
    2165                2170                2175

Leu His Pro Thr His Tyr Ser Ile Arg Ser Thr Leu Arg Met Glu
    2180                2185                2190

Leu Met Gly Cys Asp Leu Asn Ser Cys Ser Met Pro Leu Gly Met
    2195                2200                2205

Glu Ser Lys Ala Ile Ser Asp Ala Gln Ile Thr Ala Ser Ser Tyr
    2210                2215                2220

Phe Thr Asn Met Phe Ala Thr Trp Ser Pro Ser Gln Ala Arg Leu
    2225                2230                2235

His Leu Gln Gly Arg Thr Asn Ala Trp Arg Pro Gln Val Asn Asn
    2240                2245                2250

Pro Lys Glu Trp Leu Gln Val Asp Phe Gln Lys Thr Met Lys Val
    2255                2260                2265

Thr Gly Ile Ile Thr Gln Gly Val Lys Ser Leu Leu Thr Ser Met
    2270                2275                2280

Phe Val Lys Glu Phe Leu Ile Ser Ser Ser Gln Asp Gly His His
    2285                2290                2295

Trp Thr Leu Phe Leu Gln Asn Gly Lys Val Lys Val Phe Gln Gly
    2300                2305                2310

Asn Gln Asp Ser Phe Thr Pro Val Val Asn Ser Leu Asp Pro Pro
    2315                2320                2325

Leu Leu Thr Arg Tyr Leu Arg Ile His Pro Gln Ser Trp Val His
    2330                2335                2340

Gln Ile Ala Leu Arg Leu Glu Val Leu Gly Cys Glu Ala Gln Gln
    2345                2350                2355

Leu Tyr
    2360
```

<210> SEQ ID NO 34
<211> LENGTH: 2357
<212> TYPE: PRT
<213> ORGANISM: artificial sequence
<220> FEATURE:
<223> OTHER INFORMATION: ancestral

<400> SEQUENCE: 34

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
            20                  25                  30

Trp Asp Tyr Met Gln Ser Glu Leu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Asn Glu Ser Leu Thr Gln Ala Met
225                 230                 235                 240

Asp Pro Ala Ser Ala Arg Ala Gln Pro Glu Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
        355                 360                 365

Asp Leu Tyr Asp Ser Asp Met Asp Val Val Arg Phe Asp Asp Asn
        370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asn Asp Arg Ser Tyr Lys Ser Leu Tyr Leu
                420                 425                 430

Asn Asn Gly Pro Gln Arg Ile Gly Arg Lys Tyr Lys Val Arg Phe
            435                 440                 445

Met Ala Tyr Thr Asp Glu Thr Phe Lys Thr Arg Glu Ala Ile Gln Tyr
            450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
                500                 505                 510

Lys Gly Val Lys His Leu Lys Asp Met Pro Ile Leu Pro Gly Glu Ile
            515                 520                 525

Phe Lys Tyr Lys Trp Thr Val Thr Val Glu Asp Gly Pro Thr Lys Ser
            530                 535                 540

Asp Pro Arg Cys Leu Thr Arg Tyr Tyr Ser Ser Phe Val Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
            595                 600                 605

Glu Asn Met Gln Arg Phe Leu Pro Asn Ala Asp Gly Val Gln Pro Gln
            610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
            675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Ser Leu Leu Asn
                740                 745                 750

Glu Asn Asn Val Ile Glu Pro Arg Ser Phe Ser Gln Asn Ser Arg His
            755                 760                 765

Pro Ser Thr Arg Gln Lys Gln Phe Lys Ala Thr Thr Thr Pro Glu Asn
770                 775                 780

```
Asp Ile Glu Lys Ile Asp Pro Gln Ser Gly Glu Arg Thr Gln Leu Leu
785                 790                 795                 800

Lys Val Gln Ser Val Ser Ser Asp Leu Leu Met Leu Leu Gly Gln
            805                 810                 815

Asn Pro Thr Pro His Gly Leu Ser Leu Ser Asp Leu Gln Glu Ala Thr
                820                 825                 830

Tyr Glu Ala Asp Asp His Leu Pro Gly Ala Ile Glu Arg Asn Lys Gly
            835                 840                 845

Pro Ser Glu Val Ala His Leu Arg Pro Glu Leu His His Ser Gly Asp
850                 855                 860

Arg Val Phe Thr Pro Glu Pro Glu Leu Gln Arg Leu Asn Glu Asn
865                 870                 875                 880

Leu Gly Thr Thr Ile Thr Val Glu Leu Lys Lys Leu Asp Leu Lys Ile
                885                 890                 895

Ser Ser Ser Ser Asn Asn Leu Met Thr Ser Pro Thr Ile Pro Ser Asp
            900                 905                 910

Lys Leu Ala Ala Gly Thr Glu Lys Thr Gly Ser Leu Gly Pro Pro Asn
            915                 920                 925

Met Pro Val His Phe Ser Ser Gln Leu Gly Thr Ile Val Phe Gly Lys
    930                 935                 940

Asn Ser Ser His Leu Ile Gly Ser Gly Val Pro Leu Gly Leu Ser Glu
945                 950                 955                 960

Gly Asp Asn Asp Ser Lys Leu Leu Glu Ala Ala Leu Met Asn Ser Gln
                965                 970                 975

Glu Ser Ser Leu Gly Glu Asn Val Leu Ser Met Glu Ser Asp Arg Leu
            980                 985                 990

Phe Lys Glu Glu Arg Val His Gly  Pro Ala Ser Leu Thr  Lys Asp Asn
            995                 1000                1005

Ala Leu  Phe Lys Val Asn Ile  Ser Leu Val Lys Thr  Asn Lys Ala
    1010                1015                1020

Pro Ile  Asn Ser Thr Thr Asn  Arg Lys Thr His Ile  Asp Gly Pro
    1025                1030                1035

Thr Leu  Leu Ile Glu Asn Ser  Thr Ser Val Trp Gln  Asp Ile Ile
    1040                1045                1050

Leu Glu  Ser Asn Thr Glu Phe  Gln Glu Val Thr Ser  Leu Ile His
    1055                1060                1065

Asp Glu  Thr Phe Met Asp Lys  Asn Thr Thr Ala Leu  Gly Leu Asn
    1070                1075                1080

His Val  Ser Asn Lys Thr Thr  Ser Ser Lys Asn Met  Glu Met Val
    1085                1090                1095

His Gln  Lys Lys Glu Gly Pro  Val Pro Leu Gly Ala  Glu Asn Pro
    1100                1105                1110

Asp Thr  Ser Phe Phe Lys Met  Leu Phe Leu Pro Asp  Ser Ala Asn
    1115                1120                1125

Trp Ile  Lys Arg Thr His Gly  Lys Asn Ser Leu Ser  Ser Gly Gln
    1130                1135                1140

Arg Pro  Ser Pro Lys Gln Leu  Thr Ser Leu Gly Ser  Glu Lys Ser
    1145                1150                1155

Val Lys  Asp Gln Asn Phe Leu  Ser Glu Lys Asn Lys  Val Val Val
    1160                1165                1170

Gly Glu  Asp Glu Phe Thr Lys  Asp Thr Gly Leu Lys  Glu Met Ile
    1175                1180                1185
```

```
Phe Pro Asn Ser Lys Ser Ile Phe Leu Thr Asn Leu Ala Asn Val
    1190            1195            1200

Gln Glu Asn Asp Thr His Asn Gln Glu Lys Lys Ser Gln Glu Glu
    1205            1210            1215

Ile Glu Arg Lys Glu Lys Leu Ile Gln Glu Asn Val Val Leu Pro
    1220            1225            1230

Gln Val Tyr Thr Val Thr Gly Thr Lys Asn Phe Leu Lys Asn Leu
    1235            1240            1245

Phe Leu Leu Ser Thr Lys Gln Asn Val Glu Gly Leu Asp Glu Gly
    1250            1255            1260

Thr Tyr Thr Pro Ile Leu Gln Asp Thr Arg Ser Leu Asn Asp Ser
    1265            1270            1275

Ala Asn Arg Ala Gly Ile His Met Ala His Phe Ser Lys Ile Arg
    1280            1285            1290

Glu Glu Ala Asn Leu Glu Gly Leu Gly Asn Gln Thr Lys Gln Met
    1295            1300            1305

Val Glu Lys Tyr Pro Ser Thr Thr Arg Met Ser Pro Asn Pro Ser
    1310            1315            1320

Gln Gln Asn Val Ile Thr Gln Arg Gly Lys Arg Ala Leu Lys Gln
    1325            1330            1335

Phe Arg Leu Pro Leu Glu Glu Ile Lys Leu Glu Arg Gly Val Ile
    1340            1345            1350

Leu Asn Asp Thr Ser Thr Gln Trp Ser Lys Asn Met Lys Tyr Leu
    1355            1360            1365

Thr Gln Gly Thr Leu Thr Gln Ile Glu Tyr Asn Glu Lys Glu Lys
    1370            1375            1380

Arg Ala Ile Thr Gln Ser Leu Leu Ser Asp Cys Ser Met Arg Ser
    1385            1390            1395

His Gly Ile Ile Gln Thr Asn Gly Ser Ala Leu Pro Ile Ala Lys
    1400            1405            1410

Val Ser Ala Phe Pro Ser Ile Arg Pro Thr Asp Leu Thr Lys Ile
    1415            1420            1425

Pro Ser Gln Asp Asn Ser Ser His Leu Leu Ala Ser Ala Cys Ser
    1430            1435            1440

Tyr Thr Phe Arg Glu Arg Ser Ser Gly Val Gln Glu Ser Ser His
    1445            1450            1455

Phe Leu Gln Gly Ala Lys Arg Asn Asn Leu Ser Leu Ala Phe Leu
    1460            1465            1470

Thr Leu Glu Met Ile Arg Gly Gln Glu Lys Ile Ser Ser Leu Gly
    1475            1480            1485

Lys Ser Ala Thr Asn Pro Leu Met Tyr Lys Lys Leu Glu Asn Thr
    1490            1495            1500

Val Leu Leu Lys Pro Gly Leu Ser Glu Ala Ser Gly Lys Val Glu
    1505            1510            1515

Leu Leu Pro Lys Val His Val His Gln Glu Asp Ser Phe Pro Thr
    1520            1525            1530

Lys Thr Ser Asn Gly Ser Pro Gly His Leu Asp Leu Met Glu Glu
    1535            1540            1545

Ile Phe Leu Gln Lys Thr Gln Gly Pro Val Lys Leu Asn Lys Val
    1550            1555            1560

Asn Arg Pro Gly Lys Val Pro Phe Leu Lys Trp Ala Thr Glu Ser
    1565            1570            1575
```

```
Ser Glu Lys Thr Pro Ser Lys Leu Leu Gly Pro Leu Ala Trp Asp
    1580            1585                1590

Asn Gln Tyr Ala Thr Gln Ile Pro Arg Glu Glu Trp Lys Ser Gln
    1595            1600                1605

Glu Lys Ser Gln Lys Asn Thr Ala Phe Lys Thr Lys Asp Thr Ile
    1610            1615                1620

Leu Pro Leu Asp Pro Cys Glu Asn Asn His Ser Ile Ala Ala Ile
    1625            1630                1635

Asn Glu Gly Gln Asp Lys Pro Gln Arg Glu Ala Thr Trp Ala Lys
    1640            1645                1650

Gln Gly Gly Thr Gly Arg Leu Cys Ser Gln Asn Pro Pro Val Leu
    1655            1660                1665

Lys Arg His Gln Arg Glu Ile Thr Leu Thr Thr Leu Gln Pro Glu
    1670            1675                1680

Glu Asp Lys Ile Asp Tyr Asp Asp Thr Phe Ser Ile Glu Thr Lys
    1685            1690                1695

Arg Glu Asp Phe Asp Ile Tyr Gly Glu Asp Glu Asn Gln Gly Pro
    1700            1705                1710

Arg Ser Phe Gln Lys Arg Thr Arg His Tyr Phe Ile Ala Ala Val
    1715            1720                1725

Glu Arg Leu Trp Asp Tyr Gly Met Ser Arg Ser Pro His Ala Leu
    1730            1735                1740

Arg Asn Arg Ala Gln Ser Gly Ser Val Pro Gln Phe Lys Lys Val
    1745            1750                1755

Val Phe Gln Glu Phe Thr Asp Gly Ser Phe Thr Gln Pro Leu Tyr
    1760            1765                1770

Arg Gly Glu Leu Asn Glu His Leu Gly Leu Leu Gly Pro Tyr Ile
    1775            1780                1785

Arg Ala Glu Val Glu Asp Asn Ile Met Val Thr Phe Lys Asn Gln
    1790            1795                1800

Ala Ser Arg Pro Tyr Ser Phe Tyr Ser Ser Leu Ile Ser Tyr Glu
    1805            1810                1815

Glu Asp Gln Arg Gln Gly Ala Glu Pro Arg Lys Lys Phe Val Lys
    1820            1825                1830

Pro Asn Glu Thr Lys Ile Tyr Phe Trp Lys Val Gln His His Met
    1835            1840                1845

Ala Pro Thr Lys Asp Glu Phe Asp Cys Lys Ala Trp Ala Tyr Phe
    1850            1855                1860

Ser Asp Val Asp Leu Glu Lys Asp Met His Ser Gly Leu Ile Gly
    1865            1870                1875

Pro Leu Leu Ile Cys Arg Thr Asn Thr Leu Asn Pro Ala His Gly
    1880            1885                1890

Arg Gln Val Thr Val Gln Glu Phe Ala Leu Phe Phe Thr Ile Phe
    1895            1900                1905

Asp Glu Thr Lys Ser Trp Tyr Phe Thr Glu Asn Met Glu Arg Asn
    1910            1915                1920

Cys Arg Ala Pro Cys Asn Ile Gln Met Glu Asp Pro Thr Phe Lys
    1925            1930                1935

Glu Asn Tyr Arg Phe His Ala Ile Asn Gly Tyr Val Met Asp Thr
    1940            1945                1950

Leu Pro Gly Leu Val Met Ala Gln Asp Gln Arg Ile Arg Trp Tyr
    1955            1960                1965
```

```
Leu Leu Ser Met Gly Ser Asn Glu Asn Ile His Ser Ile His Phe
1970                1975                1980

Ser Gly His Val Phe Thr Val Arg Lys Lys Glu Glu Tyr Lys Met
1985                1990                1995

Ala Val Tyr Asn Leu Tyr Pro Gly Val Phe Glu Thr Val Glu Met
2000                2005                2010

Leu Pro Ser Lys Ala Gly Ile Trp Arg Ile Glu Cys Leu Ile Gly
2015                2020                2025

Glu His Leu Gln Ala Gly Met Ser Thr Leu Phe Leu Val Tyr Ser
2030                2035                2040

Lys Lys Cys Gln Thr Pro Leu Gly Met Ala Ser Gly Arg Ile Arg
2045                2050                2055

Asp Phe Gln Ile Thr Ala Ser Gly Gln Tyr Gly Gln Trp Ala Pro
2060                2065                2070

Lys Leu Ala Arg Leu His Tyr Ser Gly Ser Ile Asn Ala Trp Ser
2075                2080                2085

Thr Lys Asp Pro Phe Ser Trp Ile Lys Val Asp Leu Leu Ala Pro
2090                2095                2100

Met Ile Ile His Ser Ile Met Thr Gln Gly Ala Arg Gln Lys Phe
2105                2110                2115

Ser Ser Leu Tyr Ile Ser Gln Phe Ile Ile Met Tyr Ser Leu Asp
2120                2125                2130

Gly Lys Lys Trp Gln Ser Tyr Arg Gly Asn Ser Thr Gly Thr Leu
2135                2140                2145

Met Val Phe Phe Gly Asn Val Asp Ser Ser Gly Ile Lys His Asn
2150                2155                2160

Ile Phe Asn Pro Pro Ile Ile Ala Arg Tyr Ile Arg Leu His Pro
2165                2170                2175

Thr His Tyr Ser Ile Arg Ser Thr Leu Arg Met Glu Leu Met Gly
2180                2185                2190

Cys Asp Leu Asn Ser Cys Ser Met Pro Leu Gly Met Glu Asn Lys
2195                2200                2205

Ala Ile Ser Asp Ala Gln Ile Thr Ala Ser Ser Tyr Leu Asn Asn
2210                2215                2220

Met Phe Ala Thr Trp Ser Pro Ser Gln Ala Arg Leu His Leu Gln
2225                2230                2235

Gly Arg Thr Asn Ala Trp Arg Pro Gln Val Asn Asn Pro Lys Glu
2240                2245                2250

Trp Leu Gln Val Asp Phe Gln Lys Thr Met Lys Val Thr Gly Ile
2255                2260                2265

Thr Thr Gln Gly Val Lys Ser Leu Leu Thr Ser Met Tyr Val Lys
2270                2275                2280

Glu Phe Leu Ile Ser Ser Ser Gln Asp Gly His Asn Trp Thr Leu
2285                2290                2295

Phe Leu Gln Asn Gly Lys Val Lys Val Phe Gln Gly Asn Gln Asp
2300                2305                2310

Ser Phe Thr Pro Val Val Asn Ser Leu Asp Pro Pro Leu Leu Thr
2315                2320                2325

Arg Tyr Leu Arg Ile His Pro Gln Ser Trp Ala His Gln Ile Ala
2330                2335                2340

Leu Arg Leu Glu Val Leu Gly Cys Glu Ala Gln Gln Leu Tyr
2345                2350                2355
```

-continued

```
<210> SEQ ID NO 35
<211> LENGTH: 2357
<212> TYPE: PRT
<213> ORGANISM: artificial sequence
<220> FEATURE:
<223> OTHER INFORMATION: ancestral

<400> SEQUENCE: 35
```

Met Gln Ile Glu Leu Ser Thr Cys Phe Phe Leu Cys Leu Leu Pro Phe
1               5                   10                  15

Ser Phe Ser Ala Ile Arg Arg Tyr Tyr Leu Gly Ala Val Glu Leu Ser
            20                  25                  30

Trp Asp Tyr Met Gln Ser Glu Leu Leu Ser Glu Leu His Val Asp Thr
        35                  40                  45

Arg Phe Pro Pro Arg Val Pro Arg Ser Phe Pro Phe Asn Thr Ser Val
    50                  55                  60

Met Tyr Lys Lys Thr Val Phe Val Glu Phe Thr Asp Gln Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ser
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Lys Ser His Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Gly Lys Asn Glu Ser Leu Thr Gln Ala Met
225                 230                 235                 240

Asp Pro Ala Ser Ala Arg Ala Gln Pro Ala Met His Thr Ile Asn Gly
                245                 250                 255

Tyr Ile Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
        355                 360                 365

```
Asp Leu Tyr Asp Ser Asp Met Asp Val Val Arg Phe Asp Gly Asp Asn
        370                 375                 380

Ala Pro Pro Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Ser Asn Asp Arg Ser Tyr Lys Ser Leu Tyr Leu
                420                 425                 430

Asn Asn Gly Pro Gln Arg Ile Gly Arg Lys Tyr Lys Val Arg Phe
            435                 440                 445

Ile Ala Tyr Thr Asp Glu Thr Phe Lys Thr Arg Glu Ala Ile Gln Tyr
    450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Phe Pro
                500                 505                 510

Lys Gly Val Lys His Leu Lys Asp Met Pro Ile Leu Pro Gly Glu Ile
            515                 520                 525

Phe Lys Tyr Lys Trp Thr Val Thr Val Glu Asp Gly Pro Thr Lys Ser
    530                 535                 540

Asp Pro Arg Cys Leu Thr Arg Tyr Tyr Ser Ser Phe Val Asn Leu Glu
545                 550                 555                 560

Lys Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Gln Ser Trp Tyr Leu Thr
    595                 600                 605

Glu Asn Ile Gln Arg Phe Leu Pro Asn Ala Asp Gly Val Gln Pro Gln
    610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
    675                 680                 685

Thr Leu Phe Pro Phe Ser Gly Glu Thr Val Phe Met Ser Met Glu Asn
    690                 695                 700

Pro Gly Leu Trp Val Leu Gly Cys His Asn Ser Asp Phe Arg Asn Arg
705                 710                 715                 720

Gly Met Thr Ala Leu Leu Lys Val Tyr Ser Cys Asp Arg Asn Thr Gly
                725                 730                 735

Asp Tyr Tyr Glu Asp Thr Tyr Glu Asp Ile Pro Thr Phe Leu Leu Asn
            740                 745                 750

Glu Asn Asn Val Ile Glu Pro Arg Ser Phe Ser Gln Asn Ser Arg His
    755                 760                 765

Pro Ser Thr Arg Gln Lys Gln Phe Lys Ala Thr Thr Thr Pro Glu Asn
    770                 775                 780
```

```
Asp Ile Glu Lys Ile Asp Pro Gln Ser Gly Glu Arg Thr Gln Leu Leu
785                 790                 795                 800

Lys Glu Gln Ser Val Ser Ser Asp Leu Leu Met Leu Leu Gly Gln
            805                 810                 815

Asn Pro Thr Pro His Gly Leu Ser Leu Ser Asp Leu Gln Glu Ala Arg
            820                 825                 830

Asn Glu Ala Asp Asp His Leu Pro Gly Ala Ile Glu Arg Asn Lys Gly
            835                 840                 845

Pro Ser Glu Val Ala His Leu Arg Pro Glu Leu His Ser Gly Glu
            850                 855                 860

Arg Val Phe Thr Pro Glu Pro Glu Leu Pro Leu Arg Leu Asn Glu Asn
865                 870                 875                 880

Leu Gly Thr Thr Ile Thr Val Glu Leu Lys Lys Leu Asp Phe Lys Ile
                885                 890                 895

Ser Ser Ser Ser Asn Asn Leu Met Thr Ser Pro Thr Ile Pro Ser Asp
                900                 905                 910

Lys Leu Ser Ala Gly Thr Glu Lys Thr Gly Ser Leu Gly Pro Pro Asn
            915                 920                 925

Met Pro Val Asn Phe Ser Ser Gln Leu Gly Thr Ile Val Phe Gly Lys
            930                 935                 940

Asn Ser Ser His Phe Ile Gly Ser Gly Val Pro Leu Gly Leu Ser Glu
945                 950                 955                 960

Glu Asp Asn Asp Ser Lys Leu Leu Glu Ala Ala Leu Met Asn Ser Gln
                965                 970                 975

Glu Ser Ser Leu Gly Glu Asn Val Leu Ser Met Glu Ser Asp Arg Leu
            980                 985                 990

Phe Lys Glu Glu Arg Val His Gly Pro Ala Ser Leu Thr Lys Asp Asp
            995                 1000                1005

Ala Leu Phe Lys Val Asn Ile Ser Leu Val Lys Thr Asn Lys Ala
    1010                1015                1020

Pro Val Asn Ser Thr Thr Asn Arg Lys Thr His Ile Asp Asp Pro
    1025                1030                1035

Thr Leu Leu Ile Glu Asn Ser Thr Ser Val Trp Gln Asp Ile Ile
    1040                1045                1050

Leu Glu Ser Asn Thr Glu Phe Gln Glu Val Thr Ser Leu Ile His
    1055                1060                1065

Asp Glu Thr Phe Met Asp Lys Asn Thr Thr Ala Leu Gly Leu Asn
    1070                1075                1080

His Val Ser Asn Lys Thr Thr Ser Ser Lys Asn Met Glu Met Val
    1085                1090                1095

His Gln Lys Lys Glu Gly Pro Val Pro Leu Asp Ala Glu Tyr Pro
    1100                1105                1110

Asp Thr Ser Phe Phe Lys Thr Leu Phe Leu Pro Asp Ser Thr Asn
    1115                1120                1125

Trp Ile Lys Arg Thr His Gly Lys Asn Ser Leu Ser Ser Gly Gln
    1130                1135                1140

Arg Pro Ser Pro Lys Gln Leu Thr Ser Ser Gly Ser Glu Lys Ser
    1145                1150                1155

Val Lys Asp Gln Asn Phe Leu Ser Glu Lys Asn Lys Val Val Val
    1160                1165                1170

Gly Glu Asp Glu Phe Ser Lys Asp Thr Gly Leu Lys Glu Met Ile
    1175                1180                1185
```

```
Phe Pro Asn Ser Lys Ser Ile Phe Leu Thr Asn Leu Ala Asn Val
    1190                1195                1200

Gln Glu Asn Asp Thr His Asn Gln Glu Lys Lys Ser Gln Glu Glu
    1205                1210                1215

Ile Glu Arg Lys Glu Lys Leu Ile Gln Glu Asn Val Val Leu Pro
    1220                1225                1230

Gln Val Tyr Thr Val Thr Gly Thr Lys Asn Phe Leu Lys Asn Leu
    1235                1240                1245

Phe Leu Leu Ser Thr Lys Gln Asn Val Glu Gly Leu Asp Glu Gly
    1250                1255                1260

Thr Tyr Thr Pro Val Leu Gln Asp Thr Arg Ser Leu Asn Asp Ser
    1265                1270                1275

Ala Lys Arg Ala Gly Ile His Met Ala His Phe Ser Lys Ile Arg
    1280                1285                1290

Glu Glu Ala Asn Leu Glu Gly Leu Gly Asn Gln Thr Lys Gln Met
    1295                1300                1305

Val Glu Lys Tyr Pro Ser Thr Thr Arg Met Ser Pro Asn Pro Ser
    1310                1315                1320

Gln Gln Asn Val Ile Pro Gln Arg Gly Lys Arg Asp Leu Lys Gln
    1325                1330                1335

Phe Arg Leu Pro Leu Glu Glu Ile Lys Leu Glu Arg Gly Val Ile
    1340                1345                1350

Leu Asn Asp Thr Ser Thr Gln Trp Ser Lys Asn Met Lys Tyr Leu
    1355                1360                1365

Thr Gln Gly Thr Phe Thr Gln Ile Glu Tyr Asn Lys Lys Glu Lys
    1370                1375                1380

Arg Ala Ile Thr Gln Ser Phe Leu Ser Asp Cys Ser Met Arg Ser
    1385                1390                1395

His Gly Ile Ile Gln Thr Asn Gly Ser Ala Leu Pro Ile Ala Lys
    1400                1405                1410

Val Ser Ala Phe Pro Ser Ile Arg Pro Thr Asp Leu Thr Lys Ile
    1415                1420                1425

Pro Ser Gln Asp Asn Ser Ser His Leu Pro Ala Ser Ala Cys Ser
    1430                1435                1440

Tyr Thr Phe Gly Glu Arg Ser Ser Gly Val Gln Glu Ser Ser His
    1445                1450                1455

Phe Leu Gln Gly Ala Lys Arg Asn Asn Leu Ser Leu Ala Phe Leu
    1460                1465                1470

Thr Leu Glu Met Ile Arg Gly Gln Gly Lys Ile Ser Thr Leu Gly
    1475                1480                1485

Lys Ser Ala Thr Asn Pro Leu Met Tyr Lys Lys Leu Glu Asn Thr
    1490                1495                1500

Val Leu Leu Lys Pro Gly Leu Ser Glu Ala Ser Gly Lys Val Glu
    1505                1510                1515

Phe Leu Pro Lys Val His Val His Gln Glu Asp Phe Phe Pro Thr
    1520                1525                1530

Lys Thr Ser Asn Gly Ser Pro Ala His Leu Asp Leu Arg Glu Glu
    1535                1540                1545

Ile Phe Leu Gln Lys Thr Gln Gly Leu Val Lys Leu Asn Lys Val
    1550                1555                1560

Asn Arg Pro Gly Lys Val Pro Phe Leu Lys Trp Ala Thr Glu Ser
    1565                1570                1575
```

```
Ser Glu Lys Thr Pro Ser Lys Leu Leu Gly Pro Leu Ala Trp Asp
1580                1585                1590

Asn Gln Tyr Ala Thr Leu Ile Pro Arg Glu Glu Trp Lys Ser Leu
    1595                1600                1605

Glu Lys Ser Gln Lys Asn Thr Ala Phe Lys Thr Lys Asp Thr Ile
1610                1615                1620

Leu Pro Leu Asp Pro Cys Glu Asn Asn His Ser Ile Ala Ala Ile
    1625                1630                1635

Asn Glu Gly Gln Asp Lys Pro Gln Arg Glu Ala Thr Trp Val Lys
1640                1645                1650

Gln Gly Gly Thr Gly Arg Leu Cys Ser Gln Asn Pro Pro Val Leu
    1655                1660                1665

Lys Arg His Gln Arg Glu Ile Thr Leu Thr Thr Phe Gln Pro Glu
1670                1675                1680

Glu Asp Lys Ile Asp Tyr Asp Asp Thr Phe Ser Ile Glu Thr Lys
    1685                1690                1695

Arg Glu Asp Phe Asp Ile Tyr Gly Glu Asp Glu Asn Gln Gly Pro
1700                1705                1710

Arg Ser Phe Gln Lys Arg Thr Arg His Tyr Phe Ile Ala Ala Val
    1715                1720                1725

Glu Arg Leu Trp Asp Tyr Gly Met Ser Arg Ser Pro His Ala Leu
1730                1735                1740

Arg Asn Arg Ala Gln Asn Gly Asp Val Pro Gln Phe Lys Lys Val
    1745                1750                1755

Val Phe Gln Glu Phe Thr Asp Gly Ser Phe Thr Gln Pro Leu Tyr
1760                1765                1770

Arg Gly Glu Leu Asn Glu His Leu Gly Leu Leu Gly Pro Tyr Ile
    1775                1780                1785

Arg Ala Glu Val Glu Asp Asn Ile Met Val Thr Phe Lys Asn Gln
1790                1795                1800

Ala Ser Arg Pro Tyr Ser Phe Tyr Ser Ser Leu Ile Ser Tyr Glu
    1805                1810                1815

Glu Asp Gln Arg Gln Gly Ala Glu Pro Arg Lys Lys Phe Val Lys
1820                1825                1830

Pro Asn Glu Thr Lys Ile Tyr Phe Trp Lys Val Gln His His Met
    1835                1840                1845

Ala Pro Thr Lys Asp Glu Phe Asp Cys Lys Ala Trp Ala Tyr Phe
1850                1855                1860

Ser Asp Val Asp Leu Glu Lys Asp Val His Ser Gly Leu Ile Gly
    1865                1870                1875

Pro Leu Leu Ile Cys Arg Thr Asn Thr Leu Asn Ala Ala His Gly
1880                1885                1890

Arg Gln Val Thr Val Gln Glu Phe Ala Leu Phe Phe Thr Ile Phe
    1895                1900                1905

Asp Glu Thr Lys Ser Trp Tyr Phe Thr Glu Asn Met Glu Arg Asn
1910                1915                1920

Cys Arg Ala Pro Cys Asn Ile Gln Met Glu Asp Pro Thr Phe Lys
    1925                1930                1935

Glu Asn Tyr Arg Phe His Ala Ile Asn Gly Tyr Val Met Asp Thr
1940                1945                1950

Leu Pro Gly Leu Val Met Ala Gln Asp Gln Arg Ile Arg Trp Tyr
    1955                1960                1965
```

```
Leu Leu Ser Met Gly Ser Asn Glu Asn Ile His Ser Ile His Phe
    1970            1975                1980

Ser Gly His Val Phe Thr Val Arg Lys Lys Glu Glu Tyr Lys Met
    1985            1990                1995

Ala Val Tyr Asn Leu Tyr Pro Gly Val Phe Glu Thr Val Glu Met
    2000            2005                2010

Leu Pro Ser Lys Val Gly Ile Trp Arg Ile Glu Cys Leu Ile Gly
    2015            2020                2025

Glu His Leu Gln Ala Gly Met Ser Thr Leu Phe Leu Val Tyr Ser
    2030            2035                2040

Lys Lys Cys Gln Thr Pro Leu Gly Met Ala Ser Gly Arg Ile Arg
    2045            2050                2055

Asp Phe Gln Ile Thr Ala Ser Gly Gln Tyr Gly Gln Trp Ala Pro
    2060            2065                2070

Lys Leu Ala Arg Leu His Tyr Ser Gly Ser Ile Asn Ala Trp Ser
    2075            2080                2085

Thr Lys Asp Pro Phe Ser Trp Ile Lys Val Asp Leu Leu Ala Pro
    2090            2095                2100

Met Ile Ile His Ser Ile Met Thr Gln Gly Ala Arg Gln Lys Phe
    2105            2110                2115

Ser Ser Leu Tyr Ile Ser Gln Phe Ile Ile Met Tyr Ser Leu Asp
    2120            2125                2130

Gly Lys Lys Trp Gln Ser Tyr Arg Gly Asn Ser Thr Gly Thr Leu
    2135            2140                2145

Met Val Phe Phe Gly Asn Val Asp Ser Ser Gly Ile Lys His Asn
    2150            2155                2160

Ile Phe Asn Pro Pro Ile Ile Ala Arg Tyr Ile Arg Leu His Pro
    2165            2170                2175

Thr His Tyr Ser Ile Arg Ser Thr Leu Arg Met Glu Leu Met Gly
    2180            2185                2190

Cys Asp Leu Asn Ser Cys Ser Met Pro Leu Gly Met Glu Asn Lys
    2195            2200                2205

Ala Ile Ser Asp Ala Gln Ile Thr Ala Ser Ser His Leu Ser Asn
    2210            2215                2220

Met Phe Ala Thr Trp Ser Pro Ser Gln Ala Arg Leu His Leu Gln
    2225            2230                2235

Gly Arg Thr Asn Ala Trp Arg Pro Gln Val Asn Asn Pro Lys Glu
    2240            2245                2250

Trp Leu Gln Val Asp Phe Gln Lys Thr Met Lys Val Thr Gly Ile
    2255            2260                2265

Thr Thr Gln Gly Val Lys Ser Leu Leu Thr Ser Met Tyr Val Lys
    2270            2275                2280

Glu Phe Leu Ile Ser Ser Ser Gln Asp Gly His Asn Trp Thr Leu
    2285            2290                2295

Phe Leu Gln Asn Gly Lys Val Lys Val Phe Gln Gly Asn Gln Asp
    2300            2305                2310

Ser Phe Thr Pro Val Val Asn Ala Leu Asp Pro Pro Leu Phe Thr
    2315            2320                2325

Arg Tyr Leu Arg Ile His Pro Gln Ser Trp Ala His His Ile Ala
    2330            2335                2340

Leu Arg Leu Glu Val Leu Gly Cys Glu Ala Gln Gln Leu Tyr
    2345            2350                2355
```

```
<210> SEQ ID NO 36
<211> LENGTH: 2351
<212> TYPE: PRT
<213> ORGANISM: artificial sequence
<220> FEATURE:
<223> OTHER INFORMATION: ancestral

<400> SEQUENCE: 36

Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Glu Leu Leu Ser Glu Leu His Val Asp Thr
            35                  40                  45

Arg Phe Ser Pro Arg Val Pro Arg Ser Leu Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Lys Glu Lys Glu
    130                 135                 140

Asp Asp Lys Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Phe Ser His Val Asp Leu Val Lys Asp Leu Asn Ser Gly Leu
            180                 185                 190

Ile Gly Ala Leu Leu Val Cys Lys Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Asn Glu Ser Leu Thr Gln Ser Ala
225                 230                 235                 240

Gln Ala Gln His Glu Met His Thr Val Asn Gly Tyr Val Asn Arg Ser
                245                 250                 255

Leu Pro Gly Leu Thr Gly Cys His Lys Lys Ser Val Tyr Trp His Val
            260                 265                 270

Ile Gly Met Gly Thr Thr Pro Glu Val His Ser Ile Phe Leu Glu Gly
        275                 280                 285

His Thr Phe Leu Val Arg Asn His Arg Gln Ala Ser Leu Glu Ile Ser
    290                 295                 300

Pro Ile Thr Phe Leu Thr Ala Gln Thr Phe Leu Met Asp Leu Gly Gln
305                 310                 315                 320

Phe Leu Leu Phe Cys His Ile Ser Ser His Gln His Asp Gly Met Glu
                325                 330                 335

Ala Tyr Val Lys Val Asp Ser Cys Pro Glu Glu Pro Gln Leu Arg Met
            340                 345                 350

Lys Asn Asn Glu Glu Glu Asp Tyr Asp Asp Leu Tyr Asp Ser
        355                 360                 365
```

```
Asp Met Asp Val Val Arg Phe Asp Gly Asp Asn Ser Ser Pro Phe Ile
    370                 375                 380

Gln Ile Arg Ser Val Ala Lys Lys His Pro Lys Thr Trp Val His Tyr
385                 390                 395                 400

Ile Ala Ala Glu Glu Asp Trp Asp Tyr Ala Pro Ser Ala Pro Thr
                405                 410                 415

Pro Asn Asp Arg Ser Tyr Lys Asn Leu Tyr Leu Asn Asn Gly Pro Gln
            420                 425                 430

Arg Ile Gly Arg Lys Tyr Lys Val Arg Phe Met Ala Tyr Thr Asp
            435                 440                 445

Glu Thr Phe Lys Thr Arg Glu Ala Ile Gln Tyr Glu Ser Gly Ile Leu
    450                 455                 460

Gly Pro Leu Leu Tyr Gly Glu Val Gly Asp Thr Leu Leu Ile Ile Phe
465                 470                 475                 480

Lys Asn Gln Ala Ser Arg Pro Tyr Asn Ile Tyr Pro His Gly Ile Thr
                485                 490                 495

Asp Val Ser Pro Leu His Ser Gly Arg Leu Pro Lys Gly Val Lys His
            500                 505                 510

Leu Lys Asp Met Pro Ile Leu Pro Gly Glu Ile Phe Lys Tyr Lys Trp
    515                 520                 525

Thr Val Thr Val Glu Asp Gly Pro Thr Lys Ser Asp Pro Arg Cys Leu
530                 535                 540

Thr Arg Tyr Tyr Ser Ser Phe Ile Asn Leu Glu Arg Asp Leu Ala Ser
545                 550                 555                 560

Gly Leu Ile Gly Pro Leu Leu Ile Cys Tyr Lys Glu Ser Val Asp Gln
                565                 570                 575

Arg Gly Asn Gln Met Met Ser Asp Lys Arg Asn Val Ile Leu Phe Ser
            580                 585                 590

Val Phe Asp Glu Asn Arg Ser Trp Tyr Leu Thr Glu Asn Met Gln Arg
            595                 600                 605

Phe Leu Pro Asn Ala Asp Ala Val Gln Pro His Asp Pro Glu Phe Gln
    610                 615                 620

Val Ser Asn Ile Met His Ser Ile Asn Gly Tyr Val Phe Asp Asn Leu
625                 630                 635                 640

Gln Leu Ser Val Cys Leu His Glu Val Ala Tyr Trp Tyr Ile Leu Ser
                645                 650                 655

Val Gly Ala Gln Thr Asp Phe Leu Ser Val Phe Phe Ser Gly Tyr Thr
            660                 665                 670

Phe Lys His Lys Met Val Tyr Glu Asp Thr Leu Thr Leu Phe Pro Phe
    675                 680                 685

Ser Gly Glu Thr Val Phe Met Ser Met Glu Asn Pro Gly Leu Trp Val
    690                 695                 700

Leu Gly Cys His Asn Ser Asp Phe Arg Asn Arg Gly Met Thr Ala Leu
705                 710                 715                 720

Leu Lys Val Ser Ser Cys Asn Arg Asn Thr Gly Asp Tyr Tyr Glu Asp
                725                 730                 735

Thr Tyr Glu Asp Ile Pro Thr Ser Leu Leu Asn Glu Asn Asn Val Ile
            740                 745                 750

Glu Pro Arg Ser Phe Ser Gln Asn Ser Arg His Pro Ser Thr Arg Gln
            755                 760                 765

Lys Gln Phe Lys Ala Thr Thr Thr Pro Glu Asn Asp Ile Glu Lys Ile
    770                 775                 780
```

-continued

Asp Pro Gln Ser Gly Glu Arg Thr Gln Leu Leu Lys Val Gln Ser Val
785                 790                 795                 800

Ser Ser Ser Asp Leu Leu Met Leu Leu Gly Gln Asn Pro Thr Pro His
            805                 810                 815

Gly Leu Phe Leu Ser Asp Leu Gln Glu Ala Thr His Glu Ala Asp Asp
        820                 825                 830

His Leu Leu Gly Ala Ile Glu Arg Asn Lys Gly Pro Ser Glu Val Ala
    835                 840                 845

Ser Leu Arg Pro Glu Leu His His Ser Gly Asp Arg Val Phe Thr Pro
850                 855                 860

Glu Pro Glu Leu Gln Leu Arg Leu Asn Glu Asn Leu Gly Thr Thr Val
865                 870                 875                 880

Thr Val Glu Leu Lys Lys Leu Asp Leu Lys Ile Ser Ser Ser Ser Asp
                885                 890                 895

Asn Leu Met Thr Ser Pro Thr Ile Pro Ser Asp Lys Leu Ala Ala Gly
            900                 905                 910

Thr Glu Lys Thr Gly Ser Leu Gly Pro Pro Asn Met Ser Val His Phe
        915                 920                 925

Asn Ser His Leu Gly Thr Ile Val Phe Gly Lys Asn Ser Ser His Leu
    930                 935                 940

Ile Glu Ser Gly Val Pro Leu Gly Leu Ser Glu Gly Asp Asn Asp Ser
945                 950                 955                 960

Lys Leu Leu Glu Ala Ala Leu Met Asn Ser Gln Glu Ser Ser Leu Gly
                965                 970                 975

Glu Asn Val Leu Ser Met Glu Ser Asn Arg Leu Phe Lys Glu Glu Arg
            980                 985                 990

Val His Gly Pro Ala Ser Leu Ile Lys Asp Asn Ala Leu Phe Lys Val
        995                 1000                1005

Asn Ile Ser Leu Val Lys Thr Asn Lys Ala Pro Ile Asn Ser Thr
    1010                1015                1020

Thr Asn Arg Lys Thr His Val Asp Val Pro Thr Leu Leu Ile Glu
    1025                1030                1035

Asn Ser Thr Ser Val Trp Gln Asp Ile Ile Leu Glu Ser Asn Thr
    1040                1045                1050

Glu Phe Gln Glu Val Thr Ser Leu Ile His Asn Glu Thr Phe Met
    1055                1060                1065

Asp Arg Asn Thr Thr Ala Leu Gly Leu Asn His Val Ser Asn Lys
    1070                1075                1080

Thr Thr Ser Ser Lys Asn Val Glu Met Val His Gln Lys Lys Glu
    1085                1090                1095

Gly Pro Val Pro Leu Gly Ala Glu Asn Pro Asp Leu Ser Phe Phe
    1100                1105                1110

Lys Ile Leu Phe Leu Pro Asp Ser Ala Asn Trp Ile Lys Arg Thr
    1115                1120                1125

His Gly Lys Asn Ser Leu Ser Ser Gly Gln Arg Pro Ser Pro Lys
    1130                1135                1140

Gln Leu Thr Ser Leu Gly Ser Glu Lys Ser Val Lys Asp Gln Asn
    1145                1150                1155

Phe Leu Ser Glu Lys Lys Val Val Val Gly Glu Asp Glu Phe Thr
    1160                1165                1170

Lys Asp Thr Gly Leu Lys Glu Met Ile Phe Pro Asn Ser Lys Ser
    1175                1180                1185

```
Ile Phe Phe Thr Asn Leu Ala Asn Val Gln Glu Asn Asp Thr Tyr
1190                1195                1200

Asn Gln Glu Lys Lys Ser Gln Glu Glu Ile Glu Arg Lys Glu Lys
1205                1210                1215

Leu Thr Gln Glu Asn Val Val Leu Pro Gln Val Tyr Thr Val Thr
1220                1225                1230

Gly Thr Lys Asn Phe Leu Lys Asn Leu Phe Leu Thr Lys Gln Asn
1235                1240                1245

Val Thr Val Glu Gly Leu Asp Glu Gly Pro Tyr Thr Pro Ile Leu
1250                1255                1260

Gln Asp Thr Arg Ser Leu Asn Asp Ser Ala His Arg Ala Gly Ile
1265                1270                1275

His Met Ala His Phe Ser Lys Ile Arg Glu Glu Ala Asn Leu Glu
1280                1285                1290

Gly Leu Gly Asn Gln Thr Lys Gln Met Val Glu Arg Phe Pro Ser
1295                1300                1305

Thr Thr Arg Met Ser Pro Asn Pro Ser Gln His Asn Val Ile Thr
1310                1315                1320

Gln Arg Gly Lys Arg Ala Leu Lys Gln Pro Arg Leu Ser Leu Glu
1325                1330                1335

Glu Ile Lys Phe Glu Arg Gly Val Ile Leu Asn Asp Thr Ser Thr
1340                1345                1350

Gln Trp Ser Lys Asn Met Asn Tyr Leu Thr Gln Gly Thr Leu Thr
1355                1360                1365

Gln Ile Glu Tyr Asn Glu Lys Glu Lys Arg Ala Ile Thr Gln Ser
1370                1375                1380

Leu Leu Ser Asp Cys Ser Met Arg Asn His Gly Thr Ile Gln Met
1385                1390                1395

Asn Asp Ser Ala Leu Pro Ile Ala Lys Val Ser Ala Phe Pro Ser
1400                1405                1410

Ile Arg His Thr Asp Leu Thr Lys Ile Pro Ser Gln Asp Asn Ser
1415                1420                1425

Ser His Leu Pro Ala Ser Ala Cys Ser Tyr Thr Phe Arg Glu Arg
1430                1435                1440

Ser Ser Gly Val Gln Glu Ser Ser His Phe Leu Gln Gly Ala Lys
1445                1450                1455

Arg Asn Asn Leu Ser Leu Ala Phe Leu Thr Leu Glu Met Ile Arg
1460                1465                1470

Gly Gln Gly Lys Phe Ser Ser Leu Gly Lys Ser Ala Thr Asn Gln
1475                1480                1485

Pro Met Tyr Lys Lys Leu Glu Asn Thr Val Leu Leu Lys Pro Gly
1490                1495                1500

Leu Ser Glu Ala Ser Gly Lys Val Glu Leu Leu Pro Lys Val His
1505                1510                1515

Val His Gln Glu Asp Ser Phe Pro Thr Lys Thr Ser Asn Asp Ser
1520                1525                1530

Pro Gly His Leu Asp Leu Met Glu Lys Ile Phe Leu Gln Lys Thr
1535                1540                1545

Gln Gly Pro Val Lys Leu Asn Lys Val Asn Arg Pro Gly Lys Val
1550                1555                1560

Pro Phe Leu Lys Trp Ala Thr Glu Ser Ser Glu Lys Ile Pro Ser
1565                1570                1575
```

Lys Leu Leu Gly Pro Leu Ala Trp Asp Asn His Tyr Ala Thr Gln
1580            1585                1590

Ile Pro Arg Glu Glu Trp Lys Ser Gln Lys Lys Ser Gln Lys Asn
1595            1600                1605

Thr Ala Phe Lys Thr Lys Asp Thr Ile Leu Pro Leu Gly Pro Cys
1610            1615                1620

Glu Asn Asn His Ser Ile Ala Ala Ile Asn Glu Gly Gln Asp Lys
1625            1630                1635

Pro Gln Arg Glu Ala Thr Trp Ala Lys Gln Gly Glu Thr Gly Arg
1640            1645                1650

Leu Cys Ser Gln Asn Pro Pro Val Ser Lys Arg His Gln Arg Glu
1655            1660                1665

Ile Thr Leu Thr Thr Leu Gln Pro Glu Glu Asp Lys Ile Glu Tyr
1670            1675                1680

Asp Asp Thr Phe Ser Ile Glu Met Lys Arg Glu Asp Phe Asp Ile
1685            1690                1695

Tyr Gly Glu Asp Glu Asn Gln Gly Leu Arg Ser Phe Gln Lys Arg
1700            1705                1710

Thr Arg His Tyr Phe Ile Ala Ala Val Glu Arg Leu Trp Asp Tyr
1715            1720                1725

Gly Met Ser Arg Ser Pro His Ala Leu Arg Asn Arg Ala Gln Ser
1730            1735                1740

Gly Asp Val Pro Gln Phe Lys Lys Val Val Phe Gln Glu Phe Thr
1745            1750                1755

Asp Gly Ser Phe Thr Gln Pro Leu Tyr Arg Gly Glu Leu Asn Glu
1760            1765                1770

His Leu Gly Leu Leu Gly Pro Tyr Ile Arg Ala Glu Val Glu Asp
1775            1780                1785

Asn Ile Met Val Thr Phe Lys Asn Gln Ala Ser Arg Pro Tyr Ser
1790            1795                1800

Phe Tyr Ser Ser Leu Ile Ser Tyr Glu Glu Asp Gln Arg Gln Gly
1805            1810                1815

Ala Glu Pro Arg Lys Lys Phe Val Asn Pro Asn Glu Thr Lys Ile
1820            1825                1830

Tyr Phe Trp Lys Val Gln His His Met Ala Pro Thr Lys Asp Glu
1835            1840                1845

Phe Asp Cys Lys Ala Trp Ala Tyr Phe Ser Asp Val Asp Leu Glu
1850            1855                1860

Lys Asp Val His Ser Gly Leu Ile Gly Pro Leu Leu Ile Cys Arg
1865            1870                1875

Ser Asn Thr Leu Asn Pro Ala His Gly Arg Gln Val Thr Val Gln
1880            1885                1890

Glu Phe Ala Leu Phe Phe Thr Ile Phe Asp Glu Thr Lys Ser Trp
1895            1900                1905

Tyr Phe Thr Glu Asn Met Glu Arg Asn Cys Arg Ala Pro Cys Asn
1910            1915                1920

Ile Gln Lys Glu Asp Pro Thr Phe Lys Glu Asn Tyr Arg Phe His
1925            1930                1935

Ala Ile Asn Gly Tyr Val Met Asp Thr Leu Pro Gly Leu Val Met
1940            1945                1950

Ala Gln Asp Gln Lys Ile Arg Trp Tyr Leu Leu Ser Met Gly Ser
1955            1960                1965

Asn Glu Asn Ile His Ser Ile His Phe Ser Gly His Val Phe Thr
    1970            1975            1980

Val Arg Lys Lys Glu Glu Tyr Lys Met Ala Val Tyr Asn Leu Tyr
    1985            1990            1995

Pro Gly Val Phe Glu Thr Val Glu Met Leu Pro Ser Lys Val Gly
    2000            2005            2010

Ile Trp Arg Ile Glu Cys Leu Ile Gly Glu His Leu Gln Ala Gly
    2015            2020            2025

Met Ser Thr Leu Phe Leu Val Tyr Ser Lys Lys Cys Gln Thr Pro
    2030            2035            2040

Leu Gly Met Ala Ser Gly His Ile Arg Asp Phe Gln Ile Thr Ala
    2045            2050            2055

Ser Gly Gln Tyr Gly Gln Trp Ala Pro Lys Leu Ala Arg Leu His
    2060            2065            2070

Tyr Ser Gly Ser Ile Asn Ala Trp Ser Thr Lys Asp Pro Phe Ser
    2075            2080            2085

Trp Ile Lys Val Asp Leu Leu Ala Pro Met Ile Ile His Ser Ile
    2090            2095            2100

Met Thr Gln Gly Ala Arg Gln Lys Phe Ser Ser Leu Tyr Ile Ser
    2105            2110            2115

Gln Phe Ile Ile Met Tyr Ser Leu Asp Gly Lys Lys Trp Gln Ser
    2120            2125            2130

Tyr Arg Gly Asn Ser Thr Gly Thr Leu Met Val Phe Phe Gly Asn
    2135            2140            2145

Val Asp Ser Ser Gly Ile Lys His Asn Ile Phe Asn Pro Pro Ile
    2150            2155            2160

Ile Ala Arg Tyr Ile Arg Leu His Pro Thr His Tyr Ser Ile Arg
    2165            2170            2175

Ser Thr Leu Arg Met Glu Leu Met Gly Cys Asp Leu Asn Ser Cys
    2180            2185            2190

Ser Met Pro Leu Gly Met Glu Asn Lys Ala Ile Ser Asp Ala Gln
    2195            2200            2205

Ile Thr Ala Ser Ser Tyr Leu Asn Ser Met Phe Ala Thr Trp Ser
    2210            2215            2220

Pro Ser Gln Ala Arg Leu His Leu Gln Gly Arg Thr Asn Ala Trp
    2225            2230            2235

Arg Pro Gln Ala Asn Asn Pro Lys Glu Trp Leu Gln Val Asp Phe
    2240            2245            2250

Gln Lys Thr Met Lys Val Thr Gly Ile Thr Thr Gln Gly Val Lys
    2255            2260            2265

Ser Leu Leu Thr Ser Met Tyr Val Lys Glu Phe Leu Ile Ser Ser
    2270            2275            2280

Ser Gln Asp Gly His Asn Trp Thr Leu Phe Leu Gln Asn Gly Lys
    2285            2290            2295

Val Lys Val Phe Gln Gly Asn Gln Asp Ser Phe Thr Pro Val Val
    2300            2305            2310

Asn Ser Leu Asp Pro Pro Leu Leu Thr Arg Tyr Leu Arg Ile His
    2315            2320            2325

Pro Gln Ser Trp Ala His Gln Ile Ala Leu Arg Leu Glu Val Leu
    2330            2335            2340

Gly Cys Glu Ala Gln Gln Leu Tyr
    2345            2350

<210> SEQ ID NO 37
<211> LENGTH: 2331
<212> TYPE: PRT
<213> ORGANISM: artificial sequence
<220> FEATURE:
<223> OTHER INFORMATION: ancestral

<400> SEQUENCE: 37

```
Met Gln Ile Glu Leu Ser Thr Cys Phe Phe Leu Cys Leu Leu Pro Phe
1               5                   10                  15

Ser Phe Ser Ala Thr Arg Arg Tyr Tyr Leu Gly Thr Val Glu Leu Ser
            20                  25                  30

Trp Asp Tyr Met Gln Ser Glu Leu Leu Ser Glu Leu His Val Asp Thr
        35                  40                  45

Arg Phe Pro Pro Arg Val Pro Arg Ser Phe Pro Phe Asn Pro Ser Val
    50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Ile Pro Gly Glu Ser Tyr Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
        195                 200                 205

Thr Gln Thr Leu His Glu Phe Val Leu Leu Phe Ala Val Phe Asp Glu
    210                 215                 220

Gly Lys Ser Trp His Ser Glu Thr Asn Glu Ser Leu Thr Gln Ala Met
225                 230                 235                 240

Asp Pro Ala Ser Ala Arg Ala Gln Pro Glu Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Ser Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
            340                 345                 350

Pro Gln Leu Arg Met Lys Asn Asn Glu Glu Glu Glu Asp Tyr Asp Asp
        355                 360                 365
```

```
Asp Leu Tyr Asp Ser Asp Met Asp Val Val Arg Phe Asp Gly Asp Asn
        370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Asp Trp Asp Tyr Ala
                405                 410                 415

Pro Ser Val Leu Thr Pro Asn Asp Arg Ser Tyr Lys Ser Leu Tyr Leu
                420                 425                 430

Asn Asn Gly Pro Gln Gln Ile Gly Arg Lys Tyr Lys Lys Ala Arg Phe
            435                 440                 445

Met Ala Tyr Thr Asp Glu Thr Phe Lys Thr Arg Glu Ala Ile Gln Tyr
        450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510

Lys Gly Val Lys His Leu Lys Asp Met Pro Ile Leu Pro Gly Glu Ile
        515                 520                 525

Phe Lys Tyr Lys Trp Thr Val Thr Val Glu Asp Gly Pro Thr Lys Ser
        530                 535                 540

Asp Pro Arg Cys Leu Thr Arg Tyr Tyr Ser Ser Phe Val Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Asp Gly Val Gln Pro Gln
610                 615                 620

Asp Pro Glu Phe Gln Val Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
        690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asn Arg Asn Thr Gly
                725                 730                 735

Asp Tyr Tyr Glu Asp Thr Tyr Glu Asp Ile Pro Thr Ser Leu Leu Asn
            740                 745                 750

Glu Asn Asn Val Ile Glu Pro Arg Ser Phe Ser Gln Asn Ser Arg His
        755                 760                 765

Pro Ser Thr Arg Gln Lys Gln Phe Lys Ala Thr Thr Thr Pro Glu Asn
770                 775                 780
```

```
Asp Val Glu Lys Ile Asp Leu Arg Ser Gly Glu Arg Thr Gln Leu Leu
785                 790                 795                 800

Lys Val Gln Ser Val Ser Ser Asp Leu Leu Met Leu Leu Gly Gln
            805                 810                 815

Asn Pro Thr Pro His Ala Leu Ser Leu Ser Asp Leu Gln Glu Val Thr
                820                 825                 830

Tyr Glu Ala Asp Asp His Leu Pro Gly Thr Ile Glu Arg Asn Lys Gly
            835                 840                 845

Pro Ser Glu Val Ala His Leu Arg Pro Glu Leu His Ser Gly Asp
    850                 855                 860

Arg Val Phe Thr Pro Glu Pro Glu Leu Gln Leu Arg Leu Asn Glu Asn
865                 870                 875                 880

Leu Gly Thr Thr Ile Thr Val Glu Leu Lys Lys Leu Asp Leu Lys Ile
                885                 890                 895

Ser Ser Ser Ser Asn Asn Leu Met Ile Ser Pro Thr Ile Pro Ser Asp
                900                 905                 910

Lys Leu Ala Ala Gly Thr Glu Lys Thr Gly Ser Leu Gly Pro Pro Asn
            915                 920                 925

Met Pro Val His Phe Ser Ser Gln Leu Gly Thr Ile Val Phe Gly Lys
930                 935                 940

Asn Ser Ser His Leu Ile Glu Ser Ala Val Pro Leu Gly Leu Ser Glu
945                 950                 955                 960

Gly Asp Asn Asp Ser Lys Leu Ile Glu Ala Ala Leu Met Asn Ser Gln
                965                 970                 975

Glu Ser Ser Leu Glu Glu Asn Val Leu Ser Met Glu Ser Asp Arg Leu
            980                 985                 990

Phe Lys Glu Glu Arg Val His Gly Pro Val Ser Leu Thr Lys Asp Asn
            995                 1000                1005

Ala Leu Phe Lys Val Asn Phe Ser Leu Val Lys Thr Asn Lys Ala
    1010                1015                1020

Pro Ile Asn Ser Thr Thr Asn Arg Lys Thr His Ile Asp Gly Pro
    1025                1030                1035

Thr Leu Leu Ile Glu Asn Ser Thr Ser Val Trp Gln Asp Ile Ile
    1040                1045                1050

Leu Glu Ser Asn Ser Gly Phe Gln Glu Val Thr Ser Leu Ile His
    1055                1060                1065

Asp Glu Thr Phe Met Asp Lys Asn Thr Thr Ala Leu Gly Leu Asn
    1070                1075                1080

His Val Ser Asn Lys Thr Thr Ser Ser Lys Asn Met Glu Met Val
    1085                1090                1095

His Gln Lys Lys Glu Asp Pro Ala Pro Leu Gly Ala Glu Asn Pro
    1100                1105                1110

Asp Ile Ser Phe Phe Lys Met Leu Phe Leu Pro Asp Ser Ala Asn
    1115                1120                1125

Trp Ile Lys Arg Thr His Cys Lys Asn Ser Leu Ser Ser Gly Gln
    1130                1135                1140

Arg Pro Ser Pro Lys Gln Leu Thr Ser Leu Gly Ser Glu Lys Ser
    1145                1150                1155

Val Lys Asp Gln Asn Phe Leu Ser Glu Lys Asn Lys Val Val Val
    1160                1165                1170

Gly Glu Asp Glu Phe Thr Lys Asp Thr Gly Leu Lys Glu Met Ile
    1175                1180                1185
```

```
Phe Pro Asn Ser Lys Ser Ile Phe Leu Thr Asn Leu Ala Asn Val
    1190            1195                1200

Gln Glu Asn Asp Thr His Asn Gln Glu Lys Asn Ser Gln Glu Glu
    1205            1210                1215

Ile Glu Arg Lys Glu Lys Leu Ile Gln Lys Asn Val Val Leu Pro
    1220            1225                1230

Gln Val Tyr Thr Val Thr Gly Thr Lys Asn Phe Leu Lys Asn Leu
    1235            1240                1245

Phe Leu Leu Ser Thr Lys Gln Asn Val Glu Gly Leu Asp Glu Gly
    1250            1255                1260

Thr Tyr Thr Pro Ile Leu Gln Asp Thr Arg Ser Leu Asn Glu Ser
    1265            1270                1275

Ala Asn Arg Ala Arg Ile His Met Ala His Phe Ser Lys Ile Arg
    1280            1285                1290

Glu Glu Ala Asn Leu Glu Gly Leu Gly Asn Gln Thr Lys Gln Met
    1295            1300                1305

Val Glu Lys Tyr Pro Ser Thr Thr Arg Met Ser Pro Asn Pro Arg
    1310            1315                1320

Gln Gln Asn Val Ile Thr His His Gly Lys Arg Ala Leu Lys Gln
    1325            1330                1335

Phe Arg Leu Pro Gln Glu Glu Ile Lys Leu Glu Arg Gly Val Ile
    1340            1345                1350

Leu Asn Asp Thr Ser Thr Gln Trp Ser Lys Asn Met Lys Tyr Leu
    1355            1360                1365

Thr Gln Gly Thr Leu Thr Gln Ile Glu Tyr Asn Glu Lys Glu Lys
    1370            1375                1380

Arg Ala Ile Thr Gln Ser Leu Leu Ser Asp Cys Ser Val Arg Ser
    1385            1390                1395

His Gly Ile Ile Gln Thr Asn Gly Ser Ala Leu Pro Ile Ala Lys
    1400            1405                1410

Val Ser Ala Phe Pro Ser Ile Arg Pro Thr Asp Leu Thr Lys Ile
    1415            1420                1425

Pro Ser Gln Asp Asn Ser Ser His Leu Leu Ala Ser Ala Cys Ser
    1430            1435                1440

Tyr Thr Phe Arg Glu Lys Ser Ser Gly Ile Gln Glu Ser Ser His
    1445            1450                1455

Phe Leu Gln Gly Ala Lys Arg Asn Asn Leu Ser Leu Ala Phe Leu
    1460            1465                1470

Thr Leu Glu Met Ile Arg Gly Gln Gly Lys Ile Ser Ser Leu Gly
    1475            1480                1485

Lys Leu Ser Glu Ala Ser Gly Lys Val Glu Leu Leu Pro Lys Val
    1490            1495                1500

His Val His Gln Glu Asp Ser Phe Pro Thr Lys Thr Ser Asn Gly
    1505            1510                1515

Ser Pro Gly His Leu Asp Leu Met Glu Glu Ile Phe Leu Gln Lys
    1520            1525                1530

Thr Gln Gly Pro Val Lys Leu Asn Lys Val Asn Arg Pro Gly Lys
    1535            1540                1545

Ile Pro Phe Leu Lys Trp Ala Ala Glu Ser Ser Glu Lys Thr Pro
    1550            1555                1560

Ser Lys Leu Leu Gly Pro Leu Ala Thr Gln Ile Pro Arg Glu Glu
    1565            1570                1575
```

```
Trp Asn Ser Gln Glu Lys Ser Gln Lys Asn Lys Ala Phe Lys Thr
1580                1585                1590

Lys Asp Thr Ile Ser Pro Leu Asp Pro Cys Glu Asn Asn His Ser
1595                1600                1605

Ile Ala Ala Ile Asn Lys Gly Gln Asp Lys Pro Gln Arg Glu Ala
1610                1615                1620

Thr Trp Ala Lys Gln Glu Glu Thr Gly Arg Leu Cys Ser Gln Asn
1625                1630                1635

Pro Pro Val Leu Lys Arg His Gln Arg Gln Ile Thr Leu Thr Thr
1640                1645                1650

Val Gln Pro Glu Glu Asp Lys Ile Asp Tyr Asp Asp Thr Phe Ser
1655                1660                1665

Thr Glu Thr Lys Arg Glu Asp Phe Asp Ile Tyr Gly Glu Asp Glu
1670                1675                1680

Asn Gln Asp Pro Arg Ser Phe Gln Lys Arg Thr Arg His Tyr Phe
1685                1690                1695

Ile Ala Ala Val Glu Arg Leu Trp Asp Tyr Gly Met Ser Arg Ser
1700                1705                1710

Pro His Ala Leu Arg Asn Arg Ala Gln Ser Gly Asp Val Pro Gln
1715                1720                1725

Phe Lys Lys Val Val Phe Gln Glu Phe Thr Asp Gly Ser Phe Thr
1730                1735                1740

Gln Pro Leu Tyr Arg Gly Glu Leu Asn Glu His Leu Gly Leu Leu
1745                1750                1755

Gly Pro Tyr Ile Arg Ala Glu Val Glu Asp Asn Ile Met Val Thr
1760                1765                1770

Phe Lys Asn Gln Ala Ser Arg Pro Tyr Ser Phe Tyr Ser Ser Leu
1775                1780                1785

Ile Ser Tyr Glu Asp Asp Gln Arg Gln Gly Ala Glu Pro Arg Lys
1790                1795                1800

Lys Phe Val Lys Pro Asn Glu Thr Glu Val Tyr Phe Trp Lys Val
1805                1810                1815

Gln His His Met Ala Pro Thr Lys Asp Glu Phe Asp Cys Lys Ala
1820                1825                1830

Trp Ala Tyr Phe Ser Asp Val Asp Leu Asp Lys Asp Val His Ser
1835                1840                1845

Gly Leu Val Gly Pro Leu Leu Ile Cys Arg Ala Asn Thr Leu Asn
1850                1855                1860

Pro Ala His Gly Arg Gln Val Thr Val Gln Glu Phe Ala Leu Phe
1865                1870                1875

Phe Thr Ile Phe Asp Glu Thr Lys Ser Trp Tyr Phe Thr Glu Asn
1880                1885                1890

Met Glu Arg Asn Cys Arg Ala Pro Cys Asn Ile Gln Met Glu Asp
1895                1900                1905

Pro Thr Phe Lys Glu Asn Tyr Arg Phe His Ala Ile Asn Gly Tyr
1910                1915                1920

Val Met Asp Thr Leu Pro Gly Leu Val Met Ala Gln Asp Gln Arg
1925                1930                1935

Ile Arg Trp Tyr Leu Leu Ser Met Gly Ser Asn Glu Asn Ile His
1940                1945                1950

Ser Ile His Phe Ser Gly His Val Phe Thr Val Arg Lys Lys Glu
1955                1960                1965
```

```
Glu Tyr Lys Met Ala Val Tyr Asn Leu Tyr Pro Gly Val Phe Glu
    1970            1975                1980
Thr Val Glu Met Leu Pro Ser Lys Val Gly Ile Trp Arg Ile Glu
    1985            1990                1995
Cys Leu Ile Gly Glu His Leu Gln Ala Gly Met Ser Thr Leu Phe
    2000            2005                2010
Leu Val Tyr Ser Lys Lys Cys Gln Thr Pro Leu Gly Met Ala Ser
    2015            2020                2025
Gly His Ile Arg Asp Phe Gln Ile Thr Ala Ser Gly Gln Tyr Gly
    2030            2035                2040
Gln Trp Ala Pro Lys Leu Ala Arg Leu His Tyr Ser Gly Ser Ile
    2045            2050                2055
Asn Ala Trp Ser Thr Lys Asp Pro Phe Ser Trp Ile Lys Val Asp
    2060            2065                2070
Leu Leu Ala Pro Met Ile Ile His Ser Ile Met Thr Gln Gly Ala
    2075            2080                2085
Arg Gln Lys Phe Ser Ser Leu Tyr Ile Ser Gln Phe Ile Ile Met
    2090            2095                2100
Tyr Ser Leu Asp Gly Lys Lys Trp Gln Ser Tyr Arg Gly Asn Ser
    2105            2110                2115
Thr Gly Thr Leu Met Val Phe Phe Gly Asn Val Asp Ser Ser Gly
    2120            2125                2130
Ile Lys His Asn Ile Phe Asn Pro Pro Ile Ile Ala Arg Tyr Ile
    2135            2140                2145
Arg Leu His Pro Thr His Tyr Ser Ile Arg Ser Thr Leu Arg Met
    2150            2155                2160
Glu Leu Met Gly Cys Asp Leu Asn Ser Cys Ser Met Pro Leu Gly
    2165            2170                2175
Met Glu Asn Lys Ala Ile Ala Asp Ala Gln Ile Thr Ala Ser Ser
    2180            2185                2190
Tyr Leu Asn Asn Met Phe Ala Thr Trp Ser Pro Ser Gln Ala Arg
    2195            2200                2205
Leu His Leu Gln Gly Arg Thr Asn Ala Trp Arg Pro Arg Val Asn
    2210            2215                2220
Asn Pro Lys Glu Trp Leu Gln Val Asp Phe Gln Lys Thr Met Lys
    2225            2230                2235
Val Thr Gly Ile Thr Thr Gln Gly Val Lys Ser Leu Leu Thr Ser
    2240            2245                2250
Met Tyr Val Lys Glu Phe Leu Ile Ser Ser Ser Gln Asp Gly His
    2255            2260                2265
Asn Trp Thr Leu Phe Leu Gln Asn Gly Lys Val Lys Val Phe Gln
    2270            2275                2280
Gly Asn Gln Asp Ser Phe Thr Pro Val Val Asn Ser Leu Asp Pro
    2285            2290                2295
Pro Leu Leu Thr Arg Tyr Leu Arg Ile His Pro Gln Ser Trp Gly
    2300            2305                2310
His Gln Ile Ala Leu Arg Leu Glu Val Leu Gly Cys Glu Ala Gln
    2315            2320                2325
Gln Leu Tyr
    2330

<210> SEQ ID NO 38
<211> LENGTH: 2358
```

```
<212> TYPE: PRT
<213> ORGANISM: artificial sequence
<220> FEATURE:
<223> OTHER INFORMATION: ancestral

<400> SEQUENCE: 38
```

| | | | | | | | | | | | | | | |
|---|---|---|---|---|---|---|---|---|---|---|---|---|---|---|
| Met | Gln | Ile | Glu | Leu | Ser | Val | Cys | Phe | Phe | Leu | Cys | Leu | Leu | Pro | Phe |
| 1 | | | | 5 | | | | | 10 | | | | | 15 | |
| Ser | Phe | Ser | Ala | Thr | Arg | Arg | Tyr | Tyr | Leu | Gly | Ala | Val | Glu | Leu | Ser |
| | | | 20 | | | | | 25 | | | | | 30 | | |
| Trp | Asp | Tyr | Met | Gln | Ser | Asp | Leu | Leu | Ser | Glu | Leu | His | Val | Asp | Thr |
| | | | 35 | | | | | 40 | | | | | 45 | | |
| Arg | Leu | Leu | Pro | Arg | Val | Pro | Arg | Ser | Phe | Pro | Phe | Asn | Thr | Ser | Val |
| | 50 | | | | | 55 | | | | | 60 | | | | |
| Met | Phe | Lys | Lys | Thr | Val | Phe | Val | Glu | Phe | Thr | Asp | His | Leu | Phe | Asn |
| 65 | | | | | 70 | | | | | 75 | | | | | 80 |
| Ile | Ala | Lys | Pro | Arg | Pro | Pro | Trp | Met | Gly | Leu | Leu | Gly | Pro | Thr | Ile |
| | | | | 85 | | | | | 90 | | | | | 95 | |
| Arg | Ala | Glu | Val | Tyr | Asp | Thr | Val | Ile | Ile | Thr | Leu | Lys | Asn | Met | Ala |
| | | | 100 | | | | | 105 | | | | | 110 | | |
| Ser | His | Pro | Val | Ser | Leu | His | Ala | Val | Gly | Val | Ser | Tyr | Trp | Lys | Ala |
| | | | 115 | | | | | 120 | | | | | 125 | | |
| Ser | Glu | Gly | Ala | Glu | Tyr | Asp | Asp | Lys | Thr | Ser | Gln | Arg | Glu | Lys | Glu |
| | 130 | | | | | 135 | | | | | 140 | | | | |
| Asp | Asp | Lys | Val | Ile | Pro | Gly | Glu | Ser | His | Thr | Tyr | Ile | Trp | Gln | Val |
| 145 | | | | | 150 | | | | | 155 | | | | | 160 |
| Leu | Lys | Glu | Asn | Gly | Pro | Met | Ala | Ser | Asp | Pro | Pro | Cys | Leu | Thr | Tyr |
| | | | | 165 | | | | | 170 | | | | | 175 | |
| Ser | Tyr | Leu | Ser | His | Val | Asp | Leu | Val | Lys | Asp | Leu | Asn | Ser | Gly | Leu |
| | | | 180 | | | | | 185 | | | | | 190 | | |
| Ile | Gly | Ala | Leu | Leu | Val | Cys | Arg | Glu | Gly | Ser | Leu | Ala | Lys | Glu | Arg |
| | | | 195 | | | | | 200 | | | | | 205 | | |
| Thr | Gln | Thr | Leu | His | Glu | Phe | Val | Leu | Leu | Phe | Ala | Val | Phe | Asp | Glu |
| | 210 | | | | | 215 | | | | | 220 | | | | |
| Gly | Lys | Ser | Trp | His | Ser | Glu | Ala | Asn | Glu | Ser | Leu | Ala | Gln | Gly | Val |
| 225 | | | | | 230 | | | | | 235 | | | | | 240 |
| Asp | Ser | Ala | Ser | Thr | Arg | Pro | Trp | Pro | Lys | Met | Tyr | Thr | Val | Asn | Gly |
| | | | | 245 | | | | | 250 | | | | | 255 | |
| Tyr | Val | Asn | Arg | Ser | Leu | Pro | Gly | Leu | Ile | Gly | Cys | His | Arg | Lys | Ser |
| | | | 260 | | | | | 265 | | | | | 270 | | |
| Val | Tyr | Trp | His | Val | Ile | Gly | Met | Gly | Thr | Thr | Pro | Glu | Val | His | Ser |
| | | | 275 | | | | | 280 | | | | | 285 | | |
| Ile | Phe | Leu | Glu | Gly | His | Thr | Phe | Leu | Val | Arg | Asn | His | Arg | Gln | Ala |
| | 290 | | | | | 295 | | | | | 300 | | | | |
| Ser | Leu | Glu | Ile | Ser | Pro | Ile | Thr | Phe | Leu | Thr | Ala | Gln | Thr | Leu | Leu |
| 305 | | | | | 310 | | | | | 315 | | | | | 320 |
| Met | Asp | Leu | Gly | Gln | Phe | Leu | Leu | Phe | Cys | His | Ile | Pro | Ser | His | Gln |
| | | | | 325 | | | | | 330 | | | | | 335 | |
| His | Asp | Gly | Met | Glu | Ala | Tyr | Val | Lys | Val | Asp | Ser | Cys | Pro | Glu | Glu |
| | | | 340 | | | | | 345 | | | | | 350 | | |
| Pro | Gln | Leu | Arg | Lys | Lys | Asn | Asn | Glu | Glu | Glu | Glu | Asp | Tyr | Glu | Asp |
| | | | 355 | | | | | 360 | | | | | 365 | | |
| Asp | Leu | Tyr | Asp | Ser | Asp | Met | Asp | Val | Leu | Arg | Phe | Asp | Asp | Asp | Asn |
| | 370 | | | | | 375 | | | | | 380 | | | | |

```
Ser Pro Pro Phe Ile Gln Ile Arg Ser Val Ala Lys Lys His Pro Lys
385                 390                 395                 400

Thr Trp Ile His Tyr Ile Ala Glu Glu Asp Trp Asp Tyr Ala
            405                 410                 415

Pro Ala Val Leu Pro Ser Thr Asp Arg Ser Tyr Lys Ser Gln Tyr Leu
            420                 425                 430

Asn Asn Gly Thr Gln Arg Ile Gly Arg Lys Tyr Lys Val Arg Phe
            435                 440                 445

Ile Ala Tyr Thr Asp Glu Thr Phe Gln Thr Arg Glu Ala Ile Gln Tyr
450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
            485                 490                 495

Pro His Gly Ile Thr Asn Val Ser Pro Leu His Ser Gly Arg Leu Pro
            500                 505                 510

Lys Gly Val Lys His Leu Lys Asp Leu Gln Ile Met Pro Gly Glu Ile
            515                 520                 525

Phe Lys Tyr Lys Trp Thr Val Thr Val Glu Asp Gly Pro Thr Lys Ser
            530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
            565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
            595                 600                 605

Glu Asn Met Gln Arg Phe Leu Pro Asn Ala Ala Gly Val Gln Pro Gln
            610                 615                 620

Asp Pro Glu Phe Gln Ala Ser Asn Met Met Tyr Ser Ile Asn Gly Tyr
625                 630                 635                 640

Val Phe Asp Asn Leu Gln Leu Ser Val Cys Leu His Glu Val Ala Tyr
            645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Phe Glu Asp Thr Leu
            675                 680                 685

Thr Leu Phe Pro Phe Ser Gly Glu Thr Val Phe Met Ser Met Glu Asn
            690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Asp
            725                 730                 735

Asp Tyr Tyr Glu Asp Thr Tyr Glu Asp Ile Pro Thr Tyr Leu Leu Asn
            740                 745                 750

Glu Asn Ser Val Ile Glu Pro Arg Ser Phe Ser Gln Asn Ser Arg His
            755                 760                 765

Pro Ser Pro Arg Gln Lys Gln Phe Lys Ala Thr Thr Ala Pro Glu Asn
            770                 775                 780

Asp Ile Glu Lys Met Asp Pro Arg Phe Gly Glu Arg Thr Gln Leu Leu
785                 790                 795                 800
```

```
Lys Ala Gln Ser Val Ser Ser Asp Leu Leu Met Leu Gly Gln
            805                 810                 815

Ser Pro Thr Pro His Gly Leu Ser Leu Ser Asp Leu Gln Glu Ala Lys
            820                 825                 830

Tyr Glu Ala Ile Pro Asp Asp Pro Ser Pro Gly Ala Ile Glu Asn Lys
            835                 840                 845

Glu Gly Pro Ser Glu Val Ala His Leu Arg Pro Glu Leu His His Ser
        850                 855                 860

Glu Asp Met Val Phe Thr Pro Glu Pro Gly Leu Gln Leu Arg Leu Asn
865                 870                 875                 880

Glu Asn Leu Glu Thr Thr Ile Thr Glu Asp Leu Lys Lys Leu Asp Leu
            885                 890                 895

Lys Val Ser Ser Ser Asn Asn Val Met Thr Ser Pro Ile Ser Ser
            900                 905                 910

Ser Asp Asn Leu Pro Ala Asp Thr Glu Lys Thr Asp Ser Leu Gly Pro
            915                 920                 925

Leu Asn Thr Pro Val His Phe Ser Ser Gln Leu Gly Thr Ile Leu Phe
            930                 935                 940

Gly Lys Lys Ser Ser Pro Leu Ile Gly Ser Gly Val Pro Leu Asn Leu
945                 950                 955                 960

Ser Glu Arg Asp Asn Asp Ser Thr Leu Leu Glu Ala Ala Leu Met Ser
            965                 970                 975

Ser Gln Glu Ser Ser Leu Gly Lys Lys Val Ser Ser Met Glu Ser Asp
            980                 985                 990

Arg Leu Phe Lys Glu Lys Lys Val His Gly Pro Ala Ser Leu Thr Lys
            995                 1000                1005

Asp Asn Ala Leu Phe Lys Val Asn Ile Ser Leu Val Lys Thr Asn
        1010                1015                1020

Lys Thr Pro Asn Asn Ser Thr Asn Arg Lys Thr His Ile Asp
        1025                1030                1035

Gly Pro Thr Leu Leu Asn Glu Asn Ser Thr Ser Gly Trp Gln Asp
        1040                1045                1050

Ile Leu Lys Asn Asp Thr Glu Phe Gln Glu Val Thr Ser Leu Ile
        1055                1060                1065

His Asn Glu Met Phe Met Asp Lys Asn Thr Thr Ala Leu Gly Leu
        1070                1075                1080

Asn His Val Ser Asn Lys Thr Thr Ser Ser Lys Asp Met Glu Met
        1085                1090                1095

Val His Gln Lys Lys Glu Asp Pro Val Ser Leu Asp Ala Glu Asn
        1100                1105                1110

Pro Asp Met Ser Phe Phe Lys Met Leu Phe Leu Pro Asp Ser Ala
        1115                1120                1125

Asn Trp Ile Lys Arg Thr His Gly Lys Asn Ser Leu Ser Ser Glu
        1130                1135                1140

Gln Gly Pro Ser Pro Lys Gln Leu Ile Ser Leu Gly Ser Glu Asn
        1145                1150                1155

Ser Val Lys Asp Gln Asn Phe Leu Ser Glu Lys Asn Lys Val Ala
        1160                1165                1170

Val Gly Glu Asp Glu Phe Thr Lys Asp Thr Gly Phe Lys Glu Met
        1175                1180                1185

Ile Phe Pro Asn Ser Lys Ser Ile Phe Leu Thr Asn Leu Ala Asn
        1190                1195                1200
```

-continued

| | | | | | | | | | | | |
|---|---|---|---|---|---|---|---|---|---|---|---|
|Val|Gln 1205|Glu|Asn|Asp|Thr 1210|Gln|Asn|Glu|Lys 1215|Lys|Phe|Gln|Glu|

Val Gln Glu Asn Asp Thr Gln Asn Glu Lys Lys Phe Gln Glu
    1205                1210             1215

Glu Ile Glu Arg Lys Glu Thr Leu Ile Gln Glu Asn Val Gly Leu
    1220                1225             1230

Pro Gln Val Phe Pro Val Thr Gly Thr Lys Asn Phe Leu Lys Thr
    1235                1240             1245

Leu Phe Leu Leu Ser Thr Arg Gln Asn Val Thr Val Glu Gly Leu
    1250                1255             1260

Asp Glu Gly Thr Tyr Ala Pro Val Leu Gln Asp Thr Arg Ser Leu
    1265                1270             1275

Asn Asp Ser Ala Asn Arg Leu Gly Leu His Met Ala His Phe Ser
    1280                1285             1290

Lys Arg Arg Glu Glu Ala Asn Leu Glu Gly Leu Arg Asn Gln Thr
    1295                1300             1305

Lys Gln Met Val Glu Lys Tyr Pro Ser Pro Thr Arg Met Ser Pro
    1310                1315             1320

Asn Pro Ser Gln Gln Asn Ala Ile Thr Gln Arg Ser Lys Arg Ala
    1325                1330             1335

Leu Lys Gln Phe Gly Pro Pro Leu Glu Glu Ile Glu Leu Glu Arg
    1340                1345             1350

Gly Leu Ile Val Asn Asp Thr Ser Thr Leu Gln Ser Arg Asn Met
    1355                1360             1365

Lys Tyr Leu Thr Gln Gly Thr Leu Thr Gln Ile Asp Tyr Asn Glu
    1370                1375             1380

Lys Glu Lys Arg Ala Ile Thr Gln Ser Pro Leu Ser Asp Cys Ser
    1385                1390             1395

Met Arg Asn His Val Ile Thr Gln Thr Asn Gly Ser Ala Leu Pro
    1400                1405             1410

Ile Ala Lys Thr Ser Ala Phe Pro Ser Ile Arg Pro Thr Asp Leu
    1415                1420             1425

Thr Lys Ile Pro Ser Gln Asp Asn Ser Ser His Leu Leu Ser Ser
    1430                1435             1440

Ala Cys Asn Tyr Thr Phe Arg Glu Lys Ser Ser Gly Val Gln Glu
    1445                1450             1455

Ser Ser His Phe Leu Gln Gly Ala Lys Arg Asn Asn Leu Ser Ser
    1460                1465             1470

Ala Ile Leu Thr Leu Asp Met Ile Arg Gly Gln Glu Lys Val Ile
    1475                1480             1485

Ser Leu Ser Ala Thr Asp Pro Leu Met Tyr Lys Lys Leu Glu Asn
    1490                1495             1500

Thr Val Leu Leu Lys Pro Gly Leu Pro Glu Ala Ser Gly Lys Val
    1505                1510             1515

Glu Leu Leu Pro Lys Ile His Val His Gln Glu Asp Pro Phe Pro
    1520                1525             1530

Thr Glu Thr Ser Asn Gly Ser Pro Gly His Leu Asp Leu Met Glu
    1535                1540             1545

Glu Ile Leu Leu Gln Lys Thr Gln Gly Ala Ile Lys Leu Asn Lys
    1550                1555             1560

Val Asn Arg Pro Gly Lys Val Pro Phe Leu Lys Gly Ala Thr Glu
    1565                1570             1575

Ser Ser Glu Lys Thr Leu Pro Lys Leu Leu Gly Pro Leu Ala Trp
    1580                1585             1590

```
Asp Asn Gln Tyr Ala Thr Gln Ile Ser Arg Glu Glu Trp Gln Ser
1595                1600                1605

Gln Glu Lys Ser Pro Lys Asn Thr Ala Phe Asn Thr Lys Asp Thr
    1610                1615                1620

Ile Ser Pro Leu Asn Pro Cys Glu Asn Asn His Ala Ile Ala Ala
1625                1630                1635

Ile Asn Glu Gly Gln Asp Arg Leu Gln Lys Glu Ala Thr Trp Ala
1640                1645                1650

Lys Gln Gly Glu Thr Glu Arg Leu Cys Ser Glu Asn Pro Pro Val
    1655                1660                1665

Leu Lys His His Pro Arg Glu Ile Thr Leu Thr Ala Leu Gln Gln
    1670                1675                1680

Glu Gln Glu Lys Ile Asp Tyr Asp Asp Ala Leu Ser Ile Glu Thr
    1685                1690                1695

Lys Arg Glu Asp Phe Asp Ile Tyr Gly Glu Asp Glu Asn Gln Gly
1700                1705                1710

Pro Arg Ser Phe Gln Lys Lys Thr Arg His Tyr Phe Ile Ala Ala
1715                1720                1725

Val Glu Arg Leu Trp Asp Tyr Gly Met Ser Lys Ser Pro His Ala
1730                1735                1740

Leu Arg Asn Arg Ala Gln Ser Gly Ser Val Pro Gln Phe Lys Lys
1745                1750                1755

Val Val Phe Gln Glu Phe Thr Asp Gly Ser Phe Thr Gln Pro Leu
1760                1765                1770

Tyr Arg Gly Glu Leu Asn Glu His Leu Gly Leu Leu Gly Pro Tyr
1775                1780                1785

Ile Arg Ala Glu Val Glu Asp Asn Ile Met Val Thr Phe Lys Asn
1790                1795                1800

Gln Ala Ser Arg Pro Tyr Ser Phe Tyr Ser Ser Leu Ile Ser Tyr
1805                1810                1815

Glu Glu Asp Gln Arg Gln Gly Thr Glu Pro Arg Lys Asn Leu Val
1820                1825                1830

Lys Pro Asn Glu Thr Lys Thr Tyr Phe Trp Lys Val Gln His His
1835                1840                1845

Met Ala Pro Thr Lys Asp Glu Phe Asp Cys Lys Ala Trp Ala Tyr
1850                1855                1860

Phe Ser Asp Val Asp Leu Glu Lys Asp Leu His Ser Gly Leu Ile
1865                1870                1875

Gly Pro Leu Leu Ile Cys Arg Thr Asn Thr Leu Asn Pro Ala His
1880                1885                1890

Gly Arg Gln Leu Thr Val Gln Glu Phe Ala Leu Phe Phe Thr Ile
    1895                1900                1905

Phe Asp Glu Thr Lys Ser Trp Tyr Phe Thr Glu Asn Met Glu Arg
1910                1915                1920

Asn Cys Lys Ala Pro Cys Asn Ile Gln Met Glu Asp Pro Thr Phe
1925                1930                1935

Lys Lys Asn Tyr Arg Phe His Ala Ile Asn Gly Tyr Val Met Asp
1940                1945                1950

Thr Leu Pro Gly Leu Val Met Ala Gln Asp Gln Arg Ile Arg Trp
1955                1960                1965

Tyr Leu Leu Ser Met Gly Ser Asn Glu Asn Ile His Ser Ile His
1970                1975                1980
```

Phe Ser Gly His Val Phe Thr Val Arg Lys Lys Glu Glu Tyr Lys
1985                1990                1995

Met Ala Val Tyr Asn Leu Tyr Pro Gly Val Phe Glu Thr Val Glu
2000                2005                2010

Met Leu Pro Ser Lys Ala Gly Ile Trp Arg Val Glu Cys Leu Ile
2015                2020                2025

Gly Glu His Leu Gln Ala Gly Met Ser Thr Leu Phe Leu Val Tyr
2030                2035                2040

Ser Lys Glu Cys Gln Thr Pro Leu Gly Met Ala Ser Gly Arg Ile
2045                2050                2055

Arg Asp Ser Gln Ile Thr Ala Ser Gly His Tyr Gly Gln Trp Ala
2060                2065                2070

Pro Lys Leu Ala Arg Leu His Tyr Thr Gly Ser Ile Asn Ala Trp
2075                2080                2085

Ser Thr Lys Asp Pro Phe Ser Trp Ile Lys Val Asp Leu Leu Ala
2090                2095                2100

Pro Met Ile Ile His Gly Ile Lys Thr Gln Gly Ala Arg Gln Lys
2105                2110                2115

Leu Ser Ser Leu Tyr Ile Ser Gln Phe Ile Ile Met Tyr Ser Leu
2120                2125                2130

Asp Gly Lys Lys Trp Gln Ser Tyr Arg Gly Asn Ser Thr Gly Thr
2135                2140                2145

Leu Met Val Phe Phe Gly Asn Val Asp Ser Ser Gly Ile Lys His
2150                2155                2160

Asn Ile Phe Asn Pro Pro Ile Ile Ala Gln Tyr Ile Arg Leu His
2165                2170                2175

Pro Thr His His Ser Ile Arg Ser Thr Leu Arg Met Glu Leu Met
2180                2185                2190

Gly Cys Asp Leu Asn Ser Cys Ser Met Pro Leu Gly Met Glu Ser
2195                2200                2205

Lys Ala Ile Ser Asp Ala Gln Ile Thr Ala Ser Ser Tyr Phe Thr
2210                2215                2220

Asn Met Phe Ala Thr Trp Ser Pro Ser Gln Ala Arg Leu His Leu
2225                2230                2235

Gln Gly Arg Thr Asn Ala Trp Arg Pro Gln Val Asn Asn Pro Lys
2240                2245                2250

Glu Trp Leu Gln Val Asp Phe Gln Lys Thr Met Lys Val Thr Gly
2255                2260                2265

Ile Thr Thr Gln Gly Ala Lys Ser Leu Leu Thr Ser Met Tyr Val
2270                2275                2280

Lys Glu Phe Leu Ile Ser Ser Ser Gln Asp Gly His His Trp Thr
2285                2290                2295

Leu Phe Leu Gln Asn Gly Lys Val Lys Val Phe Gln Gly Asn Gln
2300                2305                2310

Asp Ser Phe Thr Pro Val Val Asn Ser Leu Asp Pro Pro Leu Leu
2315                2320                2325

Thr Arg Tyr Leu Arg Ile Tyr Pro Gln Ser Trp Val His Gln Ile
2330                2335                2340

Ala Leu Arg Leu Glu Val Leu Gly Cys Gln Ser Gln Gln His Tyr
2345                2350                2355

<210> SEQ ID NO 39
<211> LENGTH: 1453
<212> TYPE: PRT

<213> ORGANISM: artificial sequence
<220> FEATURE:
<223> OTHER INFORMATION: ancestral

<400> SEQUENCE: 39

```
Met Gln Ile Ala Leu Phe Thr Cys Phe Phe Leu Ser Leu Phe Asn Phe
1               5                   10                  15

Cys Ser Ser Ala Thr Arg Arg Tyr Tyr Leu Gly Ala Val Glu Leu Ser
            20                  25                  30

Trp Asn Tyr Met Gln Ser Asp Leu Leu Ser Val Leu His Thr Asp Thr
        35                  40                  45

Arg Phe Leu Pro Arg Met Pro Thr Ser Phe Pro Phe Asn Thr Ser Ile
    50                  55                  60

Met Tyr Lys Lys Thr Val Phe Val Glu Tyr Met Asp His Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Lys Glu Gly Ser Leu Ser Lys Glu Arg
        195                 200                 205

Thr Gln Met Leu His Gln Phe Val Leu Leu Phe Ala Val Phe Asp Glu
    210                 215                 220

Gly Lys Ser Trp His Ser Glu Thr Lys Asp Ser Phe Thr Gln Ala Met
225                 230                 235                 240

Asp Ser Ala Ser Thr Arg Ala Trp Pro Lys Met His Thr Val Asn Gly
                245                 250                 255

Tyr Val Asn Arg Ser Leu Pro Gly Leu Ile Gly Cys His Arg Lys Ser
            260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
    290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
            340                 345                 350

Pro Gln Trp Gln Lys Lys Asn Asn Glu Glu Met Glu Asp Tyr Asp Asp
        355                 360                 365

Asp Leu Asp Ser Glu Met Asp Met Phe Thr Leu Asp Asp Asn Ser
    370                 375                 380
```

```
Pro Phe Ile Gln Ile Arg Ser Val Ala Lys Lys Tyr Pro Lys Thr Trp
385                 390                 395                 400

Ile His Tyr Ile Ser Ala Glu Glu Glu Asp Trp Asp Tyr Ala Pro Ser
                405                 410                 415

Val Leu Thr Ser Asp Asp Gly Ser Tyr Lys Ser Gln Tyr Leu Ser Asn
            420                 425                 430

Gly Pro His Arg Ile Gly Arg Lys Tyr Lys Val Arg Phe Ile Ala
            435                 440                 445

Tyr Thr Asp Val Thr Phe Lys Thr Arg Glu Thr Ile Gln His Glu Ser
    450                 455                 460

Gly Ile Leu Gly Pro Leu Leu Tyr Gly Glu Val Gly Asp Thr Leu Leu
465                 470                 475                 480

Ile Ile Phe Lys Asn Gln Ala Ser Arg Pro Tyr Asn Ile Tyr Pro His
                485                 490                 495

Gly Ile Thr Asp Val Ser Pro Leu His Ser Arg Arg Leu Pro Arg Gly
                500                 505                 510

Ile Lys His Val Lys Asp Leu Pro Ile Arg Pro Gly Glu Ile Phe Lys
                515                 520                 525

Tyr Lys Trp Thr Val Thr Val Glu Asp Gly Pro Thr Lys Ser Asp Pro
530                 535                 540

Arg Cys Leu Thr Arg Tyr Tyr Ser Ser Phe Ile Asn Pro Glu Arg Asp
545                 550                 555                 560

Leu Ala Ser Gly Leu Ile Gly Pro Leu Leu Ile Cys Tyr Lys Glu Ser
                565                 570                 575

Val Asp Gln Arg Gly Asn Gln Met Met Ser Asp Lys Arg Asn Val Ile
                580                 585                 590

Leu Phe Ser Val Phe Asp Glu Asn Gln Ser Trp Tyr Ile Thr Glu Asn
                595                 600                 605

Met Gln Arg Phe Leu Pro Asn Ala Ala Asp Thr Gln Pro Gln Asp Pro
    610                 615                 620

Glu Phe Gln Ala Ser Asn Ile Met His Ser Ile Asn Gly Tyr Val Phe
625                 630                 635                 640

Asp Ser Leu Gln Leu Thr Val Cys Leu His Glu Val Ala Tyr Trp Tyr
                645                 650                 655

Ile Leu Ser Val Gly Ala Gln Thr Asp Phe Leu Ser Ile Phe Phe Ser
                660                 665                 670

Gly Tyr Thr Phe Lys His Lys Met Val Tyr Glu Asp Thr Leu Thr Leu
                675                 680                 685

Phe Pro Phe Ser Gly Glu Thr Val Phe Met Ser Met Glu Asn Pro Gly
    690                 695                 700

Leu Trp Val Leu Gly Cys His Asn Ser Asp Phe Arg Lys Arg Gly Met
705                 710                 715                 720

Thr Ala Leu Leu Lys Val Ser Ser Cys Asp Lys Ser Thr Ser Asp Tyr
                725                 730                 735

Tyr Glu Glu Ile Tyr Glu Asp Ile Pro Thr Gln Leu Val Asn Asp Asn
                740                 745                 750

Asn Val Ile Glu Pro Arg Ser Phe Phe Gln Asn Pro Pro Val Leu Lys
            755                 760                 765

Arg His Gln Arg Glu Leu Ser Ala Leu Gln Ser Glu Gln Glu Ala Thr
            770                 775                 780

Asp Tyr Asp Asp Ser Ile Thr Ile Glu Thr Asn Glu Asp Phe Asp Ile
785                 790                 795                 800
```

-continued

Tyr Gly Glu Asp Ile Lys Gln Gly Pro Arg Ser Phe Gln Gln Lys Thr
                    805                 810                 815

Arg His Tyr Phe Ile Ala Ala Val Glu Arg Leu Trp Asp Tyr Gly Met
            820                 825                 830

Ser Thr Ser Pro His Val Leu Arg Asn Arg Asp Gln Ser Gly Asn Ala
            835                 840                 845

Pro Gln Phe Lys Lys Val Val Phe Gln Glu Phe Thr Asp Gly Ser Phe
850                 855                 860

Ser Gln Pro Leu Tyr Arg Gly Glu Leu Asn Glu His Leu Gly Leu Leu
865                 870                 875                 880

Gly Pro Tyr Ile Arg Ala Glu Val Glu Asp Asn Ile Met Val Thr Phe
                885                 890                 895

Lys Asn Gln Ala Ser Arg Pro Tyr Ser Phe Tyr Ser Ser Leu Ile Ser
                900                 905                 910

Tyr Lys Glu Asp Gln Arg Gln Gly Glu Glu Pro Arg Arg Asn Phe Val
            915                 920                 925

Lys Pro Asn Glu Thr Lys Ile Tyr Phe Trp Lys Val Gln His His Met
            930                 935                 940

Ala Pro Thr Glu Asp Glu Phe Asp Cys Lys Ala Trp Ala Tyr Phe Ser
945                 950                 955                 960

Asp Val Asp Leu Glu Arg Asp Met His Ser Gly Leu Ile Gly Pro Leu
                965                 970                 975

Leu Ile Cys His Thr Asn Thr Leu Asn Pro Ala His Gly Arg Gln Val
                980                 985                 990

Ala Val Gln Glu Phe Ala Leu Phe Phe Thr Ile Phe Asp Glu Thr Lys
            995                 1000                1005

Ser Trp Tyr Phe Thr Glu Asn Val Glu Arg Asn Cys Lys Thr Pro
    1010                1015                1020

Cys Asn Ile Gln Met Glu Asp Pro Thr Leu Lys Glu Asn Tyr Arg
    1025                1030                1035

Phe His Ala Ile Asn Gly Tyr Val Met Asp Thr Leu Pro Gly Leu
    1040                1045                1050

Val Met Ala Gln Asp Gln Arg Ile Arg Trp Tyr Leu Leu Ser Met
    1055                1060                1065

Gly Ser Asn Glu Asn Ile Gln Ser Ile His Phe Ser Gly His Val
    1070                1075                1080

Phe Thr Val Arg Lys Lys Glu Glu Tyr Lys Met Ala Val Tyr Asn
    1085                1090                1095

Leu Tyr Pro Gly Val Phe Glu Thr Val Glu Met Leu Pro Ser Arg
    1100                1105                1110

Ala Gly Ile Trp Arg Val Glu Cys Leu Ile Gly Glu His Leu Gln
    1115                1120                1125

Ala Gly Met Ser Thr Leu Phe Leu Val Tyr Ser Lys Gln Cys Gln
    1130                1135                1140

Ile Pro Leu Gly Met Ala Ser Gly Ser Ile Arg Asp Phe Gln Ile
    1145                1150                1155

Thr Ala Ser Gly His Tyr Gly Gln Trp Ala Pro Asn Leu Ala Arg
    1160                1165                1170

Leu His His Ser Gly Ser Ile Asn Ala Trp Ser Thr Lys Glu Pro
    1175                1180                1185

Phe Ser Trp Ile Lys Val Asp Leu Leu Thr Pro Met Ile Ile His
    1190                1195                1200

Gly Ile Lys Thr Gln Gly Ala Arg Gln Lys Phe Ser Ser Leu Tyr
    1205                1210                1215

Ile Ser Gln Phe Ile Ile Met Tyr Ser Leu Asp Gly Lys Lys Trp
    1220                1225                1230

Leu Ser Tyr Arg Gly Asn Ser Thr Gly Thr Leu Met Val Phe Phe
    1235                1240                1245

Gly Asn Val Asp Ser Ser Gly Ile Lys His Asn Ser Phe Asn Pro
    1250                1255                1260

Pro Ile Ile Ala Arg Tyr Ile Arg Leu His Pro Thr His Ser Ser
    1265                1270                1275

Ile Arg Ser Thr Leu Arg Met Glu Leu Met Gly Cys Asp Leu Asn
    1280                1285                1290

Ser Cys Ser Ile Pro Leu Gly Met Glu Asn Lys Val Ile Ser Asp
    1295                1300                1305

Thr Gln Ile Thr Ala Ser Ser Tyr Phe Thr Asn Met Phe Ala Thr
    1310                1315                1320

Trp Ser Pro Ser Gln Ala Arg Leu His Leu Gln Gly Arg Thr Asn
    1325                1330                1335

Ala Trp Arg Pro Gln Val Asn Asp Pro Lys Glu Trp Leu Gln Val
    1340                1345                1350

Asp Leu Gln Lys Thr Met Lys Val Thr Gly Ile Ile Thr Gln Gly
    1355                1360                1365

Val Lys Ser Leu Phe Thr Ser Met Phe Val Lys Glu Phe Leu Ile
    1370                1375                1380

Ser Ser Ser Gln Asp Gly His His Trp Thr His Ile Leu His Asn
    1385                1390                1395

Gly Lys Val Lys Val Phe Gln Gly Asn Gln Asp Ser Ser Thr Pro
    1400                1405                1410

Met Val Asn Ser Leu Asp Pro Pro Leu Leu Thr Arg Tyr Leu Arg
    1415                1420                1425

Ile His Pro Gln Ile Trp Glu His Gln Ile Ala Leu Arg Leu Glu
    1430                1435                1440

Ile Leu Gly Cys Glu Ala Gln Gln Leu Tyr
    1445                1450

<210> SEQ ID NO 40
<211> LENGTH: 1458
<212> TYPE: PRT
<213> ORGANISM: artificial sequence
<220> FEATURE:
<223> OTHER INFORMATION: ancestral

<400> SEQUENCE: 40

Met Gln Ile Glu Leu Ser Thr Cys Phe Phe Leu Cys Leu Leu Gln Phe
1               5                   10                  15

Ser Phe Ser Ala Thr Arg Arg Tyr Tyr Leu Gly Ala Val Glu Leu Ser
                20                  25                  30

Trp Asp Tyr Met Gln Ser Asp Leu Leu Ser Glu Leu His Val Asp Thr
            35                  40                  45

Arg Phe Pro Pro Arg Val Pro Arg Ser Phe Pro Phe Asn Thr Ser Val
        50                  55                  60

Met Tyr Lys Lys Thr Val Phe Val Glu Phe Thr Asp His Leu Phe Asn
65                  70                  75                  80

Ile Ala Lys Pro Arg Pro Pro Trp Met Gly Leu Leu Gly Pro Thr Ile
                85                  90                  95

```
Arg Ala Glu Val Tyr Asp Thr Val Val Ile Thr Leu Lys Asn Met Ala
            100                 105                 110

Ser His Pro Val Ser Leu His Ala Val Gly Val Ser Tyr Trp Lys Ala
            115                 120                 125

Ser Glu Gly Ala Glu Tyr Asp Asp Gln Thr Ser Gln Arg Glu Lys Glu
            130                 135                 140

Asp Asp Lys Val Phe Pro Gly Ser His Thr Tyr Val Trp Gln Val
145                 150                 155                 160

Leu Lys Glu Asn Gly Pro Met Ala Ser Asp Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Ala Lys Glu Arg
            195                 200                 205

Thr Gln Thr Leu His Gln Phe Val Leu Leu Phe Ala Val Phe Asp Glu
            210                 215                 220

Gly Lys Ser Trp His Ser Glu Thr Lys Asp Ser Leu Thr Gln Ala Met
225                 230                 235                 240

Asp Ser Ala Ser Ala Arg Ala Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Val His Ser
                275                 280                 285

Ile Phe Leu Glu Gly His Thr Phe Leu Val Arg Asn His Arg Gln Ala
            290                 295                 300

Ser Leu Glu Ile Ser Pro Ile Thr Phe Leu Thr Ala Gln Thr Leu Leu
305                 310                 315                 320

Met Asp Leu Gly Gln Phe Leu Leu Phe Cys His Ile Ser Ser His Gln
                325                 330                 335

His Asp Gly Met Glu Ala Tyr Val Lys Val Asp Ser Cys Pro Glu Glu
                340                 345                 350

Pro Gln Leu Arg Met Lys Asn Asn Glu Glu Glu Asp Tyr Asp Asp
            355                 360                 365

Asp Leu Tyr Asp Ser Glu Met Asp Val Val Arg Phe Asp Asp Asp Asn
370                 375                 380

Ser Pro Pro Phe Ile Gln Ile Arg Ser Val Ala Lys Lys His Pro Lys
385                 390                 395                 400

Thr Trp Val His Tyr Ile Ala Ala Glu Glu Glu Asp Trp Asp Tyr Ala
                405                 410                 415

Pro Ser Val Leu Thr Pro Asp Asp Arg Ser Tyr Lys Ser Gln Tyr Leu
                420                 425                 430

Asn Asn Gly Pro Gln Arg Ile Gly Arg Lys Tyr Lys Lys Val Arg Phe
            435                 440                 445

Met Ala Tyr Thr Asp Val Thr Phe Lys Thr Arg Glu Ala Ile Gln Tyr
            450                 455                 460

Glu Ser Gly Ile Leu Gly Pro Leu Leu Tyr Gly Glu Val Gly Asp Thr
465                 470                 475                 480

Leu Leu Ile Ile Phe Lys Asn Gln Ala Ser Arg Pro Tyr Asn Ile Tyr
                485                 490                 495

Pro His Gly Ile Thr Asp Val Ser Pro Leu His Ser Gly Arg Leu Pro
            500                 505                 510
```

```
Lys Gly Val Lys His Leu Lys Asp Leu Pro Ile Leu Pro Gly Glu Ile
            515                 520                 525

Phe Lys Tyr Lys Trp Thr Val Thr Val Glu Asp Gly Pro Thr Lys Ser
        530                 535                 540

Asp Pro Arg Cys Leu Thr Arg Tyr Tyr Ser Ser Phe Ile Asn Leu Glu
545                 550                 555                 560

Arg Asp Leu Ala Ser Gly Leu Ile Gly Pro Leu Leu Ile Cys Tyr Lys
                565                 570                 575

Glu Ser Val Asp Gln Arg Gly Asn Gln Met Met Ser Asp Lys Arg Asn
            580                 585                 590

Val Ile Leu Phe Ser Val Phe Asp Glu Asn Arg Ser Trp Tyr Leu Thr
        595                 600                 605

Glu Asn Met Gln Arg Phe Leu Pro Asn Ala Ala Gly Val Gln Pro Gln
        610                 615                 620

Asp Pro Glu Phe Gln Ala Ser Asn Ile Met His Ser Ile Asn Gly Tyr
625                 630                 635                 640

Val Phe Asp Ser Leu Gln Leu Ser Val Cys Leu His Glu Val Ala Tyr
                645                 650                 655

Trp Tyr Ile Leu Ser Val Gly Ala Gln Thr Asp Phe Leu Ser Val Phe
            660                 665                 670

Phe Ser Gly Tyr Thr Phe Lys His Lys Met Val Tyr Glu Asp Thr Leu
        675                 680                 685

Thr Leu Phe Pro Phe Ser Gly Glu Thr Val Phe Met Ser Met Glu Asn
        690                 695                 700

Pro Gly Leu Trp Val Leu Gly Cys His Asn Ser Asp Phe Arg Asn Arg
705                 710                 715                 720

Gly Met Thr Ala Leu Leu Lys Val Ser Ser Cys Asp Arg Asn Thr Gly
                725                 730                 735

Asp Tyr Tyr Glu Asp Thr Tyr Glu Asp Ile Pro Thr Tyr Leu Leu Ser
            740                 745                 750

Glu Asn Asn Val Ile Glu Pro Arg Ser Phe Ser Gln Asn Pro Pro Val
        755                 760                 765

Leu Lys Arg His Gln Arg Glu Ile Thr Leu Thr Thr Leu Gln Ser Glu
        770                 775                 780

Gln Glu Glu Ile Asp Tyr Asp Asp Thr Ile Ser Ile Glu Thr Lys Arg
785                 790                 795                 800

Glu Asp Phe Asp Ile Tyr Gly Glu Asp Glu Asn Gln Gly Pro Arg Ser
                805                 810                 815

Phe Gln Lys Arg Thr Arg His Tyr Phe Ile Ala Ala Val Glu Arg Leu
            820                 825                 830

Trp Asp Tyr Gly Met Ser Arg Ser Pro His Val Leu Arg Asn Arg Ala
        835                 840                 845

Gln Ser Gly Ser Val Pro Gln Phe Lys Lys Val Val Phe Gln Glu Phe
        850                 855                 860

Thr Asp Gly Ser Phe Thr Gln Pro Leu Tyr Arg Gly Glu Leu Asn Glu
865                 870                 875                 880

His Leu Gly Leu Leu Gly Pro Tyr Ile Arg Ala Glu Val Glu Asp Asn
                885                 890                 895

Ile Met Val Thr Phe Lys Asn Gln Ala Ser Arg Pro Tyr Ser Phe Tyr
            900                 905                 910

Ser Ser Leu Ile Ser Tyr Glu Glu Asp Gln Arg Gln Gly Ala Glu Pro
        915                 920                 925
```

-continued

Arg Lys Asn Phe Val Lys Pro Asn Glu Thr Leu Thr Tyr Phe Trp Lys
            930                 935                 940

Val Gln His His Met Ala Pro Thr Lys Asp Glu Phe Asp Cys Lys Ala
945                 950                 955                 960

Trp Ala Tyr Phe Ser Asp Val Asp Leu Glu Lys Asp Met His Ser Gly
                965                 970                 975

Leu Ile Gly Pro Leu Leu Ile Cys His Thr Asn Thr Leu Asn Pro Ala
            980                 985                 990

His Gly Arg Gln Val Thr Val Gln Glu Phe Ala Leu Phe Phe Thr Ile
        995                 1000                1005

Phe Asp Glu Thr Lys Ser Trp Tyr Phe Thr Glu Asn Met Glu Arg
    1010                1015                1020

Asn Cys Arg Ala Pro Cys Asn Ile Gln Met Glu Asp Pro Thr Phe
    1025                1030                1035

Lys Glu Asn Tyr Arg Phe His Ala Ile Asn Gly Tyr Val Met Asp
    1040                1045                1050

Thr Leu Pro Gly Leu Val Met Ala Gln Asp Gln Arg Ile Arg Trp
    1055                1060                1065

Tyr Leu Leu Ser Met Gly Ser Asn Glu Asn Ile His Ser Ile His
    1070                1075                1080

Phe Ser Gly His Val Phe Thr Val Arg Lys Lys Glu Glu Tyr Lys
    1085                1090                1095

Met Ala Val Tyr Asn Leu Tyr Pro Gly Val Phe Glu Thr Val Glu
    1100                1105                1110

Met Leu Pro Ser Lys Ala Gly Ile Trp Arg Val Glu Cys Leu Ile
    1115                1120                1125

Gly Glu His Leu His Ala Gly Met Ser Thr Leu Phe Leu Val Tyr
    1130                1135                1140

Ser Lys Gln Cys Gln Thr Pro Leu Gly Met Ala Ser Gly His Ile
    1145                1150                1155

Arg Asp Phe Gln Ile Thr Ala Ser Gly Gln Tyr Gly Gln Trp Ala
    1160                1165                1170

Pro Lys Leu Ala Arg Leu His Tyr Ser Gly Ser Ile Asn Ala Trp
    1175                1180                1185

Ser Thr Lys Glu Pro Phe Ser Trp Ile Lys Val Asp Leu Leu Ala
    1190                1195                1200

Pro Met Ile Ile His Gly Ile Lys Thr Gln Gly Ala Arg Gln Lys
    1205                1210                1215

Phe Ser Ser Leu Tyr Ile Ser Gln Phe Ile Ile Met Tyr Ser Leu
    1220                1225                1230

Asp Gly Lys Lys Trp Gln Thr Tyr Arg Gly Asn Ser Thr Gly Thr
    1235                1240                1245

Leu Met Val Phe Phe Gly Asn Val Asp Ser Ser Gly Ile Lys His
    1250                1255                1260

Asn Ile Phe Asn Pro Pro Ile Ile Ala Arg Tyr Ile Arg Leu His
    1265                1270                1275

Pro Thr His Tyr Ser Ile Arg Ser Thr Leu Arg Met Glu Leu Met
    1280                1285                1290

Gly Cys Asp Leu Asn Ser Cys Ser Met Pro Leu Gly Met Glu Ser
    1295                1300                1305

Lys Ala Ile Ser Asp Ala Gln Ile Thr Ala Ser Ser Tyr Phe Thr
    1310                1315                1320

```
Asn Met Phe Ala Thr Trp Ser Pro Ser Gln Ala Arg Leu His Leu
    1325                1330                1335

Gln Gly Arg Thr Asn Ala Trp Arg Pro Gln Val Asn Asn Pro Lys
    1340                1345                1350

Glu Trp Leu Gln Val Asp Phe Gln Lys Thr Met Lys Val Thr Gly
    1355                1360                1365

Ile Thr Thr Gln Gly Val Lys Ser Leu Leu Thr Ser Met Tyr Val
    1370                1375                1380

Lys Glu Phe Leu Ile Ser Ser Gln Asp Gly His His Trp Thr
    1385                1390                1395

Leu Phe Leu Gln Asn Gly Lys Val Lys Val Phe Gln Gly Asn Gln
    1400                1405                1410

Asp Ser Phe Thr Pro Val Val Asn Ser Leu Asp Pro Pro Leu Leu
    1415                1420                1425

Thr Arg Tyr Leu Arg Ile His Pro Gln Ser Trp Val His Gln Ile
    1430                1435                1440

Ala Leu Arg Leu Glu Val Leu Gly Cys Glu Ala Gln Gln Leu Tyr
    1445                1450                1455
```

<210> SEQ ID NO 41
<211> LENGTH: 10
<212> TYPE: PRT
<213> ORGANISM: artificial sequence
<220> FEATURE:
<223> OTHER INFORMATION: ancestral

<400> SEQUENCE: 41

```
Ser Arg Pro Pro Ser Ala Ser Ala Pro Lys
1               5                   10
```

<210> SEQ ID NO 42
<211> LENGTH: 1463
<212> TYPE: PRT
<213> ORGANISM: artificial sequence
<220> FEATURE:
<223> OTHER INFORMATION: ancestral

<400> SEQUENCE: 42

```
Met Gln Ile Ala Leu Phe Thr Cys Phe Phe Leu Ser Leu Phe Asn Phe
1               5                   10                  15

Cys Ser Ser Ala Thr Arg Arg Tyr Tyr Leu Gly Ala Val Glu Leu Ser
                20                  25                  30

Trp Asn Tyr Met Gln Ser Asp Leu Leu Ser Val Leu His Thr Asp Thr
            35                  40                  45

Arg Phe Leu Pro Arg Met Pro Thr Ser Phe Pro Phe Asn Thr Ser Ile
    50                  55                  60

Met Tyr Lys Lys Thr Val Phe Val Glu Tyr Met Asp His Leu Phe Asn
65                  70                  75                  80

Ile Ala Lys Pro Arg Pro Pro Trp Met Gly Leu Leu Gly Pro Thr Ile
                85                  90                  95

Trp Thr Glu Val His Asp Thr Val Val Ile Thr Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Arg Glu Lys Glu
    130                 135                 140

Asp Asp Lys Val Phe Pro Gly Glu Ser His Thr Tyr Val Trp Gln Val
145                 150                 155                 160
```

```
Leu Lys Glu Asn Gly Pro Met Ala Ser Asp Pro Cys Leu Thr Tyr
            165                 170                 175

Ser Tyr Leu Ser His Val Asp Leu Val Lys Asp Leu Asn Ser Gly Leu
        180                 185                 190

Ile Gly Ala Leu Leu Val Cys Lys Glu Gly Ser Leu Ser Lys Glu Arg
        195                 200                 205

Thr Gln Met Leu His Gln Phe Val Leu Leu Phe Ala Val Phe Asp Glu
        210                 215                 220

Gly Lys Ser Trp His Ser Glu Thr Lys Asp Ser Phe Thr Gln Ala Met
225                 230                 235                 240

Asp Ser Ala Ser Thr Arg Ala Trp Pro Lys Met His Thr Val Asn Gly
                245                 250                 255

Tyr Val Asn Arg Ser Leu Pro Gly Leu Ile Gly Cys His Arg Lys Ser
                260                 265                 270

Val Tyr Trp His Val Ile Gly Met Gly Thr Thr Pro Glu Val His Ser
        275                 280                 285

Ile Phe Leu Glu Gly His Thr Phe Leu Val Arg Asn His Arg Gln Ala
        290                 295                 300

Ser Leu Glu Ile Ser Pro Ile Thr Phe Leu Thr Ala Gln Thr Leu Leu
305                 310                 315                 320

Ile Asp Leu Gly Gln Phe Leu Leu Phe Cys His Ile Ser Ser His Lys
                325                 330                 335

His Asp Gly Met Glu Ala Tyr Val Lys Val Asp Ser Cys Pro Glu Glu
                340                 345                 350

Pro Gln Trp Gln Lys Lys Asn Asn Glu Glu Met Glu Asp Tyr Asp Asp
        355                 360                 365

Asp Leu Asp Ser Glu Met Asp Met Phe Thr Leu Asp Asp Asp Asn Ser
        370                 375                 380

Pro Phe Ile Gln Ile Arg Ser Val Ala Lys Lys His Pro Lys Thr Trp
385                 390                 395                 400

Val His Tyr Ile Ala Ala Glu Glu Glu Asp Trp Asp Tyr Ala Pro Leu
                405                 410                 415

Val Leu Ala Pro Asp Asp Arg Ser Tyr Lys Ser Gln Tyr Leu Asn Asn
                420                 425                 430

Gly Pro Gln Arg Ile Gly Arg Lys Tyr Lys Lys Val Arg Phe Met Ala
        435                 440                 445

Tyr Thr Asp Val Thr Phe Lys Thr Arg Glu Ala Ile Gln His Glu Ser
        450                 455                 460

Gly Ile Leu Gly Pro Leu Leu Tyr Gly Glu Val Gly Asp Thr Leu Leu
465                 470                 475                 480

Ile Ile Phe Lys Asn Gln Ala Ser Arg Pro Tyr Asn Ile Tyr Pro His
                485                 490                 495

Gly Ile Thr Asp Val Arg Pro Leu Tyr Ser Arg Arg Leu Pro Lys Gly
                500                 505                 510

Val Lys His Leu Lys Asp Phe Pro Ile Leu Pro Gly Glu Ile Phe Lys
        515                 520                 525

Tyr Lys Trp Thr Val Thr Val Glu Asp Gly Pro Thr Lys Ser Asp Pro
        530                 535                 540

Arg Cys Leu Thr Arg Tyr Tyr Ser Ser Phe Val Asn Met Glu Arg Asp
545                 550                 555                 560

Leu Ala Ser Gly Leu Ile Gly Pro Leu Leu Ile Cys Tyr Lys Glu Ser
                565                 570                 575
```

```
Val Asp Gln Arg Gly Asn Gln Ile Met Ser Asp Lys Arg Asn Val Ile
            580                 585                 590

Leu Phe Ser Val Phe Asp Glu Asn Arg Ser Trp Tyr Leu Thr Glu Asn
        595                 600                 605

Ile Gln Arg Phe Leu Pro Asn Pro Ala Gly Val Gln Leu Glu Asp Pro
    610                 615                 620

Glu Phe Gln Ala Ser Asn Ile Met His Ser Ile Asn Gly Tyr Val Phe
625                 630                 635                 640

Asp Ser Leu Gln Leu Ser Val Cys Leu His Glu Val Ala Tyr Trp Tyr
                645                 650                 655

Ile Leu Ser Ile Gly Ala Gln Thr Asp Phe Leu Ser Val Phe Phe Ser
            660                 665                 670

Gly Tyr Thr Phe Lys His Lys Met Val Tyr Glu Asp Thr Leu Thr Leu
        675                 680                 685

Phe Pro Phe Ser Gly Glu Thr Val Phe Met Ser Met Glu Asn Pro Gly
    690                 695                 700

Leu Trp Ile Leu Gly Cys His Asn Ser Asp Phe Arg Asn Arg Gly Met
705                 710                 715                 720

Thr Ala Leu Leu Lys Val Ser Ser Cys Asp Lys Asn Thr Gly Asp Tyr
                725                 730                 735

Tyr Glu Asp Ser Tyr Glu Asp Ile Ser Ala Tyr Leu Leu Ser Lys Asn
            740                 745                 750

Asn Ala Ile Glu Pro Arg Ser Phe Ala Gln Asn Ser Arg Pro Pro Ser
        755                 760                 765

Ala Ser Ala Pro Lys Pro Pro Val Leu Lys Arg His Gln Arg Glu Leu
    770                 775                 780

Ser Ala Leu Gln Ser Glu Gln Glu Ala Thr Asp Tyr Asp Asp Ser Ile
785                 790                 795                 800

Thr Ile Glu Thr Asn Glu Asp Phe Asp Ile Tyr Gly Glu Asp Ile Lys
                805                 810                 815

Gln Gly Pro Arg Ser Phe Gln Gln Lys Thr Arg His Tyr Phe Ile Ala
            820                 825                 830

Ala Val Glu Arg Leu Trp Asp Tyr Gly Met Ser Thr Ser Pro His Val
        835                 840                 845

Leu Arg Asn Arg Asp Gln Ser Gly Asn Ala Pro Gln Phe Lys Lys Val
850                 855                 860

Val Phe Gln Glu Phe Thr Asp Gly Ser Phe Ser Gln Pro Leu Tyr Arg
865                 870                 875                 880

Gly Glu Leu Asn Glu His Leu Gly Leu Leu Gly Pro Tyr Ile Arg Ala
                885                 890                 895

Glu Val Glu Asp Asn Ile Met Val Thr Phe Lys Asn Gln Ala Ser Arg
            900                 905                 910

Pro Tyr Ser Phe Tyr Ser Ser Leu Ile Ser Tyr Lys Glu Asp Gln Arg
        915                 920                 925

Gln Gly Glu Glu Pro Arg Arg Asn Phe Val Lys Pro Asn Glu Thr Lys
    930                 935                 940

Ile Tyr Phe Trp Lys Val Gln His His Met Ala Pro Thr Glu Asp Glu
945                 950                 955                 960

Phe Asp Cys Lys Ala Trp Ala Tyr Phe Ser Asp Val Asp Leu Glu Arg
                965                 970                 975

Asp Met His Ser Gly Leu Ile Gly Pro Leu Leu Ile Cys His Thr Asn
            980                 985                 990
```

Thr Leu Asn Pro Ala His Gly Arg Gln Val Ala Val Gln Glu Phe Ala
    995                 1000                1005

Leu Phe Phe Thr Ile Phe Asp Glu Thr Lys Ser Trp Tyr Phe Thr
    1010                1015                1020

Glu Asn Val Glu Arg Asn Cys Lys Thr Pro Cys Asn Ile Gln Met
    1025                1030                1035

Glu Asp Pro Thr Leu Lys Glu Asn Tyr Arg Phe His Ala Ile Asn
    1040                1045                1050

Gly Tyr Val Met Asp Thr Leu Pro Gly Leu Val Met Ala Gln Asp
    1055                1060                1065

Gln Arg Ile Arg Trp Tyr Leu Leu Ser Met Gly Ser Asn Glu Asn
    1070                1075                1080

Ile Gln Ser Ile His Phe Ser Gly His Val Phe Thr Val Arg Lys
    1085                1090                1095

Lys Glu Glu Tyr Lys Met Ala Val Tyr Asn Leu Tyr Pro Gly Val
    1100                1105                1110

Phe Glu Thr Val Glu Met Leu Pro Ser Arg Ala Gly Ile Trp Arg
    1115                1120                1125

Val Glu Cys Leu Ile Gly Glu His Leu Gln Ala Gly Met Ser Thr
    1130                1135                1140

Leu Phe Leu Val Tyr Ser Lys Lys Cys Gln Thr Pro Leu Gly Met
    1145                1150                1155

Ala Ser Gly His Ile Arg Asp Phe Gln Ile Thr Ala Ser Gly Gln
    1160                1165                1170

Tyr Gly Gln Trp Ala Pro Lys Leu Ala Arg Leu His Tyr Ser Gly
    1175                1180                1185

Ser Ile Asn Ala Trp Ser Thr Lys Glu Pro Phe Ser Trp Ile Lys
    1190                1195                1200

Val Asp Leu Leu Ala Pro Met Ile Ile His Gly Ile Lys Thr Gln
    1205                1210                1215

Gly Ala Arg Gln Lys Phe Ser Ser Leu Tyr Ile Ser Gln Phe Ile
    1220                1225                1230

Ile Met Tyr Ser Leu Asp Gly Lys Lys Trp Gln Thr Tyr Arg Gly
    1235                1240                1245

Asn Ser Thr Gly Thr Leu Met Val Phe Phe Gly Asn Val Asp Ser
    1250                1255                1260

Ser Gly Ile Lys His Asn Ile Phe Asn Pro Pro Ile Ile Ala Arg
    1265                1270                1275

Tyr Ile Arg Leu His Pro Thr His Tyr Ser Ile Arg Ser Thr Leu
    1280                1285                1290

Arg Met Glu Leu Met Gly Cys Asp Leu Asn Ser Cys Ser Met Pro
    1295                1300                1305

Leu Gly Met Glu Ser Lys Ala Ile Ser Asp Ala Gln Ile Thr Ala
    1310                1315                1320

Ser Ser Tyr Phe Thr Asn Met Phe Ala Thr Trp Ser Pro Ser Lys
    1325                1330                1335

Ala Arg Leu His Leu Gln Gly Arg Ser Asn Ala Trp Arg Pro Gln
    1340                1345                1350

Val Asn Asn Pro Lys Glu Trp Leu Gln Val Asp Phe Gln Lys Thr
    1355                1360                1365

Met Lys Val Thr Gly Val Thr Thr Gln Gly Val Lys Ser Leu Leu
    1370                1375                1380

-continued

Thr Ser Met Tyr Val Lys Glu Phe Leu Ile Ser Ser Ser Gln Asp
    1385                1390                1395

Gly His Gln Trp Thr Leu Phe Phe Gln Asn Gly Lys Val Lys Val
    1400                1405                1410

Phe Gln Gly Asn Gln Asp Ser Phe Thr Pro Val Val Asn Ser Leu
    1415                1420                1425

Asp Pro Pro Leu Leu Thr Arg Tyr Leu Arg Ile His Pro Gln Ser
    1430                1435                1440

Trp Val His Gln Ile Ala Leu Arg Met Glu Val Leu Gly Cys Glu
    1445                1450                1455

Ala Gln Asp Leu Tyr
    1460

<210> SEQ ID NO 43
<211> LENGTH: 5
<212> TYPE: PRT
<213> ORGANISM: artificial sequence
<220> FEATURE:
<223> OTHER INFORMATION: ancestral

<400> SEQUENCE: 43

Thr Asp Val Thr Phe
1               5

<210> SEQ ID NO 44
<211> LENGTH: 4
<212> TYPE: PRT
<213> ORGANISM: artificial sequence
<220> FEATURE:
<223> OTHER INFORMATION: ancestral

<400> SEQUENCE: 44

Ile Ala Leu Phe
1

<210> SEQ ID NO 45
<211> LENGTH: 4
<212> TYPE: PRT
<213> ORGANISM: artificial sequence
<220> FEATURE:
<223> OTHER INFORMATION: ancestral

<400> SEQUENCE: 45

Phe Phe Leu Ser
1

<210> SEQ ID NO 46
<211> LENGTH: 4
<212> TYPE: PRT
<213> ORGANISM: artificial sequence
<220> FEATURE:
<223> OTHER INFORMATION: ancestral

<400> SEQUENCE: 46

Phe Leu Ser Leu
1

<210> SEQ ID NO 47
<211> LENGTH: 4
<212> TYPE: PRT
<213> ORGANISM: artificial sequence
<220> FEATURE:
<223> OTHER INFORMATION: ancestral

<400> SEQUENCE: 47

Leu Ser Leu Phe
1

<210> SEQ ID NO 48
<211> LENGTH: 4
<212> TYPE: PRT
<213> ORGANISM: artificial sequence
<220> FEATURE:
<223> OTHER INFORMATION: ancestral

<400> SEQUENCE: 48

Ser Leu Phe Asn
1

<210> SEQ ID NO 49
<211> LENGTH: 4
<212> TYPE: PRT
<213> ORGANISM: artificial sequence
<220> FEATURE:
<223> OTHER INFORMATION: ancestral

<400> SEQUENCE: 49

Leu Phe Asn Phe
1

<210> SEQ ID NO 50
<211> LENGTH: 4
<212> TYPE: PRT
<213> ORGANISM: artificial sequence
<220> FEATURE:
<223> OTHER INFORMATION: ancestral

<400> SEQUENCE: 50

Phe Asn Phe Cys
1

<210> SEQ ID NO 51
<211> LENGTH: 4
<212> TYPE: PRT
<213> ORGANISM: artificial sequence
<220> FEATURE:
<223> OTHER INFORMATION: ancestral

<400> SEQUENCE: 51

Asn Phe Cys Ser
1

<210> SEQ ID NO 52
<211> LENGTH: 4
<212> TYPE: PRT
<213> ORGANISM: artificial sequence
<220> FEATURE:
<223> OTHER INFORMATION: ancestral

<400> SEQUENCE: 52

Phe Cys Ser Ser
1

<210> SEQ ID NO 53
<211> LENGTH: 4
<212> TYPE: PRT
<213> ORGANISM: artificial sequence
<220> FEATURE:
<223> OTHER INFORMATION: ancestral

```
<400> SEQUENCE: 53

Cys Ser Ser Ala
1

<210> SEQ ID NO 54
<211> LENGTH: 4
<212> TYPE: PRT
<213> ORGANISM: artificial sequence
<220> FEATURE:
<223> OTHER INFORMATION: ancestral

<400> SEQUENCE: 54

Ser Ser Ala Thr
1

<210> SEQ ID NO 55
<211> LENGTH: 4
<212> TYPE: PRT
<213> ORGANISM: artificial sequence
<220> FEATURE:
<223> OTHER INFORMATION: ancestral

<400> SEQUENCE: 55

Leu Ser Trp Asn
1

<210> SEQ ID NO 56
<211> LENGTH: 4
<212> TYPE: PRT
<213> ORGANISM: artificial sequence
<220> FEATURE:
<223> OTHER INFORMATION: ancestral

<400> SEQUENCE: 56

Trp Asn Tyr Met
1

<210> SEQ ID NO 57
<211> LENGTH: 4
<212> TYPE: PRT
<213> ORGANISM: artificial sequence
<220> FEATURE:
<223> OTHER INFORMATION: ancestral

<400> SEQUENCE: 57

Asn Tyr Met Gln
1

<210> SEQ ID NO 58
<211> LENGTH: 4
<212> TYPE: PRT
<213> ORGANISM: artificial sequence
<220> FEATURE:
<223> OTHER INFORMATION: ancestral

<400> SEQUENCE: 58

Asp Leu Leu Ser
1

<210> SEQ ID NO 59
<211> LENGTH: 4
<212> TYPE: PRT
<213> ORGANISM: artificial sequence
<220> FEATURE:
<223> OTHER INFORMATION: ancestral
```

```
<400> SEQUENCE: 59

Leu Leu Ser Val
1

<210> SEQ ID NO 60
<211> LENGTH: 4
<212> TYPE: PRT
<213> ORGANISM: artificial sequence
<220> FEATURE:
<223> OTHER INFORMATION: ancestral

<400> SEQUENCE: 60

Leu Ser Val Leu
1

<210> SEQ ID NO 61
<211> LENGTH: 4
<212> TYPE: PRT
<213> ORGANISM: artificial sequence
<220> FEATURE:
<223> OTHER INFORMATION: ancestral

<400> SEQUENCE: 61

Ser Val Leu His
1

<210> SEQ ID NO 62
<211> LENGTH: 4
<212> TYPE: PRT
<213> ORGANISM: artificial sequence
<220> FEATURE:
<223> OTHER INFORMATION: ancestral

<400> SEQUENCE: 62

Val Leu His Thr
1

<210> SEQ ID NO 63
<211> LENGTH: 4
<212> TYPE: PRT
<213> ORGANISM: artificial sequence
<220> FEATURE:
<223> OTHER INFORMATION: ancestral

<400> SEQUENCE: 63

Leu His Thr Asp
1

<210> SEQ ID NO 64
<211> LENGTH: 4
<212> TYPE: PRT
<213> ORGANISM: artificial sequence
<220> FEATURE:
<223> OTHER INFORMATION: ancestral

<400> SEQUENCE: 64

His Thr Asp Thr
1

<210> SEQ ID NO 65
<211> LENGTH: 4
<212> TYPE: PRT
<213> ORGANISM: artificial sequence
<220> FEATURE:
<223> OTHER INFORMATION: ancestral
```

```
<400> SEQUENCE: 65

Thr Asp Thr Arg
1

<210> SEQ ID NO 66
<211> LENGTH: 4
<212> TYPE: PRT
<213> ORGANISM: artificial sequence
<220> FEATURE:
<223> OTHER INFORMATION: ancestral

<400> SEQUENCE: 66

Thr Arg Phe Leu
1

<210> SEQ ID NO 67
<211> LENGTH: 4
<212> TYPE: PRT
<213> ORGANISM: artificial sequence
<220> FEATURE:
<223> OTHER INFORMATION: ancestral

<400> SEQUENCE: 67

Arg Phe Leu Pro
1

<210> SEQ ID NO 68
<211> LENGTH: 4
<212> TYPE: PRT
<213> ORGANISM: artificial sequence
<220> FEATURE:
<223> OTHER INFORMATION: ancestral

<400> SEQUENCE: 68

Phe Leu Pro Arg
1

<210> SEQ ID NO 69
<211> LENGTH: 4
<212> TYPE: PRT
<213> ORGANISM: artificial sequence
<220> FEATURE:
<223> OTHER INFORMATION: ancestral

<400> SEQUENCE: 69

Leu Pro Arg Met
1

<210> SEQ ID NO 70
<211> LENGTH: 4
<212> TYPE: PRT
<213> ORGANISM: artificial sequence
<220> FEATURE:
<223> OTHER INFORMATION: ancestral

<400> SEQUENCE: 70

Pro Arg Met Pro
1

<210> SEQ ID NO 71
<211> LENGTH: 4
<212> TYPE: PRT
<213> ORGANISM: artificial sequence
<220> FEATURE:
<223> OTHER INFORMATION: ancestral
```

<400> SEQUENCE: 71

Arg Met Pro Thr
1

<210> SEQ ID NO 72
<211> LENGTH: 4
<212> TYPE: PRT
<213> ORGANISM: artificial sequence
<220> FEATURE:
<223> OTHER INFORMATION: ancestral

<400> SEQUENCE: 72

Pro Thr Ser Phe
1

<210> SEQ ID NO 73
<211> LENGTH: 4
<212> TYPE: PRT
<213> ORGANISM: artificial sequence
<220> FEATURE:
<223> OTHER INFORMATION: ancestral

<400> SEQUENCE: 73

Thr Ser Phe Pro
1

<210> SEQ ID NO 74
<211> LENGTH: 4
<212> TYPE: PRT
<213> ORGANISM: artificial sequence
<220> FEATURE:
<223> OTHER INFORMATION: ancestral

<400> SEQUENCE: 74

Asn Thr Ser Ile
1

<210> SEQ ID NO 75
<211> LENGTH: 4
<212> TYPE: PRT
<213> ORGANISM: artificial sequence
<220> FEATURE:
<223> OTHER INFORMATION: ancestral

<400> SEQUENCE: 75

Thr Ser Ile Met
1

<210> SEQ ID NO 76
<211> LENGTH: 4
<212> TYPE: PRT
<213> ORGANISM: artificial sequence
<220> FEATURE:
<223> OTHER INFORMATION: ancestral

<400> SEQUENCE: 76

Ser Ile Met Tyr
1

<210> SEQ ID NO 77
<211> LENGTH: 4
<212> TYPE: PRT
<213> ORGANISM: artificial sequence
<220> FEATURE:
<223> OTHER INFORMATION: ancestral

```
<400> SEQUENCE: 77

Ile Met Tyr Lys
1

<210> SEQ ID NO 78
<211> LENGTH: 4
<212> TYPE: PRT
<213> ORGANISM: artificial sequence
<220> FEATURE:
<223> OTHER INFORMATION: ancestral

<400> SEQUENCE: 78

Met Tyr Lys Lys
1

<210> SEQ ID NO 79
<211> LENGTH: 4
<212> TYPE: PRT
<213> ORGANISM: artificial sequence
<220> FEATURE:
<223> OTHER INFORMATION: ancestral

<400> SEQUENCE: 79

Phe Val Glu Tyr
1

<210> SEQ ID NO 80
<211> LENGTH: 4
<212> TYPE: PRT
<213> ORGANISM: artificial sequence
<220> FEATURE:
<223> OTHER INFORMATION: ancestral

<400> SEQUENCE: 80

Val Glu Tyr Met
1

<210> SEQ ID NO 81
<211> LENGTH: 4
<212> TYPE: PRT
<213> ORGANISM: artificial sequence
<220> FEATURE:
<223> OTHER INFORMATION: ancestral

<400> SEQUENCE: 81

Glu Tyr Met Asp
1

<210> SEQ ID NO 82
<211> LENGTH: 4
<212> TYPE: PRT
<213> ORGANISM: artificial sequence
<220> FEATURE:
<223> OTHER INFORMATION: ancestral

<400> SEQUENCE: 82

Tyr Met Asp His
1

<210> SEQ ID NO 83
<211> LENGTH: 4
<212> TYPE: PRT
<213> ORGANISM: artificial sequence
<220> FEATURE:
<223> OTHER INFORMATION: ancestral
```

<400> SEQUENCE: 83

Met Asp His Leu
1

<210> SEQ ID NO 84
<211> LENGTH: 4
<212> TYPE: PRT
<213> ORGANISM: artificial sequence
<220> FEATURE:
<223> OTHER INFORMATION: ancestral

<400> SEQUENCE: 84

Asp His Leu Phe
1

<210> SEQ ID NO 85
<211> LENGTH: 4
<212> TYPE: PRT
<213> ORGANISM: artificial sequence
<220> FEATURE:
<223> OTHER INFORMATION: ancestral

<400> SEQUENCE: 85

Pro Thr Ile Trp
1

<210> SEQ ID NO 86
<211> LENGTH: 4
<212> TYPE: PRT
<213> ORGANISM: artificial sequence
<220> FEATURE:
<223> OTHER INFORMATION: ancestral

<400> SEQUENCE: 86

Thr Ile Trp Thr
1

<210> SEQ ID NO 87
<211> LENGTH: 4
<212> TYPE: PRT
<213> ORGANISM: artificial sequence
<220> FEATURE:
<223> OTHER INFORMATION: ancestral

<400> SEQUENCE: 87

Ile Trp Thr Glu
1

<210> SEQ ID NO 88
<211> LENGTH: 4
<212> TYPE: PRT
<213> ORGANISM: artificial sequence
<220> FEATURE:
<223> OTHER INFORMATION: ancestral

<400> SEQUENCE: 88

Trp Thr Glu Val
1

<210> SEQ ID NO 89
<211> LENGTH: 4
<212> TYPE: PRT
<213> ORGANISM: artificial sequence
<220> FEATURE:
<223> OTHER INFORMATION: ancestral

```
<400> SEQUENCE: 89

Thr Glu Val His
1

<210> SEQ ID NO 90
<211> LENGTH: 4
<212> TYPE: PRT
<213> ORGANISM: artificial sequence
<220> FEATURE:
<223> OTHER INFORMATION: ancestral

<400> SEQUENCE: 90

Glu Val His Asp
1

<210> SEQ ID NO 91
<211> LENGTH: 4
<212> TYPE: PRT
<213> ORGANISM: artificial sequence
<220> FEATURE:
<223> OTHER INFORMATION: ancestral

<400> SEQUENCE: 91

Val His Asp Thr
1

<210> SEQ ID NO 92
<211> LENGTH: 4
<212> TYPE: PRT
<213> ORGANISM: artificial sequence
<220> FEATURE:
<223> OTHER INFORMATION: ancestral

<400> SEQUENCE: 92

His Asp Thr Val
1

<210> SEQ ID NO 93
<211> LENGTH: 4
<212> TYPE: PRT
<213> ORGANISM: artificial sequence
<220> FEATURE:
<223> OTHER INFORMATION: ancestral

<400> SEQUENCE: 93

Phe Pro Gly Glu
1

<210> SEQ ID NO 94
<211> LENGTH: 4
<212> TYPE: PRT
<213> ORGANISM: artificial sequence
<220> FEATURE:
<223> OTHER INFORMATION: ancestral

<400> SEQUENCE: 94

Pro Gly Glu Ser
1

<210> SEQ ID NO 95
<211> LENGTH: 4
<212> TYPE: PRT
<213> ORGANISM: artificial sequence
<220> FEATURE:
<223> OTHER INFORMATION: ancestral
```

```
<400> SEQUENCE: 95

Gly Glu Ser His
1

<210> SEQ ID NO 96
<211> LENGTH: 4
<212> TYPE: PRT
<213> ORGANISM: artificial sequence
<220> FEATURE:
<223> OTHER INFORMATION: ancestral

<400> SEQUENCE: 96

Glu Ser His Thr
1

<210> SEQ ID NO 97
<211> LENGTH: 4
<212> TYPE: PRT
<213> ORGANISM: artificial sequence
<220> FEATURE:
<223> OTHER INFORMATION: ancestral

<400> SEQUENCE: 97

Leu Val Cys Lys
1

<210> SEQ ID NO 98
<211> LENGTH: 4
<212> TYPE: PRT
<213> ORGANISM: artificial sequence
<220> FEATURE:
<223> OTHER INFORMATION: ancestral

<400> SEQUENCE: 98

Val Cys Lys Glu
1

<210> SEQ ID NO 99
<211> LENGTH: 4
<212> TYPE: PRT
<213> ORGANISM: artificial sequence
<220> FEATURE:
<223> OTHER INFORMATION: ancestral

<400> SEQUENCE: 99

Cys Lys Glu Gly
1

<210> SEQ ID NO 100
<211> LENGTH: 4
<212> TYPE: PRT
<213> ORGANISM: artificial sequence
<220> FEATURE:
<223> OTHER INFORMATION: ancestral

<400> SEQUENCE: 100

Gly Ser Leu Ser
1

<210> SEQ ID NO 101
<211> LENGTH: 4
<212> TYPE: PRT
<213> ORGANISM: artificial sequence
<220> FEATURE:
<223> OTHER INFORMATION: ancestral
```

```
<400> SEQUENCE: 101

Ser Leu Ser Lys
1

<210> SEQ ID NO 102
<211> LENGTH: 4
<212> TYPE: PRT
<213> ORGANISM: artificial sequence
<220> FEATURE:
<223> OTHER INFORMATION: ancestral

<400> SEQUENCE: 102

Leu Ser Lys Glu
1

<210> SEQ ID NO 103
<211> LENGTH: 4
<212> TYPE: PRT
<213> ORGANISM: artificial sequence
<220> FEATURE:
<223> OTHER INFORMATION: ancestral

<400> SEQUENCE: 103

Ser Lys Glu Arg
1

<210> SEQ ID NO 104
<211> LENGTH: 4
<212> TYPE: PRT
<213> ORGANISM: artificial sequence
<220> FEATURE:
<223> OTHER INFORMATION: ancestral

<400> SEQUENCE: 104

Arg Thr Gln Met
1

<210> SEQ ID NO 105
<211> LENGTH: 4
<212> TYPE: PRT
<213> ORGANISM: artificial sequence
<220> FEATURE:
<223> OTHER INFORMATION: ancestral

<400> SEQUENCE: 105

Thr Gln Met Leu
1

<210> SEQ ID NO 106
<211> LENGTH: 4
<212> TYPE: PRT
<213> ORGANISM: artificial sequence
<220> FEATURE:
<223> OTHER INFORMATION: ancestral

<400> SEQUENCE: 106

Gln Met Leu His
1

<210> SEQ ID NO 107
<211> LENGTH: 4
<212> TYPE: PRT
<213> ORGANISM: artificial sequence
<220> FEATURE:
<223> OTHER INFORMATION: ancestral
```

<400> SEQUENCE: 107

Met Leu His Gln
1

<210> SEQ ID NO 108
<211> LENGTH: 4
<212> TYPE: PRT
<213> ORGANISM: artificial sequence
<220> FEATURE:
<223> OTHER INFORMATION: ancestral

<400> SEQUENCE: 108

Leu His Gln Phe
1

<210> SEQ ID NO 109
<211> LENGTH: 4
<212> TYPE: PRT
<213> ORGANISM: artificial sequence
<220> FEATURE:
<223> OTHER INFORMATION: ancestral

<400> SEQUENCE: 109

His Gln Phe Val
1

<210> SEQ ID NO 110
<211> LENGTH: 4
<212> TYPE: PRT
<213> ORGANISM: artificial sequence
<220> FEATURE:
<223> OTHER INFORMATION: ancestral

<400> SEQUENCE: 110

Gln Phe Val Leu
1

<210> SEQ ID NO 111
<211> LENGTH: 4
<212> TYPE: PRT
<213> ORGANISM: artificial sequence
<220> FEATURE:
<223> OTHER INFORMATION: ancestral

<400> SEQUENCE: 111

Lys Asp Ser Phe
1

<210> SEQ ID NO 112
<211> LENGTH: 4
<212> TYPE: PRT
<213> ORGANISM: artificial sequence
<220> FEATURE:
<223> OTHER INFORMATION: ancestral

<400> SEQUENCE: 112

Asp Ser Phe Thr
1

<210> SEQ ID NO 113
<211> LENGTH: 4
<212> TYPE: PRT
<213> ORGANISM: artificial sequence
<220> FEATURE:
<223> OTHER INFORMATION: ancestral

```
<400> SEQUENCE: 113

Ser Phe Thr Gln
1

<210> SEQ ID NO 114
<211> LENGTH: 4
<212> TYPE: PRT
<213> ORGANISM: artificial sequence
<220> FEATURE:
<223> OTHER INFORMATION: ancestral

<400> SEQUENCE: 114

Phe Thr Gln Ala
1

<210> SEQ ID NO 115
<211> LENGTH: 4
<212> TYPE: PRT
<213> ORGANISM: artificial sequence
<220> FEATURE:
<223> OTHER INFORMATION: ancestral

<400> SEQUENCE: 115

Thr Gln Ala Met
1

<210> SEQ ID NO 116
<211> LENGTH: 4
<212> TYPE: PRT
<213> ORGANISM: artificial sequence
<220> FEATURE:
<223> OTHER INFORMATION: ancestral

<400> SEQUENCE: 116

Gln Ala Met Asp
1

<210> SEQ ID NO 117
<211> LENGTH: 4
<212> TYPE: PRT
<213> ORGANISM: artificial sequence
<220> FEATURE:
<223> OTHER INFORMATION: ancestral

<400> SEQUENCE: 117

Ala Met Asp Ser
1

<210> SEQ ID NO 118
<211> LENGTH: 4
<212> TYPE: PRT
<213> ORGANISM: artificial sequence
<220> FEATURE:
<223> OTHER INFORMATION: ancestral

<400> SEQUENCE: 118

Met Asp Ser Ala
1

<210> SEQ ID NO 119
<211> LENGTH: 4
<212> TYPE: PRT
<213> ORGANISM: artificial sequence
<220> FEATURE:
<223> OTHER INFORMATION: ancestral
```

<400> SEQUENCE: 119

Asp Ser Ala Ser
1

<210> SEQ ID NO 120
<211> LENGTH: 4
<212> TYPE: PRT
<213> ORGANISM: artificial sequence
<220> FEATURE:
<223> OTHER INFORMATION: ancestral

<400> SEQUENCE: 120

Ser Ala Ser Thr
1

<210> SEQ ID NO 121
<211> LENGTH: 4
<212> TYPE: PRT
<213> ORGANISM: artificial sequence
<220> FEATURE:
<223> OTHER INFORMATION: ancestral

<400> SEQUENCE: 121

Ala Ser Thr Arg
1

<210> SEQ ID NO 122
<211> LENGTH: 4
<212> TYPE: PRT
<213> ORGANISM: artificial sequence
<220> FEATURE:
<223> OTHER INFORMATION: ancestral

<400> SEQUENCE: 122

Ser Thr Arg Ala
1

<210> SEQ ID NO 123
<211> LENGTH: 4
<212> TYPE: PRT
<213> ORGANISM: artificial sequence
<220> FEATURE:
<223> OTHER INFORMATION: ancestral

<400> SEQUENCE: 123

Thr Arg Ala Trp
1

<210> SEQ ID NO 124
<211> LENGTH: 4
<212> TYPE: PRT
<213> ORGANISM: artificial sequence
<220> FEATURE:
<223> OTHER INFORMATION: ancestral

<400> SEQUENCE: 124

Leu Leu Ile Asp
1

<210> SEQ ID NO 125
<211> LENGTH: 4
<212> TYPE: PRT
<213> ORGANISM: artificial sequence
<220> FEATURE:
<223> OTHER INFORMATION: ancestral

```
<400> SEQUENCE: 125

Leu Ile Asp Leu
1

<210> SEQ ID NO 126
<211> LENGTH: 4
<212> TYPE: PRT
<213> ORGANISM: artificial sequence
<220> FEATURE:
<223> OTHER INFORMATION: ancestral

<400> SEQUENCE: 126

Ile Asp Leu Gly
1

<210> SEQ ID NO 127
<211> LENGTH: 4
<212> TYPE: PRT
<213> ORGANISM: artificial sequence
<220> FEATURE:
<223> OTHER INFORMATION: ancestral

<400> SEQUENCE: 127

Ser Ser His Lys
1

<210> SEQ ID NO 128
<211> LENGTH: 4
<212> TYPE: PRT
<213> ORGANISM: artificial sequence
<220> FEATURE:
<223> OTHER INFORMATION: ancestral

<400> SEQUENCE: 128

Ser His Lys His
1

<210> SEQ ID NO 129
<211> LENGTH: 4
<212> TYPE: PRT
<213> ORGANISM: artificial sequence
<220> FEATURE:
<223> OTHER INFORMATION: ancestral

<400> SEQUENCE: 129

His Lys His Asp
1

<210> SEQ ID NO 130
<211> LENGTH: 4
<212> TYPE: PRT
<213> ORGANISM: artificial sequence
<220> FEATURE:
<223> OTHER INFORMATION: ancestral

<400> SEQUENCE: 130

Lys His Asp Gly
1

<210> SEQ ID NO 131
<211> LENGTH: 4
<212> TYPE: PRT
<213> ORGANISM: artificial sequence
<220> FEATURE:
<223> OTHER INFORMATION: ancestral
```

<400> SEQUENCE: 131

Glu Pro Gln Trp
1

<210> SEQ ID NO 132
<211> LENGTH: 4
<212> TYPE: PRT
<213> ORGANISM: artificial sequence
<220> FEATURE:
<223> OTHER INFORMATION: ancestral

<400> SEQUENCE: 132

Pro Gln Trp Gln
1

<210> SEQ ID NO 133
<211> LENGTH: 4
<212> TYPE: PRT
<213> ORGANISM: artificial sequence
<220> FEATURE:
<223> OTHER INFORMATION: ancestral

<400> SEQUENCE: 133

Gln Trp Gln Lys
1

<210> SEQ ID NO 134
<211> LENGTH: 4
<212> TYPE: PRT
<213> ORGANISM: artificial sequence
<220> FEATURE:
<223> OTHER INFORMATION: ancestral

<400> SEQUENCE: 134

Trp Gln Lys Lys
1

<210> SEQ ID NO 135
<211> LENGTH: 4
<212> TYPE: PRT
<213> ORGANISM: artificial sequence
<220> FEATURE:
<223> OTHER INFORMATION: ancestral

<400> SEQUENCE: 135

Gln Lys Lys Asn
1

<210> SEQ ID NO 136
<211> LENGTH: 4
<212> TYPE: PRT
<213> ORGANISM: artificial sequence
<220> FEATURE:
<223> OTHER INFORMATION: ancestral

<400> SEQUENCE: 136

Lys Lys Asn Asn
1

<210> SEQ ID NO 137
<211> LENGTH: 4
<212> TYPE: PRT
<213> ORGANISM: artificial sequence
<220> FEATURE:
<223> OTHER INFORMATION: ancestral

```
<400> SEQUENCE: 137

Asn Glu Glu Met
1

<210> SEQ ID NO 138
<211> LENGTH: 4
<212> TYPE: PRT
<213> ORGANISM: artificial sequence
<220> FEATURE:
<223> OTHER INFORMATION: ancestral

<400> SEQUENCE: 138

Glu Glu Met Glu
1

<210> SEQ ID NO 139
<211> LENGTH: 4
<212> TYPE: PRT
<213> ORGANISM: artificial sequence
<220> FEATURE:
<223> OTHER INFORMATION: ancestral

<400> SEQUENCE: 139

Glu Met Glu Asp
1

<210> SEQ ID NO 140
<211> LENGTH: 4
<212> TYPE: PRT
<213> ORGANISM: artificial sequence
<220> FEATURE:
<223> OTHER INFORMATION: ancestral

<400> SEQUENCE: 140

Met Glu Asp Tyr
1

<210> SEQ ID NO 141
<211> LENGTH: 4
<212> TYPE: PRT
<213> ORGANISM: artificial sequence
<220> FEATURE:
<223> OTHER INFORMATION: ancestral

<400> SEQUENCE: 141

Asp Asp Leu Asp
1

<210> SEQ ID NO 142
<211> LENGTH: 4
<212> TYPE: PRT
<213> ORGANISM: artificial sequence
<220> FEATURE:
<223> OTHER INFORMATION: ancestral

<400> SEQUENCE: 142

Asp Leu Asp Ser
1

<210> SEQ ID NO 143
<211> LENGTH: 4
<212> TYPE: PRT
<213> ORGANISM: artificial sequence
<220> FEATURE:
<223> OTHER INFORMATION: ancestral
```

```
<400> SEQUENCE: 143

Leu Asp Ser Glu
1

<210> SEQ ID NO 144
<211> LENGTH: 4
<212> TYPE: PRT
<213> ORGANISM: artificial sequence
<220> FEATURE:
<223> OTHER INFORMATION: ancestral

<400> SEQUENCE: 144

Glu Met Asp Met
1

<210> SEQ ID NO 145
<211> LENGTH: 4
<212> TYPE: PRT
<213> ORGANISM: artificial sequence
<220> FEATURE:
<223> OTHER INFORMATION: ancestral

<400> SEQUENCE: 145

Met Asp Met Phe
1

<210> SEQ ID NO 146
<211> LENGTH: 4
<212> TYPE: PRT
<213> ORGANISM: artificial sequence
<220> FEATURE:
<223> OTHER INFORMATION: ancestral

<400> SEQUENCE: 146

Asp Met Phe Thr
1

<210> SEQ ID NO 147
<211> LENGTH: 4
<212> TYPE: PRT
<213> ORGANISM: artificial sequence
<220> FEATURE:
<223> OTHER INFORMATION: ancestral

<400> SEQUENCE: 147

Met Phe Thr Leu
1

<210> SEQ ID NO 148
<211> LENGTH: 4
<212> TYPE: PRT
<213> ORGANISM: artificial sequence
<220> FEATURE:
<223> OTHER INFORMATION: ancestral

<400> SEQUENCE: 148

Phe Thr Leu Asp
1

<210> SEQ ID NO 149
<211> LENGTH: 4
<212> TYPE: PRT
<213> ORGANISM: artificial sequence
<220> FEATURE:
<223> OTHER INFORMATION: ancestral
```

```
<400> SEQUENCE: 149

Thr Leu Asp Asp
1

<210> SEQ ID NO 150
<211> LENGTH: 4
<212> TYPE: PRT
<213> ORGANISM: artificial sequence
<220> FEATURE:
<223> OTHER INFORMATION: ancestral

<400> SEQUENCE: 150

Leu Asp Asp Asp
1

<210> SEQ ID NO 151
<211> LENGTH: 4
<212> TYPE: PRT
<213> ORGANISM: artificial sequence
<220> FEATURE:
<223> OTHER INFORMATION: ancestral

<400> SEQUENCE: 151

Leu Ser Ala Leu
1

<210> SEQ ID NO 152
<211> LENGTH: 4
<212> TYPE: PRT
<213> ORGANISM: artificial sequence
<220> FEATURE:
<223> OTHER INFORMATION: ancestral

<400> SEQUENCE: 152

Ser Ala Leu Gln
1

<210> SEQ ID NO 153
<211> LENGTH: 4
<212> TYPE: PRT
<213> ORGANISM: artificial sequence
<220> FEATURE:
<223> OTHER INFORMATION: ancestral

<400> SEQUENCE: 153

Ala Leu Gln Ser
1

<210> SEQ ID NO 154
<211> LENGTH: 4
<212> TYPE: PRT
<213> ORGANISM: artificial sequence
<220> FEATURE:
<223> OTHER INFORMATION: ancestral

<400> SEQUENCE: 154

Leu Gln Ser Glu
1

<210> SEQ ID NO 155
<211> LENGTH: 4
<212> TYPE: PRT
<213> ORGANISM: artificial sequence
<220> FEATURE:
<223> OTHER INFORMATION: ancestral
```

<400> SEQUENCE: 155

Gln Ser Glu Gln
1

<210> SEQ ID NO 156
<211> LENGTH: 4
<212> TYPE: PRT
<213> ORGANISM: artificial sequence
<220> FEATURE:
<223> OTHER INFORMATION: ancestral

<400> SEQUENCE: 156

Ser Glu Gln Glu
1

<210> SEQ ID NO 157
<211> LENGTH: 4
<212> TYPE: PRT
<213> ORGANISM: artificial sequence
<220> FEATURE:
<223> OTHER INFORMATION: ancestral

<400> SEQUENCE: 157

Glu Gln Glu Ala
1

<210> SEQ ID NO 158
<211> LENGTH: 4
<212> TYPE: PRT
<213> ORGANISM: artificial sequence
<220> FEATURE:
<223> OTHER INFORMATION: ancestral

<400> SEQUENCE: 158

Gln Glu Ala Thr
1

<210> SEQ ID NO 159
<211> LENGTH: 4
<212> TYPE: PRT
<213> ORGANISM: artificial sequence
<220> FEATURE:
<223> OTHER INFORMATION: ancestral

<400> SEQUENCE: 159

Glu Ala Thr Asp
1

<210> SEQ ID NO 160
<211> LENGTH: 4
<212> TYPE: PRT
<213> ORGANISM: artificial sequence
<220> FEATURE:
<223> OTHER INFORMATION: ancestral

<400> SEQUENCE: 160

Ala Thr Asp Tyr
1

<210> SEQ ID NO 161
<211> LENGTH: 4
<212> TYPE: PRT
<213> ORGANISM: artificial sequence
<220> FEATURE:
<223> OTHER INFORMATION: ancestral

```
<400> SEQUENCE: 161

Thr Asp Tyr Asp
1

<210> SEQ ID NO 162
<211> LENGTH: 4
<212> TYPE: PRT
<213> ORGANISM: artificial sequence
<220> FEATURE:
<223> OTHER INFORMATION: ancestral

<400> SEQUENCE: 162

Tyr Asp Asp Ser
1

<210> SEQ ID NO 163
<211> LENGTH: 4
<212> TYPE: PRT
<213> ORGANISM: artificial sequence
<220> FEATURE:
<223> OTHER INFORMATION: ancestral

<400> SEQUENCE: 163

Asp Asp Ser Ile
1

<210> SEQ ID NO 164
<211> LENGTH: 4
<212> TYPE: PRT
<213> ORGANISM: artificial sequence
<220> FEATURE:
<223> OTHER INFORMATION: ancestral

<400> SEQUENCE: 164

Asp Ser Ile Thr
1

<210> SEQ ID NO 165
<211> LENGTH: 4
<212> TYPE: PRT
<213> ORGANISM: artificial sequence
<220> FEATURE:
<223> OTHER INFORMATION: ancestral

<400> SEQUENCE: 165

Ser Ile Thr Ile
1

<210> SEQ ID NO 166
<211> LENGTH: 4
<212> TYPE: PRT
<213> ORGANISM: artificial sequence
<220> FEATURE:
<223> OTHER INFORMATION: ancestral

<400> SEQUENCE: 166

Ile Thr Ile Glu
1

<210> SEQ ID NO 167
<211> LENGTH: 4
<212> TYPE: PRT
<213> ORGANISM: artificial sequence
<220> FEATURE:
<223> OTHER INFORMATION: ancestral
```

```
<400> SEQUENCE: 167

Thr Ile Glu Thr
1

<210> SEQ ID NO 168
<211> LENGTH: 4
<212> TYPE: PRT
<213> ORGANISM: artificial sequence
<220> FEATURE:
<223> OTHER INFORMATION: ancestral

<400> SEQUENCE: 168

Ile Glu Thr Asn
1

<210> SEQ ID NO 169
<211> LENGTH: 4
<212> TYPE: PRT
<213> ORGANISM: artificial sequence
<220> FEATURE:
<223> OTHER INFORMATION: ancestral

<400> SEQUENCE: 169

Glu Thr Asn Glu
1

<210> SEQ ID NO 170
<211> LENGTH: 4
<212> TYPE: PRT
<213> ORGANISM: artificial sequence
<220> FEATURE:
<223> OTHER INFORMATION: ancestral

<400> SEQUENCE: 170

Thr Asn Glu Asp
1

<210> SEQ ID NO 171
<211> LENGTH: 4
<212> TYPE: PRT
<213> ORGANISM: artificial sequence
<220> FEATURE:
<223> OTHER INFORMATION: ancestral

<400> SEQUENCE: 171

Asn Glu Asp Phe
1

<210> SEQ ID NO 172
<211> LENGTH: 4
<212> TYPE: PRT
<213> ORGANISM: artificial sequence
<220> FEATURE:
<223> OTHER INFORMATION: ancestral

<400> SEQUENCE: 172

Asp Ile Tyr Gly
1

<210> SEQ ID NO 173
<211> LENGTH: 4
<212> TYPE: PRT
<213> ORGANISM: artificial sequence
<220> FEATURE:
<223> OTHER INFORMATION: ancestral
```

```
<400> SEQUENCE: 173

Ile Tyr Gly Glu
1

<210> SEQ ID NO 174
<211> LENGTH: 4
<212> TYPE: PRT
<213> ORGANISM: artificial sequence
<220> FEATURE:
<223> OTHER INFORMATION: ancestral

<400> SEQUENCE: 174

Tyr Gly Glu Asp
1

<210> SEQ ID NO 175
<211> LENGTH: 4
<212> TYPE: PRT
<213> ORGANISM: artificial sequence
<220> FEATURE:
<223> OTHER INFORMATION: ancestral

<400> SEQUENCE: 175

Gly Glu Asp Ile
1

<210> SEQ ID NO 176
<211> LENGTH: 4
<212> TYPE: PRT
<213> ORGANISM: artificial sequence
<220> FEATURE:
<223> OTHER INFORMATION: ancestral

<400> SEQUENCE: 176

Glu Asp Ile Lys
1

<210> SEQ ID NO 177
<211> LENGTH: 4
<212> TYPE: PRT
<213> ORGANISM: artificial sequence
<220> FEATURE:
<223> OTHER INFORMATION: ancestral

<400> SEQUENCE: 177

Asp Ile Lys Gln
1

<210> SEQ ID NO 178
<211> LENGTH: 4
<212> TYPE: PRT
<213> ORGANISM: artificial sequence
<220> FEATURE:
<223> OTHER INFORMATION: ancestral

<400> SEQUENCE: 178

Ile Lys Gln Gly
1

<210> SEQ ID NO 179
<211> LENGTH: 4
<212> TYPE: PRT
<213> ORGANISM: artificial sequence
<220> FEATURE:
<223> OTHER INFORMATION: ancestral
```

```
<400> SEQUENCE: 179

Lys Gln Gly Pro
1

<210> SEQ ID NO 180
<211> LENGTH: 4
<212> TYPE: PRT
<213> ORGANISM: artificial sequence
<220> FEATURE:
<223> OTHER INFORMATION: ancestral

<400> SEQUENCE: 180

Gln Gly Pro Arg
1

<210> SEQ ID NO 181
<211> LENGTH: 4
<212> TYPE: PRT
<213> ORGANISM: artificial sequence
<220> FEATURE:
<223> OTHER INFORMATION: ancestral

<400> SEQUENCE: 181

Met Ser Thr Ser
1

<210> SEQ ID NO 182
<211> LENGTH: 4
<212> TYPE: PRT
<213> ORGANISM: artificial sequence
<220> FEATURE:
<223> OTHER INFORMATION: ancestral

<400> SEQUENCE: 182

Ser Thr Ser Pro
1

<210> SEQ ID NO 183
<211> LENGTH: 4
<212> TYPE: PRT
<213> ORGANISM: artificial sequence
<220> FEATURE:
<223> OTHER INFORMATION: ancestral

<400> SEQUENCE: 183

Thr Ser Pro His
1

<210> SEQ ID NO 184
<211> LENGTH: 4
<212> TYPE: PRT
<213> ORGANISM: artificial sequence
<220> FEATURE:
<223> OTHER INFORMATION: ancestral

<400> SEQUENCE: 184

Arg Asn Arg Asp
1

<210> SEQ ID NO 185
<211> LENGTH: 4
<212> TYPE: PRT
<213> ORGANISM: artificial sequence
<220> FEATURE:
<223> OTHER INFORMATION: ancestral
```

```
<400> SEQUENCE: 185

Asn Arg Asp Gln
1

<210> SEQ ID NO 186
<211> LENGTH: 4
<212> TYPE: PRT
<213> ORGANISM: artificial sequence
<220> FEATURE:
<223> OTHER INFORMATION: ancestral

<400> SEQUENCE: 186

Arg Asp Gln Ser
1

<210> SEQ ID NO 187
<211> LENGTH: 4
<212> TYPE: PRT
<213> ORGANISM: artificial sequence
<220> FEATURE:
<223> OTHER INFORMATION: ancestral

<400> SEQUENCE: 187

Asp Gln Ser Gly
1

<210> SEQ ID NO 188
<211> LENGTH: 4
<212> TYPE: PRT
<213> ORGANISM: artificial sequence
<220> FEATURE:
<223> OTHER INFORMATION: ancestral

<400> SEQUENCE: 188

Gln Ser Gly Asn
1

<210> SEQ ID NO 189
<211> LENGTH: 4
<212> TYPE: PRT
<213> ORGANISM: artificial sequence
<220> FEATURE:
<223> OTHER INFORMATION: ancestral

<400> SEQUENCE: 189

Ser Gly Asn Ala
1

<210> SEQ ID NO 190
<211> LENGTH: 4
<212> TYPE: PRT
<213> ORGANISM: artificial sequence
<220> FEATURE:
<223> OTHER INFORMATION: ancestral

<400> SEQUENCE: 190

Gly Asn Ala Pro
1

<210> SEQ ID NO 191
<211> LENGTH: 4
<212> TYPE: PRT
<213> ORGANISM: artificial sequence
<220> FEATURE:
<223> OTHER INFORMATION: ancestral
```

<400> SEQUENCE: 191

Asn Ala Pro Gln
1

<210> SEQ ID NO 192
<211> LENGTH: 4
<212> TYPE: PRT
<213> ORGANISM: artificial sequence
<220> FEATURE:
<223> OTHER INFORMATION: ancestral

<400> SEQUENCE: 192

Ala Pro Gln Phe
1

<210> SEQ ID NO 193
<211> LENGTH: 4
<212> TYPE: PRT
<213> ORGANISM: artificial sequence
<220> FEATURE:
<223> OTHER INFORMATION: ancestral

<400> SEQUENCE: 193

Gly Ser Phe Ser
1

<210> SEQ ID NO 194
<211> LENGTH: 4
<212> TYPE: PRT
<213> ORGANISM: artificial sequence
<220> FEATURE:
<223> OTHER INFORMATION: ancestral

<400> SEQUENCE: 194

Ser Phe Ser Gln
1

<210> SEQ ID NO 195
<211> LENGTH: 4
<212> TYPE: PRT
<213> ORGANISM: artificial sequence
<220> FEATURE:
<223> OTHER INFORMATION: ancestral

<400> SEQUENCE: 195

Phe Ser Gln Pro
1

<210> SEQ ID NO 196
<211> LENGTH: 4
<212> TYPE: PRT
<213> ORGANISM: artificial sequence
<220> FEATURE:
<223> OTHER INFORMATION: ancestral

<400> SEQUENCE: 196

Ser Gln Pro Leu
1

<210> SEQ ID NO 197
<211> LENGTH: 4
<212> TYPE: PRT
<213> ORGANISM: artificial sequence
<220> FEATURE:
<223> OTHER INFORMATION: ancestral

```
<400> SEQUENCE: 197

Ile Ser Tyr Lys
1

<210> SEQ ID NO 198
<211> LENGTH: 4
<212> TYPE: PRT
<213> ORGANISM: artificial sequence
<220> FEATURE:
<223> OTHER INFORMATION: ancestral

<400> SEQUENCE: 198

Ser Tyr Lys Glu
1

<210> SEQ ID NO 199
<211> LENGTH: 4
<212> TYPE: PRT
<213> ORGANISM: artificial sequence
<220> FEATURE:
<223> OTHER INFORMATION: ancestral

<400> SEQUENCE: 199

Tyr Lys Glu Asp
1

<210> SEQ ID NO 200
<211> LENGTH: 4
<212> TYPE: PRT
<213> ORGANISM: artificial sequence
<220> FEATURE:
<223> OTHER INFORMATION: ancestral

<400> SEQUENCE: 200

Lys Glu Asp Gln
1

<210> SEQ ID NO 201
<211> LENGTH: 4
<212> TYPE: PRT
<213> ORGANISM: artificial sequence
<220> FEATURE:
<223> OTHER INFORMATION: ancestral

<400> SEQUENCE: 201

Arg Gln Gly Glu
1

<210> SEQ ID NO 202
<211> LENGTH: 4
<212> TYPE: PRT
<213> ORGANISM: artificial sequence
<220> FEATURE:
<223> OTHER INFORMATION: ancestral

<400> SEQUENCE: 202

Gln Gly Glu Glu
1

<210> SEQ ID NO 203
<211> LENGTH: 4
<212> TYPE: PRT
<213> ORGANISM: artificial sequence
<220> FEATURE:
<223> OTHER INFORMATION: ancestral
```

```
<400> SEQUENCE: 203

Gly Glu Glu Pro
1

<210> SEQ ID NO 204
<211> LENGTH: 4
<212> TYPE: PRT
<213> ORGANISM: artificial sequence
<220> FEATURE:
<223> OTHER INFORMATION: ancestral

<400> SEQUENCE: 204

Glu Glu Pro Arg
1

<210> SEQ ID NO 205
<211> LENGTH: 4
<212> TYPE: PRT
<213> ORGANISM: artificial sequence
<220> FEATURE:
<223> OTHER INFORMATION: ancestral

<400> SEQUENCE: 205

Glu Pro Arg Arg
1

<210> SEQ ID NO 206
<211> LENGTH: 4
<212> TYPE: PRT
<213> ORGANISM: artificial sequence
<220> FEATURE:
<223> OTHER INFORMATION: ancestral

<400> SEQUENCE: 206

Pro Arg Arg Asn
1

<210> SEQ ID NO 207
<211> LENGTH: 4
<212> TYPE: PRT
<213> ORGANISM: artificial sequence
<220> FEATURE:
<223> OTHER INFORMATION: ancestral

<400> SEQUENCE: 207

Arg Arg Asn Phe
1

<210> SEQ ID NO 208
<211> LENGTH: 4
<212> TYPE: PRT
<213> ORGANISM: artificial sequence
<220> FEATURE:
<223> OTHER INFORMATION: ancestral

<400> SEQUENCE: 208

Arg Asn Phe Val
1

<210> SEQ ID NO 209
<211> LENGTH: 4
<212> TYPE: PRT
<213> ORGANISM: artificial sequence
<220> FEATURE:
<223> OTHER INFORMATION: ancestral
```

```
<400> SEQUENCE: 209

Glu Thr Lys Ile
1

<210> SEQ ID NO 210
<211> LENGTH: 4
<212> TYPE: PRT
<213> ORGANISM: artificial sequence
<220> FEATURE:
<223> OTHER INFORMATION: ancestral

<400> SEQUENCE: 210

Thr Lys Ile Tyr
1

<210> SEQ ID NO 211
<211> LENGTH: 4
<212> TYPE: PRT
<213> ORGANISM: artificial sequence
<220> FEATURE:
<223> OTHER INFORMATION: ancestral

<400> SEQUENCE: 211

Lys Ile Tyr Phe
1

<210> SEQ ID NO 212
<211> LENGTH: 4
<212> TYPE: PRT
<213> ORGANISM: artificial sequence
<220> FEATURE:
<223> OTHER INFORMATION: ancestral

<400> SEQUENCE: 212

Ile Tyr Phe Trp
1

<210> SEQ ID NO 213
<211> LENGTH: 4
<212> TYPE: PRT
<213> ORGANISM: artificial sequence
<220> FEATURE:
<223> OTHER INFORMATION: ancestral

<400> SEQUENCE: 213

Asp Leu Glu Arg
1

<210> SEQ ID NO 214
<211> LENGTH: 4
<212> TYPE: PRT
<213> ORGANISM: artificial sequence
<220> FEATURE:
<223> OTHER INFORMATION: ancestral

<400> SEQUENCE: 214

Leu Glu Arg Asp
1

<210> SEQ ID NO 215
<211> LENGTH: 4
<212> TYPE: PRT
<213> ORGANISM: artificial sequence
<220> FEATURE:
<223> OTHER INFORMATION: ancestral
```

```
<400> SEQUENCE: 215

Glu Arg Asp Met
1

<210> SEQ ID NO 216
<211> LENGTH: 4
<212> TYPE: PRT
<213> ORGANISM: artificial sequence
<220> FEATURE:
<223> OTHER INFORMATION: ancestral

<400> SEQUENCE: 216

Arg Asp Met His
1

<210> SEQ ID NO 217
<211> LENGTH: 4
<212> TYPE: PRT
<213> ORGANISM: artificial sequence
<220> FEATURE:
<223> OTHER INFORMATION: ancestral

<400> SEQUENCE: 217

Asp Met His Ser
1

<210> SEQ ID NO 218
<211> LENGTH: 4
<212> TYPE: PRT
<213> ORGANISM: artificial sequence
<220> FEATURE:
<223> OTHER INFORMATION: ancestral

<400> SEQUENCE: 218

Met His Ser Gly
1

<210> SEQ ID NO 219
<211> LENGTH: 4
<212> TYPE: PRT
<213> ORGANISM: artificial sequence
<220> FEATURE:
<223> OTHER INFORMATION: ancestral

<400> SEQUENCE: 219

Leu Ile Cys His
1

<210> SEQ ID NO 220
<211> LENGTH: 4
<212> TYPE: PRT
<213> ORGANISM: artificial sequence
<220> FEATURE:
<223> OTHER INFORMATION: ancestral

<400> SEQUENCE: 220

Ile Cys His Thr
1

<210> SEQ ID NO 221
<211> LENGTH: 4
<212> TYPE: PRT
<213> ORGANISM: artificial sequence
<220> FEATURE:
<223> OTHER INFORMATION: ancestral
```

```
<400> SEQUENCE: 221

Cys His Thr Asn
1

<210> SEQ ID NO 222
<211> LENGTH: 4
<212> TYPE: PRT
<213> ORGANISM: artificial sequence
<220> FEATURE:
<223> OTHER INFORMATION: ancestral

<400> SEQUENCE: 222

His Thr Asn Thr
1

<210> SEQ ID NO 223
<211> LENGTH: 4
<212> TYPE: PRT
<213> ORGANISM: artificial sequence
<220> FEATURE:
<223> OTHER INFORMATION: ancestral

<400> SEQUENCE: 223

Thr Asn Thr Leu
1

<210> SEQ ID NO 224
<211> LENGTH: 4
<212> TYPE: PRT
<213> ORGANISM: artificial sequence
<220> FEATURE:
<223> OTHER INFORMATION: ancestral

<400> SEQUENCE: 224

Thr Leu Asn Pro
1

<210> SEQ ID NO 225
<211> LENGTH: 4
<212> TYPE: PRT
<213> ORGANISM: artificial sequence
<220> FEATURE:
<223> OTHER INFORMATION: ancestral

<400> SEQUENCE: 225

Leu Asn Pro Ala
1

<210> SEQ ID NO 226
<211> LENGTH: 4
<212> TYPE: PRT
<213> ORGANISM: artificial sequence
<220> FEATURE:
<223> OTHER INFORMATION: ancestral

<400> SEQUENCE: 226

Asn Pro Ala His
1

<210> SEQ ID NO 227
<211> LENGTH: 4
<212> TYPE: PRT
<213> ORGANISM: artificial sequence
<220> FEATURE:
<223> OTHER INFORMATION: ancestral
```

```
<400> SEQUENCE: 227

Pro Ala His Gly
1

<210> SEQ ID NO 228
<211> LENGTH: 4
<212> TYPE: PRT
<213> ORGANISM: artificial sequence
<220> FEATURE:
<223> OTHER INFORMATION: ancestral

<400> SEQUENCE: 228

Arg Gln Val Ala
1

<210> SEQ ID NO 229
<211> LENGTH: 4
<212> TYPE: PRT
<213> ORGANISM: artificial sequence
<220> FEATURE:
<223> OTHER INFORMATION: ancestral

<400> SEQUENCE: 229

Gln Val Ala Val
1

<210> SEQ ID NO 230
<211> LENGTH: 4
<212> TYPE: PRT
<213> ORGANISM: artificial sequence
<220> FEATURE:
<223> OTHER INFORMATION: ancestral

<400> SEQUENCE: 230

Val Ala Val Gln
1

<210> SEQ ID NO 231
<211> LENGTH: 4
<212> TYPE: PRT
<213> ORGANISM: artificial sequence
<220> FEATURE:
<223> OTHER INFORMATION: ancestral

<400> SEQUENCE: 231

Ala Val Gln Glu
1

<210> SEQ ID NO 232
<211> LENGTH: 4
<212> TYPE: PRT
<213> ORGANISM: artificial sequence
<220> FEATURE:
<223> OTHER INFORMATION: ancestral

<400> SEQUENCE: 232

Arg Asn Cys Lys
1

<210> SEQ ID NO 233
<211> LENGTH: 4
<212> TYPE: PRT
<213> ORGANISM: artificial sequence
<220> FEATURE:
<223> OTHER INFORMATION: ancestral
```

```
<400> SEQUENCE: 233

Asn Cys Lys Thr
1

<210> SEQ ID NO 234
<211> LENGTH: 4
<212> TYPE: PRT
<213> ORGANISM: artificial sequence
<220> FEATURE:
<223> OTHER INFORMATION: ancestral

<400> SEQUENCE: 234

Cys Lys Thr Pro
1

<210> SEQ ID NO 235
<211> LENGTH: 4
<212> TYPE: PRT
<213> ORGANISM: artificial sequence
<220> FEATURE:
<223> OTHER INFORMATION: ancestral

<400> SEQUENCE: 235

Lys Thr Pro Cys
1

<210> SEQ ID NO 236
<211> LENGTH: 4
<212> TYPE: PRT
<213> ORGANISM: artificial sequence
<220> FEATURE:
<223> OTHER INFORMATION: ancestral

<400> SEQUENCE: 236

Thr Pro Cys Asn
1

<210> SEQ ID NO 237
<211> LENGTH: 4
<212> TYPE: PRT
<213> ORGANISM: artificial sequence
<220> FEATURE:
<223> OTHER INFORMATION: ancestral

<400> SEQUENCE: 237

Glu Asn Ile Gln
1

<210> SEQ ID NO 238
<211> LENGTH: 4
<212> TYPE: PRT
<213> ORGANISM: artificial sequence
<220> FEATURE:
<223> OTHER INFORMATION: ancestral

<400> SEQUENCE: 238

Asn Ile Gln Ser
1

<210> SEQ ID NO 239
<211> LENGTH: 4
<212> TYPE: PRT
<213> ORGANISM: artificial sequence
<220> FEATURE:
<223> OTHER INFORMATION: ancestral
```

```
<400> SEQUENCE: 239

Ile Gln Ser Ile
1

<210> SEQ ID NO 240
<211> LENGTH: 4
<212> TYPE: PRT
<213> ORGANISM: artificial sequence
<220> FEATURE:
<223> OTHER INFORMATION: ancestral

<400> SEQUENCE: 240

Gln Ser Ile His
1

<210> SEQ ID NO 241
<211> LENGTH: 4
<212> TYPE: PRT
<213> ORGANISM: artificial sequence
<220> FEATURE:
<223> OTHER INFORMATION: ancestral

<400> SEQUENCE: 241

Leu Pro Ser Arg
1

<210> SEQ ID NO 242
<211> LENGTH: 4
<212> TYPE: PRT
<213> ORGANISM: artificial sequence
<220> FEATURE:
<223> OTHER INFORMATION: ancestral

<400> SEQUENCE: 242

Pro Ser Arg Ala
1

<210> SEQ ID NO 243
<211> LENGTH: 4
<212> TYPE: PRT
<213> ORGANISM: artificial sequence
<220> FEATURE:
<223> OTHER INFORMATION: ancestral

<400> SEQUENCE: 243

Ser Arg Ala Gly
1

<210> SEQ ID NO 244
<211> LENGTH: 4
<212> TYPE: PRT
<213> ORGANISM: artificial sequence
<220> FEATURE:
<223> OTHER INFORMATION: ancestral

<400> SEQUENCE: 244

Arg Ala Gly Ile
1

<210> SEQ ID NO 245
<211> LENGTH: 4
<212> TYPE: PRT
<213> ORGANISM: artificial sequence
<220> FEATURE:
<223> OTHER INFORMATION: ancestral
```

```
<400> SEQUENCE: 245

Arg His Gln Arg
1

<210> SEQ ID NO 246
<211> LENGTH: 24
<212> TYPE: PRT
<213> ORGANISM: artificial sequence
<220> FEATURE:
<223> OTHER INFORMATION: ancestral

<400> SEQUENCE: 246

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 247
<211> LENGTH: 4
<212> TYPE: PRT
<213> ORGANISM: artificial sequence
<220> FEATURE:
<223> OTHER INFORMATION: ancestral

<400> SEQUENCE: 247

Cys Leu Leu Gln
1

<210> SEQ ID NO 248
<211> LENGTH: 4
<212> TYPE: PRT
<213> ORGANISM: artificial sequence
<220> FEATURE:
<223> OTHER INFORMATION: ancestral

<400> SEQUENCE: 248

Leu Leu Gln Phe
1

<210> SEQ ID NO 249
<211> LENGTH: 4
<212> TYPE: PRT
<213> ORGANISM: artificial sequence
<220> FEATURE:
<223> OTHER INFORMATION: ancestral

<400> SEQUENCE: 249

Leu Gln Phe Ser
1

<210> SEQ ID NO 250
<211> LENGTH: 4
<212> TYPE: PRT
<213> ORGANISM: artificial sequence
<220> FEATURE:
<223> OTHER INFORMATION: ancestral

<400> SEQUENCE: 250

Gln Phe Ser Phe
1

<210> SEQ ID NO 251
<211> LENGTH: 4
<212> TYPE: PRT
<213> ORGANISM: artificial sequence
<220> FEATURE:
```

<223> OTHER INFORMATION: ancestral

<400> SEQUENCE: 251

Leu Leu Ser Glu
1

<210> SEQ ID NO 252
<211> LENGTH: 4
<212> TYPE: PRT
<213> ORGANISM: artificial sequence
<220> FEATURE:
<223> OTHER INFORMATION: ancestral

<400> SEQUENCE: 252

Leu Ser Glu Leu
1

<210> SEQ ID NO 253
<211> LENGTH: 4
<212> TYPE: PRT
<213> ORGANISM: artificial sequence
<220> FEATURE:
<223> OTHER INFORMATION: ancestral

<400> SEQUENCE: 253

Glu Leu His Val
1

<210> SEQ ID NO 254
<211> LENGTH: 4
<212> TYPE: PRT
<213> ORGANISM: artificial sequence
<220> FEATURE:
<223> OTHER INFORMATION: ancestral

<400> SEQUENCE: 254

Arg Val Pro Arg
1

<210> SEQ ID NO 255
<211> LENGTH: 4
<212> TYPE: PRT
<213> ORGANISM: artificial sequence
<220> FEATURE:
<223> OTHER INFORMATION: ancestral

<400> SEQUENCE: 255

Val Pro Arg Ser
1

<210> SEQ ID NO 256
<211> LENGTH: 4
<212> TYPE: PRT
<213> ORGANISM: artificial sequence
<220> FEATURE:
<223> OTHER INFORMATION: ancestral

<400> SEQUENCE: 256

Pro Thr Ile Arg
1

<210> SEQ ID NO 257
<211> LENGTH: 4
<212> TYPE: PRT
<213> ORGANISM: artificial sequence
<220> FEATURE:
<223> OTHER INFORMATION: ancestral

```
<400> SEQUENCE: 257

Thr Ile Arg Ala
1

<210> SEQ ID NO 258
<211> LENGTH: 4
<212> TYPE: PRT
<213> ORGANISM: artificial sequence
<220> FEATURE:
<223> OTHER INFORMATION: ancestral

<400> SEQUENCE: 258

Ile Arg Ala Glu
1

<210> SEQ ID NO 259
<211> LENGTH: 4
<212> TYPE: PRT
<213> ORGANISM: artificial sequence
<220> FEATURE:
<223> OTHER INFORMATION: ancestral

<400> SEQUENCE: 259

Asn Glu Glu Glu
1

<210> SEQ ID NO 260
<211> LENGTH: 4
<212> TYPE: PRT
<213> ORGANISM: artificial sequence
<220> FEATURE:
<223> OTHER INFORMATION: ancestral

<400> SEQUENCE: 260

Glu Glu Glu Asp
1

<210> SEQ ID NO 261
<211> LENGTH: 4
<212> TYPE: PRT
<213> ORGANISM: artificial sequence
<220> FEATURE:
<223> OTHER INFORMATION: ancestral

<400> SEQUENCE: 261

Cys Asp Arg Asn
1

<210> SEQ ID NO 262
<211> LENGTH: 4
<212> TYPE: PRT
<213> ORGANISM: artificial sequence
<220> FEATURE:
<223> OTHER INFORMATION: ancestral

<400> SEQUENCE: 262

Glu Asp Thr Tyr
1

<210> SEQ ID NO 263
<211> LENGTH: 4
<212> TYPE: PRT
<213> ORGANISM: artificial sequence
<220> FEATURE:
<223> OTHER INFORMATION: ancestral
```

```
<400> SEQUENCE: 263

Pro Thr Tyr Leu
1

<210> SEQ ID NO 264
<211> LENGTH: 4
<212> TYPE: PRT
<213> ORGANISM: artificial sequence
<220> FEATURE:
<223> OTHER INFORMATION: ancestral

<400> SEQUENCE: 264

Leu Ser Glu Asn
1

<210> SEQ ID NO 265
<211> LENGTH: 4
<212> TYPE: PRT
<213> ORGANISM: artificial sequence
<220> FEATURE:
<223> OTHER INFORMATION: ancestral

<400> SEQUENCE: 265

Ile Thr Leu Thr
1

<210> SEQ ID NO 266
<211> LENGTH: 4
<212> TYPE: PRT
<213> ORGANISM: artificial sequence
<220> FEATURE:
<223> OTHER INFORMATION: ancestral

<400> SEQUENCE: 266

Ser Ile Glu Thr
1

<210> SEQ ID NO 267
<211> LENGTH: 4
<212> TYPE: PRT
<213> ORGANISM: artificial sequence
<220> FEATURE:
<223> OTHER INFORMATION: ancestral

<400> SEQUENCE: 267

Ile Glu Thr Lys
1

<210> SEQ ID NO 268
<211> LENGTH: 4
<212> TYPE: PRT
<213> ORGANISM: artificial sequence
<220> FEATURE:
<223> OTHER INFORMATION: ancestral

<400> SEQUENCE: 268

Glu Thr Lys Arg
1

<210> SEQ ID NO 269
<211> LENGTH: 4
<212> TYPE: PRT
<213> ORGANISM: artificial sequence
<220> FEATURE:
<223> OTHER INFORMATION: ancestral
```

<400> SEQUENCE: 269

Thr Lys Arg Glu
1

<210> SEQ ID NO 270
<211> LENGTH: 4
<212> TYPE: PRT
<213> ORGANISM: artificial sequence
<220> FEATURE:
<223> OTHER INFORMATION: ancestral

<400> SEQUENCE: 270

Lys Arg Glu Asp
1

<210> SEQ ID NO 271
<211> LENGTH: 4
<212> TYPE: PRT
<213> ORGANISM: artificial sequence
<220> FEATURE:
<223> OTHER INFORMATION: ancestral

<400> SEQUENCE: 271

Arg Glu Asp Phe
1

<210> SEQ ID NO 272
<211> LENGTH: 4
<212> TYPE: PRT
<213> ORGANISM: artificial sequence
<220> FEATURE:
<223> OTHER INFORMATION: ancestral

<400> SEQUENCE: 272

Gln Lys Arg Thr
1

<210> SEQ ID NO 273
<211> LENGTH: 4
<212> TYPE: PRT
<213> ORGANISM: artificial sequence
<220> FEATURE:
<223> OTHER INFORMATION: ancestral

<400> SEQUENCE: 273

Val Glu Gln Leu
1

<210> SEQ ID NO 274
<211> LENGTH: 4
<212> TYPE: PRT
<213> ORGANISM: artificial sequence
<220> FEATURE:
<223> OTHER INFORMATION: ancestral

<400> SEQUENCE: 274

Glu Gly Leu Trp
1

<210> SEQ ID NO 275
<211> LENGTH: 4
<212> TYPE: PRT
<213> ORGANISM: artificial sequence
<220> FEATURE:
<223> OTHER INFORMATION: ancestral

```
<400> SEQUENCE: 275

Gly Met Ser Arg
1

<210> SEQ ID NO 276
<211> LENGTH: 4
<212> TYPE: PRT
<213> ORGANISM: artificial sequence
<220> FEATURE:
<223> OTHER INFORMATION: ancestral

<400> SEQUENCE: 276

Met Ser Arg Ser
1

<210> SEQ ID NO 277
<211> LENGTH: 4
<212> TYPE: PRT
<213> ORGANISM: artificial sequence
<220> FEATURE:
<223> OTHER INFORMATION: ancestral

<400> SEQUENCE: 277

Ser Arg Ser Pro
1
```

FACTOR VIII PROTEINS HAVING ANCESTRAL SEQUENCES, EXPRESSION VECTORS, AND USES RELATED THERETO

CROSS REFERENCE TO RELATED APPLICATIONS

This application is a continuation of U.S. patent application Ser. No. 16/874,121, filed May 14, 2020, which is a continuation of U.S. patent application Ser. No. 15/547,742, filed Jul. 31, 2017, which is a U.S. national stage application under 35 USC § 371 of PCT/US2016/015092, filed Jan. 27, 2016, which claims benefit of U.S. Provisional Application No. 62/109,964 filed Jan. 30, 2015, hereby incorporated by reference in its entirety.

STATEMENT REGARDING FEDERALLY FUNDED RESEARCH

This invention was made with government support under Grants R01 HL092179 and U54 HL112309 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is EMY_061US2 SEQ_LIST.txt. The text file is 415 KB, was created on Jun. 1, 2021, and is being submitted electronically via EFS-Web. The information the text file is identical to the sequence listing contained in the application.

BACKGROUND

Mutations in the coagulation factor VIII gene result in a decreased or defective coagulation factor (FVIII) protein that gives rise to hemophilia A characterized by uncontrolled bleeding. Treatment of hemophilia A typically entails lifelong, multi-weekly intravenous infusion of either human plasma-derived or recombinant FVIII products. Patients treated with FVIII replacement products often develop neutralizing antibodies that render future treatment ineffective. Thus, there is a need to identify improved therapies.

Gene therapies are typically based on genetically engineered viruses designed to deliver functional transgenes to the patient so that their own cells can biosynthesize a missing or defective protein. Clinical advancements have been made using recombinant adeno-associated viral (rAAV) vectors for the expression of blood factors in the liver. McIntosh et al. report therapeutic levels of FVIII following administration of rAAV vector encoding a human factor VIII variant. Blood. 2013, 121(17):3335-44. See also Brown et al. Molecular Therapy, Methods & Clinical Development (2014) 1, 14036; Doering et al. J. Biol. Chem. 2004, 279:6546-6552; Zakas et al., J Thromb Haemost, 2015, 13(1):72-81; and U.S. Patent Application Publication US20040197875.

References cited herein are not an admission of prior art.

SUMMARY

This disclosure relates to recombinant or chimeric FVIII proteins, variants, and vectors encoding the proteins containing one or more ancestral mutations. In certain embodiments, one or more protein domains comprise amino acid sequences that are derived from ancestrally reconstructed amino acid sequences. In certain embodiments, the disclosure relates to pharmaceutical compositions comprising the proteins or vectors and related methods of inducing blood clotting.

In certain embodiments, ancestral domain mutations are those contained in SEQ ID NO: 2, 11, 20, and 29-38. In certain embodiments, the ancestral domain is a sequence within the A1 domain, A2 domain, activation peptide(ap) domain, A3 domain, C1 domain, or C2 domain optionally having a signaling peptide (sp) domain. In certain embodiments, the FVIII variant comprises a deleted B domain.

In certain embodiments, FVIII variant comprises an A1 domain, an A2 domain, a RHQR sequence (SEQ ID NO: 245), an A3 domain, a C1 domain, and a C2 domain.

In certain embodiments, FVIII variant comprises an A1 domain, an A2 domain, an activation peptide (ap) domain, an A3 domain, a C1 domain, and a C2 domain. In certain embodiments, the FVIII variant optionally comprises a deleted B domain.

In certain embodiments, the FVIII variant comprises a linker of between two and fifty, or two and twenty five, or two and fifteen amino acids between the A2 domain and the an activation peptide (ap) domain.

In certain embodiments, the ancestral sp domain is SEQ ID NO: 3, 12, or 21 or variants thereof. In certain embodiments, the ancestral A1 domain is SEQ ID NO: 4, 13, or 22 or variants thereof.

In certain embodiments, the ancestral A2 domain is SEQ ID NO: 5, 14, or 23 or variants thereof. In certain embodiments, the ancestral B domain is SEQ ID NO: 6, 15, or 24 or variants thereof. In certain embodiments, the ancestral ap domain is SEQ ID NO: 7, 16 or 25 or variants thereof. In certain embodiments, the ancestral A3 domain is SEQ ID NO: 8, 17, or 26 or variants thereof. In certain embodiments, the ancestral C1 domain is SEQ ID NO: 9, 18, or 27 or variants thereof. In certain embodiments, the ancestral C2 domain is SEQ ID NO: 10, 19, or 28 or variants thereof. In certain embodiments, the variants are those having greater than 80, 85, 90, 95, 96, 97, 98, or 99% identity or similarity to the domains. In certain embodiments, the variants are those having one, two, or more amino acid substitutions or conservative substitutions. In certain embodiments, the variants are those having one, two, three, four, five, six seven, eight, nine, or more amino acid substitutions, deletions, or additions.

In certain embodiments, the recombinant FVIII protein has SEQ ID NO: 39, 40, or 42 or variants thereof. In certain embodiments, the variants are those having greater than 80, 85, 90, 95, 96, 97, 98, or 99% identity or similarity to the proteins including or not including the signaling peptide. In certain embodiments, the variants are those having one, two, or more amino acid substitutions or conservative substitutions. In certain embodiments, the variants are those having one, two, three, four, five, six seven, eight, nine, or more amino acid substitutions, deletions, or additions.

In certain embodiments, the disclosure relates to recombinant or chimeric FVIII protein having one or more ancestral sequences or variants thereof such as SEQ ID NOs: 44-244 and 247-277 in the corresponding domains. In certain embodiments, the disclosure relates to recombinant FVIII protein having an ancestral domain selected from a signaling peptide (sp) domain, A1 domain, activation peptide (ap) domain, and A3 domain wherein one or more amino acids in B-domain are optionally deleted or the B-domain has one or more naturally or non-naturally occurring substitutions.

In certain embodiments, the recombinant or chimeric FVIII protein has the E434V mutation as reported in FIG. 1 of US20040197875 wherein the protein has an A2 domain having TDVTF (SEQ ID NO: 43)

In certain embodiments, the disclosure relates to nucleic acids encoding a recombinant or chimeric FVIII protein disclosed herein.

In certain embodiments, the disclosure relates to vectors comprising a promotor nucleic acid sequence in operable combination with a heterologous nucleic acid sequence encoding a recombinant or chimeric FVIII protein disclosed herein. In certain embodiments, the vector comprises a liver-specific promotor and 5' and 3' AAV inverted terminal repeats (ITRs).

In certain embodiments, the disclosure contemplates lentiviral gene therapy targeting hematopoietic stem cells. In certain embodiments, the vector is a retroviral or lentiviral vector such as a self-inactivating lentiviral vector derived from HIV-1. In certain embodiments, the vector contains an internal constitutive promoter such as EF1-alpha, PGK or UbC or a cell specific promoter such as GPIb-alpha, CD68, or beta globin LCR.

In certain embodiments, the disclosure contemplates pharmaceutical compositions comprising a recombinant or chimeric FVIII protein and a pharmaceutically acceptable excipient.

In certain embodiments, the disclosure contemplates methods of inducing blood clotting comprising administering an effective amount of a pharmaceutical composition disclosed herein to a subject in need thereof. In certain embodiments, the subject is at risk for, suspected of, exhibiting symptoms of, or diagnosed with a blood clotting disorder, e.g., wherein the subject is diagnosed with hemophilia A or acquired hemophilia.

In certain embodiments, the disclosure contemplates pharmaceutical composition comprising a vector of encoding a protein disclosed herein.

In certain embodiments, the disclosure contemplates method of inducing blood clotting comprising administering an effective amount of a pharmaceutical composition comprising a vector encoding a protein disclosed herein to a subject in need thereof wherein the subject is diagnosed with hemophilia A or acquired hemophilia under conditions such that the protein is expressed inducing blood clotting. In certain embodiments, the subject is unlikely to respond to exogenous FVIII infusions.

In certain embodiments, the disclosure relates to expression systems comprising nucleic acids or vectors comprising nucleic acids disclosed herein.

In certain embodiments, the disclosure relates to methods of inducing blood clotting comprising administering an effective amount of allogenic or autologous cells transduced ex vivo with a vector to express a FVIII disclosed herein.

Figure 1:
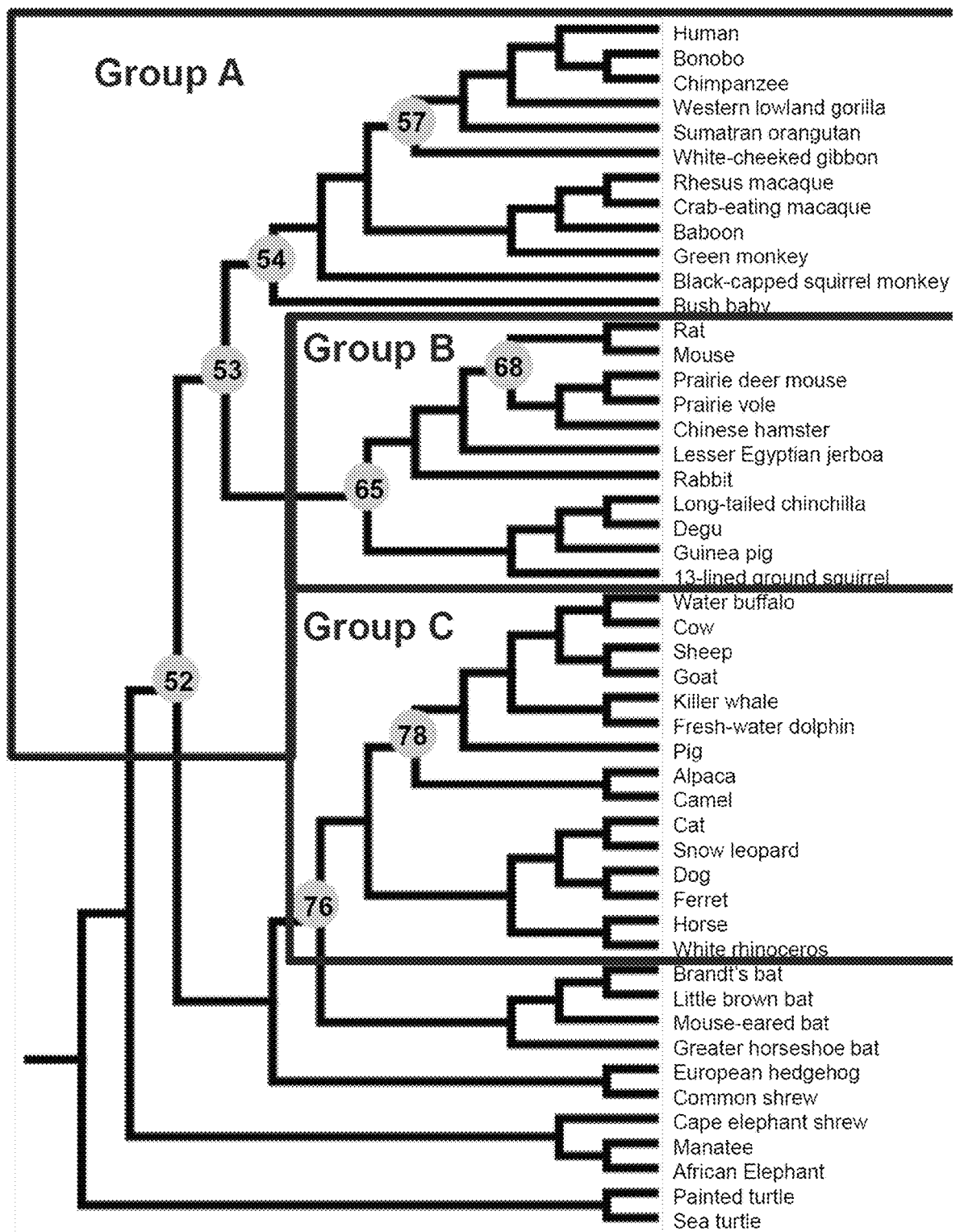
FIG. 1 shows a phylogenetic tree that was constructed for mammalian FVIII genes using known amino acid sequences. The ancestral intermediary nodes that were reconstructed through gene synthesis are numbered within the circles. These B-domain deleted genes have been codon optimized for human cell expression and have been subcloned into the mammalian expression plasmid ReNeo.
Figure 2:
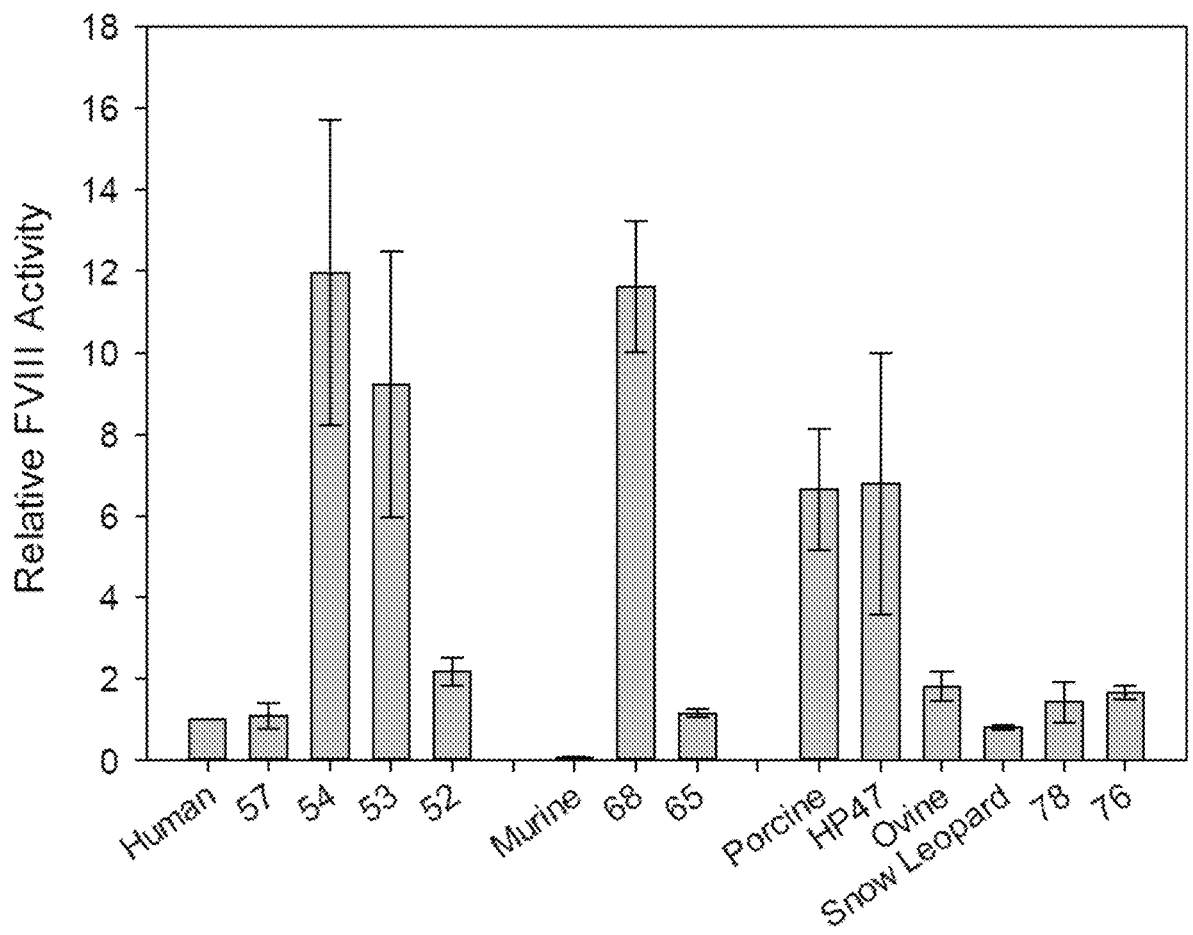
FIG. 2 shows relative FVIII activity data where HEK293T-17 cells were transiently transfected with FVIII plasmid via PEI. Twenty-four hours after replacing DMEM media with serum-free Aim-V, supernatant was assayed for FVIII activity via one-stage coagulation assay and shown as the mean fold increase over human FVIII from two separate experiments. Total activity was normalized to cell counts taken at the time of the FVIII detection and then normalized to human FVIII activity levels.
Figure 3:
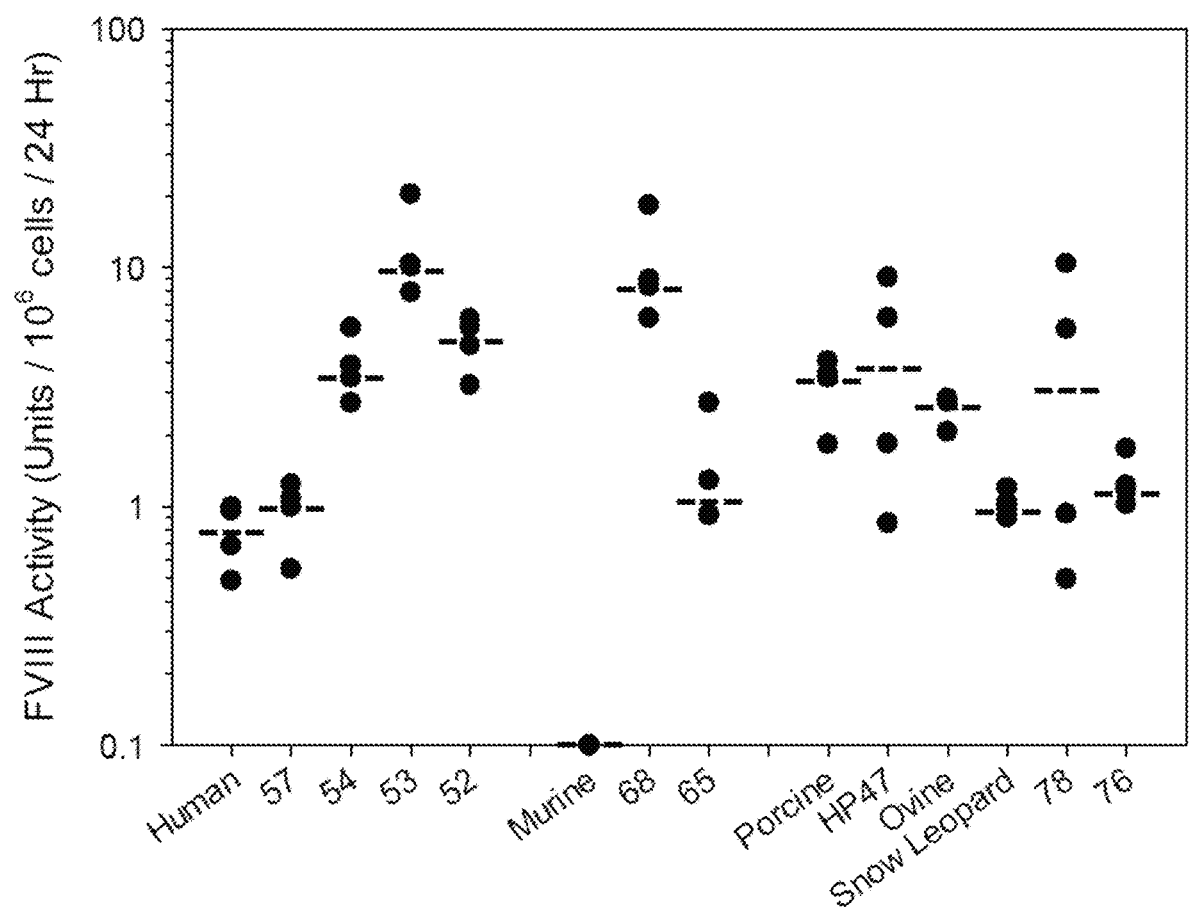
FIG. 3 shows activity data. Stable BHK-M clones were generated using G418 selection following transfection of FVIII plasmid with Lipofectamine 2000. Twenty-four clones were selected from each FVIII treatment. Shown are the FVIII activity levels of the 4 highest producing clones as determined by one-stage coagulation and normalized to cell counts. Dashed lines indicate the median value for each FVIII treatment. Of the ancestral FVIII sequences, production of nodes 52, 53, and 68 FVIII is significantly different from human FVIII. Furthermore, ancestral nodes 53 and 68 produce significantly higher concentrations of FVIII compared to porcine FVIII.
Figure 4:
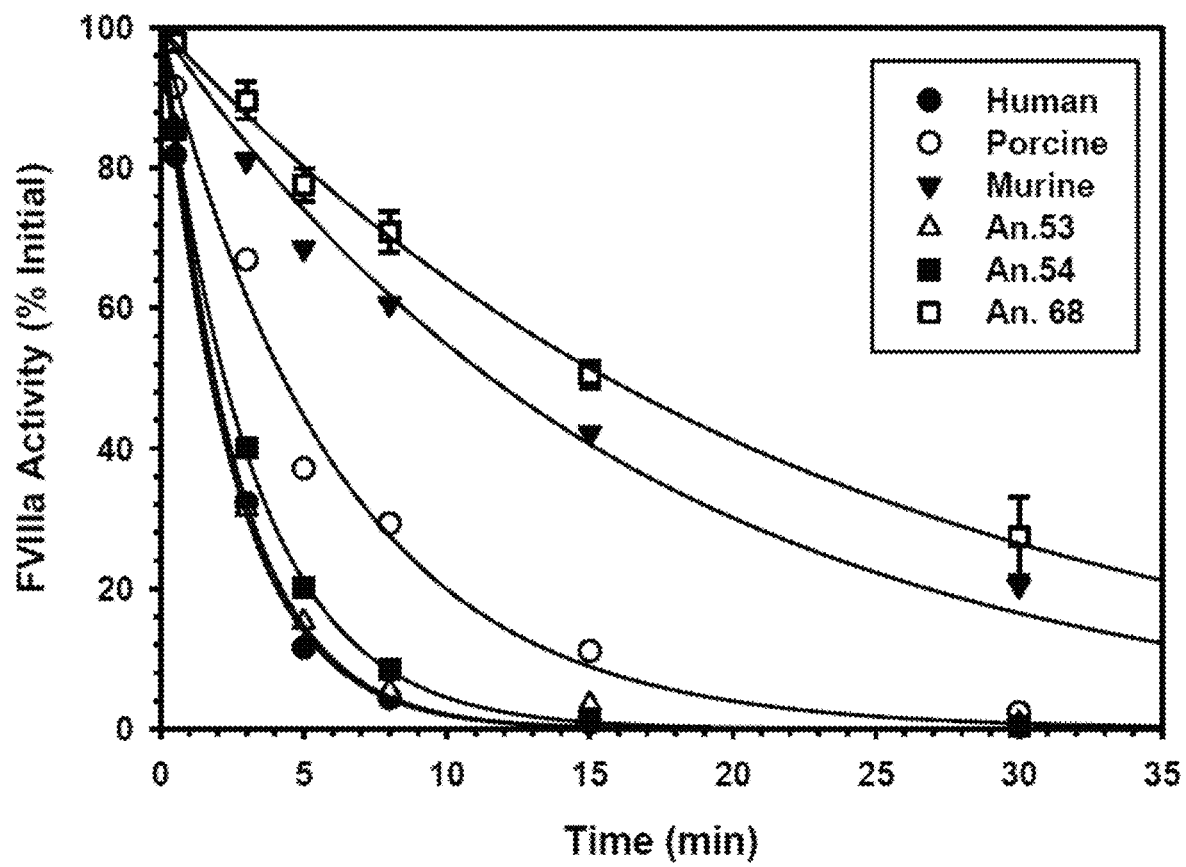
FIG. 4 shows the decay rate of 1 nM ancestral node 68 FVIIIa determined by chromogenic Xase assay. FVIII protein from the top producing BHK-M clone was collected and purified from serum-free media using one-step ion-exchange chromatography. FVIII was captured with an SPHP HiTrap column and eluted with an increasing concentration of NaCl. Compared to the human FVIII half-life of 1.8 minutes, the ancestral node 68 protein displays a 9-fold prolonged half-life of 16.2 minutes, n=1. Of note, node 68 retains 75% identity to murine FVIII and 71% identity to porcine FVIII.

FIG. 5 shows data on cross-reactivity of inhibitory mouse anti-human monoclonal antibodies (MAbs) to An-53 (black circles) and An-68 (white circles) via direct ELISA. MAbs were selected for high potency (>1000 BU/mg) and specificity to the A2 or C2 domain. Epitope groups within the domain are listed in parentheses. Cross-reactivity to ancestral FVIII is defined as the percent absorbance compared to human FVIII.

FIG. 6 shows data on the ability to the E434 mutant in A2 to evade 4A4 inhibition.

FIG. 7 shows a schematic of a AAV-FVIII plasmid. FVIII was human codon optimized and subcloned into an AAV expression cassette under the liver-directed HLP promoter.

FIG. 8 shows data comparing An-53 (white) and ET3 (black) FVIII levels following hydrodynamic injection in mice at two doses of AAV-FVIII plasmid DNA. Circles represent 3 μg and downward triangles represent 0.75 μg per mouse. FVIII activity was measured by two-stage chromogenic assay compared to a FACT standard and error bars represent standard deviation of 4 mice.

FIG. 9 shows SDS-PAGE analysis of An-53 and An-68 following two-step ion-exchange. SC: single chain; HC: heavy chain; LC: light chain; cLC: cleaved light chain; A1 and A2: FVIII A domains

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.
Figure 5:
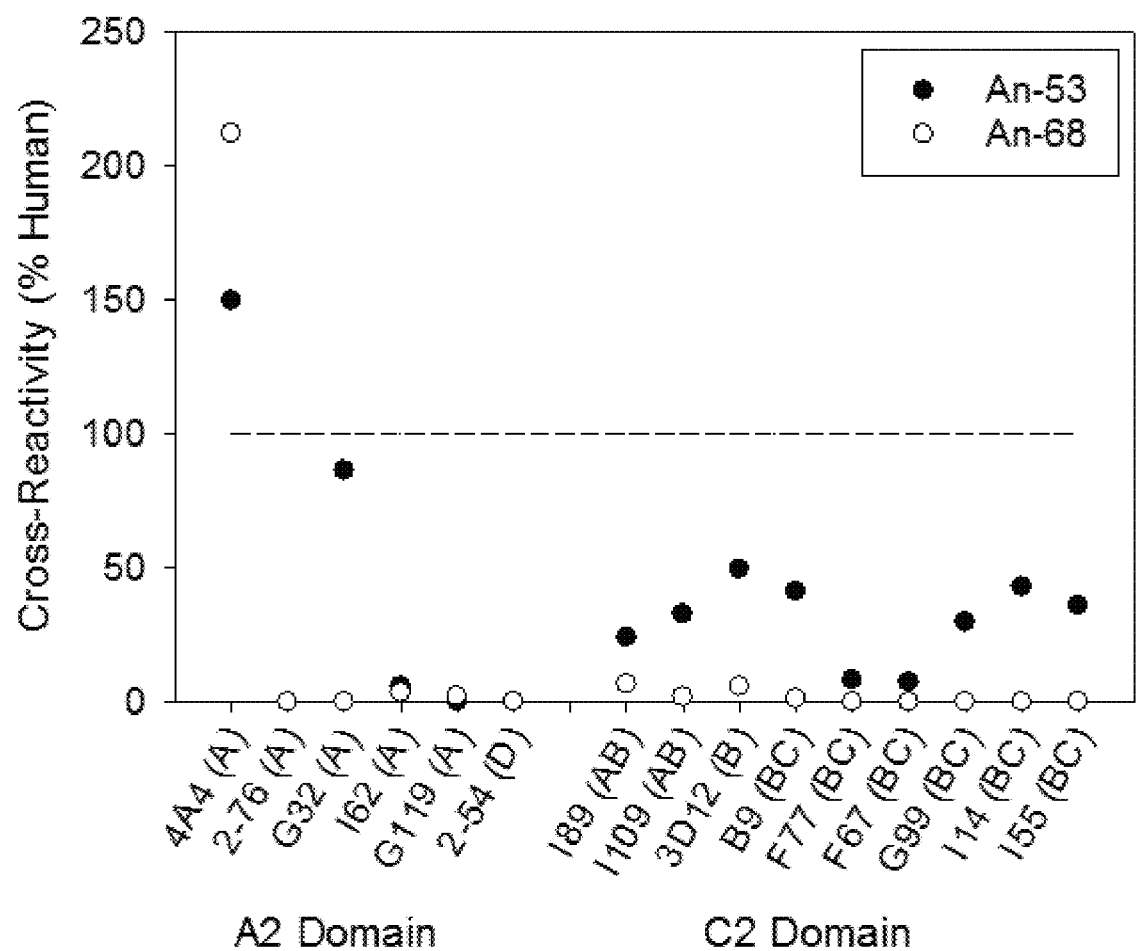
Figure 6:
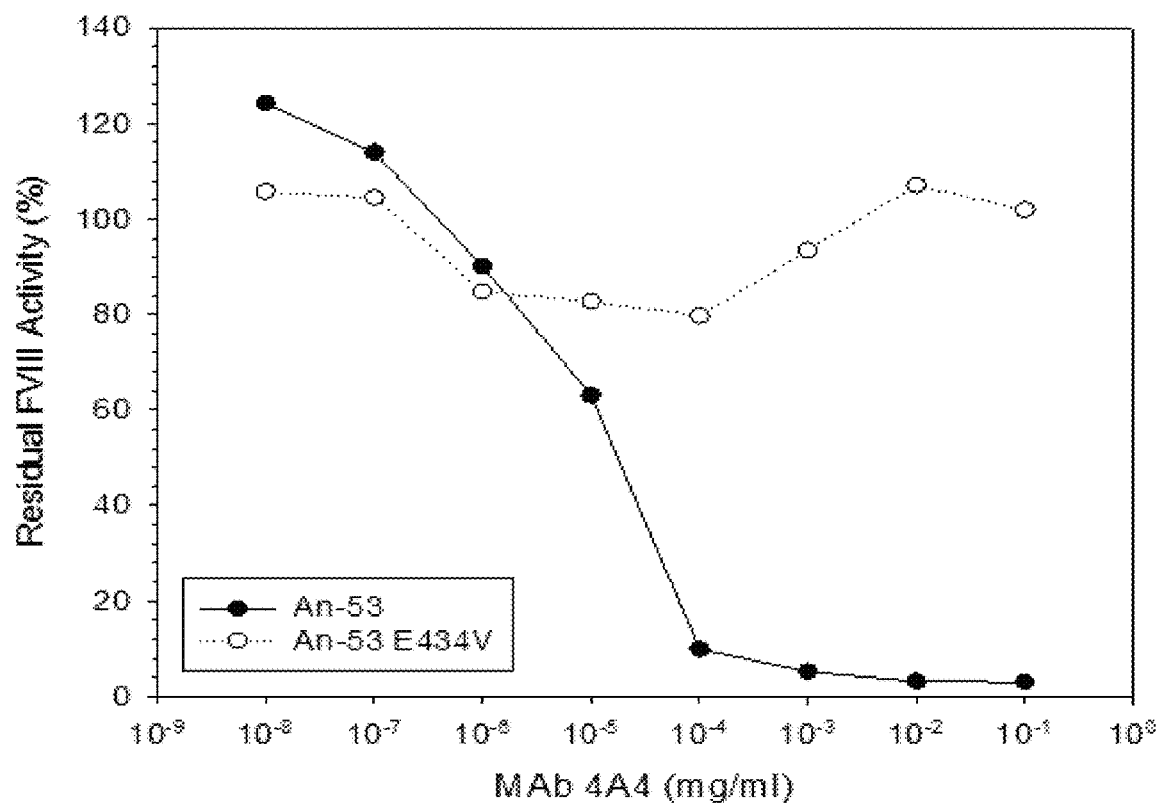
Figure 7:
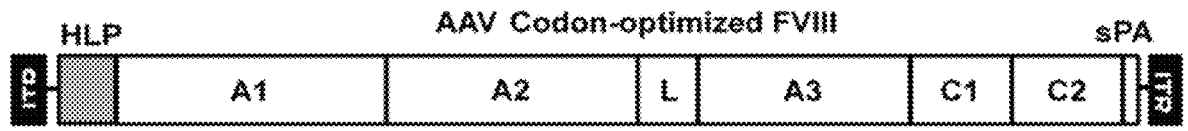

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, a "non-naturally occurring" sequence is one for which no organisms produce or ever produced through the course of natural events. A protein is non-naturally occurring if one or more amino acids are substituted such that the entire amino acid sequence was never produced due to the course of natural events.

As used herein, an "ancestral mutations" refer to alterations in nucleic acid sequencing that results in amino acid substitutions in the corresponding protein when compared to the consensus human sequence, i.e., SEQ ID NO: 1. A position of the amino acid substitution can be identified by reference to numerical positions within SEQ ID NO: 1 with or without reference to the protein having the signal peptide. With regard to mutations, it is common to refer to the numbering system above wherein FVIII does not contain the signal peptide as it is typically cleaved during cellular processing. As used herein, a "unique ancestral mutation" refers to an ancestral mutation also not found in the sequence for any known primates or mammals.

The terms "protein" and "polypeptide" refer to compounds comprising amino acids joined via peptide bonds and are used interchangeably.

As used herein, where "amino acid sequence" is recited herein, it refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycosylations and addition of lipid moieties.

The term "nucleic acid" refers to a polymer of nucleotides, or polynucleotides. The term is used to designate a single molecule, or a collection of molecules. Nucleic acids may be single stranded or double stranded of self-complementary, and may include coding regions and regions of various control elements.

The terms "a nucleic acid sequence encoding" a specified polypeptide refers to a nucleic acid sequence comprising the coding region of a gene or in other words the nucleic acid sequence which encodes a protein. The coding region may be present in either a cDNA, genomic DNA, or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The term "chimera" when used in reference to a polypeptide of polynucleotide refers to the expression product of two or more coding sequences obtained from different genes, that have been cloned together and that, after translation, act as a single polypeptide sequence such that the single or whole polypeptide sequence, or nucleotide sequence, is not naturally occurring. Chimeric polypeptides are also referred to as "hybrid" polypeptides. The coding sequences include those obtained from the same or from different species of organisms.

The term "heterologous nucleic acid" refers to a nucleic acid that is not in its natural environment (i.e., has been altered by the hand of man). For example, a heterologous nucleic acid includes a gene from one species introduced into another species. A heterologous nucleic acid also includes a gene native to an organism that has been altered in some way (e.g., mutated, added in multiple copies, linked to a non-native promoter or enhancer sequence, etc.). Heterologous viral nucleic acids are distinguished from endogenous viral genes in that the heterologous gene sequences are typically joined to nucleotide sequences comprising regulatory elements such as promoters that are not found naturally associated with the gene for the protein encoded by the heterologous gene or with viral gene sequences in the chromosome, or are associated with portions of the chromosome not found in nature (e.g., genes expressed in loci where the gene is not normally expressed).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids or nucleotide (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro and cell free systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro and cell-free protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

In certain embodiments, the disclosure relates to the recombinant vectors comprising a nucleic acid encoding a polypeptide disclosed herein or chimeric protein thereof. In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, a beta globin polyA signal, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil.

Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (at1D), UDP-glucose:galactose-1-phosphate uridyltransferasel (galT), feedback-insensitive a subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the nucleic acids disclosed herein may be a part of any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. In certain embodiments, a vector may be an adeno-associated virus or human adeno-associated virus (containing AAV genes or sequences) vector, e.g., having nucleic acid sequences derived from AAV1, AAV2, AAV3, AAV4, AAV5, AAV6, AAV7, AAV8, AAV9 serotypes or combinations. In certain embodiments, the nucleic acid sequences derived from AAV1, AAV2, AAV3, AAV4, AAV5, AAV6, AAV7, AAV8, AAV9 serotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment. In certain embodiments, a vector may be a lentivirus based (containing lentiviral genes or sequences) vector, e.g., having nucleic acid sequences derived from VSVG or GP64 pseudotypes or both. In certain embodiments, the nucleic acid sequences derived from VSVG or GP64 pseudotypes may be at least one or two or more genes or gene fragments of more than 1000, 500, 400, 300, 200, 100, 50, or 25 continuous nucleotides or nucleotides sequences with greater than 50, 60, 70, 80, 90, 95 or 99% identity to the gene or fragment.

The selected vector may be delivered by any suitable method, including intravenous injection, ex-vivo transduction, transfection, electroporation, liposome delivery, membrane fusion techniques, high velocity DNA-coated pellets, viral infection and protoplast fusion. CpG DNA motifs are typically removed because they may lead to gene methylation and silencing. See Bird, DNA methylation and the frequency of CpG in animal DNA, 1980, Nucleic Acids Res, 8: 1499-1504. CpG removal also helps the vector evade immune detection, enhancing the safety and efficacy of the vector. See J Clin Invest. 2013, 123(7):2994-3001, entitled "CpG-depleted adeno-associated virus vectors evade immune detection."

Blood Coagulation Factors

The blood clothing system is a proteolytic cascade. Blood clotting factors are present in the plasma as a zymogen, in other words in an inactive form, which on activation undergoes proteolytic cleavage to release the active factor from the precursor molecule. The ultimate goal is to produce thrombin. Thrombin converts fibrinogen into fibrin, which forms a clot.

Factor X is the first molecule of the common pathway and is activated by a complex of molecules containing activated factor IX (FIXa), factor VIII, calcium, and phospholipids which are on the platelet surface. Factor VIII is activated by thrombin, and it facilitates the activation of factor X by FIXa. Factor VIII (FVIII), contains multiple domains (A1-A2-B-ap-A3-C1-C2) and circulates in blood in an inactivated form bound to von Willebrand factor (VWF). The C2 domain is involved with FVIII binding to VWF. Thrombin cleaves FVIII causing dissociation with VWF ultimately leading to fibrin formation through factor IX (FIX). Congenital hemophilia A is associated with genetic mutations in the FVIII gene and results in impaired clotting due to lower than normal levels of circulating FVIII. Hemophilia B is similarly associated with genetic mutations in the FIX gene.

A treatment option for a patient diagnosed with hemophilia A is the exogenous administration of recombinant FVIII sometimes referred to as FVIII replacement therapy. In some patients, this therapy can lead to the development of antibodies that bind to the administered FVIII protein. Subsequently, the FVIII-antibody bound conjugates, typically referred to as inhibitors, interfere with or retard the ability of FVIII to cause blood clotting. Inhibitory autoantibodies also sometimes occur spontaneously in a subject that is not genetically at risk of having hemophilia, termed acquired hemophilia. Inhibitory antibodies assays are typically performed prior to exogenous FVIII treatment in order to determine whether the anti-coagulant therapy will be effective.

A "Bethesda assay" has historically been used to quantitate the inhibitory strength the concentration of factor VIII binding antibodies. In the assay, serial dilutions of plasma from a patient, e.g., prior to having surgery, are prepared and each dilution is mixed with an equal volume of normal plasma as a source of FVIII. After incubating for a couple hours, the activities of factor VIII in each of the diluted mixtures are measured. Having antibody inhibitor concentrations that prevent factor VIII clotting activity after multiple repeated dilutions indicates a heightened risk of uncontrolled bleeding. Patients with inhibitor titers after about ten dilutions are felt to be unlikely to respond to exogenous FVIII infusions to stop bleeding. A Bethesda titer is defined as the reciprocal of the dilution that results in 50% inhibition of FVIII activity present in normal human plasma. A Bethesda titer greater than 10 is considered the threshold of response to FVIII replacement therapy.

In certain embodiments, the disclosure relates to methods of inducing blood clotting comprising administering an effective amount of a recombinant or chimeric protein disclosed herein or viral particle or capsid comprising a vector comprising a nucleic acid encoding a blood clotting factor as disclosed herein to a subject in need thereof.

In certain embodiments, the subject is diagnosed with hemophilia A or acquired hemophilia or unlikely to respond to exogenous FVIII infusions.

In certain embodiments, the protein, capsid, or vector is administered in combination with an immunosuppressive agent, e.g., ciclosporin, tacrolimus, sirolimus, cyclophosphamide, methotrexate, azathioprine, mercaptopurine, fluorouracil, mycophenolic acid, dactinomycin, fingolimod, T-cell receptor antibody or binding protein, muromonab-CD3, IL-2 receptor antibody or binding protein, basiliximab, daclizumab, recombinant IFN-beta, TNF-alpha antibody or binding protein, infliximab, etanercept, adalimumab, or combinations thereof.

In certain embodiments, modified cells are re-administered in combination with irradiation, busulfan, and/or anti-thymocyte globulin, e.g., when using lentiviral gene therapy targeting hematopoietic stem cells.

Treating patients with inhibitors to FVIII has also been accomplished by methods of immune tolerance induction (ITT) which typically involves the daily infusion of FVIII until circulating inhibitor/antibody levels decline. However, 20-30% of patients fail to become tolerant after an immune tolerance induction (ITT) therapy. Persistence of FVIII inhibitors is associated with increased risks of morbidity and mortality. In certain embodiments, the disclosure relates to methods of immune tolerance induction comprising administering an effective amount of a recombinant or chimeric protein disclosed herein or a vector or a capsid as disclosed herein to a subject in need thereof.

Vector-Mediated Gene Transfer

In certain embodiments, the disclosure relates to methods of treating a subject diagnosed with a genetic trait that results in expression of a mutated or truncated non-functional protein by administering an effective amount of a vector disclosed herein. In certain embodiments, the vector is configured to express a functional protein from the liver. In certain embodiments, the vector is configured to express a protein in any cells such as hematopoietic stem cells or other hematocytes in vivo or by ex vivo transduction.

As used herein, the liver specific promotor refers to the sequences in the 5' direction of the transcriptional start site of the protein to be produced. McIntosh et al. report an rAAV vector encoding a human factor VIII variant using a hybrid liver-specific promoter (HLP). Blood. 2013, 121(17):3335-44. Brown et al. report liver-directed adeno-associated viral vector delivery of a bioengineered FVIII. Molecular Therapy, Methods & Clinical Development (2014) 1, 14036.

In certain embodiments, the vector comprises a viral nucleic acid sequence of greater than 10, 20, 30, 40, 50, 100, or 200 nucleotides. In certain embodiments, the viral nucleic acid sequence is a segment of human adeno-associated virus (hAAV) of serotypes 1, 2, 3B, 4, 5, 6, 7, 8, 9 or combinations or variants thereof, typically comprising an AAV inverted terminal repeat.

Adeno-associated virus (AAV), Parvovirus family, is an icosahedral virus with single-stranded linear DNA genomes. The life cycle of AAV includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

The nucleic acid and promotor sequences disclosed herein are useful in production of rAAV, and are also useful as antisense delivery vectors, gene therapy vectors, or vaccine vectors. In certain embodiments, the disclosure provides for gene delivery vectors, and host cells which contain the nucleic acid sequences disclosed herein.

In certain embodiments, the disclosure relates to virus particles, e.g., capsids, containing the nucleic acid sequences encoding promotors and proteins disclosed herein. The virus particles, capsids, and recombinant vectors are useful in delivery of a heterologous gene or other nucleic acid sequences to a target cell. The nucleic acids may be readily utilized in a variety of vector systems, capsids, and host cells. In certain embodiments, the nucleic acids are in vectors contained within a capsid comprising cap proteins, including AAV capsid proteins vp1, vp2, vp3 and hypervariable regions.

Adeno-associated virus (AAV) has a biphasic life cycle consisting of both a productive and a latent phase. In the presence of helper virus, Adenovirus (Ad), or Herpesvirus (HSV), AAV undergoes a productive infection. Lacking a helper virus, AAV latently infects by integration into the host genome. AAV is capable of undergoing site-specific integration into the human genome. The ability to integrate site specifically is one of the attractive features for using this virus as a vector for human gene therapy.

Inverted terminal repeats (ITRs) in AAVs are cis elements used for targeted integration. Traditional AAV-mediated site-specific integration uses the AAV Rep78/68 proteins and ITRs which contain the Rep-binding site (RBS) and AAVS1 which is a sequence present at the integration site. See Linden et al. (1996) entitled "The recombination signals for adeno-associated virus site-specific integration." Proc Natl Acad Sci USA 93(15):7966-7972.

AAV vectors typically contain a transgene expression cassette between the ITRs that replaces the rep and cap genes. Vector particles are produced by the co-transfection of cells with a plasmid containing the vector genome and a packaging/helper construct that expresses the rep and cap proteins in trans. During infection, AAV vector genomes enter the cell nucleus and can persist in multiple molecular states. One common outcome is the conversion of the AAV genome to a double-stranded circular episome by second-strand synthesis or complementary strand pairing.

The AAV ITRs, and other selected AAV components described herein, may be readily selected from among any AAV serotype, including, without limitation, AAV1, AAV2, AAV3, AAV4, AAV5, AAV6, AAV7, AAV8, AAV9 and function variants thereof. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In certain embodiments, this disclosure provides for a nucleic acids disclosed herein the encoded proteins or wherein the nucleic acids are part of an expression cassette or transgene. See e.g., US Pat. App. Pub. 20150139953. In certain embodiments, the expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

In certain embodiments, the disclosure provides for a method of generating a recombinant adeno-associated virus (AAV) having an AAV serotype capsid, or a portion thereof. Such a method involves culturing a host cell which contains a nucleic acid sequence encoding an adeno-associated virus (AAV) serotype capsid protein; a functional rep gene; an expression cassette composed of AAV inverted terminal repeats (ITRs) and a transgene; and sufficient helper functions to permit packaging of the expression cassette into the AAV capsid protein. See e.g., US Pat. App. Pub. 20150139953.

The components for culturing in the host cell to package an AAV expression cassette in an AAV capsid may be provided to the host cell in trans. Alternatively, any one or more of the components (e.g., expression cassette, rep sequences, cap sequences, and/or helper functions) may be provided by a stable host cell which has been engineered to contain one or more of the required components using methods known to those of skill in the art. Most suitably, such a stable host cell will contain the component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may be accomplished using techniques known to the skilled artisan. In preferred embodiment, standard transfection techniques are used, e.g., CaPO4 transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

One of skill in the art will readily understand that the AAV techniques can be adapted for use in these and other viral vector systems for in vitro, ex vivo or in vivo gene delivery. The in certain embodiments the disclosure contemplates the use of nucleic acids and vectors disclosed herein in a variety of rAAV and non-rAAV vector systems. Such vectors systems may include, e.g., lentiviruses, retroviruses, poxviruses, vaccinia viruses, and adenoviral systems, among others.

For example, in certain embodiments, the disclosure contemplates expression of FVIII by lentiviral vectors through in vivo administration or ex vivo transduction. Allogenic or autologous CD34+ cells can be isolated and mixed ex vivo with a lentiviral vector hying nucleic acids encoding a FVIII protein disclosed herein under conditions such that the lentiviral vector integrates into the cells nucleic acids, e.g. DNA, sufficiently to produce or allow production the encoded FVIII protein. The cells are then infused or re-infused into a subject, wherein the subject optionally received a myeloablative treatment, under conditions such that hematopoietic stem cells or resulting cells or hematocytes express the protein. See Cartier et al. Science. 2009, 326(5954):818-23. Sanber et al. report the construction of stable packaging cell lines for clinical lentiviral vector production. Sci Rep. 2015, 5:9021. Hu et al. report production of replication-defective human immunodeficiency type 1 virus vector particles using helper-dependent adenovirus vectors. See Mol Ther Methods Clin Dev. 2015, 2:15004.

Therapeutics

Recombinant or chimeric proteins and virus particles, capsids, or vectors encoding proteins disclosed herein can be delivered, e.g., to liver via the hepatic artery, the portal vein, or intravenously to yield therapeutic levels of therapeutic proteins or clotting factors in the blood. The recombinant or chimeric proteins and capsid or vector is preferably suspended in a physiologically compatible carrier, may be administered to a patient. Suitable carriers may be readily selected by one of skill in the art in view of the indication. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, the compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant or chimeric proteins and virus particles, capsids, or vectors will depend primarily on factors such as the condition being treated, the age, weight and health of the patient, and may thus vary among patients. For example, a therapeutically effective human dosage of the protein is generally in the range of from about 0.1 ml to about 100 ml of solution containing concentrations of from about $1 \times 10^9$ to $1 \times 10^{16}$ genomes, virus vectors, or gene modified cells produced by ex vivo transduction.

Therapeutic proteins encoded by the nucleic acids (e.g., operably in combination with promoters) reported herein include those used for treatment of hemophilia, including hemophilia hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

Administration of only the chain defective is contemplated in patients because most persons with hemophilia contain a mutation or deletion in only one of the chains (e.g., heavy or light chain). Thus, in certain embodiments, the disclosure relates to recombinant or chimeric proteins of a light chain containing the A3, C1 and C2 domains or a heavy chain consisting of the A1 and A2 domains. In some embodiments, the therapeutic protein or as encoded by the nucleic acids (e.g., operably in combination with promoters) reported herein comprises the Factor VIII heavy chain which encodes the 19 amino acid signal sequence, as well as the human beta globin polyadenylation sequence or growth hormone (hGH) polyadenylation sequence. In alternative embodiments, the A1 and A2 domains, as well as 5 amino acids from the N-terminus of the B domain, and/or 8 amino acids of the C-terminus of the B domain, as well as the A3, C1 and C2 domains. In yet other embodiments, the protein or nucleic acids encoding Factor VIII is a heavy chain and light chain provided in a single protein or nucleic acid separated by 42 nucleic acids/14 amino acids of the B domain. See U.S. Pat. No. 6,200,560.

As used herein, a therapeutically effective amount is an amount of protein or vector that produces sufficient amounts of Factor VIII to decrease the time it takes for the blood of a subject to clot. Generally, severe hemophiliacs having less than 1% of normal levels of Factor VIII have a whole blood clotting time of greater than 60 minutes as compared to approximately 10 minutes for non-hemophiliacs.

The recombinant or chimeric proteins or vectors may contain an amino acid sequence or nucleic acid coding for fragments of Factor VIII which is itself not biologically active, yet when administered into the subject improves or restores the blood clotting time. For example, the Factor VIII protein comprises two polypeptide chains: a heavy chain and a light chain separated by a B-domain which is cleaved during processing. Co-transducing recipient cells with the Factor VIII heavy and light chains leads to the expression of biologically active Factor VIII. Administration of only the chain defective is contemplated in patients because most hemophiliacs contain a mutation or deletion in only one of the chains (e.g., heavy or light chain).

Thus, in certain embodiments, the disclosure relates to vectors disclosed herein having nucleic acids encoding a light chain containing the A3, C1 and C2 domains or a heavy chain consisting of the A1 and A2 domains.

Bioengineering Coagulation Factor VIII Through Ancestral Protein Reconstruction

The development of transformative hemophilia A therapeutics has been hindered by the size, instability, immunogenicity and biosynthetic inefficiency of coagulation factor VIII (FVIII). Through the study of FVIII orthologs from existing vertebrate species, unique molecular, cellular and biochemical properties that can overcome the limitations of human FVIII were discovered. This approach facilitated the development of recombinant porcine FVIII for acquired hemophilia A and has enabled low resolution mapping and bioengineering of functional sequence determinants into human FVIII.

A mammalian FVIII phylogenetic tree with corresponding ancestral node (An) sequences was constructed through Bayesian inference using both DNA and amino acid-based models in PAML Version 4.1 (FIG. 1). Initially, 14 An-FVIII sequences were selected for reconstruction and subsequent molecular, cellular, biochemical and immunological characterization. Each An-FVIII displayed activity in coagulation assays utilizing human hemophilia A plasma as a substrate thus demonstrating evolutionary mammalian compatibility. Infusion of highly purified preparations of several An-FVIIIs into hemophilia A mice also corrected the bleeding phenotype following a tail transection bleeding challenge confirming in vivo functionality.

To study biosynthetic efficiency, secreted FVIII activity and mRNA transcript levels were analyzed following transfection of An-FVIII plasmids into HEK293 and BHK-M cell lines. An-53, common ancestor to rodents and primates, and An-68, ancestor to a subset of current rodents, displayed the highest FVIII biosynthetic efficiencies that were 12 and 15 fold greater than human FVIII, respectively. These two An-FVIII sequences share 95 and 87% amino acid identity to human FVIII, respectively. In contrast, intermediate ancestors between An-53 and human FVIII, designated An-55, -56 and -57, do not display enhanced biosynthetic efficiency suggesting that the functional sequence determinant of high expression was lost during primate evolution.

Testing whether high expression ancestral FVIIIs would be enabling to gene therapy approaches, An-53, An-68 and human FVIII cDNAs were placed in an AAV expression cassette under the control of a liver-directed promoter and the resulting plasmid DNA was infused hydrodynamically into hemophilia A mice. An-53 and An-68, but not human FVIII vector treated animals, achieved sustained, therapeutic plasma FVIII activity levels over 4 weeks (0.1-0.6 IU/ml versus<0.01 IU/ml, respectively). Recombinant An-FVIIIs were expressed, purified and biochemically characterized by SDS-PAGE, specific activity, decay following thrombin activation and inhibitor recognition. Early mammalian and all primate lineage thrombin-activated An-FVIII(a) displayed half-lives between 1.5-2.2 min that were not distinguishable from human FVIII.

Modern murine, porcine, and ovine FVIIIa display significantly longer half-lives. An-68 and An-78 display prolonged half-lives of 16 and 7 min, respectively. Lastly, the immune recognition of An-FVIIIs by a panel of A2 and C2 domain targeting inhibitory murine monoclonal antibodies as well as hemophilia A inhibitor patient plasmas was examined and many examples of reduced reactivity were revealed, which may enable the development of less immunogenic FVIII products.

Factor VIII domain boundaries refer to the human FVIII amino acid sequence numbering as follows; residues 1-19 (Signal Sequence), 20-391 (A1), 392-759 (A2), 760-1667 (B), 1668-1708 (ap), 1709-2038 (A3), 2039-2191 (C1) and 2192-2351 (C2). Gitschier et al., Nature, 1984, 312,326-330.

```
(SEQ ID NO: 1):
   1 MQIELSTCFF LCLLRFCFSA TRRYYLGAVE LSWDYMQSDL GELPVDARFP PRVPKSFPFN

61 TSVVYKKTLF VEFTDHLFNI AKPRPPWMGL LGPTIQAEVY DTVVITLKNM ASHPVSLHAV

GVSYWKASEG AEYDDQTSQR EKEDDKVFPG GSHTYVWQVL KENGPMASDP LCLTYSYLSH

VDLVKDLNSG LIGALLVCRE GSLAKEKTQT LHKFILLFAV FDEGKSWHSE TKNSLMQDRD

AASARAWPKM HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE EPQLRMKNNE

EAEDYDDDLT DSEMDVVRFD DDNSPSFIQI RSVAKKHPKT WVHYIAAEEE DWDYAPLVLA

421 PDDRSYKSQY LNNGPQRIGR KYKKVRFMAY TDETFKTREA IQHESGILGP LLYGEVGDTL

LIIFKNQASR PYNIYPHGIT DVRPLYSRRL PKGVKHLKDF PILPGEIFKY KWTVTVEDGP

TKSDPRCLTR YYSSFVNMER DLASGLIGPL LICYKESVDQ RGNQIMSDKR NVILFSVFDE

NRSWYLTENI QRFLPNPAGV QLEDPEFQAS NIMHSINGYV FDSLQLSVCL HEVAYWYILS

IGAQTDFLSV FFSGYTFKHK MVYEDTLTLF PFSGETVFMS MENPGLWILG CHNSDFRNRG

MTALLKVSSC DKNTGDYYED SYEDISAYLL SKNNAIEPRS FSQNSRHPST RQKQFNATTI

781 PENDIEKTDP WFAHRTPMPK IQNVSSSDLL MLLRQSPTPH GLSLSDLQEA KYETFSDDPS

PGAIDSNNSL SEMTHFRPQL HHSGDMVFTP ESGLQLRLNE KLGTTAATEL KKLDFKVSST

SNNLISTIPS DNLAAGTDNT SSLGPPSMPV HYDSQLDTTL FGKKSSPLTE SGGPLSLSEE

NNDSKLLESG LMNSQESSWG KNVSSTESGR LFKGKRAHGP ALLTKDNALF KVSISLLKTN

1021 KTSNNSATNR KTHIDGPSLL IENSPSVWQN ILESDTEFKK VTPLIHDRML MDKNATALRL

NHMSNKTTSS KNMEMVQQKK EGPIPPDAQN PDMSFFKMLF LPESARWIQR THGKNSLNSG

QGPSPKQLVS LGPEKSVEGQ NFLSEKNKVV VGKGEFTKDV GLKEMVFPSS RNLFLTNLDN

1201 LHENNTHNQE KKIQEEIEKK ETLIQENVVL PQIHTVTGTK NFMKNLFLLS TRQNVEGSYD

GAYAPVLQDF RSLNDSTNRT KKHTAHFSKK GEEENLEGLG NQTKQIVEKY ACTTRISPNT

SQQNFVTQRS KRALKQFRLP LEETELEKRI IVDDTSTQWS KNMKHLTPST LTQIDYNEKE

1381 KGAITQSPLS DCLTRSHSIP QANRSPLPIA KVSSFPSIRP IYLTRVLFQD NSSHLPAASY

RKKDSGVQES SHFLQGAKKN NLSLAILTLE MTGDQREVGS LGTSATNSVT YKKVENTVLP
```

```
1501 KPDLPKTSGK VELLPKVHIY QKDLFPTETS NGSPGHLDLV EGSLLQGTEG AIKWNEANRP

GKVPFLRVAT ESSAKTPSKL LDPLAWDNHY GTQIPKEEWK SQEKSPEKTA FKKKDTILSL

1621 NACESNHAIA AINEGQNKPE IEVTWAKQGR TERLCSQNPP VLKRHQREIT RTTLQSDQEE

IDYDDTISVE MKKEDFDIYD EDENQSPRSF QKKTRHYFIA AVERLWDYGM SSSPHVLRNR

1741 AQSGSVPQFK KVVFQEFTDG SFTQPLYRGE LNEHLGLLGP YIRAEVEDNI MVTFRNQASR

PYSFYSSLIS YEEDQRQGAE PRKNFVKPNE TKTYFWKVQH HMAPTKDEFD CKAWAYFSDV

1861 DLEKDVHSGL IGPLLVCHTN TLNPAHGRQV TVQEFALFFT IFDETKSWYF TENMERNCRA

PCNIQMEDPT FKENYRFHAI NGYIMDTLPG LVMAQDQRIR WYLLSMGSNE NIHSIHFSGH

VFTVRKKEEY KMALYNLYPG VFETVEMLPS KAGIWRVECL IGEHLHAGMS TLFLVYSNKC

QTPLGMASGH IRDFQITASG QYGQWAPKLA RLHYSGSINA WSTKEPFSWI KVDLLAPMII

HGIKTQGARQ KFSSLYISQF IIMYSLDGKK WQTYRGNSTG TLMVFFGNVD SSGIKHNIFN

2161 PPIIARYIRL HPTHYSIRST LRMELMGCDL NSCSMPLGME SKAISDAQIT ASSYFTNMFA

TWSPSKARLH LQGRSNAWRP QVNNPKEWLQ VDFQKTMKVT GVTTQGVKSL LTSMYVKEFL

ISSSQDGHQW TLFFQNGKVK VFQGNQDSFT PVVNSLDPPL LTRYLRIHPQ SWVHQIALRM

2341 EVLGCEAQDL Y
```

HSQ is B domain deleted human factor VIII. ET3 is a B domain deleted FVIII hybrid that contains human and porcine domains, i.e., sequence (A1 and A3 porcine) with a linker in the deleted B domain. ET3 utilizes a 24 amino acid porcine sequence-derived OL linker sequence, i.e., porcine-derived sequence SFAQNSRPPSASAPKPPVLRRHQR (SEQ ID NO: 246). Both HSQ and ET3 contain the RHQR (SEQ ID NO: 245) recognition sequence for PACE/furin processing sequence for the B-domain.

In certain embodiments, the recombinant or chimeric FVIII protein further comprises a linker amino acid sequence between two and fifty, or two and twenty five, or two and fifteen amino acids between the A2 domain and the an activation peptide(ap) domain. In certain embodiments, the linker comprises RHQR (SEQ ID NO: 245), SRPP-SASAPK (SEQ ID NO: 41), or SFAQNSRPP-SASAPKPPVLRRHQR (SEQ ID NO: 246).

In certain embodiments, the disclosure relates to FVIII proteins comprising one, two, more, or combinations of ancestral mutation(s). In certain embodiments, the disclosure relates to a recombinant or chimeric FVIII protein comprising one or more ancestral mutations wherein optionally one or more amino acids in B-domain are deleted, and wherein the sequence does not naturally occur.

```
The sequence for Node number 68 is:
                                                        SEQ ID NO: 2
MQIALFTCFFLSLFNFCSSATRRYYLGAVELSWNYMQSDLLSVLHTDTRFLPRMPTSFPF

NTSIMYKKTVFVEYMDHLFNIAKPRPPWMGLLGPTIWTEVHDTVVITLKNMASHPVSLH

AVGVSYWKASEGAEYEDQTSQREKEDDKVFPGESHTYVWQVLKENGPMASDPPCLTY

SYLSHVDLVKDLNSGLIGALLVCKEGSLSKERTQMLHQFVLLFAVFDEGKSWHSETKDS

FTQAMDSASTRAWPKMHTVNGYVNRSLPGLIGCHRKSVYWHVIGMGTTPEVHSIFLEG

HTFLVRNHRQASLEISPITFLTAQTLLIDLGQFLLFCHISSHKHDGMEAYVKVDSCPEEPQ

WQKKNNEEMEDYDDDLDSEMDMFTLDDDNSPFIQIRSVAKKYPKTWIHYISAEEEDWD

YAPSVLTSDDGSYKSQYLSNGPHRIGRKYKKVRFIAYTDETFKTRETIQHESGILGPLLY

GEVGDTLLIIFKNQASRPYNIYPHGITDVSPLHSRRLPRGIKHVKDLPIRPGEIFKYKWTVT

VEDGPTKSDPRCLTRYYSSFINPERDLASGLIGPLLICYKESVDQRGNQMMSDKRNVILF

SVFDENQSWYITENMQRFLPNAADTQPQDPEFQASNIMHSINGYVFDSLQLTVCLHEVA

YWYILSVGAQTDFLSIFFSGYTFKHKMVYEDTLTLFPPFSGETVFMSMENPGLWVLGCHN

SDFRKRGMTALLKVSSCDKSTSDYYEEIYEDIPTQLVNDNNVIEPRSFFQNSNHPNTRKK

KFKATTIPENDIEKIEPQFGETAEMLKVQSVSSSDLLMLLGQSPTPHGLSLSDNQEAIYEA

IPDDHSPDAIDSNEGPSKVTQLRPELHHSGKIVFTPEPGLQLRSNKNLETTIEVKWKKLDL
```

-continued

QVSSLPNNLMTTTILSDNLTATSEKTDSSGSPDMPVHFSSKLSTTAFGKKSYPLIGSHVPL

NISERNSDSNLLDATLMNNQESSLGDNISSMENDRLLKEKRFHGIALLTKDNTLFKDNIS

LMKTNKTYNHSTTNGKAHIDSPTSIENSTAVLQDTILKINSEIQEVTSLIHDGTLSGKNTT

YLRLNHMLNRTTSSKNKEIFHQKDEDPVPQDTENTIMPFFKMLFLPESANWMKRTNGN

NSLNSEQGPSPKQLVYLMLEKSVKNQNFLSEKNKVIVEQDEFTKDTGLKDMVFPSNMSI

FLTTLANVQENDMHNQEKNIQEEIEKEALIEEKVVLPQVHIATGSKNFLKDIFFLGTRQN

VSLDEDIYVPVLQDISSINNSTNTVEIHMAHFFKRREDEETNSEGLVNKTREMVKNYPSQ

KNIITQRSKRALGQFRLPLASTQWPQTMNYLTQSIITQIDHSKEGEKSITQSSLSDSSMIKS

TTQTNSSGLHIVKTSAFPPTDLKRIPFQDKFFHVLASSYTYDFKTKSSRIQESSHFLKETKI

NNSSLAILPWEMIINQGKFASPGTSNTNSVTYKKLENIVLLKPVLPEESGKVELLPQVSIH

EEELLPTETSHGSPGHLDLMKEVFLQKTQGPIKWNKAKRHGESELKGTTESSEKTPSKLL

DHLAWDNHYAAQIPKDKWKSKEKSPEITSIKREDTILSLNPHENNHSIVANEKQNWPQR

EATWVKQGQTQRLCSQNPPVLKRHQRELSALQSEQEATDYDDSITIETNEDFDIYGEDIK

QGPRSFQQKTRHYFIAAVERLWDYGMSTSPHVLRNRDQSGNAPQFKKVVFQEFTDGSF

SQPLYRGELNEHLGLLGPYIRAEVEDNIMVTFKNQASRPYSFYSSLISYKEDQRQGEEPR

RNFVKPNETKIYFWKVQHHMAPTEDEFDCKAWAYFSDVDLERDMHSGLIGPLLICHTN

TLNPAHGRQVAVQEFALFFTIFDETKSWYFTENVERNCKTPCNIQMEDPTLKENYRFHAI

NGYVMDTLPGLVMAQDQRIRWYLLSMGSNENIQSIHFSGHVFTVRKKEEYKMAVYNL

YPGVFETVEMLPSRAGIWRVECLIGEHLQAGMSTLFLVYSKQCQIPLGMASGSIRDFQIT

ASGHYGQWAPNLARLHHSGSINAWSTKEPFSWIKVDLLTPMIIHGIKTQGARQKFSSLYI

SQFIIMYSLDGKKWLSYRGNSTGTLMVFFGNVDSSGIKHNSFNPPIIARYIRLHPTHSSIRS

TLRMELMGCDLNSCSIPLGMENKVISDTQITASSYFTNMFATWSPSQARLHLQGRTNAW

RPQVNDPKEWLQVDLQKTMKVTGIITQGVKSLFTSMFVKEFLISSSQDGHHWTHILHNG

KVKVFQGNQDSSTPMVNSLDPPLLTRYLRIHPQIWEHQIALRLEILGCEAQQLY

Accordingly the sequences for sp-A1-A2-B-aq-A3-C1-C2:
                (signal peptide, sp domain, SEQ ID NO: 3)
MQIALFTCFFLSLFNFCSS (A1 domain SEQ ID NO: 4)
ATRRYYLGAVELSWNYMQSDLLSVLHTDTRFLPRMPTSFPFNTSIMYKKTVFVEYMDH

LFNIAKPRPPWMGLLGPTIWTEVHDTVVITLKNMASHPVSLHAVGVSYWKASEGAEYE

DQTSQREKEDDKVFPGESHTYVWQVLKENGPMASDPPCLTYSYLSHVDLVKDLNSGLI

GALLVCKEGSLSKERTQMLHQFVLLFAVFDEGKSWHSETKDSFTQAMDSASTRAWPK

MHTVNGYVNRSLPGLIGCHRKSVYWHVIGMGTTPEVHSIFLEGHTFLVRNHRQASLEIS

PITFLTAQTLLIDLGQFLLFCHISSHKHDGMEAYVKVDSCPEEPQWQKKNNEEMEDYDD

DLDSEMDMFTLDDDNSPFIQIRS (A2 domain SEQ ID NO: 5)
VAKKYPKTWIHYISAEEEDWDYAPSVLTSDDGSYKSQYLSNGPHRIGRKYKKVRFIAYT

DETFKTRETIQHESGILGPLLYGEVGDTLLIIFKNQASRPYNIYPHGITDVSPLHSRRLPRGI

KHVKDLPIRPGEIFKYKWTVTVEDGPTKSDPRCLTRYYSSFINPERDLASGLIGPLLICYK

ESVDQRGNQMMSDKRNVILFSVFDENQSWYITENMQRFLPNAADTQPQDPEFQASNIM

HSINGYVFDSLQLTVCLHEVAYWYILSVGAQTDFLSIFFSGYTFKHKMVYEDTLTLFPFS

GETVFMSMENPGLWVLGCHNSDFRKRGMTALLKVSSCDKSTSDYYEEIYEDIPTQLVN

DNNVIEPR (B domain SEQ ID NO: 6)
SFFQNSNHPNTRKKKFKATTIPENDIEKIEPQFGETAEMLKVQSVSSSDLLMLLGQSPTPH

GLSLSDNQEAIYEAIPDDHSPDAIDSNEGPSKVTQLRPELHHSGKIVFTPEPGLQLRSNKN

LETTIEVKWKKLDLQVSSLPNNLMTTTILSDNLTATSEKTDSSGSPDMPVHFSSKLSTTA

FGKKSYPLIGSHVPLNISERNSDSNLLDATLMNNQESSLGDNISSMENDRLLKEKRFHGI

ALLTKDNTLFKDNISLMKTNKTYNHSTTNGKAHIDSPTSIENSTAVLQDTILKINSEIQEV

TSLIHDGTLSGKNTTYLRLNHMLNRTTSSKNKEIFHQKDEDPVPQDTENTIMPFFKMLFL

PESANWMKRTNGNNSLNSEQGPSPKQLVYLMLEKSVKNQNFLSEKNKVIVEQDEFTKD

TGLKDMVFPSNMSIFLTTLANVQENDMHNQEKNIQEEIEKEALIEEKVVLPQVHIATGSK

NFLKDIFFLGTRQNVSLDEDIYVPVLQDISSINNSTNTVEIHMAHFFKRREDEETNSEGLV

NKTREMVKNYPSQKNIITQRSKRALGQFRLPLASTQWPQTMNYLTQSIITQIDHSKEGEK

SITQSSLSDSSMIKSTTQTNSSGLHIVKTSAFPPTDLKRIPFQDKFFHVLASSYTYDFKTKS

SRIQESSHFLKETKINNSSLAILPWEMIINQGKFASPGTSNTNSVTYKKLENIVLLKPVLPE

ESGKVELLPQVSIHEEELLPTETSHGSPGHLDLMKEVFLQKTQGPIKWNKAKRHGESELK

GTTESSEKTPSKLLDHLAWDNHYAAQIPKDKWKSKEKSPEITSIKREDTILSLNPHENNH

SIVANEKQNWPQREATWVKQGQTQRLCSQNPPVLKRHQR (ap domain SEQ ID NO: 7)
ELSALQSEQEATDYDDSITIETNEDFDIYGEDIKQGPR (A3 domain SEQ ID NO: 8)
SFQQKTRHYFIAAVERLWDYGMSTSPHVLRNRDQSGNAPQFKKVVFQEFTDGSFSQPL

YRGELNEHLGLLGPYIRAEVEDNIMVTFKNQASRPYSFYSSLISYKEDQRQGEEPRRNFV

KPNETKIYFWKVQHHMAPTEDEFDCKAWAYFSDVDLERDMHSGLIGPLLICHTNTLNP

AHGRQVAVQEFALFFTIFDETKSWYFTENVERNCKTPCNIQMEDPTLKENYRFHAINGY

VMDTLPGLVMAQDQRIRWYLLSMGSNENIQSIHFSGHVFTVRKKEEYKMAVYNLYPG

VFETVEMLPSRAGIWRVECLIGEHLQAGMSTLFLVYSK (C1 domain SEQ ID NO: 9)
QCQIPLGMASGSIRDFQITASGHYGQWAPNLARLHHSGSINAWSTKEPFSWIKVDLLTP

MIIHGIKTQGARQKFSSLYISQFIIMYSLDGKKWLSYRGNSTGTLMVFFGNVDSSGIKHN

SFNPPIIARYIRLHPTHSSIRSTLRMELMGCDLN (C2 domain SEQ ID NO: 10)
SCSIPLGMENKVISDTQITASSYFTNMFATWSPSQARLHLQGRTNAWRPQVNDPKEWLQ

VDLQKTMKVTGIITQGVKSLFTSMFVKEFLISSSQDGHHWTHILHNGKVKVFQGNQDSS

TPMVNSLDPPLLTRYLRIHPQIWEHQIALRLEILGCEAQQLY

The sequence for Node number 54 is:
SEQ ID NO: 11
MQIELSTCFFLCLLQFSFSATRRYYLGAVELSWDYMQSDLLSELHVDTRFPPRVPRSFPF

NTSVMYKKTVFVEFTDHLFNIAKPRPPWMGLLGPTIQAEVYDTVVITLKNMASHPVSLH

AVGVSYWKASEGAEYDDQTSQREKEDDKVFPGESHTYVWQVLKENGPMASDPPCLTY

SYLSHVDLVKDLNSGLIGALLVCREGSLAKERTQTLHKFVLLFAVFDEGKSWHSETKDS

LMQDMDSASARAWPKMHTVNGYVNRSLPGLIGCHRKSVYWHVIGMGTTPEVHSIFLE

GHTFLVRNHRQASLEISPITFLTAQTLLMDLGQFLLFCHISSHQHDGMEAYVKVDSCPEE

PQLRMKNNEEEEDYDDDLADSEMDVVRFDDDNSPSFIQIRSVAKKHPKTWVHYIAAEE

EDWDYAPSVLTPDDRSYKSQYLNNGPQRIGRKYKKVRFMAYTDETFKTREAIQYESGIL

GPLLYGEVGDTLLIIFKNQASRPYNIYPHGITDVRPLHSGRLPKGVKHLKDLPILPGEIFK

-continued

```
YKWTVTVEDGPTKSDPRCLTRYYSSFINLERDLASGLIGPLLICYKESVDQRGNQMMSD
KRNVILFSVFDENRSWYLTENMQRFLPNAAGVQPQDPEFQASNIMHSINGYVFDSLQLS
VCLHEVAYWYILSIGAQTDFLSVFFSGYTFKHKMVYEDTLTLFPFSGETVFMSMENPGL
WVLGCHNSDFRNRGMTALLKVSSCDRNTGDYYEDTYEDISTYLLSENNVIEPRSFSQNS
RHPSTRQKQFKATTIPENDIEKIDPQFGERTQMLKVQSVSSSDLLMLLGQSPTPHGLSLSD
LQEATYEAIPDDHSPGAIDSNEGPSEVAHLRPELHHSGDMVFTPEPGLQLRLNENLGTTI
AVELKKLDLKVSSSSNNLMTSPTIPSDNLAAGTEKTGSLGPPNMPVHFDSQLDTTVFGK
KSSPLIGSGVPLSLSERNNDSKLLEAALMNSQESSLGKNVSSMESDRLFKEKRAHGPALL
TKDNALFKVNISLVKTNKTSNNSTTNRKTHIDGPTLLIENSTSVWQDILESDTEFQEVTSL
IHDKMLMDKNTTALRLNHVSNKTTSSKNMEMVHQKKEGPVPPDAENPDMSFFKMLFL
PESANWIKRTHGKNSLNSGQGPSPKQLISLGSEKSVKDQNFLSEKNKVVVGEDEFTKDT
GLKEMIFPSSRNIFLTNLANVHENDTHNQEKKIQEEIERKETLIQENVVLPQVYTVTGTK
NFMKNLFLLSTRQNVEGLDEGAYAPVLQDTRSLNDSTNRTEIHMAHFSKKREEENLEGL
GNQTKQMVEKYPSTTRMSPNPSQQNVITQRGKRALKQFRLPLEETELEKGLIVDDTSTQ
WSKNMKYLTQSTLTQIDYNEKEKKAITQSPLSDCLMRNHSITQTNSSALPIAKVSAFPSIR
PTDLTRVPSQDNSSHLLASAYRKKSSGVQESSHFLQGAKRNNLSLAILTLEMIGNQRKV
GSLGTSATNSVMYKKLENTVLLKPGLPEASGKVELLPKVHIHQKDLFPTETSNGSPGHL
DLMEEILLQKTQGAIKWNKTNRPGKVPFLKGATESSEKTPSKLLGPLAWDNQYATQIPK
EEWKSQEKSPENTAFKTKDTILSLNPCESNHAIAAINEGQDRPQREATWAKQGGTGRLC
SQNPPVLKRHQREITLTTLQSDQEEIDYDDTISIETKREDFDIYGEDENQSPRSFQKKTRH
YFIAAVERLWDYGMSRSPHVLRNRAQSGSVPQFKKVVFQEFTDGSFTQPLYRGELNEHL
GLLGPYIRAEVEDNIMVTFKNQASRPYSFYSSLISYEEDQRQGAEPRKNFVKPNETKTYF
WKVQHHMAPTKDEFDCKAWAYFSDVDLEKDMHSGLIGPLLICHTNTLNPAHGRQVTV
QEFALFFTIFDETKSWYFTENMERNCRAPCNIQMEDPTFKENYRFHAINGYVMDTLPGL
VMAQDQRIRWYLLSMGSNENIHSIHFSGHVFTVRKKEEYKMAVYNLYPGVFETVEMLP
SKAGIWRVECLIGEHLHAGMSTLFLVYSKQCQTPLGMASGHIRDFQITASGQYGQWAP
KLARLHYSGSINAWSTKEPFSWIKVDLLAPMIIHGIKTQGARQKFSSLYISQFIIMYSLDG
KKWQTYRGNSTGTLMVFFGNVDSSGIKHNIFNPPIIARYIRLHPTHYSIRSTLRMELMGC
DLNSCSMPLGMESKAISDAQITASSYFTNMFATWSPSQARLHLQGRTNAWRPQVNNPK
EWLQVDFQKTMKVTGITTQGVKSLLTSMYVKEFLISSSQDGHHWTLFFQNGKVKVFQG
NQDSFTPVVNSLDPPLLTRYLRIHPQSWVHQIALRLEVLGCEAQQLY
```

Accordingly the sequences for sp-A1-A2-B-aq-A3-C1-C2:

(sp, Signal Peptide, SEQ ID NO: 12)
MQIELSTCFFLCLLQFSFS (A1 SEQ ID NO: 13)
```
ATRRYYLGAVELSWDYMQSDLLSELHVDTRFPPRVPRSFPFNTSVMYKKTVFVEFTDH
LFNIAKPRPPWMGLLGPTIQAEVYDTVVITLKNMASHPVSLHAVGVSYWKASEGAEYD
DQTSQREKEDDKVFPGESHTYVWQVLKENGPMASDPPCLTYSYLSHVDLVKDLNSGLI
GALLVCREGSLAKERTQTLHKFVLLFAVFDEGKSWHSETKDSLMQDMDSASARAWPK
MHTVNGYVNRSLPGLIGCHRKSVYWHVIGMGTTPEVHSIFLEGHTFLVRNHRQASLEIS
PITFLTAQTLLMDLGQFLLFCHISSHQHDGMEAYVKVDSCPEEPQLRMKNNEEEEDYDD
DLADSEMDVVRFDDDNSPSFIQIRS
```

```
                                                (A2 SEQ ID NO: 14)
VAKKHPKTWVHYIAAEEEDWDYAPSVLTPDDRSYKSQYLNNGPQRIGRKYKKVRFMA

YTDETFKTREAIQYESGILGPLLYGEVGDTLLIIFKNQASRPYNIYPHGITDVRPLHSGRLP

KGVKHLKDLPILPGEIFKYKWTVTVEDGPTKSDPRCLTRYYSSFINLERDLASGLIGPLLI

CYKESVDQRGNQMMSDKRNVILFSVFDENRSWYLTENMQRFLPNAAGVQPQDPEFQA

SNIMHSINGYVFDSLQLSVCLHEVAYWYILSIGAQTDFLSVFFSGYTFKHKMVYEDTLTL

FPFSGETVFMSMENPGLWVLGCHNSDFRNRGMTALLKVSSCDRNTGDYYEDTYEDIST

YLLSENNVIEPR (B SEQ ID NO: 15)
SFSQNSRHPSTRQKQFKATTIPENDIEKIDPQFGERTQMLKVQSVSSSDLLMLLGQSPTPH

GLSLSDLQEATYEAIPDDHSPGAIDSNEGPSEVAHLRPELHHSGDMVFTPEPGLQLRLNE

NLGTTIAVELKKLDLKVSSSSNNLMTSPTIPSDNLAAGTEKTGSLGPPNMPVHFDSQLDT

TVFGKKSSPLIGSGVPLSLSERNNDSKLLEAALMNSQESSLGKNVSSMESDRLFKEKRAH

GPALLTKDNALFKVNISLVKTNKTSNNSTTNRKTHIDGPTLLIENSTSVWQDILESDTEFQ

EVTSLIHDKMLMDKNTTALRLNHVSNKTTSSKNMEMVHQKKEGPVPPDAENPDMSFF

KMLFLPESANWIKRTHGKNSLNSGQGPSPKQLISLGSEKSVKDQNFLSEKNKVVVGEDE

FTKDTGLKEMIFPSSRNIFLTNLANVHENDTHNQEKKIQEEIERKETLIQENVVLPQVYTV

TGTKNFMKNLFLLSTRQNVEGLDEGAYAPVLQDTRSLNDSTNRTEIHMAHFSKKREEEN

LEGLGNQTKQMVEKYPSTTRMSPNPSQQNVITQRGKRALKQFRLPLEETELEKGLIVDD

TSTQWSKNMKYLTQSTLTQIDYNEKEKKAITQSPLSDCLMRNHSITQTNSSALPIAKVSA

FPSIRPTDLTRVPSQDNSSHLLASAYRKKSSGVQESSHFLQGAKRNNLSLAILTLEMIGNQ

RKVGSLGTSATNSVMYKKLENTVLLKPGLPEASGKVELLPKVHIHQKDLFPTETSNGSP

GHLDLMEEILLQKTQGAIKWNKTNRPGKVPFLKGATESSEKTPSKLLGPLAWDNQYAT

QIPKEEWKSQEKSPENTAFKTKDTILSLNPCESNHAIAAINEGQDRPQREATWAKQGGTG

RLCSQNPPVLKRHQR (ap SEQ ID NO : 16)
EITLTTLQSDQEEIDYDDTISIETKREDFDIYGEDENQSPR (A3 SEQ ID NO: 17)
SFQKKTRHYFIAAVERLWDYGMSRSPHVLRNRAQSGSVPQFKKVVFQEFTDGSFTQPLY

RGELNEHLGLLGPYIRAEVEDNIMVTFKNQASRPYSFYSSLISYEEDQRQGAEPRKNFVK

PNETKTYFWKVQHHMAPTKDEFDCKAWAYFSDVDLEKDMHSGLIGPLLICHTNTLNPA

HGRQVTVQEFALFFTIFDETKSWYFTENMERNCRAPCNIQMEDPTFKENYRFHAINGYV

MDTLPGLVMAQDQRIRWYLLSMGSNENIHSIHFSGHVFTVRKKEEYKMAVYNLYPGVF

ETVEMLPSKAGIWRVECLIGEHLHAGMSTLFLVYSK (C1 SEQ ID NO: 18)
QCQTPLGMASGHIRDFQITASGQYGQWAPKLARLHYSGSINAWSTKEPFSWIKVDLLAP

MIIHGIKTQGARQKFSSLYISQFIIMYSLDGKKWQTYRGNSTGTLMVFFGNVDSSGIKHNI

FNPPIIARYIRLHPTHYSIRSTLRMELMGCDLN (C2 SEQ ID NO: 19)
SCSMPLGMESKAISDAQITASSYFTNMFATWSPSQARLHLQGRTNAWRPQVNNPKEWL

QVDFQKTMKVTGITTQGVKSLLTSMYVKEFLISSSQDGHHWTLFFQNGKVKVFQGNQD

SFTPVVNSLDPPLLTRYLRIHPQSWVHQIALRLEVLGCEAQQLY
```

-continued

The sequence for Node number 53 is:

SEQ ID NO: 20

MQIELSTCFFLCLLQFSFSATRRYYLGAVELSWDYMQSDLLSELHVDTRFPPRVPRSFPF
NTSVMYKKTVFVEFTDHLFNIAKPRPPWMGLLGPTIRAEVYDTVVITLKNMASHPVSLH
AVGVSYWKASEGAEYDDQTSQREKEDDKVFPGESHTYVWQVLKENGPMASDPPCLTY
SYLSHVDLVKDLNSGLIGALLVCREGSLAKERTQTLHQFVLLFAVFDEGKSWHSETKDS
LTQAMDSASARAWPKMHTVNGYVNRSLPGLIGCHRKSVYWHVIGMGTTPEVHSIFLEG
HTFLVRNHRQASLEISPITFLTAQTLLMDLGQFLLFCHISSHQHDGMEAYVKVDSCPEEP
QLRMKNNEEEEDYDDDLYDSEMDVVRFDDDNSPPFIQIRSVAKKHPKTWVHYIAAEEE
DWDYAPSVLTPDDRSYKSQYLNNGPQRIGRKYKKVRFMAYTDETFKTREAIQYESGILG
PLLYGEVGDTLLIIFKNQASRPYNIYPHGITDVSPLHSGRLPKGVKHLKDLPILPGEIFKYK
WTVTVEDGPTKSDPRCLTRYYSSFINLERDLASGLIGPLLICYKESVDQRGNQMMSDKR
NVILFSVFDENRSWYLTENMQRFLPNAAGVQPQDPEFQASNIMHSINGYVFDSLQLSVC
LHEVAYWYILSVGAQTDFLSVFFSGYTFKHKMVYEDTLTLFPFSGETVFMSMENPGLW
VLGCHNSDFRNRGMTALLKVSSCDRNTGDYYEDTYEDIPTYLLSENNVIEPRSFSQNSR
HPSTRQKQFKATTIPENDIEKIDPQFGERTQMLKVQSVSSSDLLMLLGQSPTPHGLSLSDL
QEATYEAIPDDHSPGAIDSNEGPSEVAHLRPELHHSGDMVFTPEPGLQLRLNENLGTTIA
VELKKLDLKVSSSSNNLMTSPTIPSDNLAAGTEKTGSLGPPNMPVHFSSQLGTTVFGKKS
SPLIGSGVPLNLSERNNDSKLLEAALMNSQESSLGKNVSSMESDRLFKEKRVHGPALLT
KDNALFKVNISLVKTNKTSNNSTTNRKTHIDGPTLLIENSTSVWQDIILESDTEFQEVTSLI
HDEMLMDKNTTALRLNHVSNKTTSSKNMEMVHQKKEGPVPPDAENPDMSFFKMLFLP
ESANWIKRTHGKNSLNSGQGPSPKQLISLGSEKSVKDQNFLSEKNKVVVGEDEFTKDTG
LKEMIFPNSRSIFLTNLANVQENDTHNQEKKFQEEIERKETLIQENVVLPQVYTVTGTKN
FLKNLFLLSTRQNVEGLDEGTYAPVLQDTRSLNDSTNRAEIHMAHFSKRREEENLEGLG
NQTKQMVEKYPSTTRMSPNPSQQNVITQRGKRALKQFRLPLEETELEKGLIVDDTSTQW
SKNMKYLTQSTLTQIDYNEKEKKAITQSPLSDCSMRNHSITQTNSSALPIAKVSAFPSIRP
TDLTKIPSQDNSSHLLASAYSYTFREKSSGVQESSHFLQGAKRNNLSLAILTLEMIRNQEK
VGSLGTSATNSVMYKKLENTVLLKPGLPEASGKVELLPKVHIHQEDLFPTETSNGSPGH
LDLMEEILLQKTQGAIKWNKTNRPGKVPFLKGATESSEKTPSKLLGPLAWDNQYATQIP
KEEWKSQEKSPKNTAFKTKDTILSLNPCENNHAIAAINEGQDRPQREATWAKQGGTGRL
CSQNPPVLKRHQREITLTTLQSEQEEIDYDDTISIETKREDFDIYGEDENQGPRSFQKRTR
HYFIAAVERLWDYGMSRSPHVLRNRAQSGSVPQFKKVVFQEFTDGSFTQPLYRGELNE
HLGLLGPYIRAEVEDNIMVTFKNQASRPYSFYSSLISYEEDQRQGAEPRKNFVKPNETKT
YFWKVQHHMAPTKDEFDCKAWAYFSDVDLEKDMHSGLIGPLLICHTNTLNPAHGRQV
TVQEFALFFTIFDETKSWYFTENMERNCRAPCNIQMEDPTFKENYRFHAINGYVMDTLP
GLVMAQDQRIRWYLLSMGSNENIEISIHFSGHVFTVRKKEEYKMAVYNLYPGVFETVEM
LPSKAGIWRVECLIGEHLHAGMSTLFLVYSKQCQTPLGMASGHIRDFQITASGQYGQWA
PKLARLHYSGSINAWSTKEPFSWIKVDLLAPMIIHGIKTQGARQKFSSLYISQFIIMYSLD
GKKWQTYRGNSTGTLMVFFGNVDSSGIKHNIFNPPIIARYIRLHPTHYSIRSTLRMELMG
CDLNSCSMPLGMESKAISDAQITASSYFTNMFATWSPSQARLHLQGRTNAWRPQVNNP

KEWLQVDFQKTMKVTGITTQGVKSLLTSMYVKEFLISSSQDGHHWTLFLQNGKVKVFQ

GNQDSFTPVVNSLDPPLLTRYLRIHPQSWVHQIALRLEVLGCEAQQLY

Accordingly the sequences for sp-A1 -A2-B-aq-A3-C1-C2:

(sp, Signal Peptide, SEQ ID NO: 21)
MQIELSTCFFLCLLQFSFS (A1 SEQ ID NO: 22)
ATRRYYLGAVELSWDYMQSDLLSELHVDTRFPPRVPRSFPFNTSVMYKKTVFVEFTDH

LFNIAKPRPPWMGLLGPTIRAEVYDTVVITLKNMASHPVSLHAVGVSYWKASEGAEYD

DQTSQREKEDDKVFPGESHTYVWQVLKENGPMASDPPCLTYSYLSHVDLVKDLNSGLI

GALLVCREGSLAKERTQTLHQFVLLFAVFDEGKSWHSETKDSLTQAMDSASARAWPK

MHTVNGYVNRSLPGLIGCHRKSVYWHVIGMGTTPEVHSIFLEGHTFLVRNHRQASLEIS

PITFLTAQTLLMDLGQFLLFCHISSHQHDGMEAYVKVDSCPEEPQLRMKNNEEEEDYDD

DLYDSEMDVVRFDDDNSPPFIQIRS (A2 SEQ ID NO: 23)
VAKKHPKTWVHYIAAEEEDWDYAPSVLTPDDRSYKSQYLNNGPQRIGRKYKKVRFMA

YTDETFKTREAIQYESGILGPLLYGEVGDTLLIIFKNQASRPYNIYPHGITDVSPLHSGRLP

KGVKHLKDLPILPGEIFKYKWTVTVEDGPTKSDPRCLTRYYSSFINLERDLASGLIGPLLI

CYKESVDQRGNQMMSDKRNVILFSVFDENRSWYLTENMQRFLPNAAGVQPQDPEFQA

SNIMHSINGYVFDSLQLSVCLHEVAYWYILSVGAQTDFLSVFFSGYTFKHKMVYEDTLT

LFPFSGETVFMSMENPGLWVLGCHNSDFRNRGMTALLKVSSCDRNTGDYYEDTYEDIP

TYLLSENNVIEPR (B SEQ ID NO: 24)
SFSQNSRHPSTRQKQFKATTIPENDIEKIDPQFGERTQMLKVQSVSSSDLLMLLGQSPTPH

GLSLSDLQEATYEAIPDDHSPGAIDSNEGPSEVAHLRPELHHSGDMVFTPEPGLQLRLNE

NLGTTIAVELKKLDLKVSSSSNNLMTSPTIPSDNLAAGTEKTGSLGPPNMPVHFSSQLGT

TVFGKKSSPLIGSGVPLNLSERNNDSKLLEAALMNSQESSLGKNVSSMESDRLFKEKRV

HGPALLTKDNALFKVNISLVKTNKTSNNSTTNRKTHIDGPTLLIENSTSVWQDIILESDTE

FQEVTSLIHDEMLMDKNTTALRLNHVSNKTTSSKNMEMVHQKKEGPVPPDAENPDMSF

FKMLFLPESANWIKRTHGKNSLNSGQGPSPKQLISLGSEKSVKDQNFLSEKNKVVVGED

EFTKDTGLKEMIFPNSRSIFLTNLANVQENDTHNQEKKFQEEIERKETLIQENVVLPQVYT

VTGTKNFLKNLFLLSTRQNVEGLDEGTYAPVLQDTRSLNDSTNRAEIHMAHFSKRREEE

NLEGLGNQTKQMVEKYPSTTRMSPNPSQQNVITQRGKRALKQFRLPLEETELEKGLIVD

DTSTQWSKNMKYLTQSTLTQIDYNEKEKKAITQSPLSDCSMRNHSITQTNSSALPIAKVS

AFPSIRPTDLTKIPSQDNSSHLLASAYSYTFREKSSGVQESSHFLQGAKRNNLSLAILTLE

MIRNQEKVGSLGTSATNSVMYKKLENTVLLKPGLPEASGKVELLPKVHIHQEDLFPTET

SNGSPGHLDLMEEILLQKTQGAIKWNKTNRPGKVPFLKGATESSEKTPSKLLGPLAWDN

QYATQIPKEEWKSQEKSPKNTAFKTKDTILSLNPCENNHAIAAINEGQDRPQREATWAK

QGGTGRLCSQNPPVLKRHQR (ap SEQ ID NO: 25)
EITLTTLQSEQEEIDYDDTISIETKREDFDIYGEDENQGPR (A3 SEQ ID NO: 26)
SFQKRTRHYFIAAVERLWDYGMSRSPHVLRNRAQSGSVPQFKKVVFQEFTDGSFTQPLY

RGELNEHLGLLGPYIRAEVEDNIMVTFKNQASRPYSFYSSLISYEEDQRQGAEPRKNFVK

PNETKTYFWKVQHHMAPTKDEFDCKAWAYFSDVDLEKDMHSGLIGPLLICHTNTLNPA

-continued

```
HGRQVTVQEFALFFTIFDETKSWYFTENMERNCRAPCNIQMEDPTFKENYRFHAINGYV

MDTLPGLVMAQDQRIRWYLLSMGSNENIHSIHFSGHVFTVRKKEEYKMAVYNLYPGVF

ETVEMLPSKAGIWRVECLIGEHLHAGMSTLFLVYSK (C1 SEQ ID NO: 27)
QCQTPLGMASGHIRDFQITASGQYGQWAPKLARLHYSGSINAWSTKEPFSWIKVDLLAP

MIIHGIKTQGARQKFSSLYISQFIIMYSLDGKKWQTYRGNSTGTLMVFFGNVDSSGIKHNI

FNPPIIARYIRLHPTHYSIRSTLRMELMGCDLN (C2 SEQ ID NO: 28)
SCSMPLGMESKAISDAQITASSYFTNMFATWSPSQARLHLQGRTNAWRPQVNNPKEWL

QVDFQKTMKVTGITTQGVKSLLTSMYVKEFLISSSQDGHHWTLFLQNGKVKVFQGNQD

SFTPVVNSLDPPLLTRYLRIHPQSWVHQIALRLEVLGCEAQQLY
```

The sequence for Node number 50 is: SEQ ID NO: 29. The sequence for Node number 52 is: SEQ ID NO: 30. The sequence for Node number 57 is: SEQ ID NO: 31. The sequence for Node number 59 is: SEQ ID NO: 32. The sequence for Node number 65 is: SEQ ID NO: 33. The sequence for Node number 76 is: SEQ ID NO: 34. The sequence for Node number 78 is: SEQ ID NO: 35. The sequence for Node number 87 is: SEQ ID NO: 36. The sequence for Node number 90 is: SEQ ID NO: 37. The sequence for Node number 95 is: SEQ ID NO: 38.

```
                                                   SEQ ID NO: 29
MRIELPCCFFLCLLPFSFGATRRYYLGAVELSWDYVHSDLLSVLHVPTGFPGRVGRKFPF

STSVRYKKTVFVEFTDHLFTIAKPRPPWMGLLGPTIRAEVYDTVVVTLKNLASHPFSLHA

VGVTYWKASEGAGYDDETSQREKEDDKVDPGKTHTYVWEVLKDNGPTASDPPCLTYS

YLSYVDLVKDLNSGLIGALLVCRPGALAKDGTQTLHEFVLLFAVFDEGKSWYPEPNESL

TQALDTGTPRPWPKLHTVNGYVNGSLPGLIGCHKRPVYWHVIGLGTTPEVHSIFLEGHT

FLVRNHRHATLEISPITFLTAQTLLTDLGRFLLFCHIPAHQHDGMEAYVKVDVCPEEPKL

RMRADAPEEDYYDDLYDLDMDVIRFDDDDSPPFIGVRAFAKKHPKTWIHYIAAEEVDW

DYAPIVPTYLDRSYKSQYLEAGPQRIGRKYKKVRFVAYTDGTFKTRKVIQYDTGILGPLL

YGEVGDTLLIVFKNLASRPYNIYPHGLTSVSPLHPGRLPKGVKHLKDLPILPGEIFKYKW

TVTVEDGPTGSDPRCLTRYYYSFINPVRDLASGLIGPLLICYKESVDQRGNQMMSDKRR

FILFSVFDENRSWYLTENTQRFCPDAAGVQPQDPEFYASNVMHSINGYVFDNLHLKLCL

HEVAYWYVLSVGAQTDFLSVFFSGYTFKHKMVFEDTLTLFPFSGETVFMSMEKPGLWV

LGCLNPDFRDRGMWALLKVSSCDRDPGLYYGDDYDLIPTYLLNENNVLEPRGFPKNKR

WPRLCLRKFKAVTSPEKDIEKLDPQFGERTQCLRAQPLKFSDLLMLLGQNPDPHGLSLS

DLTEATYEPIPYDSFPGPVGNSTGPSEVVHLRPELHHAGDAGFYPEGGLLLFGKERLGPT

VAVELKKLDLKLHKSVDNVMFSPTAPLDNLEKGLKGTGTLGPLKEPVRFSGHLGPTVF

GKKETGLIGSGVPLQLSDRDHDSRLLERVLLNDEESPLGLNVTSLKPDRPFKDKRVHGP

ASLTKDNALFKGNITLVKLDKTPDNTTTNRKTYVDGPALLKENGTPVWLDILENDTRFQ

EVASLGFYETFQDGKLTAPGLDHVLNKTTSSKNGEVFFEKKVEPVPLDAERPPAPFFKD

LFLPRTANWLLDTHGKADLRAGQGPSPKQLISLGSDKSGDGEHFLSAKSKVRLGPDKFT

KGTGLLEMIFPGRKDIFLTSLVTVQENDTLILGKKFQEAIERKETLIQENVDLPKLYVVAG

TRNFLKDLFLLHTRTNLTLDGPDEGDYAPLLQDTRYLNGKVPPAGVHLVHGSKLLEAA

DLEGLLHKTKRMVLDYPSTTRTAPKPCDQNCITHRGKRALKQFGLPLEETELERGLVDK

DRALKGRKNMGYLTGGTLTKIDYNDRAKRLVARPPLVDCTARDHGVTGTDGPAGPIRG

VSAFPPIRPTDLTKLPSHDNSSHLPAAACGYTFREKSSGVRGGSHFLQGAKRTSLTSAYL
```

-continued

```
TLKTIRGEEKVSSLGTSADTPPTYKKLENTVLLKPGLPEVVGKVEGLPKPHVWEADLFPT

PTGNGTPGHLDLKEEWLLQKLQGAIKLSKVKRPGDFPFLKGATEILEKRPSKLLGPLPW

DGQYLTQILRDEWKLKHKSPKNTVFKTKDAILPLSGCENVHGVDGINEGRDRLQKAAT

WAKQGGTERLCSREPPVLKNHKREITLTTLQPEKEKIDYDDYLKPETDRDDFDIYGEDE

NQGPRTFTGRTRHYFIAAVERLWDYGMSRPPHFLRNRARGGRVPFFKKVVFRGFLDGSF

TQPLYRGELDEHLGLLGPYIRAEVDDVIMVTFKNLASRPYSFYSSLLPYEGGLGQGSEPR

KEVVKPGELRTYFWKVLPHMAPTVDEFDCKAWAYFSDVDLEKDLHSGLVGPLLICRPG

TLSPAFGRQLTVQEFALLFTIFDETKSWYFTENMERNCPPPCQIQPDDPDFRRSYRFHAIN

GYVMDTLPGLVMAQDQRVRWYLLSVGGTEDIHSVYFHGHVFTVRKKHEYRMGVYNL

YPGVFGTVEMLPSKPGIWRVECLVGEHLQAGMSTLFLVYDPKCQTPLGLASGHIRDAQI

TASGQYGQWAPRLARLHYSGSVNAWSTKDPFSWIKVDLLRPMILHGIKTQGARQKFSS

LYISQFIIFYGLDGKRWKRYRGNATGTLMVFFGNVDATGVKHNRFNPPIIARYIRLHPTH

YSIRTTLRMELIGCDLNSCSMPLGMENKAISDAQITASSYFTNMFATWAPSQARLHLQG

RTNAWRPKVNSPKEWLQVDFEKTMRVTGIVTQGAKSLLTSMYVKEFLVSSSQDGHRW

TPFLQDGKVKVFKGNQDHFTPVVNSLDPPLLTRYLRIHPRRWVHHIALRLEFLGCDAQQ

LY
```

SEQ ID NO: 30
```
MQIELSTCFFLCLLPFSFSATRRYYLGAVELSWDYMQSDLLSELHVDTRFPPRVPRSFPF

NTSVMYKKTVFVEFTDHLFNIAKPRPPWMGLLGPTIRAEVYDTVVITLKNMASHPVSLH

AVGVSYWKASEGAEYDDQTSQREKEDDKVIPGESHTYVWQVLKENGPMASDPPCLTY

SYLSHVDLVKDLNSGLIGALLVCREGSLAKERTQTLHEFVLLFAVFDEGKSWHSETNES

LTQAMDSASARAWPKMHTVNGYVNRSLPGLIGCHRKSVYWHVIGMGTTPEVHSIFLEG

HTFLVRNHRQASLEISPITFLTAQTLLMDLGQFLLFCHISSHQHDGMEAYVKVDSCPEEP

QLRMKNNEEEEDYDDDLYDSDMDVVRFDDDNSPPFIQIRSVAKKHPKTWVHYIAAEEE

DWDYAPSVLTPNDRSYKSQYLNNGPQRIGRKYKKVRFMAYTDETFKTREAIQYESGILG

PLLYGEVGDTLLIIFKNQASRPYNIYPHGITDVSPLHSGRLPKGVKHLKDLPILPGEIFKYK

WTVTVEDGPTKSDPRCLTRYYSSFINLERDLASGLIGPLLICYKESVDQRGNQMMSDKR

NVILFSVFDENRSWYLTENMQRFLPNAAGVQPQDPEFQASNIMHSINGYVFDSLQLSVC

LHEVAYWYILSVGAQTDFLSVFFSGYTFKHKMVYEDTLTLFPPFSGETVFMSMENPGLW

VLGCHNSDFRNRGMTALLKVSSCDRNTGDYYEDTYEDIPTYLLNENNVIEPRSFSQNSR

HPSTRQKQFKATTTPENDIEKIDPQFGERTQLLKVQSVSSSDLLMLLGQSPTPHGLSLSDL

QEATYEAIPDDHSPGAIESNEGPSEVAHLRPELHHSGDMVFTPEPGLQLRLNENLGTTITV

ELKKLDLKVSSSSNNLMTSPTIPSDNLAAGTEKTGSLGPPNMPVHFSSQLGTIVFGKKSSP

LIGSGVPLNLSERDNDSKLLEAALMNSQESSLGKNVSSMESDRLFKEKRVHGPASLTKD

NALFKVNISLVKTNKTPNNSTTNRKTHIDGPTLLIENSTSVWQDILENDTEFQEVTSLIHD

EMFMDKNTTALGLNHVSNKTTSSKNMEMVHQKKEGPVPLDAENPDMSFFKMLFLPDS

ANWIKRTHGKNSLSSGQGPSPKQLISLGSEKSVKDQNFLSEKNKVVVGEDEFTKDTGLK

EMIFPNSKSIFLTNLANVQENDTHNQEKKFQEEIERKETLIQENVVLPQVYTVTGTKNFL

KNLFLLSTRQNVTVEGLDEGTYAPVLQDTRSLNDSANRAGIHMAHFSKRREEAETNLEG

LGNQTKQMVEKYPSTTRMSPNPSQQNVITQRGKRALKQFRLPLEEIELERGLIVNDTSTQ

WSKNMKYLTQGTLTQIDYNEKEKRAITQSPLSDCSMRNHSITQTNGSALPIAKVSAFPSI
```

-continued

RPTDLTKIPSQDNSSHLLASACSYTFREKSSGVQESSHFLQGAKRNNLSLAILTLEMIRGQ

EKVSSLGTSATNPLMYKKLENTVLLKPGLPEASGKVELLPKVHVHQEDLFPTETSNGSP

GHLDLMEEILLQKTQGAIKLNKVNRPGKVPFLKGATESSEKTPSKLLGPLAWDNQYATQ

IPREEWKSQEKSPKNTAFKTKDTILPLNPCENNHAIAAINEGQDRPQREATWAKQGGTG

RLCSQNPPVLKRHQREITLTTLQPEQEKIDYDDTISIETKREDFDIYGEDENQGPRSFQKR

TRHYFIAAVERLWDYGMSRSPHALRNRAQSGSVPQFKKVVFQEFTDGSFTQPLYRGEL

NEHLGLLGPYIRAEVEDNIMVTFKNQASRPYSFYSSLISYEEDQRQGAEPRKNFVKPNET

KTYFWKVQHHMAPTKDEFDCKAWAYFSDVDLEKDMHSGLIGPLLICRTNTLNPAHGR

QVTVQEFALFFTIFDETKSWYFTENMERNCRAPCNIQMEDPTFKENYRFHAINGYVMDT

LPGLVMAQDQRIRWYLLSMGSNENIHSIHFSGHVFTVRKKEEYKMAVYNLYPGVFETV

EMLPSKAGIWRVECLIGEHLQAGMSTLFLVYSKQCQTPLGMASGRIRDFQITASGQYGQ

WAPKLARLHYSGSINAWSTKDPFSWIKVDLLAPMIIHGIKTQGARQKFSSLYISQFIIMYS

LDGKKWQSYRGNSTGTLMVFFGNVDSSGIKHNIFNPPIIARYIRLHPTHYSIRSTLRMEL

MGCDLNSCSMPLGMESKAISDAQITASSYFTNMFATWSPSQARLHLQGRTNAWRPQVN

NPKEWLQVDFQKTMKVTGITTQGVKSLLTSMYVKEFLISSSQDGHHWTLFLQNGKVKV

FQGNQDSFTPVVNSLDPPLLTRYLRIHPQSWVHQIALRLEVLGCEAQQLY

SEQ ID NO: 31
MQIELSTCFFLCLLRFCFSATRRYYLGAVELSWDYMQSDLGELPVDTRFPPRVPRSFPFN

TSVVYKKTVFVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASDPLCLTYS

YLSHVDLVKDLNSGLIGALLVCREGSLAKEKTQTLHKFVLLFAVFDEGKSWHSETKNSL

MQDRDAASARAWPKMHTVNGYVNRSLPGLIGCHRKSVYWHVIGMGTTPEVHSIFLEG

HTFLVRNHRQASLEISPITFLTAQTLLMDLGQFLLFCHISSHQHDGMEAYVKVDSCPEEP

QLRMKNNEEAEDYDDDLTDSEMDVVRFDDDNSPSFIQIRSVAKKHPKTWVHYIAAEEE

DWDYAPSVLAPDDRSYKSQYLNNGPQRIGRKYKKVRFMAYTDETEKTREAIQHESGIL

GPLLYGEVGDTLLIIFKNQASRPYNIYPHGITDVRPLYSRRLPKGVKHLKDFPILPGEIFKY

KWTVTVEDGPTKSDPRCLTRYYSSFINMERDLASGLIGPLLICYKESVDQRGNQIMSDKR

NVILFSVFDENRSWYLTENIQRFLPNPAGVQLEDPEFQASNIMHSINGYVFDSLQLSVCL

HEVAYWYILSIGAQTDFLSVFFSGYTFKHKMVYEDTLTLFPFSGETVFMSMENPGLWIL

GCHNSDFRNRGMTALLKVSSCDKNTGDYYEDSYEDISTYLLSKNNAIEPRSFSQNSRHPS

TRQKQFNATTIPENDIEKTDPWFAHRTPMPKVQNVSSSDLLMLLRQSPTPHGLSLSDLQE

AKYETFSDDPSPGAIDSNNSLSEMTHFRPQLHHSGDMVFTPEPGLQLRLNEKLGTTAATE

LKKLDFKVSSTSNNLISTIPSDNLAAGTDNTSSLGPPNMPVHYDSQLDTTLFGKKSSPLIE

SGGPLSLSEENNDSKLLESGLMNSQESSWGKNVSSTESGRLFKEKRAHGPALLTKDNAL

FKVSISLLKTNKTSNNSATNRKTHIDGPSLLIENSPSVWQNILESDTEFQKVTPLIHDRML

MDKNATALRLNHMSNKTTSSKNMEMVQQKKEGPIPPDAENPDMSFFKMLFLPESANWI

QRTHGKNSLNSGQGPSPKQLVSLGPEKSVEGQNFLSEKNKVVVGKGEFTKDVGLKEMV

FPSSRNLFLTNLDNLHENNTHNQEKKIQEEIERKETLIQENVVLPQIHTVTGTKNFMKNLF

LLSTRQNVEGSYEGAYAPVLQDFRSLNDSTNRTKKHTAHFSKKGEEENLEGLGNQTKQI

VEKYPRTTRISPNPSQQNFVTQRGKRALKQFRLPLEETELEKRIIVDDTSTQWSKNMKHL

TPSTLTQIDYNEKEKGAITQSPLSDCLTRSHSITQANRSPLPIAKVSSFPSIRPIDLTRVLFQ

-continued

DNSSHLPAPSYRKKDSGVQESSHFLQGAKKNNLSLAILTLEMTGDQREVGSLGTSATNS

VTYKKVENTVLLKPGLPKTSGKVELLPKVHIYQKDLFPTETSNGSPGHLDLVEGSLLQET

EGAIKWNEANRPGKIPFLRVATESSAKTPSKLLGPLAWDNHYGTQIPKEEWKSQEKSPE

KTAFKKKDTILSLNACESNHAIAAINEGQNKPEIEVTWAKQGGTERLCSQNPPVLKRHQ

REITLTTLQSDQEEIDYDDTISVEMKKEDFDIYDEDENQSPRSFQKKTRHYFIAAVERLW

DYGMSSSPHVLRNRAQSGSVPQFKKVVFQEFTDGSFTQPLYRGELNEHLGLLGPYIRAE

VEDNIMVTFKNQASRPYSFYSSLISYEEDQRQGAEPRKNFVKPNETKTYFWKVQHHMA

PTKDEFDCKAWAYFSDVDLEKDVHSGLIGPLLVCHTNTLNPAHGRQVTVQEFALFFTIF

DETKSWYFTENMERNCRAPCNIQMEDPITKENYRFHAINGYIMDTLPGLVMAQDQRIR

WYLLSMGSNENIHSIHFSGHVFTVRKKEEYKMAVYNLYPGVFETVEMLPSKAGIWRVE

CLIGEHLHAGMSTLFLVYSNKCQTPLGMASGHIRDFQITASGQYGQWAPKLARLHYSGS

INAWSTKEPFSWIKVDLLAPMIIHGIKTQGARQKFSSLYISQFIIMYSLDGKKWQTYRGNS

TGTLMVFFGNVDSSGIKHNIFNPPIIARYIRLHPTHYSIRSTLRMELMGCDLNSCSMPLGM

ESKAISDAQITASSYFTNMFATWSPSKARLHLQGRSNAWRPQVNNPKEWLQVDFQKTM

KVTGITTQGVKSLLTSMYVKEFLISSSQDGHHWTLFFQNGKVKVFQGNQDSFTPVVNSL

DPPLLTRYLRIHPQSWVHQIALRMEVLGCEAQELY

SEQ ID NO: 32
MQIELSTCFFLCLLRFCFSATRRYYLGAVELSWDYMQSDLGELPVDARFPPRVPKSFPFN

TSVVYKKTVFVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASDPLCLTYS

YLSHVDLVKDLNSGLIGALLVCREGSLAKEKTQTLHKFILLFAVFDEGKSWHSETKNSL

MQDRDAASARAWPKMHTVNGYVNRSLPGLIGCHRKSVYWHVIGMGTTPEVHSIFLEG

HTFLVRNHRQASLEISPITFLTAQTLLMDLGQFLLFCHISSHQHDGMEAYVKVDSCPEEP

QLRMKNNEEAEDYDDDLTDSEMDVVRFDDDNSPSFIQIRSVAKKHPKTWVHYIAAEEE

DWDYAPLVLAPDDRSYKSQYLNNGPQRIGRKYKKVRFMAYTDETFKTREAIQHESGIL

GPLLYGEVGDTLLIIFKNQASRPYNIYPHGITDVRPLYSRRLPKGVKHLKDFPILPGEIFKY

KWTVTVEDGPTKSDPRCLTRYYSSFINMERDLASGLIGPLLICYKESVDQRGNQIMSDKR

NVILFSVFDENRSWYLTENTQRFLPNPAGVQLEDPEFQASNIMHSINGYVFDSLQLSVCL

HEVAYWYILSIGAQTDFLSVFFSGYTFKHKMVYEDTLTLFPFSGETVFMSMENPGLWIL

GCHNSDFRNRGMTALLKVSSCDKNTGDYYEDSYEDISAYLLSKNNAIEPRSFSQNSRHP

STRQKQFNATTIPENDIEKTDPWFAHRTPMPKVQNVSSSDLLMLLRQSPTPHGLSLSDLQ

EAKYETFSDDPSPGAIDSNNSLSEMTHFRPQLHHSGDMVFTPESGLQLRLNEKLGTTAAT

ELKKLDFKVSSTSNNLISTIPSDNLAAGTDNTSSLGPPSMPVHYDSQLDTTLFGKKSSPLT

ESGGPLSLSEENNDSKLLESGLMNSQESSWGKNVSSTESGRLFKGKRAHGPALLTKDNA

LFKVSISLLKTNKTSNNSATNRKTHIDGPSLLIENSPSVWQNILESDTEFQKVTPLIHDRM

LMDKNATALRLNHMSNKTTSSKNMEMVQQKKEGPIPPDAENPDMSFFKMLFLPESAS

WIQRTHGKNSLNSGQGPSPKQLVSLGPEKSVEGQNFLSEKNKVVVGKGEFTKDVGLKE

MVFPSSRNLFLTNLDNLHENNTHNQEKKIQEEIERKETLIQENVVLPQIHTVTGTKNFMK

NLFLLSTRQNVEGSYEGAYAPVLQDFRSLNDSTNRTKKHTAHFSKKGEEENLEGLGNQT

KQIVEKYACTTRISPNTSQQNFVTQRSKRALKQFRLPLEETELEKRIIVDDTSTQWSKNM

KHLTPSTLTQIDYNEKEKGAITQSPLSDCLTRSHSIPQANRSPLPIAKVSSFPSIRPIYLTRV

-continued

LFQDNSSHLPAASYRKKDSGVQESSHFLQGAKKNNLSLAILTLEMTGDQREVGSLGTSA

TNSVTYKKVENTVLPKPGLPKTSGKVELLPKVHIYQKDLFPTETSNGSPGHLDLVEGSLL

QETEGAIKWNEANRPGKIPFLRVATESSAKTPSKLLGPLAWDNHYGTQIPKEEWKSQEK

SPEKTAFKKKDTILSLNACESNHAIAAINEGQNKPEIEVTWAKQGRTERLCSQNPPVLKR

HQREITRTTLQSDQEEIDYDDTISVEMKKEDFDIYDEDENQSPRSFQKKTRHYFIAAVERL

WDYGMSSSPHVLRNRAQSGSVPQFKKVVFQEFTDGSFTQPLYRGELNEHLGLLGPYIRA

EVEDNIMVTFKNQASRPYSFYSSLISYEEDQRQGAEPRKNFVKPNETKTYFWKVQHHM

APTKDEFDCKAWAYFSDVDLEKDVHSGLIGPLLVCHTNTLNPAHGRQVTVQEFALFFTI

FDETKSWYFTENMERNCRAPCNIQMEDPTFKENYRFHAINGYIMDTLPGLVMAQDQRI

RWYLLSMGSNENIHSIHFSGHVFTVRKKEEYKMALYNLYPGVFETVEMLPSKAGIWRV

ECLIGEHLHAGMSTLFLVYSNKCQTPLGMASGHIRDFQITASGQYGQWAPKLARLHYSG

SINAWSTKEPFSWIKVDLLAPMIIHGIKTQGARQKFSSLYISQFIIMYSLDGKKWQTYRGN

STGTLMVFFGNVDSSGIKHNIFNPPIIARYIRLHPTHYSIRSTLRMELMGCDLNSCSMPLG

MESKAISDAQITASSYFTNMFATWSPSKARLHLQGRSNAWRPQVNNPKEWLQVDFQKT

MKVTGITTQGVKSLLTSMYVKEFLISSSQDGHHWTLFFQNGKVKVFQGNQDSFTPVVN

SLDPPLLTRYLRIHPQSWVHQIALRMEVLGCEAQDLY

SEQ ID NO: 33
MQIELSTCFFLCLLQFSFSATRRYYLGAVELSWDYMQSDLLSELHVDTRFPPRMPRSFPF

NTSVMYKKTVFVEFTDHLFNIAKPRPPWMGLLGPTIWAEVYDTVVITLKNMASHPVSL

HAVGVSYWKASEGAEYDDQTSQREKEDDKVFPGESHTYVWQVLKENGPMASDPPCLT

YSYLSHVDLVKDLNSGLIGALLVCREGSLAKERTQMLHQFVLLFAVFDEGKSWHSETK

GSLTQAMDSASARAWPKMHTVNGYVNRSLPGLIGCHRKSVYWHVIGMGTTPEVHSIFL

EGHTFLVRNHRQASLEISPITFLTAQTLLMDLGQFLLFCHISSHQHDGMEAYVKVDSCPE

EPQLRMKNNEEEEDYDDDLLDSEMDVFRFDDDNSPPFIQIRSVAKKHPKTWIHYIAAEE

EDWDYAPSVLTSDDRSYKSQYLNNGPQRIGRKYKKVRFMAYTDETFKTRETIQYESGIL

GPLLYGEVGDTLLIIFKNQASRPYNIYPHGITDVSPLHSGRLPKGVKHLKDLPILPGEIFKY

KWTVTVEDGPTKSDPRCLTRYYSSFINLERDLASGLIGPLLICYKESVDQRGNQMMSDK

RNVILFSVFDENRSWYLTENMQRFLPNAAGVQPQDPEFQASNIMHSINGYVFDSLQLSV

CLHEVAYWYILSVGAQTDFLSVFFSGYTFKHKMVYEDTLTLFPPFSGETVFMSMENPGL

WVLGCHNSDFRNRGMTALLKVSSCDRNTGDYYEDTYEDIPTYLLSENNVIEPRSFSQNS

RHPSTRQKQFKATTIPENDIEKIDPQFGERTQMLKVQSVSSSDLLMLLGQSPTPHGLSLSD

LQEATYEAIPDDHSPGAIDSNEGPSEVAHLRPELHHSGDIVFTPEPGLQLRLNENLGTTIA

VELKKLDLKVSSSPNNLMTSPTIPSDNLAAGTEKTGSLGPPNMPVHFSSQLSTTVFGKKS

SPLIGSGVPLNLSERNNDSKLLEAALMNSQESSLGKNVSSMESDRLFKEKRVHGPALLT

KDNALFKVNISLIKTNKTSNNSTTNRKTHIDGPTLLIENSTSVWQDTILESDTEFQEVTSLI

HDEMLMDKNTTALRLNHVSNKTTSSKNMEMVHQKKEGPVPPDAENPDMSFFKMLFLP

ESANWIKRTHGKNSLNSGQGPSPKQLISLGSEKSVKDQNFLSEKNKVVVGEDEFTKDTG

LKEMIFPNNRSIFLTNLANVQENDTHNQEKKFQEEIERKEALIQENVVLPQVYTVTGTKN

FLKNLFLLSTRQNIGLDEGTYAPVLQDTRSLNDSTNRAEIHMAHFSKRREEEETNLEGLG

NQTKQMVEKYPSTTRMSPNPSQQNVITQRGKRALKQFRLPLEETELEKGLIVDDTSTQW

SKNMKYLTQSTLTQIDYNEKEKKAITQSPLSDSPMRNHSITQMNSSALPIAKISAFPSIRPT

-continued

DLTKIPSQDNSSHFLASAYNYTFREKSSGVQESSHFLQGAKRNNLSLAILPLEMIRNQEK

VGSLGTSATNSVMYKKLENTVLLKPGLPEASGKVELLPKVPIHQEDLFPTETSHGSPGHL

DLMEEILLQKTQGAIKWNKTNRPGKVPFLKGATESSEKTPSKLLGPLAWDNQYATQIPK

EEWKSQEKSPKNTAFKTKDTILSLNPCENNHAIAAINEGQDRPQREATWAKQGGTGRLC

SQNPPVLKRHQREITLTTLQSEQEEIDYDDTISIETKREDFDIYGEDENQGPRSFQKRTRH

YFIAAVERLWDYGMSRSPHVLRNRDQSGSVPQFKKVVFQEFTDGSFTQPLYRGELNEHL

GLLGPYIRAEVEDNIMVTFKNQASRPYSFYSSLISYKEDQRQGAEPRKNFVKPNETKTYF

WKVQHHMAPTKDEFDCKAWAYFSDVDLEKDMHSGLIGPLLICHTNTLNPAHGRQVTV

QEFALFFTIFDETKSWYFTENMERNCRAPCNIQMEDPTFKENYRFHAINGYVMDTLPGL

VMAQDQRIRWYLLSMGSNENIHSIHFSGHVFTVRKKEEYKMAVYNLYPGVFETVEMLP

SKAGIWRVECLIGEHLHAGMSTLFLVYSKQCQIPLGMASGHIRDFQITASGQYGQWAPK

LARLHYSGSINAWSTKEPFSWIKVDLLAPMIIHGIKTQGARQKFSSLYISQFIIMYSLDGK

KWQTYRGNSTGTLMVFFGNVDSSGIKHNIFNPPIIARYIRLHPTHYSIRSTLRMELMGCD

LNSCSMPLGMESKAISDAQITASSYFTNMFATWSPSQARLHLQGRTNAWRPQVNNPKE

WLQVDFQKTMKVTGIITQGVKSLLTSMFVKEFLISSSQDGHHWTLFLQNGKVKVFQGN

QDSFTPVVNSLDPPLLTRYLRIHPQSWVHQIALRLEVLGCEAQQLY

SEQ ID NO: 34
MQIELSTCFFLCLLPFSFSATRRYYLGAVELSWDYMQSELLSELHVDTRFPPRVPRSFPFN

TSVMYKKTVFVEFTDHLFNIAKPRPPWMGLLGPTIRAEVYDTVVITLKNMASHPVSLHA

VGVSYWKASEGAEYEDQTSQREKEDDKVIPGESHTYVWQVLKENGPMASDPPCLTYS

YLSHVDLVKDLNSGLIGALLVCREGSLAKERTQTLHEFVLLFAVFDEGKSWHSETNESL

TQAMDPASARAQPEMHTVNGYVNRSLPGLIGCHKKSVYWHVIGMGTTPEVHSIFLEGH

TFLVRNHRQASLEISPITFLTAQTLLMDLGQFLLFCHISSHQHDGMEAYVKVDSCPEEPQ

LRMKNNEEEEDYDDDLYDSDMDVVRFDDDNSPPFIQIRSVAKKHPKTWVHYIAAEEED

WDYAPSVLTPNDRSYKSLYLNNGPQRIGRKYKKVRFMAYTDETFKTREAIQYESGILGP

LLYGEVGDTLLIIFKNQASRPYNIYPHGITDVSPLHSGRLPKGVKHLKDMPILPGEIFKYK

WTVTVEDGPTKSDPRCLTRYYSSFVNLERDLASGLIGPLLICYKESVDQRGNQMMSDKR

NVILFSVFDENRSWYLTENMQRFLPNADGVQPQDPEFQVSNIMHSINGYVFDSLQLSVC

LHEVAYWYILSVGAQTDFLSVFFSGYTFKHKMVYEDTLTLFPFSGETVFMSMENPGLW

VLGCHNSDFRNRGMTALLKVSSCDRNTGDYYEDTYEDIPTSLLNENNVIEPRSFSQNSR

HPSTRQKQFKATTTPENDIEKIDPQSGERTQLLKVQSVSSSDLLMLLGQNPTPHGLSLSD

LQEATYEADDHLPGAIERNKGPSEVAHLRPELHHSGDRVFTPEPELQLRLNENLGTTITV

ELKKLDLKISSSSNNLMTSPTIPSDKLAAGTEKTGSLGPPNMPVHFSSQLGTIVFGKNSSH

LIGSGVPLGLSEGDNDSKLLEAALMNSQESSLGENVLSMESDRLFKEERVHGPASLTKD

NALFKVNISLVKTNKAPINSTTNRKTHIDGPTLLTENSTSVWQDIILESNTEFQEVTSLIHD

ETFMDKNTTALGLNHVSNKTTSSKNMEMVHQKKEGPVPLGAENPDTSFFKMLFLPDSA

NWIKRTHGKNSLSSGQRPSPKQLTSLGSEKSVKDQNFLSEKNKVVVGEDEFTKDTGLKE

MIFPNSKSIFLTNLANVQENDTHNQEKKSQEEIERKEKLIQENVVLPQVYTVTGTKNFLK

NLFLLSTKQNVEGLDEGTYTPILQDTRSLNDSANRAGIHMAHFSKIREEANLEGLGNQTK

QMVEKYPSTTRMSPNPSQQNVITQRGKRALKQFRLPLEEIKLERGVILNDTSTQWSKNM

KYLTQGTLTQIEYNEKEKRAITQSLLSDCSMRSHGIIQTNGSALPIAKVSAFPSIRPTDLTK

-continued

IPSQDNSSHLLASACSYTFRERSSGVQESSHFLQGAKRNNLSLAFLTLEMIRGQEKISSLG
KSATNPLMYKKLENTVLLKPGLSEASGKVELLPKVHVHQEDSFPTKTSNGSPGHLDLME
EIFLQKTQGPVKLNKVNRPGKVPFLKWATESSEKTPSKLLGPLAWDNQYATQIPREEWK
SQEKSQKNTAFKTKDTILPLDPCENNHSIAAINEGQDKPQREATWAKQGGTGRLCSQNP
PVLKRHQREITLTTLQPEEDKIDYDDTFSIETKREDFDIYGEDENQGPRSFQKRTRHYFIA
AVERLWDYGMSRSPHALRNRAQSGSVPQFKKVVFQEFTDGSFTQPLYRGELNEHLGLL
GPYIRAEVEDNIMVTFKNQASRPYSFYSSLISYEEDQRQGAEPRKKFVKPNETKIYFWKV
QHHMAPTKDEFDCKAWAYFSDVDLEKDMHSGLIGPLLICRTNTLNPAHGRQVTVQEFA
LFFTIFDETKSWYFTENMERNCRAPCNIQMEDPTFKENYRFHAINGYVMDTLPGLVMAQ
DQRIRWYLLSMGSNENIHSIHFSGHVFTVRKKEEYKMAVYNLYPGVFETVEMLPSKAGI
WRIECLIGEHLQAGMSTLFLVYSKKCQTPLGMASGRIRDFQITASGQYGQWAPKLARLH
YSGSINAWSTKDPFSWIKVDLLAPMIIHSIMTQGARQKFSSLYISQFIIMYSLDGKKWQSY
RGNSTGTLMVFFGNVDSSGIKHNIFNPPIIARYIRLHPTHYSIRSTLRMELMGCDLNSCSM
PLGMENKAISDAQITASSYLNNMFATWSPSQARLHLQGRTNAWRPQVNNPKEWLQVD
FQKTMKVTGITTQGVKSLLTSMYVKEFLISSSQDGHNWTLFLQNGKVKVFQGNQDSFTP
VVNSLDPPLLTRYLRIHPQSWAHQIALRLEVLGCEAQQLY

SEQ ID NO: 35
MQIELSTCFFLCLLPFSFSAIRRYYLGAVELSWDYMQSELLSELHVDTRFPPRVPRSFPFN
TSVMYKKTVFVEFTDQLFNIAKPRPPWMGLLGPTIQAEVYDTVVITLKNMASHPVSLHA
VGVSYWKSSEGAEYEDQTSQREKEDDKVIPGKSHTYVWQVLKENGPTASDPPCLTYSY
LSHVDLVKDLNSGLIGALLVCREGSLTKERTQTLHEFVLLFAVFDEGKSWHSGKNESLT
QAMDPASARAQPAMHTINGYINRSLPGLIGCHKKSVYWHVIGMGTTPEVHSIFLEGHTF
LVRNHRQASLEISPITFLTAQTLLMDLGQFLLFCHISSHQHDGMEAYVKVDSCPEEPQLR
MKNNEEEEDYDDDLYDSDMDVVRFDGDNAPPFIQIRSVAKKHPKTWVHYIAAEEEDW
DYAPSVLTSNDRSYKSLYLNNGPQRIGRKYKKVRFIAYTDETFKTREAIQYESGILGPLL
YGEVGDTLLIIFKNQASRPYNIYPHGITDVSPLHSGRFPKGVKHLKDMPILPGEIFKYKWT
VTVEDGPTKSDPRCLTRYYSSFVNLEKDLASGLIGPLLICYKESVDQRGNQMMSDKRNV
ILFSVFDENQSWYLTENIQRFLPNADGVQPQDPEFQVSNIMHSINGYVFDSLQLSVCLHE
VAYWYILSVGAQTDFLSVFFSGYTFKHKMVYEDTLTLFPFSGETVFMSMENPGLWVLG
CHNSDFRNRGMTALLKVYSCDRNTGDYYEDTYEDIPTFLLNENNVIEPRSFSQNSRHPST
RQKQFKATTTPENDIEKIDPQSGERTQLLKEQSVSSSDLLMLLGQNPTPHGLSLSDLQEA
RNEADDHLPGAIERNKGPSEVAHLRPELHHSGERVFTPEPELPLRLNENLGTTITVELKK
LDFKISSSSNNLMTSPTIPSDKLSAGTEKTGSLGPPNMPVNFSSQLGTIVFGKNSSHFIGSG
VPLGLSEEDNDSKLLEAALMNSQESSLGENVLSMESDRLFKEERVHGPASLTKDDALFK
VNISLVKTNKAPVNSTTNRKTHIDDPTLLIENSTSVWQDIILESNTEFQEVTSLIHDETFMD
KNTTALGLNHVSNKTTSSKNMEMVHQKKEGPVPLDAEYPDTSFFKTLFLPDSTNWIKRT
HGKNSLSSGQRPSPKQLTSSGSEKSVKDQNFLSEKNKVVVGEDEFSKDTGLKEMIFPNS
KSIFLTNLANVQENDTHNQEKKSQEEIERKEKLIQENVVLPQVYTVTGTKNFLKNLFLLS
TKQNVEGLDEGTYTPVLQDTRSLNDSAKRAGIHMAHFSKIREEANLEGLGNQTKQMVE
KYPSTTRMSPNPSQQNVIPQRGKRDLKQFRLPLEEIKLERGVILNDTSTQWSKNMKYLT
QGTFTQIEYNKKEKRAITQSFLSDCSMRSHGIIQTNGSALPIAKVSAFPSIRPTDLTKIPSQ

```
DNSSHLPASACSYTFGERSSGVQESSHFLQGAKRNNLSLAFLTLEMIRGQGKISTLGKSA

TNPLMYKKLENTVLLKPGLSEASGKVEFLPKVHVHQEDFFPTKTSNGSPAHLDLREEIFL

QKTQGLVKLNKVNRPGKVPFLKWATESSEKTPSKLLGPLAWDNQYATLIPREEWKSLE

KSQKNTAFKTKDTILPLDPCENNHSIAAINEGQDKPQREATWVKQGGTGRLCSQNPPVL

KRHQREITLTTFQPEEDKIDYDDTFSIETKREDFDIYGEDENQGPRSFQKRTRHYFIAAVE

RLWDYGMSRSPHALRNRAQNGDVPQFKKVVFQEFTDGSFTQPLYRGELNEHLGLLGPY

IRAEVEDNIMVTFKNQASRPYSFYSSLISYEEDQRQGAEPRKKFVKPNETKIYFWKVQHH

MAPTKDEFDCKAWAYFSDVDLEKDVHSGLIGPLLICRTNTLNAAHGRQVTVQEFALFFT

IFDETKSWYFTENMERNCRAPCNIQMEDPTFKENYRFHAINGYVMDTLPGLVMAQDQR

IRWYLLSMGSNENIHSIHFSGHVFTVRKKEEYKMAVYNLYPGVFETVEMLPSKVGIWRI

ECLIGEHLQAGMSTLFLVYSKKCQTPLGMASGRIRDFQITASGQYGQWAPKLARLHYSG

SINAWSTKDPFSWIKVDLLAPMIIHSIMTQGARQKFSSLYISQFIIMYSLDGKKWQSYRG

NSTGTLMVFFGNVDSSGIKHNIFNPPIIARYIRLHPTHYSIRSTLRMELMGCDLNSCSMPL

GMENKAISDAQITASSHLSNMFATWSPSQARLHLQGRTNAWRPQVNNPKEWLQVDFQ

KTMKVTGITTQGVKSLLTSMYVKEFLISSSQDGHNWTLFLQNGKVKVFQGNQDSFTPV

VNALDPPLFTRYLRIHPQSWAHHIALRLEVLGCEAQQLY

SEQ ID NO: 36
MQIELSTCFFLCLLPFSFSATRRYYLGAVELSWDYMQSELLSELHVDTRFSPRVPRSLPFN

TSVMYKKTVFVEFTDHLFNIAKPRPPWMGLLGPTIRAEVYDTVVITLKNMASHPVSLHA

VGVSYWKASEGAEYEDQTSQKEKEDDKVIPGESHTYVWQVLKENGPMASDPPCLTYS

YFSHVDLVKDLNSGLIGALLVCKEGSLAKERTQTLHEFVLLFAVFDEGKSWHSETNESL

TQSAQAQHEMHTVNGYVNRSLPGLTGCHKKSVYWHVIGMGTTPEVHSIFLEGHTFLVR

NHRQASLEISPITFLTAQTFLMDLGQFLLFCHISSHQHDGMEAYVKVDSCPEEPQLRMKN

NEEEEDYDDDLYDSDMDVVRFDGDNSSPFIQIRSVAKKHPKTWVHYIAAEEEDWDYAP

SAPTPNDRSYKNLYLNNGPQRIGRKYKKVRFMAYTDETFKTREAIQYESGILGPLLYGE

VGDTLLIIFKNQASRPYNIYPHGITDVSPLHSGRLPKGVKHLKDMPILPGEIFKYKWTVTV

EDGPTKSDPRCLTRYYSSFINLERDLASGLIGPLLICYKESVDQRGNQMMSDKRNVILFS

VFDENRSWYLTENMQRFLPNADAVQPHDPEFQVSNIMHSINGYVFDNLQLSVCLHEVA

YWYILSVGAQTDFLSVFFSGYTFKHKMVYEDTLTLFPPFSGETVFMSMENPGLWVLGCH

NSDFRNRGMTALLKVSSCNRNTGDYYEDTYEDIPTSLLNENNVIEPRSFSQNSRHPSTRQ

KQFKATTTPENDIEKIDPQSGERTQLLKVQSVSSSDLLMLLGQNPTPHGLFLSDLQEATH

EADDHLLGAIERNKGPSEVASLRPELHHSGDRVFTPEPELQLRLNENLGTTVTVELKKLD

LKISSSSDNLMTSPTIPSDKLAAGTEKTGSLGPPNMSVHFNSHLGTIVFGKNSSHLIESGVP

LGLSEGDNDSKLLEAALMNSQESSLGENVLSMESNRLFKEERVHGPASLIKDNALFKVN

ISLVKTNKAPINSTTNRKTHVDVPTLLIENSTSVWQDIILESNTEFQEVTSLIHNETFMDRN

TTALGLNHVSNKTTSSKNVEMVHQKKEGPVPLGAENPDLSFFKILFLPDSANWIKRTHG

KNSLSSGQRPSPKQLTSLGSEKSVKDQNFLSEKKVVVGEDEFTKDTGLKEMIFPNSKSIFF

TNLANVQENDTYNQEKKSQEEIERKEKLTQENVVLPQVYTVTGTKNFLKNLFLTKQNV

TVEGLDEGPYTPILQDTRSLNDSAHRAGIHMAHFSKIREEANLEGLGNQTKQMVERFPS

TTRMSPNPSQHNVITQRGKRALKQPRLSLEEIKFERGVILNDTSTQWSKNMNYLTQGTL

TQIEYNEKEKRAITQSLLSDCSMRNHGTIQMNDSALPIAKVSAFPSIRHTDLTKIPSQDNS
```

-continued

SHLPASACSYTFRERSSGVQESSHFLQGAKRNNLSLAFLTLEMIRGQGKFSSLGKSATNQ

PMYKKLENTVLLKPGLSEASGKVELLPKVHVHQEDSFPTKTSNDSPGHLDLMEKIFLQK

TQGPVKLNKVNRPGKVPFLKWATESSEKIPSKLLGPLAWDNHYATQIPREEWKSQKKS

QKNTAFKTKDTILPLGPCENNHSIAAINEGQDKPQREATWAKQGETGRLCSQNPPVSKR

HQREITLTTLQPEEDKIEYDDTFSIEMKREDFDIYGEDENQGLRSFQKRTRHYFIAAVERL

WDYGMSRSPHALRNRAQSGDVPQFKKVVFQEFTDGSFTQPLYRGELNEHLGLLGPYIR

AEVEDNIMVTFKNQASRPYSFYSSLISYEEDQRQGAEPRKKFVNPNETKIYFWKVQHHM

APTKDEFDCKAWAYFSDVDLEKDVHSGLIGPLLICRSNTLNPAHGRQVTVQEFALFFTIF

DETKSWYFTENMERNCRAPCNIQKEDPTFKENYRFHAINGYVMDTLPGLVMAQDQKIR

WYLLSMGSNENIHSIHFSGHVFTVRKKEEYKMAVYNLYPGVFETVEMLPSKVGIWRIEC

LIGEHLQAGMSTLFLVYSKKCQTPLGMASGHIRDFQITASGQYGQWAPKLARLHYSGSI

NAWSTKDPFSWIKVDLLAPMIIHSIMTQGARQKFSSLYISQFIIMYSLDGKKWQSYRGNS

TGTLMVFFGNVDSSGIKHNIFNPPIIARYIRLHPTHYSIRSTLRMELMGCDLNSCSMPLGM

ENKAISDAQITASSYLNSMFATWSPSQARLHLQGRTNAWRPQANNPKEWLQVDFQKT

MKVTGITTQGVKSLLTSMYVKEFLISSSQDGHNWTLFLQNGKVKVFQGNQDSFTPVVN

SLDPPLLTRYLRIHPQSWAHQIALRLEVLGCEAQQLY

SEQ ID NO: 37
MQIELSTCFFLCLLPFSFSATRRYYLGTVELSWDYMQSELLSELHVDTRFPPRVPRSFPFN

PSVMYKKTVFVEFTDHLFNIAKPRPPWMGLLGPTIRAEVYDTVVITLKNMASHPVSLHA

VGVSYWKASEGAEYEDQTSQREKEDDKVIPGESYTYVWQVLKENGPMASDPPCLTYS

YLSHVDLVKDLNSGLIGALLVCREGSLAKERTQTLHEFVLLFAVFDEGKSWHSETNESL

TQAMDPASARAQPEMHTVNGYVNRSLPGLIGCHKKSVYWHVIGMGTTPEVHSIFLEGH

TFLVRNHRQASLEISPISFLTAQTLLMDLGQFLLFCHISSHQHDGMEAYVKVDSCPEEPQ

LRMKNNEEEEDYDDDLYDSDMDVVRFDGDNSPPFIQIRSVAKKHPKTWVHYIAAEEED

WDYAPSVLTPNDRSYKSLYLNNGPQQIGRKYKKARFMAYTDETFKTREAIQYESGILGP

LLYGEVGDTLLIIFKNQASRPYNIYPHGITDVSPLHSGRLPKGVKHLKDMPILPGEIFKYK

WTVTVEDGPTKSDPRCLTRYYSSFVNLERDLASGLIGPLLICYKESVDQRGNQMMSDKR

NVILFSVFDENRSWYLTENMQRFLPNADGVQPQDPEFQVSNIMHSINGYVFDSLQLSVC

LHEVAYWYILSVGAQTDFLSVFFSGYTFKHKMVYEDTLTLFPPFSGETVFMSMENPGLW

VLGCHNSDFRNRGMTALLKVSSCNRNTGDYYEDTYEDIPTSLLNENNVIEPRSFSQNSR

HPSTRQKQFKATTTPENDVEKIDLRSGERTQLLKVQSVSSSDLLMLLGQNPTPHALSLSD

LQEVTYEADDHLPGTIERNKGPSEVAHLRPELHHSGDRVFTPEPELQLRLNENLGTTITV

ELKKLDLKISSSSNNLMISPTIPSDKLAAGTEKTGSLGPPNMPVHFSSQLGTIVFGKNSSH

LIESAVPLGLSEGDNDSKLIEAALMNSQESSLEENVLSMESDRLFKEERVHGPVSLTKDN

ALFKVNFSLVKTNKAPINSTTNRKTHIDGPTLLIENSTSVWQDIILESNSGEQEVTSLIHDE

TFMDKNTTALGLNHVSNKTTSSKNMEMVHQKKEDPAPLGAENPDISFFKMLFLPDSAN

WIKRTHCKNSLSSGQRPSPKQLTSLGSEKSVKDQNFLSEKNKVVVGEDEFTKDTGLKEM

IFPNSKSIFLTNLANVQENDTHNQEKNSQEEIERKEKLIQKNVVLPQVYTVTGTKNFLKN

LFLLSTKQNVEGLDEGTYTPILQDTRSLNESANRARIHMAHFSKIREEANLEGLGNQTKQ

MVEKYPSTTRMSPNPRQQNVITHHGKRALKQFRLPQEEIKLERGVILNDTSTQWSKNMK

YLTQGTLTQIEYNEKEKRAITQSLLSDCSVRSHGIIQTNGSALPIAKVSAFPSIRPTDLTKIP

-continued

SQDNSSHLLASACSYTFREKSSGIQESSHFLQGAKRNNLSLAFLTLEMIRGQGKISSLGKL

SEASGKVELLPKVHVHQEDSFPTKTSNGSPGHLDLMEEIFLQKTQGPVKLNKVNRPGKIP

FLKWAAESSEKTPSKLLGPLATQIPREEWNSQEKSQKNKAFKTKDTISPLDPCENNHSIA

AINKGQDKPQREATWAKQEETGRLCSQNPPVLKRHQRQITLTTVQPEEDKIDYDDTFST

ETKREDFDIYGEDENQDPRSFQKRTRHYFIAAVERLWDYGMSRSPHALRNRAQSGDVP

QFKKVVFQEFTDGSFTQPLYRGELNEHLGLLGPYIRAEVEDNIMVTFKNQASRPYSFYSS

LISYEDDQRQGAEPRKKFVKPNETEVYFWKVQHHMAPTKDEFDCKAWAYFSDVDLDK

DVHSGLVGPLLICRANTLNPAHGRQVTVQEFALFFTIFDETKSWYFTENMERNCRAPCNI

QMEDPTFKENYRFHAINGYVMDTLPGLVMAQDQRIRWYLLSMGSNENIHSIHESGHVF

TVRKKEEYKMAVYNLYPGVFETVEMLPSKVGIWRIECLIGEHLQAGMSTLFLVYSKKC

QTPLGMASGHIRDFQITASGQYGQWAPKLARLHYSGSINAWSTKDPFSWIKVDLLAPMI

IHSIMTQGARQKFSSLYISQFIIMYSLDGKKWQSYRGNSTGTLMVFFGNVDSSGIKHNIFN

PPIIARYIRLHPTHYSIRSTLRMELMGCDLNSCSMPLGMENKAIADAQITASSYLNNMFA

TWSPSQARLHLQGRTNAWRPRVNNPKEWLQVDFQKTMKVTGITTQGVKSLLTSMYVK

EFLISSSQDGHNWTLFLQNGKVKVFQGNQDSFTPVVNSLDPPLLTRYLRIHPQSWGHQIA

LRLEVLGCEAQQLY

SEQ ID NO: 38
MQIELSVCFFLCLLPFSFSATRRYYLGAVELSWDYMQSDLLSELHVDTRLLPRVPRSFPF

NTSVMFKKTVFVEFTDHLFNIAKPRPPWMGLLGPTIRAEVYDTVIITLKNMASHPVSLHA

VGVSYWKASEGAEYDDKTSQREKEDDKVIPGESHTYIWQVLKENGPMASDPPCLTYSY

LSHVDLVKDLNSGLIGALLVCREGSLAKERTQTLHEFVLLFAVFDEGKSWHSEANESLA

QGVDSASTRPWPKMYTVNGYVNRSLPGLIGCHRKSVYWHVIGMGTTPEVHSIFLEGHT

FLVRNHRQASLEISPITFLTAQTLLMDLGQFLLFCHIPSHQHDGMEAYVKVDSCPEEPQL

RKKNNEEEEDYEDDLYDSDMDVLRFDDDNSPPFIQIRSVAKKHPKTWIHYIAAEEEDWD

YAPAVLPSTDRSYKSQYLNNGTQRIGRKYKKVRFIAYTDETFQTREAIQYESGILGPLLY

GEVGDTLLIIFKNQASRPYNIYPHGITNVSPLHSGRLPKGVKHLKDLQIMPGEIFKYKWT

VTVEDGPTKSDPRCLTRYYSSFINLERDLASGLIGPLLICYKESVDQRGNQMMSDKRNVI

LFSVFDENRSWYLTENMQRFLPNAAGVQPQDPEFQASNMMYSINGYVFDNLQLSVCLH

EVAYWYILSVGAQTDFLSVFFSGYTFKHKMVFEDTLTLFPFSGETVFMSMENPGLWVL

GCHNSDFRNRGMTALLKVSSCDRNTDDYYEDTYEDIPTYLLNENSVIEPRSFSQNSRHPS

PRQKQFKATTAPENDIEKMDPRFGERTQLLKAQSVSSSDLLMLLGQSPTPHGLSLSDLQE

AKYEAIPDDPSPGAIENKEGPSEVAHLRPELHHSEDMVFTPEPGLQRLRLNENLETTITEDL

KKLDLKVSSSSNNVMTSPISSSDNLPADTEKTDSLGPLNTPVHFSSQLGTILFGKKSSPLIG

SGVPLNLSERDNDSTLLEAALMSSQESSLGKKVSSMESDRLFKEKKVHGPASLTKDNAL

FKVNISLVKTNKTPNNSTTNRKTHIDGPTLLNENSTSGWQDILKNDTEFQEVTSLIHNEM

FMDKNTTALGLNHVSNKTTSSKDMEMVHQKKEDPVSLDAENPDMSFFKMLFLPDSAN

WIKRTHGKNSLSSEQGPSPKQLISLGSENSVKDQNFLSEKNKVAVGEDEFTKDTGFKEMI

FPNSKSIFLTNLANVQENDTQNQEKKFQEEIERKETLIQENVGLPQVFPVTGTKNFLKTLF

LLSTRQNVTVEGLDEGTYAPVLQDTRSLNDSANRLGLHMAHFSKRREEANLEGLRNQT

KQMVEKYPSPTRMSPNPSQQNAITQRSKRALKQFGPPLEEIELERGLIVNDTSTLQSRNM

KYLTQGTLTQIDYNEKEKRAITQSPLSDCSMRNHVITQTNGSALPIAKTSAFPSIRPTDLT

-continued

KIPSQDNSSHLLSSACNYTFREKSSGVQESSHFLQGAKRNNLSSAILTLDMIRGQEKVISL
SATDPLMYKKLENTVLLKPGLPEASGKVELLPKIHVHQEDPFPTETSNGSPGHLDLMEEI
LLQKTQGAIKLNKVNRPGKVPFLKGATESSEKTLPKLLGPLAWDNQYATQISREEWQSQ
EKSPKNTAFNTKDTISPLNPCENNHAIAAINEGQDRLQKEATWAKQGETERLCSENPPVL
KHHPREITLTALQQEQEKIDYDDALSIETKREDFDIYGEDENQGPRSFQKKTRHYFIAAV
ERLWDYGMSKSPHALRNRAQSGSVPQFKKVVFQEFTDGSFTQPLYRGELNEHLGLLGP
YIRAEVEDNIMVTFKNQASRPYSFYSSLISYEEDQRQGTEPRKNLVKPNETKTYFWKVQ
HEIMAPTKDEFDCKAWAYFSDVDLEKDLHSGLIGPLLICRTNTLNPAHGRQLTVQEFALF
FTIFDETKSWYFTENMERNCKAPCNIQMEDPTFKKNYRFHAINGYVMDTLPGLVMAQD
QRIRWYLLSMGSNENIHSIHFSGHVFTVRKKEEYKMAVYNLYPGVFETVEMLPSKAGIW
RVECLIGEHLQAGMSTLFLVYSKECQTPLGMASGRIRDSQITASGHYGQWAPKLARLHY
TGSINAWSTKDPFSWIKVDLLAPMIIHGIKTQGARQKLSSLYISQFIIMYSLDGKKWQSYR
GNSTGTLMVFFGNVDSSGIKHNIFNPPIIAQYIRLHPTHHSIRSTLRMELMGCDLNSCSMP
LGMESKAISDAQITASSYFTNMFATWSPSQARLHLQGRTNAWRPQVNNPKEWLQVDFQ
KTMKVTGITTQGAKSLLTSMYVKEFLISSSQDGHHWTLFLQNGKVKVFQGNQDSFTPV
VNSLDPPLLTRYLRIYPQSWVHQIALRLEVLGCQSQQHY

SEQ ID NO: 39
MQIALFTCFFLSLFNFCSSATRRYYLGAVELSWNYMQSDLLSVLHTDTRFLPRMPTSFPF
NTSIMYKKTVFVEYMDHLFNIAKPRPPWMGLLGPTIWTEVHDTVVITLKNMASHPVSLH
AVGVSYWKASEGAEYEDQTSQREKEDDKVFPGESHTYVWQVLKENGPMASDPPCLTY
SYLSHVDLVKDLNSGLIGALLVCKEGSLSKERTQMLHQFVLLFAVFDEGKSWHSETKDS
FTQAMDSASTRAWPKMHTVNGYVNRSLPGLIGCHRKSVYWHVIGMGTTPEVHSIFLEG
HTFLVRNHRQASLEISPITFLTAQTLLIDLGQFLLFCHISSHKHDGMEAYVKVDSCPEEPQ
WQKKNNEEMEDYDDDLDSEMDMFTLDDDNSPFIQIRSVAKKYPKTWIHYISAEEEDWD
YAPSVLTSDDGSYKSQYLSNGPHRIGRKYKKVRFIAYTDVTFKTRETIQHESGILGPLLY
GEVGDTLLIIFKNQASRPYNIYPHGITDVSPLHSRRLPRGIKHVKDLPIRPGEIFKYKWTVT
VEDGPTKSDPRCLTRYYSSFINPERDLASGLIGPLLICYKESVDQRGNQMMSDKRNVILF
SVFDENQSWYITENMQRFLPNAADTQPQDPEFQASNIMHSINGYVFDSLQLTVCLHEVA
YWYILSVGAQTDFLSIFFSGYTFKHKMVYEDTLTLFPFSGETVFMSMENPGLWVLGCHN
SDFRKRGMTALLKVSSCDKSTSDYYEEIYEDIPTQLVNDNNVIEPRSFFQNPPVLKRHQR
ELSALQSEQEATDYDDSITIETNEDFDIYGEDIKQGPRSFQQKTRHYFIAAVERLWDYGM
STSPHVLRNRDQSGNAPQFKKVVFQEFTDGSFSQPLYRGELNEHLGLLGPYIRAEVEDNI
MVTFKNQASRPYSFYSSLISYKEDQRQGEEPRRNFVKPNETKIYFWKVQHFIMAPTEDEF
DCKAWAYFSDVDLERDMHSGLIGPLLICHTNTLNPAHGRQVAVQEFALFFTIFDETKSW
YFTENVERNCKTPCNIQMEDPTLKENYRFHAINGYVMDTLPGLVMAQDQRIRWYLLSM
GSNENIQSIHFSGHVFTVRKKEEYKMAVYNLYPGVFETVEMLPSRAGIWRVECLIGEHL
QAGMSTLFLVYSKQCQIPLGMASGSIRDFQITASGHYGQWAPNLARLHHSGSINAWSTK
EPFSWIKVDLLTPMIIHGIKTQGARQKFSSLYISQFIIMYSLDGKKWLSYRGNSTGTLMVF
FGNVDSSGIKHNSFNPPIIARYIRLHPTHSSIRSTLRMELMGCDLNSCSIPLGMENKVISDT

-continued

QITASSYFTNMFATWSPSQARLHLQGRTNAWRPQVNDPKEWLQVDLQKTMKVTGIITQ
GVKSLFTSMFVKEFLISSSQDGHHWTHILHNGKVKVFQGNQDSSTPMVNSLDPPLLTRY
LRIHPQIWEHQIALRLEILGCEAQQLY

SEQ ID NO: 40
MQIELSTCFFLCLLQFSFSATRRYYLGAVELSWDYMQSDLLSELHVDTRFPPRVPRSFPF
NTSVMYKKTVFVEFTDHLFNIAKPRPPWMGLLGPTIRAEVYDTVVITLKNMASHPVSLH
AVGVSYWKASEGAEYDDQTSQREKEDDKVFPGESHTYVWQVLKENGPMASDPPCLTY
SYLSHVDLVKDLNSGLIGALLVCREGSLAKERTQTLHQFVLLFAVFDEGKSWHSETKDS
LTQAMDSASARAWPKMHTVNGYVNRSLPGLIGCHRKSVYWHVIGMGTTPEVHSIFLEG
HTFLVRNHRQASLEISPITFLTAQTLLMDLGQFLLFCHISSHQHDGMEAYVKVDSCPEEP
QLRMKNNEEEEDYDDDLYDSEMDVVRFDDDNSPPFIQIRSVAKKHPKTWVHYIAAEEE
DWDYAPSVLTPDDRSYKSQYLNNGPQRIGRKYKKVRFMAYTDVTFKTREAIQYESGIL
GPLLYGEVGDTLLIIFKNQASRPYNIYPHGITDVSPLHSGRLPKGVKHLKDLPILPGEIFKY
KWTVTVEDGPTKSDPRCLTRYYSSFINLERDLASGLIGPLLICYKESVDQRGNQMMSDK
RNVILFSVFDENRSWYLTENMQRFLPNAAGVQPQDPEFQASNIMHSINGYVFDSLQLSV
CLHEVAYWYILSVGAQTDFLSVFFSGYTFKHKMVYEDTLTLFPPFSGETVFMSMENPGL
WVLGCHNSDFRNRGMTALLKVSSCDRNTGDYYEDTYEDIPTYLLSENNVIEPRSFSQNP
PVLKRHQREITLTTLQSEQEEIDYDDTISIETKREDFDIYGEDENQGPRSFQKRTRHYFIAA
VERLWDYGMSRSPHVLRNRAQSGSVPQFKKVVFQEFTDGSFTQPLYRGELNEHLGLLG
PYIRAEVEDNIMVTFKNQASRPYSFYSSLISYEEDQRQGAEPRKNFVKPNETKTYFWKV
QHHMAPTKDEFDCKAWAYFSDVDLEKDMHSGLIGPLLICHTNTLNPAHGRQVTVQEFA
LFFTIFDETKSWYFTENMERNCRAPCNIQMEDPTFKENYRFHAINGYVMDTLPGLVMAQ
DQRIRWYLLSMGSNENIHSIHFSGHVFTVRKKEEYKMAVYNLYPGVFETVEMLPSKAGI
WRVECLIGEHLHAGMSTLFLVYSKQCQTPLGMASGHIRDFQITASGQYGQWAPKLARL
HYSGSINAWSTKEPFSWIKVDLLAPMIIHGIKTQGARQKFSSLYISQFIIMYSLDGKKWQT
YRGNSTGTLMVFFGNVDSSGIKHNIFNPPIIARYIRLHPTHYSIRSTLRMELMGCDLNSCS
MPLGMESKAISDAQITASSYFTNMFATWSPSQARLHLQGRTNAWRPQVNNPKEWLQV
DFQKTMKVTGITTQGVKSLLTSMYVKEFLISSSQDGHHWTLFLQNGKVKVFQGNQDSF
TPVVNSLDPPLLTRYLRIHPQSWVHQIALRLEVLGCEAQQLY

SEQ ID NO: 42:
MQIALFTCFFLSLFNFCSSATRRYYLGAVELSWNYMQSDLLSVLHTDTRFLPRMPTSFPF
NTSIMYKKTVFVEYMDHLFNIAKPRPPWMGLLGPTIWTEVHDTVVITLKNMASHPVSLH
AVGVSYWKASEGAEYEDQTSQREKEDDKVFPGESHTYVWQVLKENGPMASDPPCLTY
SYLSHVDLVKDLNSGLIGALLVCKEGSLSKERTQMLHQFVLLFAVFDEGKSWHSETKDS
FTQAMDSASTRAWPKMHTVNGYVNRSLPGLIGCHRKSVYWHVIGMGTTPEVHSIFLEG
HTFLVRNHRQASLEISPITFLTAQTLLIDLGQFLLFCHISSHKHDGMEAYVKVDSCPEEPQ
WQKKNNEEMEDYDDDLDSEMDMFTLDDDNSPFIQIRSVAKKHPKTWVHYIAAEEEDW
DYAPLVLAPDDRSYKSQYLNNGPQRIGRKYKKVRFMAYTDVTFKTREAIQHESGILGPL
LYGEVGDTLLIIFKNQASRPYNIYPHGITDVRPLYSRRLPKGVKHLKDFPILPGEIFKYKW
TVTVEDGPTKSDPRCLTRYYSSFVNMERDLASGLIGPLLICYKESVDQRGNQIMSDKRN
VILFSVFDENRSWYLTENTQRFLPNPAGVQLEDPEFQASNIMHSINGYVFDSLQLSVCLHE

-continued

```
VAYWYILSIGAQTDFLSVFFSGYTFKHKMVYEDTLTLFPFSGETVFMSMENPGLWILGC

HNSDFRNRGMTALLKVSSCDKNTGDYYEDSYEDISAYLLSKNNAIEPRSFAQNSRPPSAS

APKPPVLKRHQRELSALQSEQEATDYDDSITIETNEDFDIYGEDIKQGPRSFQQKTRHYFI

AAVERLWDYGMSTSPHVLRNRDQSGNAPQFKKVVFQEFTDGSFSQPLYRGELNEHLGL

LGPYIRAEVEDNIMVTFKNQASRPYSFYSSLISYKEDQRQGEEPRRNFVKPNETKIYFWK

VQHHMAPTEDEFDCKAWAYFSDVDLERDMHSGLIGPLLICHTNTLNPAHGRQVAVQEF

ALFFTIFDETKSWYFTENVERNCKTPCNIQMEDPTLKENYRFHAINGYVMDTLPGLVMA

QDQRIRWYLLSMGSNENIQSIHFSGHVFTVRKKEEYKMAVYNLYPGVFETVEMLPSRA

GIWRVECLIGEHLQAGMSTLFLVYSKKCQTPLGMASGHIRDFQITASGQYGQWAPKLAR

LHYSGSINAWSTKEPFSWIKVDLLAPMIIHGIKTQGARQKFSSLYISQFIIMYSLDGKKWQ

TYRGNSTGTLMVFFGNVDSSGIKHNIFNPPIIARYIRLHPTHYSIRSTLRMELMGCDLNSC

SMPLGMESKAISDAQITASSYFTNMFATWSPSKARLHLQGRSNAWRPQVNNPKEWLQV

DFQKTMKVTGVTTQGVKSLLTSMYVKEFLISSSQDGHQWTLFFQNGKVKVFQGNQDSF

TPVVNSLDPPLLTRYLRIHPQSWVHQIALRMEVLGCEAQDLY
```

In certain embodiments, the disclosure contemplate recombinant, chimeric, non-naturally occurring sequences comprising one or more of the sequences of four or more continuous amino acids found in Ancestral Nodes disclosed herein, e.g., 68 or 53.

In certain embodiments, the sp domain comprises one or more sequences selected from; IALF (SEQ ID NO: 44), FFLS (SEQ ID NO: 45), FLSL (SEQ ID NO: 46), LSLF (SEQ ID NO: 47), SLFN (SEQ ID NO: 48), LFNF (SEQ ID NO: 49), FNFC (SEQ ID NO: 50), NFCS (SEQ ID NO: 51), FCSS (SEQ ID NO: 52), CSSA (SEQ ID NO: 53), SSAT (SEQ ID NO: 54).

In certain embodiments, the A1 domain comprises one or more sequences selected from; LSWN (SEQ ID NO: 55), WNYM (SEQ ID NO: 56), NYMQ (SEQ ID NO: 57), DLLS (SEQ ID NO: 58), LLSV (SEQ ID NO: 59), LSVL (SEQ ID NO: 60), SVLH (SEQ ID NO: 61), VLHT (SEQ ID NO: 62), LHTD (SEQ ID NO: 63), HTDT (SEQ ID NO: 64), TDTR (SEQ ID NO: 65), TRFL (SEQ ID NO: 66), RFLP (SEQ ID NO: 67), FLPR (SEQ ID NO: 68), LPRM (SEQ ID NO: 69), PRMP (SEQ ID NO: 70), RMPT (SEQ ID NO: 71), PTSF (SEQ ID NO: 72), TSFP (SEQ ID NO: 73), NTSI (SEQ ID NO: 74), TSIM (SEQ ID NO: 75), SIMY (SEQ ID NO: 76), IMYK (SEQ ID NO: 77), MYKK (SEQ ID NO: 78), FVEY (SEQ ID NO: 79), VEYM (SEQ ID NO: 80), EYMD (SEQ ID NO: 81), YMDH (SEQ ID NO: 82), MDHL (SEQ ID NO: 83), DHLF (SEQ ID NO: 84), PTIW (SEQ ID NO: 85), TIWT (SEQ ID NO: 86), IWTE (SEQ ID NO: 87), WTEV (SEQ ID NO: 88), TEVH (SEQ ID NO: 89), EVHD (SEQ ID NO: 90), VHDT (SEQ ID NO: 91), HDTV (SEQ ID NO: 92), FPGE (SEQ ID NO: 93), PGES (SEQ ID NO: 94), GESH (SEQ ID NO: 95), ESHT (SEQ ID NO: 96), LVCK (SEQ ID NO: 97), VCKE (SEQ ID NO: 98), CKEG (SEQ ID NO: 99), GSLS (SEQ ID NO: 100), SLSK (SEQ ID NO: 101), LSKE (SEQ ID NO: 102), SKER (SEQ ID NO: 103), RTQM (SEQ ID NO: 104), TQML (SEQ ID NO: 105), QMLH (SEQ ID NO: 106), MLHQ (SEQ ID NO: 107), LHQF (SEQ ID NO: 108), HQFV (SEQ ID NO: 109), QFVL (SEQ ID NO: 110), KDSF (SEQ ID NO: 111), DSFT (SEQ ID NO: 112), SFTQ (SEQ ID NO: 113), FTQA (SEQ ID NO: 114), TQAM (SEQ ID NO: 115), QAMD (SEQ ID NO: 116), AMDS (SEQ ID NO: 117), MDSA (SEQ ID NO: 118), DSAS (SEQ ID NO: 119), SAST (SEQ ID NO: 120), ASTR (SEQ ID NO: 121), STRA (SEQ ID NO: 122), TRAW (SEQ ID NO: 123), LLID (SEQ ID NO: 124), LIDL (SEQ ID NO: 125), IDLG (SEQ ID NO: 126), SSHK (SEQ ID NO: 127), SHKH (SEQ ID NO: 128), HKHD (SEQ ID NO: 129), KHDG (SEQ ID NO: 130), EPQW (SEQ ID NO: 131), PQWQ (SEQ ID NO: 132), QWQK (SEQ ID NO: 133), WQKK (SEQ ID NO: 134), QKKN (SEQ ID NO: 135), KKNN (SEQ ID NO: 136), NEEM (SEQ ID NO: 137), EEME (SEQ ID NO: 138), EMED (SEQ ID NO: 139), MEDY (SEQ ID NO: 140), DDLD (SEQ ID NO: 141), DLDS (SEQ ID NO: 142), LDSE (SEQ ID NO: 143), EMDM (SEQ ID NO: 144), MDMF (SEQ ID NO: 145), DMFT (SEQ ID NO: 146), MFTL (SEQ ID NO: 147), FTLD (SEQ ID NO: 148), TLDD (SEQ ID NO: 149), LDDD (SEQ ID NO: 150).

In certain embodiments, the ap domain comprises one or more sequences selected from; LSAL (SEQ ID NO: 151), SALQ (SEQ ID NO: 152), ALQS (SEQ ID NO: 153), LQSE (SEQ ID NO: 154), QSEQ (SEQ ID NO: 155), SEQE (SEQ ID NO: 156), EQEA (SEQ ID NO: 157), QEAT (SEQ ID NO: 158), EATD (SEQ ID NO: 159), ATDY (SEQ ID NO: 160), TDYD (SEQ ID NO: 161), YDDS (SEQ ID NO: 162), DDSI (SEQ ID NO: 163), DSIT (SEQ ID NO: 164), SITI (SEQ ID NO: 165), ITIE (SEQ ID NO: 166), TIET (SEQ ID NO: 167), IETN (SEQ ID NO: 168), ETNE (SEQ ID NO: 169), TNED (SEQ ID NO: 170), NEDF (SEQ ID NO: 171), DIYG (SEQ ID NO: 172), IYGE (SEQ ID NO: 173), YGED (SEQ ID NO: 174), GEDI (SEQ ID NO: 175), EDIK (SEQ ID NO: 176), DIKQ (SEQ ID NO: 177), IKQG (SEQ ID NO: 178), KQGP (SEQ ID NO: 179), QGPR (SEQ ID NO: 180).

In certain embodiments, the A3 domain comprises one or more sequences selected from; MSTS (SEQ ID NO: 181), STSP (SEQ ID NO: 182), TSPH (SEQ ID NO: 183), RNRD (SEQ ID NO: 184), NRDQ (SEQ ID NO: 185), RDQS (SEQ ID NO: 186), DQSG (SEQ ID NO: 187), QSGN (SEQ ID NO: 188), SGNA (SEQ ID NO: 189), GNAP (SEQ ID NO: 190), NAPQ (SEQ ID NO: 191), APQF (SEQ ID NO: 192), GSFS (SEQ ID NO: 193), SFSQ (SEQ ID NO: 194), FSQP (SEQ ID NO: 195), SQPL (SEQ ID NO: 196), ISYK (SEQ ID NO: 197), SYKE (SEQ ID NO: 198), YKED (SEQ ID NO: 199), KEDQ (SEQ ID NO: 200), RQGE (SEQ ID NO: 201), QGEE (SEQ ID NO: 202), GEEP (SEQ ID NO: 203), EEPR (SEQ ID NO: 204), EPRR (SEQ ID NO: 205), PRRN (SEQ ID NO: 206), RRNF (SEQ ID NO: 207), RNFV (SEQ ID NO: 208), ETKI (SEQ ID NO: 209), TKIY (SEQ ID NO: 210), KIYF (SEQ ID NO: 211), IYFW (SEQ ID NO: 212), DLER (SEQ ID NO: 213), LERD (SEQ ID NO: 214), ERDM (SEQ ID NO: 215), RDMH (SEQ ID NO: 216), DMHS (SEQ ID NO: 217), MHSG (SEQ ID NO: 218), LICH (SEQ ID NO: 219), ICHT (SEQ ID NO: 220), CHTN (SEQ ID NO: 221), HTNT (SEQ ID NO: 222), TNTL (SEQ ID NO: 223), TLNP (SEQ ID NO: 224), LNPA (SEQ ID NO: 225), NPAH (SEQ ID NO: 226), PAHG (SEQ ID NO: 227), RQVA (SEQ ID NO: 228), QVAV (SEQ ID NO: 229), VAVQ (SEQ ID NO: 230), AVQE (SEQ ID NO: 231), RNCK (SEQ ID NO: 232), NCKT (SEQ ID NO: 233), CKTP (SEQ ID NO: 234), KTPC (SEQ ID NO: 235), TPCN (SEQ ID NO: 236), ENIQ (SEQ ID NO: 237), NIQS (SEQ ID NO: 238), IQSI (SEQ ID NO: 239), QSIH (SEQ ID NO: 240), LPSR (SEQ ID NO: 241), PSRA (SEQ ID NO: 242), SRAG (SEQ ID NO: 243), RAGI (SEQ ID NO: 244).

In certain embodiments, the recombinant or chimeric protein comprises one or more of the sequences found to be unique in Ancestral Nodes 53 selected from in the sp domain, CLLQ (SEQ ID NO: 247), LLQF (SEQ ID NO: 248), LQFS (SEQ ID NO: 249), QFSF (SEQ ID NO: 250). In the A1 domain LLSE (SEQ ID NO: 251), LSEL (SEQ ID NO: 252), ELHV (SEQ ID NO: 253), RVPR (SEQ ID NO: 254), VPRS (SEQ ID NO: 255), PTIR (SEQ ID NO: 256), TIRA (SEQ ID NO: 257), IRAE (SEQ ID NO: 258), NEEE (SEQ ID NO: 259), EEED (SEQ ID NO: 260), CDRN (SEQ ID NO: 261), EDTY (SEQ ID NO: 262), PTYL (SEQ ID NO: 263), LSEN (SEQ ID NO: 264). In the activation peptide domain, ITLT (SEQ ID NO: 265), SIET (SEQ ID NO: 266), IETK (SEQ ID NO: 267), ETKR (SEQ ID NO: 268), TKRE (SEQ ID NO: 269), KRED (SEQ ID NO: 270), REDF (SEQ ID NO: 271), QKRT (SEQ ID NO: 272). In the A3 domain, VEQL (SEQ ID NO: 273), EGLW (SEQ ID NO: 274), GMSR (SEQ ID NO: 275), MSRS (SEQ ID NO: 276), SRSP (SEQ ID NO: 277).

Ancestral Protein Reconstruction

Recombinant porcine FVIII was approved by the FDA for the treatment of hemophilia A patients who have developed an autoimmune response to endogenous FVIII. Porcine FVIII displays reduce cross-reactivity toward antibody inhibitors developed against human FVIII. It is desirable to find FVIII sequences that have improved activity because it is possible that the frequency of infusion may be lessened while still achieving full prophylaxis. Murine FVIII (mFVIII) has displayed the longest observed half-life following activation.

A phylogenetic tree was constructed based on known orthologous FVIII sequences. Ancestral FVIII sequences were reconstructed and expressed in multiple cell lines. The ancestral FVIII sequences produced functional proteins that complexed with human coagulation factors. A sequence for the common ancestor of primates and rodents demonstrates higher biosynthesis/secretion than more evolved primates. Several ancestral FVIII sequences are expressed at greater levels than human FVIII in transient and recombinant expression systems.

Recombinant Proteins with the B domain deleted were produced.

```
The B-domain deleted sequence for Node number 68 having the
E434V mutation is:
                                                    SEQ ID NO: 39
MQIALFTCFFLSLFNFCSSATRRYYLGAVELSWNYMQSDLLSVLHTDTRFLPRMPTSFPF

NTSIMYKKTVFVEYMDHLFNIAKPRPPWMGLLGPTIWTEVHDTVVITLKNMASHPVSLH

AVGVSYWKASEGAEYEDQTSQREKEDDKVFPGESHTYVWQVLKENGPMASDPPCLTY

SYLSHVDLVKDLNSGLIGALLVCKEGSLSKERTQMLHQFVLLFAVFDEGKSWHSETKDS

FTQAMDSASTRAWPKMHTVNGYVNRSLPGLIGCHRKSVYWHVIGMGTTPEVHSIFLEG

HTFLVRNHRQASLEISPITFLTAQTLLIDLGQFLLFCHISSHKHDGMEAYVKVDSCPEEPQ

WQKKNNEEMEDYDDDLDSEMDMFTLDDDNSPFIQIRSVAKKYPKTWIHYISAEEEDWD

YAPSVLTSDDGSYKSQYLSNGPHRIGRKYKKVRFIAYTDV [E434V mutation]

TFKTRETIQHESGILGPLLYGEVGDTLLIIFKNQASRPYNIYPHGITDVSPLHSRRLPRGIK

HVKDLPIRPGEIFKYKWTVTVEDGPTKSDPRCLTRYYSSFINPERDLASGLIGPLLICYKE

SVDQRGNQMMSDKRNVILFSVFDENQSWYITENMQRFLPNAADTQPQDPEFQASNIMH

SINGYVFDSLQLTVCLHEVAYWYILSVGAQTDFLSIFFSGYTFKHKMVYEDTLTLFPFSG

ETVFMSMENPGLWVLGCHNSDFRKRGMTALLKVSSCDKSTSDYYEEIYEDIPTQLVND

NNVIEPRSFFQN [B-domain deletion]

PPVLKRHQRELSALQSEQEATDYDDSITIETNEDFDIYGEDIKQGPRSFQQKTRHYFIAAV

ERLWDYGMSTSPHVLRNRDQSGNAPQFKKVVFQEFTDGSFSQPLYRGELNEHLGLLGP

YIRAEVEDNIMVTFKNQASRPYSFYSSLISYKEDQRQGEEPRRNFVKPNETKIYFWKVQH

HMAPTEDEFDCKAWAYFSDVDLERDMHSGLIGPLLICHTNTLNPAHGRQVAVQEFALF

FTIFDETKSWYFTENVERNCKTPCNIQMEDPTLKENYRFHAINGYVMDTLPGLVMAQD
```

-continued

QRIRWYLLSMGSNENIQSIHFSGHVFTVRKKEEYKMAVYNLYPGVFETVEMLPSRAGIW

RVECLIGEHLQAGMSTLFLVYSKQCQIPLGMASGSIRDFQITASGHYGQWAPNLARLHH

SGSINAWSTKEPFSWIKVDLLTPMIIHGIKTQGARQKFSSLYISQFIIMYSLDGKKWLSYR

GNSTGTLMVFFGNVDSSGIKHNSFNPPIIARYIRLHPTHSSIRSTLRMELMGCDLNSCSIPL

GMENKVISDTQITASSYFTNMFATWSPSQARLHLQGRTNAWRPQVNDPKEWLQVDLQ

KTMKVTGIITQGVKSLFTSMFVKEFLISSSQDGHHWTHILHNGKVKVFQGNQDSSTPMV

NSLDPPLLTRYLRIHPQIWEHQIALRLEILGCEAQQLY

The B-domain deleted sequence for Node number 53 having E434V mutation is:

SEQ ID NO: 40

MQIELSTCFFLCLLQFSFSATRRYYLGAVELSWDYMQSDLLSELHVDTRFPPRVPRSFPF

NTSVMYKKTVFVEFTDHLFNIAKPRPPWMGLLGPTIRAEVYDTVVITLKNMASHPVSLH

AVGVSYWKASEGAEYDDQTSQREKEDDKVFPGESHTYVWQVLKENGPMASDPPCLTY

SYLSHVDLVKDLNSGLIGALLVCREGSLAKERTQTLHQFVLLFAVFDEGKSWHSETKDS

LTQAMDSASARAWPKMHTVNGYVNRSLPGLIGCHRKSVYWHVIGMGTTPEVHSIFLEG

HTFLVRNHRQASLEISPITFLTAQTLLMDLGQFLLFCHISSHQHDGMEAYVKVDSCPEEP

QLRMKNNEEEEDYDDDLYDSEMDVVRFDDDNSPPFIQIRSVAKKHPKTWVHYIAAEEE

DWDYAPSVLTPDDRSYKSQYLNNGPQRIGRKYKKVRFMAYTDV [E434V mutation]

TFKTREAIQYESGILGPLLYGEVGDTLLIIFKNQASRPYNIYPHGITDVSPLHSGRLPKGVK

HLKDLPILPGEIFKYKWTVTVEDGPTKSDPRCLTRYYSSFINLERDLASGLIGPLLICYKES

VDQRGNQMMSDKRNVILFSVFDENRSWYLTENMQRFLPNAAGVQPQDPEFQASNIMH

SINGYVFDSLQLSVCLHEVAYWYILSVGAQTDFLSVFFSGYTFKHKMVYEDTLTLFPFSG

ETVFMSMENPGLWVLGCHNSDFRNRGMTALLKVSSCDRNTGDYYEDTYEDIPTYLLSE

NNVIEPRSFSQN [B-domain deletion]

PPVLKRHQREITLTTLQSEQEEIDYDDTISIETKREDFDIYGEDENQGPRSFQKRTRHYFIA

AVERLWDYGMSRSPHVLRNRAQSGSVPQFKKVVFQEFTDGSFTQPLYRGELNEHLGLL

GPYIRAEVEDNIMVTFKNQASRPYSFYSSLISYEEDQRQGAEPRKNFVKPNETKTYFWK

VQHHMAPTKDEFDCKAWAYFSDVDLEKDMHSGLIGPLLICHTNTLNPAHGRQVTVQEF

ALFFTIFDETKSWYFTENMERNCRAPCNIQMEDPTFKENYRFHAINGYVMDTLPGLVMA

QDQRIRWYLLSMGSNENIHSIHFSGHVFTVRKKEEYKMAVYNLYPGVFETVEMLPSKA

GIWRVECLIGEHLHAGMSTLFLVYSKQCQTPLGMASGHIRDFQITASGQYGQWAPKLAR

LHYSGSINAWSTKEPFSWIKVDLLAPMIIHGIKTQGARQKFSSLYISQFIIMYSLDGKKWQ

TYRGNSTGTLMVFFGNVDSSGIKHNIFNPPIIARYIRLHPTHYSIRSTLRMELMGCDLNSC

SMPLGMESKAISDAQITASSYFTNMFATWSPSQARLHLQGRTNAWRPQVNNPKEWLQV

DFQKTMKVTGITTQGVKSLLTSMYVKEFLISSSQDGHHWTLFLQNGKVKVFQGNQDSF

TPVVNSLDPPLLTRYLRIHPQSWVHQIALRLEVLGCEAQQLY

Biosynthetic Rates of Ancestral FVIII Molecules

Constructs within the ancestral mammalian Orders—Primates, Rodentia and Perissodactyla were reconstructed through gene transfer and expression in human embryonic kidney (HEK) 293 and baby hamster kidney (BHK) mammalian cell lines. Each construct displayed detectable FVIII activity as determined by one-stage coagulation assay. This assay utilizes human FVIII-deficient plasma in combination with a test substance to generate a macroscopic clot capable of physically trapping a metal ball being pulled by magnetic forces. This assay also confirmed the compatibility of each An-FVIII with human coagulation factor IXa, for which FVIII serves as a cofactor, as well as factor X, the substrate of factor IXa. Following transient transfection of HEK293T-17 cells with plasmid DNA encoding the An-FVIII variants, 11-, 9-, and 4-fold enhanced FVIII activity was observed from the cells expressing the inferred primate ancestors An-54, -53, and -52, respectively, relative to existing human FVIII. However, the closest inferred An-57 shares 99% identity to hFVIII and did not display a significant difference in activity. Within the non-primate groups, An-68 demonstrated the greatest activity at 14-fold relative to hFVIII while An-65, -78, and -76 did not display different secreted activity concentrations. Of note, porcine FVIII (pFVIII) and the human porcine hybrid ET3 demonstrated 8 and 7-fold increased activity, respectively.

In Vivo $ED_{50}$ Determination of Recombinant an-FVIII

To study the in vivo efficacy of $ED_{50}$ of two An-FVIII sequences, An-53 and An-68, secreted protein was purified to homogeneity using two-step ion exchange FPLC. Purity of the protein was confirmed using SDS-PAGE, and specific activities of An-53 and An-68 were measured as 18,500 and 8770 U/mg, respectively. Hemophilia A E16 mice of 8-12 weeks were administered a single dose of FVIII and challenged via tail transection 15 minutes following injection. For the Dixon up-and-down method, doses were determined a priori based upon previous investigation of human FVIII $ED_{50}$. A bleeding event was defined as blood loss exceeding the mean plus standard deviation of wildtype C57BL/6 mice following the same challenge. Completion of this study revealed that An-53 and An-68 yielded $ED_{50}$ values of 88.6 and 47.2 U/kg, respectively. The resulting efficacies mirror the differences in specific activities.

TABLE 1

ED50 determination of An-53 and An-68 by Dixon up-and-down method via murine tail transection bleeding challenge.
Dixon Up-and-Down Method for Small Samples

| Factor VIII | Dose (U/mL) | Log (Dose) | Response: X = Bleed ○ = No Bleed | | | | | |
|---|---|---|---|---|---|---|---|---|
| An-53 | 100 | 2 | | ○ | | | | X |
| | 63.1 | 1.8 | X | | ○ | | X | |
| | 39.8 | 1.6 | | | | X | | |
| An-68 | 63.1 | 1.8 | ○ | | ○ | | | |
| | 39.8 | 1.6 | | X | | ○ | | X |
| | 25.1 | 1.4 | | | | | X | |
| Saline | 0 | N/A | X | X | | | | |
| hFVIII | 200 | 2.3 | ○ | ○ | | | | |

Antigenicity of Ancestral FVIII

An obstacle in the treatment of hemophilia A patients with protein replacement is the development of inhibitors. In naïve hemophilia A populations, infusions of picomolar concentrations of exogenous FVIII is sufficient to generate a robust adaptive immune response. Efforts to identify and remove immunogenic epitopes within human FVIII have largely utilized a panel of well characterized mouse anti-human monoclonal antibodies (MAbs).

Using a subset of MAbs with inhibitor titers over 1000 BU/mg and specificity targeting the A2 and C2 domains, ancestral FVIII were tested as an antigenic substrate via ELISA. Despite sharing 95% identity to modern human, An-53 displays markedly reduced cross-reactivity within the A2 and C2 domains. All group A MAbs are known to bind a major epitope in the highly immunogenic 484-508 loop of human FVIII, however, only MAbs 4A4 and G32 demonstrate cross-reactivity to An-53 (FIG. 5). These MAbs were explored for inhibitor titers against An-53 and show that G32 has an inhibitory titer 45-fold less compared to human FVIII while 4A4 has an equivalent titer against both human and An-53. An-53 has 4 residue substitutions within the 484-508 loop which may explain the absence of cross reactivity and/or inhibition by these potent A2 domain inhibitors. In addition to the 484-508 epitope, homolog scanning mutagenesis of human FVIII with porcine FVIII has previously shown that a major epitope of 4A4 lies within residues 403-444, but has not been defined. Alignment of several FVIII A2 domain sequences either possessing or lacking the 4A4 epitope allows for the identification of 4 residues that may be responsible for altered binding affinity. Three of these residues, Asp403, Gln410, and Asn414 are distal to the 484-508 surface loop and therefore unlikely to contribute significant binding energy. However, Glu434 is within close proximity to Ile508. Mutation of E434 to valine as observed in porcine FVIII resulted in a >4,000 fold reduction in 4A4 inhibition to undetectable levels as measured by modified Bethesda assay (FIG. 6).

Hydrodynamic Delivery of Two an-53 Plasmid DNA(Encoding AN-53 and AN-56) in an AAV Expression Cassette The use of AAV as a gene therapy application for hemophilia A has been explored extensively by many academic and commercial laboratories and recently advanced into clinical testing. An AAV-based product for hemophilia A has progressed beyond pre-clinical investigation. The major limitation to all gene therapy protocols for hemophilia A, both AAV and lentiviral, has continued to be the low level biosynthesis of FVIII at clinical achievable or predictably-safe vector doses. Given the enhanced biosynthesis observed for An-53 and An-56, despite high identity to human FVIII, in recombinant cell line systems, their utility was investigated in vivo following nucleic acid delivery to the liver of hemophilia A mice as a preclinical proxy for liver-directed AAV gene therapy.

An-53, An-56 and ET3 cDNAs were subcloned into an AAV expression cassette under the liver-specific HLP promoter (FIG. 7). Hemophilia A E16 mice were administered 3 μg linearized plasmid DNA (pDNA) diluted in TransIT®-EE delivery solution. A total volume equaling 10% of the mouse body weight was injected via tail vein within 4-7 seconds. Hydrodynamic injection results in DNA uptake predominantly in hepatocytes with other organs minimally affected. By placing transcriptional control under the HLP promoter, liver specificity was increase to better mimic the tropism of several AAV serotypes in clinical testing (e.g. AAV8).

Plasma FVIII levels were monitored over two weeks following injection. Peak FVIII levels were observed at day 3 for all constructs tested. Compared to the high-expression human/porcine hybrid ET3, An-53 demonstrated significantly increased and superphysiological peak FVIII levels of 2.37 units/mL. Interestingly, An-56 levels were detectable but did not exceed 0.06 units/mL throughout the experiment, suggesting that the sequence specificities allowing for enhanced biosynthesis in BHK-M cells did not convey an advantage in mouse hepatocytes. Using this system, liver codon optimized human FVIII at 3 μg per mouse was insufficient to yield detectable FVIII levels in empirical studies. The specific activity of An-53 generated in vivo was analyzed via an ELISA using cross-reactive anti-human MAbs compared to a recombinant An-53 standard curve. The FVIII produced de novo demonstrated a specific activity of 13,000±5100 U/mg.

Figure 8:
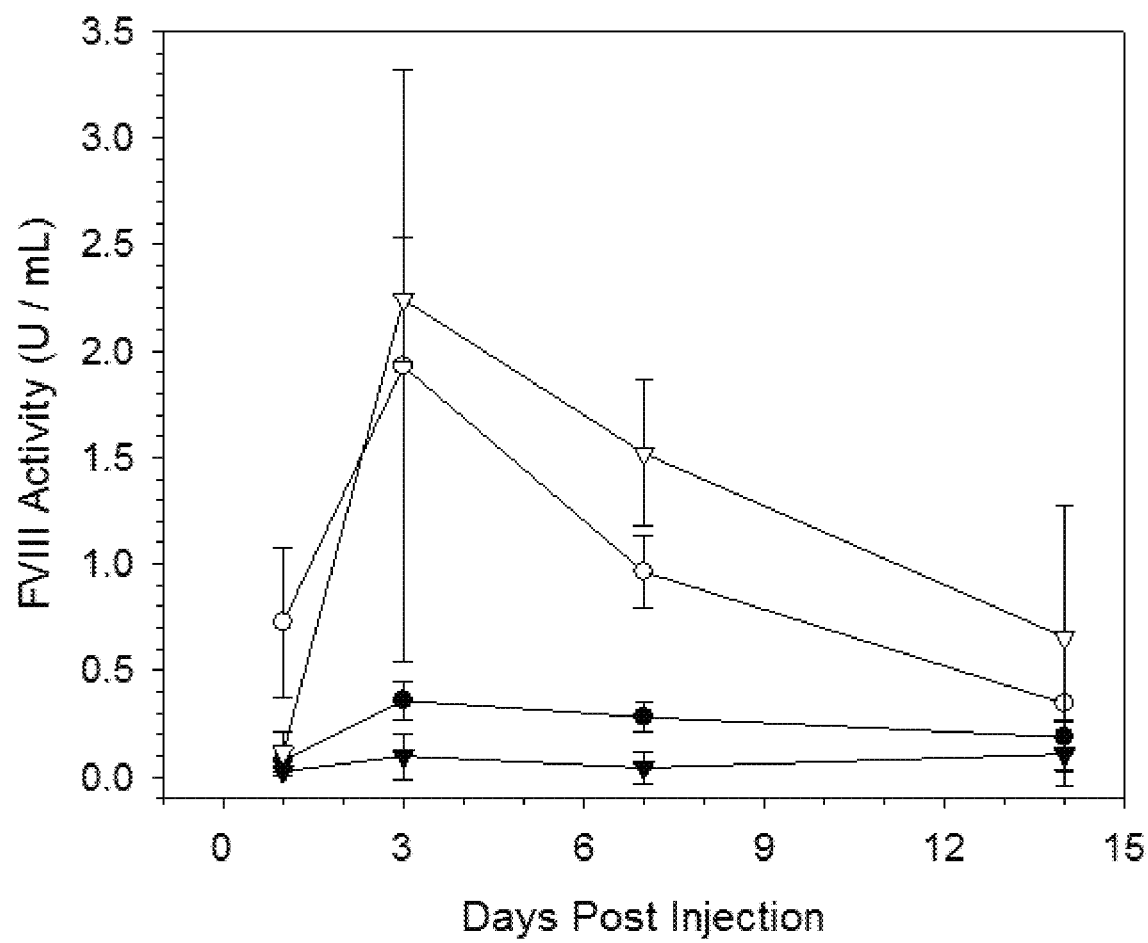
Figure 9:
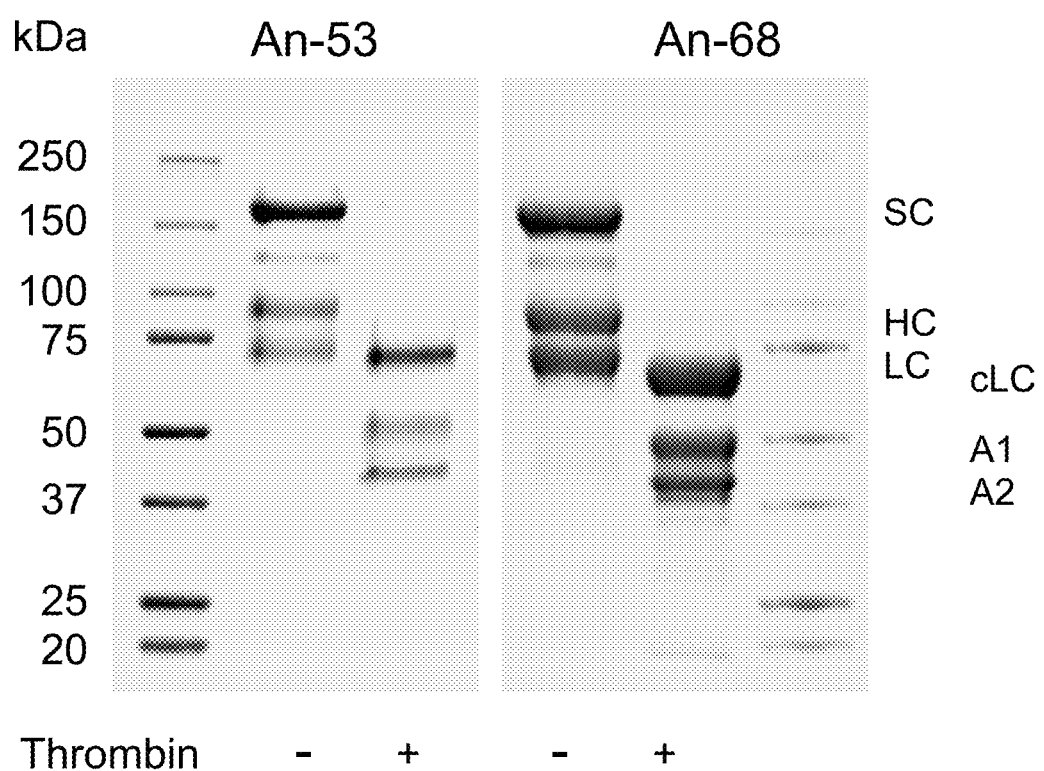

High DNA requirement in a hydrodynamic setting can be paralleled to the viral titer required to achieve therapeutic levels of FVIII. Therefore, hydrodynamic injections were conducted using two doses, a repeat of 3 μg and 4-fold lower DNA dose at 0.75 μg per mouse. Following hydrodynamic injection, ET3 DNA was observed to display the predicted dose response. An-53 DNA produced similar FVIII activity levels at 4-fold lower DNA dose. See FIG. 8.

Human and Ancestral Chimeric Sequences

It is contemplated that ancestral and human chimeric protein can be produced. In certain embodiments, the disclosure contemplates that the human FVIII B domain deleted sequences can be replaced with Ancestral A1 and A3 sequences e.g., sp-A1 (node 68)-A2 (Human E434V mutation)-(B-partially deleted Human)-linker-ap-A3 (node 68)-C1-C2 (human) SEQ ID NO: 42: MQIALFTCF-FLSLFNFCSSATRRYYLGAVELSWNYMQSDLLSVLH-TDTRFLPRMPTSFPF NTSIMYKKTVFVEYMDHLF-NIAKPRPPWMGLLGPTIWTEVHDTVVITLKN-MASHPVSLH AVGVSYWKASE-GAEYEDQTSQREKEDDKVFPGESHTYVWQVLKENGP-MASDPPCLTY SYLSHVDLVKDLNSGLIGALLVCKEGSLSK-ERTQMLHQFVLLFAVFDEGKSWHSETKDS FTQAMD-SASTRAWPKMHTVNGYVNRSLPGLIGCHRKSVY-WHVIGMGTTPEVHSIFLEG HTFLVRNHRQASLEISPITFLTAQTLLIDLGQFLL-FCHISSHKHDGMEAYVKVDSCPEEPQ WQK-KNNEEMEDYDDDLDSEMDMFTLDDDNSPFIQIRS-VAKKHPKTWVHYIAAEEEDW DYAPLVLAPDDRSYKSQYLNNGPQRIGRKYKKVRF-MAYTDV [E434V mutation] TFKTREAIQHESGILGPL-LYGEVGDTLLIIFKNQAS-RPYNIYPHGITDVRPLYSRRLPKGVK HLKDFPILPGEIFKYKWTVTVEDGPTKSDPRCL-TRYYSSFVNMERDLASGLIGPLLICYKE SVDQRGNQIMSDKRNVILFSVFDENR-SWYLTENTQRFLPNPAGVQLEDPEFQASNIMHSI NGYVFDSLQLSVCLHEVAYWYILSIGAQTDFLSVFF-SGYTFKHKMVYEDTLTLFPFSGET VFMSMEN-PGLWILGCHNSDFRNRGMTALLKVSS-CDKNTGDYYEDSYEDISAYLLSKNN AIEPRSFAQN [B-domain deletion] SRPPSASAPK [linker] PPVLKRHQRELSALQSEQEATDYDDSITI-ETNEDFDIYGEDIKQGPRSFQQKTRHYFIAAV ERLWDYGMSTSPHVLRNRDQSG-NAPQFKKVVFQEFTDGSFSQPLYRGELNEHLGLLGP YIRAEVEDNIMVTFKNQASRPYSFYSSLISYKEDQRQ-GEEPRRNFVKPNETKIYFWKVQH HMAPTEDEFDCK-AWAYFSDVDLERDMHSGLIGPLLICH-TNTLNPAHGRQVAVQEFALF FTIFDETKSWYFTENVERNCKTPCNIQMEDPTLK-ENYRFHAINGYVMDTLPGLVMAQD QRIRWYLLSMGSNENIQSIHFSGHVFTVRKKEEYK-MAVYNLYPGVFETVEMLPSRAGIW RVE-CLIGEHLQAGMSTLFLVYSKKCQTPLG-MASGHIRDFQITASGQYGQWAPKLARLH YSGSINAWSTKEPFSWIKVDLLAPMIIHGIKTQGAR-QKFSSLYISQFIIMYSLDGKKWQTY RGN-STGTLMVFFGNVDSSGIKHNIFNPPIIARYIRLHPTHY-SIRSTLRMELMGCDLNSCSM PLGMESKAISDAQI-TASSYFTNMFATWSPSKARLHLQGRSNAWRPQVNN-PKEWLQVDF QKTMKVTGVTTQGVKSLLTSMYVKE-FLISSSQDGHQWTLFFQNGKVKVFQGNQDSFTP VVNSLDPPLLTRYLRIHPQSWVHQIALRMEVLGCEA-QDLY.

The invention claimed is:

1. A vector comprising a promotor nucleic acid sequence in operable combination with a heterologous nucleic acid sequence encoding a polypeptide selected from the group consisting of SEQ ID NO: 20, SEQ ID NO: 2, SEQ ID NO: 30 and SEQ ID NO: 11.

2. The vector of claim 1, wherein the promoter is a liver-specific promotor.

3. The vector of claim 1, further comprising 5' and 3' AAV inverted terminal repeats (ITRs).

4. The vector of claim 1, wherein the vector is an adeno-associated viral vector.

5. The vector of claim 1, wherein the vector is a lentiviral vector.

6. An expression system comprising the vector of claim 1.

7. A viral particle or capsid comprising the vector of claim 1.

8. A pharmaceutical composition comprising the vector of claim 1.

9. A pharmaceutical composition comprising the viral particle or capsid of claim 6.

* * * * *